(12) United States Patent
Nakamura et al.

(10) Patent No.: US 7,906,517 B2
(45) Date of Patent: Mar. 15, 2011

(54) TRISUBSTITUTED AMINE COMPOUND

(75) Inventors: Yoshinori Nakamura, Osaka (JP);
Norimitsu Hayashi, Osaka (JP);
Takanori Higashijima, Osaka (JP);
Hitoshi Kubota, Osaka (JP); Kozo Oka, Osaka (JP)

(73) Assignee: Mitsubishi Tanabe Pharma Corporation, Osaka-shi (JP)

( * ) Notice: Subject to any disclaimer, the term of this patent is extended or adjusted under 35 U.S.C. 154(b) by 106 days.

(21) Appl. No.: 12/219,775

(22) Filed: Jul. 28, 2008

(65) Prior Publication Data
US 2009/0029994 A1    Jan. 29, 2009

Related U.S. Application Data

(63) Continuation-in-part of application No. PCT/JP2007/051861, filed on Jan. 30, 2007.

(60) Provisional application No. 60/952,706, filed on Jul. 30, 2007.

(30) Foreign Application Priority Data

Jan. 31, 2006    (JP) .................. 2006-023572
Nov. 30, 2006    (JP) .................. 2006-322853

(51) Int. Cl.
*A61K 31/44*    (2006.01)
*C07D 213/02*    (2006.01)
(52) U.S. Cl. .......... 514/256; 514/277; 544/224; 546/304
(58) Field of Classification Search .................. 514/256, 514/277; 544/224; 546/304
See application file for complete search history.

(56) References Cited

U.S. PATENT DOCUMENTS

| | | | |
|---|---|---|---|
| 5,536,718 | A | 7/1996 | Albright et al. |
| 6,685,617 | B1 | 2/2004 | Blinn et al. |
| 7,332,514 | B2 * | 2/2008 | Maeda et al. ................ 514/374 |
| 2002/0156281 | A1 | 10/2002 | Booth et al. |
| 2010/0167986 | A1 | 7/2010 | Ali et al. |

FOREIGN PATENT DOCUMENTS

| | | |
|---|---|---|
| EP | 0 129 433 A2 | 6/1984 |
| EP | 1 426 360 A1 | 6/2004 |
| EP | 1 533 292 A1 | 5/2005 |
| JP | 2003-221376 A | 8/2003 |
| WO | WO-00/17164 A1 | 3/2000 |
| WO | WO-00/17165 A1 | 3/2000 |
| WO | WO-00/17166 A1 | 3/2000 |
| WO | WO-03/063868 A1 | 8/2003 |
| WO | WO-2004/020393 A1 | 3/2004 |
| WO | WO-2005/100298 A1 | 10/2005 |
| WO | WO-2006/056854 A1 | 6/2006 |
| WO | WO-2006/073973 A2 | 7/2006 |
| WO | WO-2007/041494 A2 | 4/2007 |

OTHER PUBLICATIONS

English Translation of International Preliminary Report on Patentability, PCT/JP2007/051861, Aug. 5, 2008.
International Search Report, PCT/JP2007/051861, Dec. 6, 2007.
Massa et al., "Novel Heteroaryl Replacements of Aromatic 2-Tetrafluoroethoxy Substituents in Trifluoro-3-(tertiaryamino)-2-propanols as Potent Inhibitors of Cholesteryl Ester Transfer Protein", Biorganic & Medicinal Chemistry letters, vol. 11, pp. 1625-1628, (2001).
European Application No. 06816017.5; Office Action, Nov. 17, 2009, 6 pages.
European Application No. 6816017.5, Response filed May 27, 2010.
European Application No. 06 816 017.5, Office Action, Nov. 2, 2010, 4 pages.
U.S. Appl. No. 11/922,616, Office Action, Oct. 13, 2010, 8 pages.

* cited by examiner

*Primary Examiner* — Susannah Chung
(74) *Attorney, Agent, or Firm* — Birch, Stewart, Kolasch & Birch, LLP

(57) ABSTRACT

The present invention relates to a compound of the general formula (1):

$$A-N-R^1 \atop | \atop Y \atop | \atop B-R^2 \qquad (1)$$

wherein, Y is a methylene group, and the like; A is an optionally substituted heterocyclic group, and the like; B is an optionally substituted phenyl group, and the like; $R^1$ is an optionally substituted alkyl group, and the like; and $R^2$ is an optionally substituted amino group, and the like; or a pharmaceutically acceptable derivative thereof, which has an inhibitory activity against cholesteryl ester transfer protein (CETP), thereby being useful for prophylaxis and/or treatment of arteriosclerotic diseases, hyperlipemia or dyslipidemia, and the like.

18 Claims, No Drawings

TRISUBSTITUTED AMINE COMPOUND

This application is a Continuation-In-Part of PCT/JP2007/051861 filed on Jan. 30, 2007, which claims priority under 35 U.S.C. §119 (a) on Japanese application nos. 2006-023572 and 2006-322853 filed in Japan on Jan. 31, 2006 and Nov. 30, 2006, respectively. This application also claims priority under 35 U.S.C. §119(e) on U.S. provisional application No. 60/952,706 filed on Jul. 30, 2007. The entire contents of all of the above applications are hereby incorporated by reference in their entirety.

TECHNICAL FIELD

The present invention relates to a compound having an inhibitory activity against cholesteryl ester transfer protein (CETP) and showing an activity of increasing HDL cholesterol level and an activity of decreasing LDL cholesterol level, thereby being useful for prophylaxis and/or treatment of arteriosclerotic diseases, hyperlipemia or dyslipidemia.

BACKGROUND ART

Hypercholesterolemia, especially high serum level of low-density lipoprotein (LDL) cholesterol, has been revealed to be a risk factor of arteriosclerotic diseases by a number of epidemiological surveys. Actually, drugs capable of decreasing LDL cholesterol level such as 3-hydroxy-3-methylglutaryl-coenzyme A (HMG-CoA) reductase inhibitors have been used with the aim of preventing coronary artery diseases, and demonstrated to have some benefits in many large scale clinical tests. However, their preventive effect on coronary diseases is limited to some extent, and is not satisfactory enough yet.

Recently, low serum level of high density lipoprotein (HDL) cholesterol has been revealed to be a potent risk factor of arteriosclerotic diseases by a number of epidemiological surveys and large scale clinical tests. HDL is known to have various antiarteriosclerotic effects and attention is focused on the potentiality of drugs increasing HDL cholesterol level as a means for prevention or treatment of arteriosclerotic diseases. However, there are no drugs that can be used in a satisfactory manner for this purpose. Fibrates and HMG-CoA reductase inhibitors have only low activity of increasing HDL cholesterol level; nicotinic acid derivatives can significantly increase HDL cholesterol level, but have serious toleration issues. Accordingly, there has been a demand for a well-tolerated agent which can significantly elevate HDL cholesterol level, thereby preventing or reversing the progression of atherosclerosis.

It is known that many proteins are involved in the regulation mechanism for catabolism of various lipoproteins. Among them, the role of cholesteryl ester transfer protein (CETP) became to draw attention. CETP is a protein responsible for transfer of cholesteryl ester (CE) and triglyceride between lipoproteins, and mediate the transfer of CE from HDL to LDL or to very low density lipoprotein (VLDL). Accordingly, CETP activity affects greatly the lipid composition in lipoprotein particles. For example, it is known that administration of an active neutralizing monoclonal antibody against CETP to rabbit or hamster elevates HDL cholesterol level and lower LDL cholesterol level. Furthermore, human being having decreased or eliminated CETP activity due to gene mutation shows raised blood HDL cholesterol level and lowered blood LDL cholesterol level. On the other hand, it is known that transgenic mice and rats made to express CETP show lowered HDL cholesterol level and raised LDL cholesterol level. Thus, it is considered that CETP greatly contribute to the regulation of serum lipids, and thereby affecting the change of serum lipid profile such as decrease of HDL cholesterol level and increase of LDL cholesterol level. Accordingly, it is assumed that a high value of CETP activity would induce arteriosclerosis.

In fact, CETP activity varies depending on animal species. It is known that, arteriosclerotic lesions are readily formed by cholesterol loading in animals with high CETP activity such as rabbits, whereas such lesions hardly occur in animals with low CETP activity such as rats. Furthermore, it is confirmed that continuous suppression of CETP activity by administration of antisense oligodeoxynucleotide resulted in effects such as increase of blood HDL cholesterol level and reduction in arteriosclerotic lesions in cholesterol-fed rabbits.

The above findings indicate that CETP activity is in negative correlation with HDL cholesterol, and that inhibition of CETP activity would decrease the degree of risk for arteriosclerotic diseases. It is therefore expected that compounds capable of inhibiting CETP activity can block the transfer of cholesterol from HDL to LDL or VLDL, and thereby increasing HDL cholesterol that tends to prevent arteriosclerosis while lowering LDL cholesterol that tends to promote arteriosclerosis. In this way, such compounds can serve as a useful preventive or therapeutic agent for arteriosclerotic diseases, hyperlipemia or dyslipidemia and provide effective medical treatment for the first time.

Examples of compounds having CETP inhibitory activity include tetrahydroquinoline derivatives. See, PCT International Publication WO00/17164 pamphlet, PCT International Publication WO00/17165 pamphlet and PCT International Publication WO00/17166 pamphlet.

However, these compounds have defects. That is, they are poorly soluble in water and cannot be absorbed enough in vivo, a sufficient blood level for taking medicinal effect can hardly be achieved even when administered as an ordinary formulation for oral administration. See, WO03/63868.

Accordingly, it has been demanded to find a novel compound which eliminates the above-mentioned defects and intensive studies have been done on dibenzylamine type compounds, and the like. See, PCT International Publication WO05/100298 pamphlet, PCT International Publication WO04/020393 pamphlet, PCT International Publication WO 06/056854 pamphlet and JP 2003-221376 A.

DISCLOSURE OF INVENTION

The present invention provides compounds having an excellent inhibitory activity against CETP, thereby useful for prophylaxis and/or treatment of arteriosclerotic diseases, hyperlipemia or dyslipidemia.

The present inventors have intensively studied in order to achieve the above-mentioned objects, and have found a compound having an inhibitory activity against CETP and showing an activity of increasing HDL cholesterol level and an activity of decreasing LDL cholesterol level, and have accomplished the present invention.

BEST MODES FOR CARRYING OUT THE INVENTION

That is, the present invention provides the following embodiments:

1. A compound of the general formula (1):

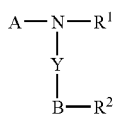

wherein, Y is a methylene group optionally substituted by a substituent(s) selected from an alkyl group and an oxo group, or a single bond;

A is (i) a group selected from an optionally substituted alkynyl group, a halogen atom, an oxo group, a hydroxy group, a cyano group, a nitro group, a carboxyl group, a sulfo group, an optionally substituted alkyl group, an optionally substituted cycloalkyl group, an optionally substituted alkenyl group, an optionally substituted alkoxy group, an optionally substituted cycloalkoxy group, an optionally substituted alkoxycarbonyl group, an optionally substituted carbamoyl group, an optionally substituted carbamimidoyl group, an optionally substituted alkylsulfanyl group, an optionally substituted alkylsulfinyl group, an optionally substituted alkylsulfonyl group, an optionally substituted amino group, an optionally substituted sulfamoyl group, an optionally substituted alkanoyl group, an optionally substituted homocyclic group, an oxy group substituted by optionally substituted homocyclic group, a carbonyl group substituted by optionally substituted homocyclic group, an optionally substituted heterocyclic group, an oxy group substituted by optionally substituted heterocyclic group, and a carbonyl group substituted by optionally substituted heterocyclic group;

(ii) a homocyclic group optionally substituted by 1 to 5 substituents selected independently from the groups as defined above in (i); or (iii) a heterocyclic group optionally substituted by 1 to 5 substituents selected independently from the groups as defined above in (i);

B is a phenyl group optionally substituted by 1 to 4 substituents selected independently from the following groups: an optionally substituted alkynyl group, a halogen atom, a hydroxy group, a cyano group, a nitro group, a carboxyl group, a sulfo group, an optionally substituted alkyl group, an optionally substituted cycloalkyl group, an optionally substituted alkenyl group, an optionally substituted alkoxy group, an optionally substituted cycloalkoxy group, an optionally substituted alkoxycarbonyl group, an optionally substituted carbamoyl group, an optionally substituted carbamimidoyl group, an optionally substituted alkylsulfanyl group, an optionally substituted alkylsulfinyl group, an optionally substituted alkylsulfonyl group, an optionally substituted amino group, an optionally substituted sulfamoyl group, an optionally substituted alkanoyl group, an optionally substituted homocyclic group, an oxy group substituted by optionally substituted homocyclic group, a carbonyl group substituted by optionally substituted homocyclic group, an optionally substituted heterocyclic group, an oxy group substituted by optionally substituted heterocyclic group, a carbonyl group substituted by optionally substituted heterocyclic group, and an alkylene group; wherein said alkylene group may have 1 to 3 heteroatoms selected independently from oxygen, sulfur and nitrogen atoms and further optionally may have a substituent(s);

$R^1$ is a hydrogen atom or an optionally substituted alkyl group; wherein the alkyl group further may optionally be substituted by a substituent(s) selected from an optionally substituted homocyclic group and an optionally substituted heterocyclic group;

$R^2$ is a group selected from an optionally substituted alkynyl group, a halogen atom, an oxo group, a hydroxy group, a cyano group, a nitro group, a carboxyl group, a sulfo group, an optionally substituted alkyl group, an optionally substituted cycloalkyl group, an optionally substituted alkenyl group, an optionally substituted alkoxy group, an optionally substituted cycloalkoxy group, an optionally substituted alkoxycarbonyl group, an optionally substituted carbamoyl group, an optionally substituted carbamimidoyl group, an optionally substituted alkylsulfanyl group, an optionally substituted alkylsulfinyl group, an optionally substituted alkylsulfonyl group, an optionally substituted amino group, an optionally substituted sulfamoyl group, an optionally substituted alkanoyl group, an optionally substituted homocyclic group, an oxy group substituted by optionally substituted homocyclic group, a carbonyl group substituted by optionally substituted homocyclic group, an optionally substituted heterocyclic group, an oxy group substituted by optionally substituted heterocyclic group, and a carbonyl group substituted by optionally substituted heterocyclic group, or a pharmaceutically acceptable derivative thereof.

2. The compound of the above embodiment 1 wherein the homocyclic group is a cycloalkyl group, a phenyl group or a naphthyl group;

the heterocyclic group is a thienyl, furyl, pyrrolyl, pyrrolinyl, oxazolyl, thiazolyl, pyrazolyl, imidazolyl, imidazolinyl, isoxazolyl, isothiazolyl, oxadiazolyl, furazanyl, thiadiazolyl, triazolyl, triazinyl, triazolidinyl, tetrazolyl, pyridyl, imidazopyridyl, pyrimidinyl, thiomorpholinyl, morpholinyl, triazinyl, pyrrolidinyl, piperidyl, pyranyl, tetrahydropyranyl, thiopyranyl, oxazinyl, thiazinyl, piperazinyl, triazinyl, oxatriazinyl, pyridazinyl, pyrazinyl, benzofuranyl, benzothiazolyl, benzoxazolyl, tetrazolopyridazinyl, triazolopyridazinyl, benzimidazolyl, quinolyl, isoquinolyl, dihydroisoquinolyl, cinnolinyl, phthalazinyl, quinazolinyl, quinoxalinyl, indolizinyl, dihydroindolyl, indolyl, quinolizinyl, naphthyridinyl, purinyl, pteridinyl, dibenzofuranyl, carbazolyl, acridinyl, phenanthridinyl, chromanyl, benzoxazinyl, phenazinyl, phenothiazinyl, phenoxazinyl, hexahydroazepinyl, imidazolidinyl, oxazolidinyl, tetrahydrofuranyl, dioxolanyl, oxiranyl, dihydropyrimidinyl, oxazolinyl, dihydrooxazinyl, dihydropyrazolyl, imidazopyridyl, dihydropyrazinyl, tetrahydroquinolyl, benzothienyl, dihydrooxazolyl, oxathiadiazolyl, dihydrooxazolyl or tetrahydroquinolyl group;

a substituent(s) for an optionally substituted alkyl group, an optionally substituted cycloalkyl group, an optionally substituted alkenyl group, an optionally substituted alkoxy group, an optionally substituted cycloalkoxy group, an optionally substituted alkoxycarbonyl group, an optionally substituted carbamoyl group, an optionally substituted carbamimidoyl group, an optionally substituted alkylsulfanyl group, an optionally substituted alkylsulfinyl group, an optionally substituted alkylsulfonyl group, an optionally substituted amino group, an optionally substituted sulfamoyl group, an optionally substituted alkanoyl group, an optionally substituted homocyclic group, an oxy group substituted by optionally substituted homocyclic group, a carbonyl group substituted by optionally substituted homocyclic group, an optionally substituted heterocyclic group, an oxy group substituted by optionally substituted heterocyclic group, a carbonyl group substituted by optionally substituted heterocyclic group, an optionally substituted phenyl group, an optionally substituted alkylsulfonyloxy group, an optionally substituted alkynyl group or an optionally substituted alkylene group is/are 1 to 5 groups selected independently from the following groups:

a halogen atom; a cyano group; a hydroxy group; a nitro group; a carboxyl group; an oxo group; a thioxo group; a sulfo group; a cycloalkyl group optionally substituted by hydroxy group, halogen atom, carboxyl group, alkoxycarbonyl group, mono- or di-alkylamino group, phenyl group or morpholinyl group; an alkoxycarbonyl group optionally substituted by hydroxy group, halogen atom, carboxyl group, alkoxycarbonyl group, mono- or di-alkylamino group, phenyl group or morpholinyl group; a carbamoyl group; a mono- or di-alkylcarbamoyl group optionally substituted by hydroxy group, halogen atom, carboxyl group, alkoxycarbonyl group, mono- or di-alkylamino group, phenyl group or morpholinyl group; an alkyl group optionally substituted by hydroxy group, halogen atom, carboxyl group, alkoxycarbonyl group, mono- or di-alkylamino group, phenyl group or morpholinyl group; an alkanoyl group optionally substituted by hydroxy group, halogen atom, carboxyl group, alkoxycarbonyl group, mono- or di-alkylamino group, phenyl group or morpholinyl group; an alkoxy group optionally substituted by hydroxy group, halogen atom, carboxyl group, alkoxycarbonyl group, mono- or di-alkylamino group, phenyl group or morpholinyl group; an alkanoyloxy group optionally substituted by hydroxy group, halogen atom, carboxyl group, alkoxycarbonyl group, mono- or di-alkylamino group, phenyl group or morpholinyl group; an alkylsulfanyl group optionally substituted by hydroxy group, halogen atom, carboxyl group, alkoxycarbonyl group, mono- or di-alkylamino group, phenyl group or morpholinyl group; an alkylsulfonyl group optionally substituted by hydroxy group, halogen atom, carboxyl group, alkoxycarbonyl group, mono- or di-alkylamino group, phenyl group or morpholinyl group; an alkylsulfinyl group optionally substituted by hydroxy group, halogen atom, carboxyl group, alkoxycarbonyl group, mono- or di-alkylamino group, phenyl group or morpholinyl group; a mono- or di-alkylsulfamoyl group optionally substituted by hydroxy group, halogen atom, carboxyl group, alkoxycarbonyl group, mono- or di-alkylamino group, phenyl group or morpholinyl group; an amino group; a mono- or di-alkylamino group optionally substituted by hydroxy group, halogen atom, carboxyl group, alkoxycarbonyl group, mono- or di-alkylamino group, phenyl group or morpholinyl group; a mono- or di-alkylsulfamoylamino group optionally substituted by hydroxy group, halogen atom, carboxyl group, alkoxycarbonyl group, mono- or di-alkylamino group, phenyl group or morpholinyl group; a mono- or di-alkylureido group optionally substituted by hydroxy group, halogen atom, carboxyl group, alkoxycarbonyl group, mono- or di-alkylamino group, phenyl group or morpholinyl group; a homocyclic group selected from a cycloalkyl group, a phenyl group and a naphthyl group; an oxy group substituted by the homocyclic group as defined above; a carbonyl group substituted by the homocyclic group as defined above; a heterocyclic group selected from a thienyl, furyl, pyrrolyl, pyrrolinyl, oxazolyl, thiazolyl, pyrazolyl, imidazolyl, imidazolinyl, isoxazolyl, isothiazolyl, oxadiazolyl, furazanyl, thiadiazolyl, triazolyl, triazinyl, triazolidinyl, tetrazolyl, pyridyl, imidazopyridyl, pyrimidinyl, thiomorpholinyl, morpholinyl, triazinyl, pyrrolidinyl, piperidyl, pyranyl, tetrahydropyranyl, thiopyranyl, oxazinyl, thiazinyl, piperazinyl, triazinyl, oxatriazinyl, pyridazinyl, pyrazinyl, benzofuranyl, benzothiazolyl, benzoxazolyl, tetrazolopyridazinyl, triazolopyridazinyl, benzimidazolyl, quinolyl, isoquinolyl, dihydroisoquinolyl, cinnolinyl, phthalazinyl, quinazolinyl, quinoxalinyl, indolinyl, dihydroindolyl, indolyl, quinolizinyl, naphthyridinyl, purinyl, pteridinyl, dibenzofuranyl, carbazolyl, acridinyl, phenanthridinyl, chromanyl, benzoxazinyl, phenazinyl, phenothiazinyl, phenoxazinyl, hexahydroazepinyl, imidazolidinyl, oxazolidinyl, tetrahydrofuranyl, dioxolanyl, oxiranyl, dihydropyrimidinyl, oxazolinyl, dihydrooxazinyl, dihydropyrazolyl, imidazopyridyl, dihydropyrazinyl, tetrahydroquinolyl, benzothienyl, dihydrooxazolyl, oxathiadiazolyl, dihydrooxazolyl and tetrahydroquinolyl groups; an oxy group substituted by the heterocyclic group as defined above; a carbonyl group substituted by the heterocyclic group as defined above; and a group of the formulae:

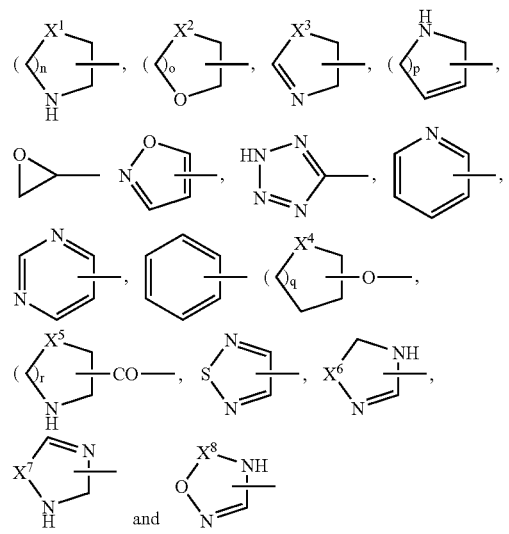

wherein $X^1$ and $X^3$ are each independently $CH_2$, NH, O, S, SO or $SO_2$; $X^2$ and $X^5$ are each independently $CH_2$, O, S, SO or $SO_2$; $X^4$ is NH, O, S, SO or $SO_2$; $X^6$ and $X^7$ are each independently O or S; $X^8$ is S or SO; and n, o, p, q and r are each independently an integer of 1 to 4, and further each of the above groups may optionally be substituted by 1 to 3 substituents selected from the following groups: halogen atom, carboxyl group, hydroxy group, cyano group, oxo group, thioxo group, alkyl group, hydroxyalkyl group, alkoxycarbonylalkyl group, carboxyalkyl group, morpholinylalkyl group, phenylalkyl group, alkanoyl group, hydroxyalkanoyl group, alkoxyalkanoyl group, alkoxy group, phenylalkoxy group, alkoxycarbonyl group, benzyloxycarbonyl group, mono- or di-alkylamino group, mono- or di-alkylcarbamoyl group, mono- or di-alkylsulfamoyl group, alkylsulfonyl group and tetrazolyl group, or a pharmaceutically acceptable derivative thereof.

3. The compound of the above embodiment 2 wherein A is a group of a formula:

$A^1$-$A^2$;

wherein $A^1$ is a phenyl, naphthyl, pyrimidinyl, pyridazinyl, pyridyl, triazolyl, tetrazolyl, oxadiazolyl, dihydropyrimidinyl, pyrazinyl, thiazolyl, oxazolyl, dihydrooxazinyl, imidazolyl, pyrazolyl or dihydropyrazinyl group;

$A^2$ is a carboxyl group; a cyano group; a nitro group; an alkyl group optionally substituted by a group selected from a hydroxy group, a cyano group, a carboxyl group, an alkoxycarbonyl group, an alkoxy group, a phenylalkoxy group, a hydroxyalkoxy group, a carboxyalkoxy group, an alkylsulfanyl group, an alkylsulfonyl group, an alkylsulfinyl group, an amino group, a mono- or di-alkylamino group, a mono- or di-alkylsulfamoylamino group, a mono- or di-alkylureido group optionally substituted by morpholinyl group, an oxiranyl group, a dialkyldioxolanyl group, a pyrrolidinyl group optionally substituted by carboxyl group, a piperidyl group optionally substituted by carboxyl group, a piperazinyl group optionally substituted by alkyl group, and a morpholinyl group; an alkenyl group optionally substituted by carboxyl group; an alkoxy group optionally substituted by a group selected from a hydroxy group, a cyano group, a carboxyl group, an alkoxycarbonyl group, an alkoxy group, a phenylalkoxy group, a hydroxyalkoxy group, a carboxyalkoxy group, an alkylsulfanyl group, an alkylsulfonyl group, an alkylsulfinyl group, an amino group, a mono- or di-alkylamino group, a mono- or di-alkylsulfamoylamino group, a mono- or di-alkylureido group optionally substituted by morpholinyl group, an oxiranyl group, a dialkyldioxolanyl group, a pyrrolidinyl group optionally substituted by carboxyl group, a piperidyl group optionally substituted by carboxyl group, a piperazinyl group optionally substituted by alkyl group, and a morpholinyl group; an alkoxycarbonyl group; a hydroxycarbamimidoyl group; an alkylsulfanyl group; an alkylsulfonyl group optionally substituted by carboxyl group; a mono- or di-alkylamino group optionally substituted by hydroxy group, carboxyl group, alkoxy group or mono- or di-alkylamino group; a morpholinyl group optionally substituted by carboxyl group, alkyl group, carboxyalkyl group or alkoxycarbonyl group; an optionally oxidized thiomorpholinyl group; a piperazinyl group optionally substituted by a group selected from an alkyl group, alkanoyl group and hydroxyalkanoyl group; a pyrrolidinyl group optionally substituted by carboxyl group, alkyl group, carboxyalkyl group or alkoxycarbonyl group; a piperidyl group optionally substituted by carboxyl group, alkyl group, carboxyalkyl group or alkoxycarbonyl group; a tetrazolyl group optionally substituted by alkyl group, hydroxyalkyl group, carboxyalkyl group or morpholinylalkyl group; an oxodihydrooxadiazolyl group; a pyrimidinyl group; or a tetrahydropyranyl group;

$R^1$ is a group of a formula:

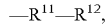

wherein $R^{11}$ is an alkylene group;

$R^{12}$ is a substituent(s) selected from a phenyl, pyridyl, pyrimidinyl, pyridazinyl, furyl, thienyl, triazolyl, tetrazolyl, oxadiazolyl, dihydropyrimidinyl, pyrazinyl, thiazolyl, oxazolyl, imidazolyl, dihydrooxazinyl, dihydropyrazinyl and pyrazolyl group;

wherein said substituent(s) may optionally be substituted by 1 to 4 substituents selected independently from halogen atom, carboxyl group, alkoxycarbonyl group, carbamoyl group, mono- or di-alkylcarbamoyl group, alkyl group, alkoxy group, hydroxy group, nitro group, cyano group, amino group, mono- or di-alkylamino group, alkanoyl group, alkylsulfanyl group, tetrazolyl group and dihydrooxazolyl group; and further each of said alkyl group, alkoxy group, mono- or di-alkylamino group, mono- or di-alkylcarbamoyl group, alkanoyl group and alkylsulfanyl group independently may optionally be substituted by 1 to 5 substituents selected independently from halogen atom, hydroxy group, alkoxy group, amino group, morpholinyl group, piperidyl group, pyrrolidinyl group, piperazinyl group, alkylpiperazinyl group and alkanoylpiperazinyl group;

$R^2$ is a halogen atom;
a hydroxy group;
a cyano group;
a nitro group;
a carboxyl group;
a sulfo group;

a cycloalkyl group optionally substituted by carboxyl group or alkoxycarbonyl group;

an alkyl group optionally substituted by a group selected from a halogen atom, a cyano group, a hydroxy group, a carboxyl group, an alkoxycarbonyl group, a tetrazolyl group, a mono- or di-alkylcarbamoyl group, an alkoxy group (said alkoxy group may optionally be substituted by phenyl group, carboxyl group or hydroxy group), an alkanoyl group, an alkanoyloxy group, an alkylsulfanyl group, an alkylsulfonyl group, an alkylsulfinyl group, an amino group, a mono- or di-alkylamino group optionally substituted by carboxyl group or alkoxy group, a mono- or di-alkylsulfamoylamino group, a mono- or di-alkylureido group optionally substituted by morpholinyl group, an oxiranyl group, a dioxolanyl group optionally substituted by alkyl group, pyrrolidinyl group optionally substituted by alkoxycarbonyl group or carboxyl group, a pyrrolidinyl group optionally substituted by alkoxycarbonylalkyl group or carboxyalkyl group, a piperidyl group optionally substituted by alkoxycarbonyl group or carboxyl group, a piperidyl group optionally substituted by alkoxycarbonylalkyl or carboxyalkyl group, a piperazinyl group optionally substituted by alkyl group, a hexahydroazepinyl group, a morpholinyl group, and a piperidyloxy group optionally substituted by alkyl group; an alkenyl group optionally substituted by a group selected from a cyano group, a hydroxy group, a carboxyl group, a benzyloxycarbonyl group and a tetrazolyl group;

an alkenyloxy group optionally substituted by carboxyl group;

an alkoxy group optionally substituted by a group selected from a halogen atom, a cyano group, a hydroxy group, a carboxyl group, an alkoxycarbonyl group, a tetrazolyl group, a carbamoyl group, a mono- or di-alkylcarbamoyl group (said mono- or di-alkylcarbamoyl group may optionally be substituted by carboxyl group, alkoxycarbonyl group or hydroxy group), an alkoxy group (said alkoxy group may optionally be substituted by carboxyl group, formyl group or hydroxy group), an alkanoyloxy group, an alkylsulfanyl group, an alkylsulfonyl group, an alkylsulfinyl group, an aminosulfonyl group, an amino group, a mono- or di-alkylamino group optionally substituted by carboxyl group or alkoxy group, a mono- or di-alkylsulfamoylamino group, a mono- or di-alkylureido group optionally substituted by morpholinyl group, a cycloalkyl group optionally substituted by carboxymethyl group, an oxiranyl group, a phenyl group optionally substituted by alkoxy group or carboxyl group, a morpholinyl group, a pyrrolidinyl group optionally substituted by alkoxycarbonyl group or carboxyl group, a pyrrolidinyl group optionally substituted by alkoxycarbonylalkyl group or carboxyalkyl group, a pyrrolidinyl group optionally substituted by oxo group, a piperidyl group optionally substituted by alkoxycarbonyl group or carboxyl group, a piperidyl group optionally substituted by alkoxycarbonylalkyl group or carboxyalkyl group, a piperazinyl group optionally substituted by alkyl group, a hexahydroazepinyl group, a pyrimidinyl group, a pyridyl group, a dioxolanyl group optionally substituted by alkyl group, an oxadiazolyl group optionally substituted by oxo group, an oxathiadiazolyl group optionally substituted by oxo group, a pyrrolidinylcarbonyl group optionally substituted by carboxyl group, a piperidyloxy group optionally substituted by alkyl group and a morpholinylcarbonyl group;

an alkoxycarbonyl group optionally substituted by phenyl group;

a carbamoyl group;

a mono- or di-alkylcarbamoyl group optionally substituted by a group selected from a carboxyl group, a morpholinyl group and an alkoxy group;

a hydroxycarbamimidoyl group;

an alkylsulfanyl group optionally substituted by a group selected from hydroxy group, carboxyl group and mono- or di-alkylcarbamoyl group; an alkylsulfinyl group;

an alkylsulfonyl group optionally substituted by a group selected from hydroxy group, carboxyl group, alkoxycarbonyl group and mono- or di-alkylcarbamoyl group;

an amino group;

a mono- or di-alkylamino group optionally substituted by a group selected from a halogen atom, a cyano group, a hydroxy group, a carboxyl group, an alkoxycarbonyl group, a tetrazolyl group, a carbamoyl group, a mono- or di-alkylcarbamoyl group (said mono- or di-alkylcarbamoyl group may optionally be substituted by carboxyl group, alkoxycarbonyl group or hydroxy group), an alkoxy group (said alkoxy group may optionally be substituted by carboxyl group, formyl group or hydroxy group), an alkanoyloxy group, an alkylsulfanyl group, an alkylsulfonyl group, an alkylsulfinyl group, an aminosulfonyl group, an amino group, a mono- or di-alkylamino group optionally substituted by carboxyl group or alkoxy group, a mono- or di-alkylsulfamoylamino group, a mono- or di-alkylureido group optionally substituted by morpholinyl group, a cycloalkyl group optionally substituted by carboxymethyl group, an oxiranyl group, a phenyl group optionally substituted by alkoxy group or carboxyl group, a morpholinyl group, a pyrrolidinyl group optionally substituted by alkoxycarbonyl group or carboxyl group, a pyrrolidinyl group optionally substituted by alkoxycarbonylalkyl or carboxyalkyl group, a pyrrolidinyl group substituted by oxo group, a piperidyl group optionally substituted by alkoxycarbonyl group or carboxyl group, a piperidyl group optionally substituted by alkoxycarbonylalkyl group or carboxyalkyl group, a piperazinyl group optionally substituted by alkyl group, a hexahydroazepinyl group, a pyrimidinyl group, a pyridyl group, a dioxolanyl group optionally substituted by alkyl group, an oxadiazolyl group optionally substituted by oxo group, an oxathiadiazolyl optionally substituted by oxo group, a pyrrolidinylcarbonyl group optionally substituted by carboxyl group, a piperidyloxy group optionally substituted by alkyl group and a morpholinylcarbonyl group;

an alkanoylamino group optionally substituted by a group selected from hydroxy group, alkoxy group, carboxyl group and amino group;

a mono- or di-alkylcarbamoylamino group optionally substituted by alkoxy group;

a morpholinylcarbonylamino group;

a sulfamoyl group;

a mono- or di-alkylsulfamoyl group;

an alkanoyl group optionally substituted by a group selected from hydroxy group, carboxyl group, alkoxycarbonyl group, alkoxy group, mono- or di-alkylamino group and morpholinyl group; or a cyclic group selected from a cycloalkyl, phenyl, naphthyl, thienyl, furyl, pyrrolyl, pyrrolinyl, oxazolyl, thiazolyl, pyrazolyl, imidazolyl, imidazolinyl, isoxazolyl, isothiazolyl, oxadiazolyl, furazanyl, thiadiazolyl, triazolyl, triazinyl, triazolidinyl, tetrazolyl, pyridyl, imidazopyridyl, pyrimidinyl, thiomorpholinyl, morpholinyl, triazinyl, pyrrolidinyl, piperidyl, pyranyl, tetrahydropyranyl, thiopyranyl, oxazinyl, thiazinyl, piperazinyl, triazinyl, oxatriazinyl, pyridazinyl, pyrazinyl, benzofuranyl, benzothiazolyl, benzoxazolyl, tetrazolopyridazinyl, triazolopyridinyl, benzimidazolyl, quinolyl, isoquinolyl, dihydroisoquinolyl, cinnolinyl, phthalazinyl, quinazolinyl, quinoxalinyl, indolizinyl, dihydroindolyl, indolyl, quinolizinyl, naphthyridinyl, purinyl, pteridinyl, dibenzofuranyl, carbazolyl, acridinyl, phenanthridinyl, chromanyl, benzoxazinyl, phenazinyl, phenothiazinyl, phenoxazinyl, hexahydroazepinyl, imidazolidinyl, oxazolidinyl, tetrahydrofuranyl, dioxolanyl, oxiranyl, dihydropyrimidinyl, oxazolinyl, dihydrooxazinyl, dihydropyrazolyl, imidazopyridyl, dihydropyrazinyl, tetrahydroquinolyl, benzothienyl, dihydrooxazolyl, oxathiadiazolyl, dihydrooxazolyl and tetrahydroquinolyl groups;

wherein said cyclic group may optionally be substituted by the following groups: a halogen atom, an alkoxyalkyl group, an alkyl group optionally substituted by 1 to 5 halogen atoms, a mono- or di-alkylaminoalkyl group, a mono- or di-alkylaminoalkoxy group, a carboxyl group, a hydroxy group, a cyano group, an oxo group, an alkyl group, a hydroxyalkyl group, an alkoxycarbonylalkyl group, a carboxyalkyl group, a morpholinylalkyl group, a phenylalkyl group, an alkanoyl group, a hydroxyalkanoyl group, an alkoxyalkanoyl group, an alkoxy group, a phenylalkoxy group, an alkoxycarbonyl group, a benzyloxycarbonyl group, a mono- or di-alkylamino group, a mono- or di-alkylcarbamoyl group, a mono- or di-alkylsulfamoyl group, an alkylsulfonyl group and a tetrazolyl group;

wherein the substituents defined as above may further be substituted by a substituent(s) selected from the following groups:

a halogen atom, an alkoxyalkyl group, an alkyl group optionally substituted by 1 to 5 halogen atoms, a mono- or di-alkylaminoalkyl group, a mono- or di-alkylaminoalkoxy group, a carboxyl group, a hydroxy group, a cyano group, an oxo group, an alkyl group, a hydroxyalkyl group, an alkoxycarbonylalkyl group, a carboxyalkyl group, a morpholinylalkyl group, a phenylalkyl group, an alkanoyl group, a hydroxyalkanoyl group, an alkoxyalkanoyl group, an alkoxy group, a phenylalkoxy group, an alkoxycarbonyl group, a benzyloxycarbonyl group, a mono- or di-alkylamino group, a mono- or di-alkylcarbamoyl group, a mono- or di-alkylsulfamoyl group, an alkylsulfonyl group and a tetrazolyl group, or a pharmaceutically acceptable derivative thereof.

4. The compound of the above embodiment 1 wherein Y is a methylene group optionally substituted by a substituent(s) selected from an alkyl group and an oxo group, or a single bond;

A is a group of a formula:

$$-A^1-A^2;$$

wherein $A^1$ is a heterocyclic group or a homocyclic group;

$A^2$ is an optionally substituted homocyclic group, an optionally substituted alkylsulfanyl group, an optionally substituted alkylsulfinyl group, an optionally substituted alkylsulfonyl group, an optionally substituted alkyl group, a nitro group, a hydroxy group, a cyano group, an optionally substituted alkenyl group, an optionally substituted heterocyclic group, a substituted alkoxy group, a halogen atom, an amino group substituted by 1 to 2 substituents, or a hydrogen atom;

B is a phenyl group optionally substituted by 1 to 4 substituents selected independently from a cyano group, a halogen atom, an optionally substituted alkylsulfanyl group, an optionally substituted alkylsulfinyl group, an optionally substituted alkylsulfonyl group, an amino group substituted by 1 to 2 substituents, a hydroxy group, an optionally substituted heterocyclic group, an optionally substituted cycloalkoxy group, a carboxyl group, an optionally substituted cycloalkyl group, an optionally substituted carbamoyl group, an optionally substituted alkyl group, and an optionally substituted alkoxy group;

R¹ is a hydrogen atom, an alkyl group substituted by a heterocyclic group or an alkyl group substituted by a homocyclic group; wherein said heterocyclic group, homocyclic group or alkyl group may further have a substituent(s);

R² is an optionally substituted alkylsulfanyl group, an optionally substituted alkylsulfinyl group, an optionally substituted alkylsulfonyl group, a cyano group, an optionally substituted alkenyl group, an amino group optionally substituted by 1 to 2 substituents, a halogen atom, an optionally substituted alkoxy group, an optionally substituted carbamoyl group, an oxy group substituted by optionally substituted heterocyclic group, a hydroxy group, an optionally substituted heterocyclic group, an optionally substituted homocyclic group, an oxy group substituted by optionally substituted homocyclic group, an optionally substituted alkyl group or a nitro group;

provided that when Y is a methylene group and A² is a halogen atom, a hydrogen atom, a nitro group, a hydroxy group or a cyano group, then R² is not an optionally substituted alkyl group, an optionally substituted alkenyl group, an optionally substituted alkoxy group, or an amino group optionally substituted by 1 to 2 substituents, or a pharmaceutically acceptable derivative thereof.

5. The compound of the above embodiment 4 wherein Y is a methylene group optionally substituted by a substituent(s) selected from an alkyl group and an oxo group;

A¹ is a heterocyclic group;

A² is an optionally substituted heterocyclic group, an optionally substituted alkyl group, a substituted alkoxy group, a halogen atom, an amino group optionally substituted by 1 to 2 substituents, or a hydrogen atom;

B is a phenyl group optionally substituted by 1 to 4 groups selected independently from a cyano group, a halogen atom, a hydroxy group, an optionally substituted cycloalkyl group, an optionally substituted cycloalkoxy group, an optionally substituted piperidyl group, a cycloalkyl group, a cycloalkoxy group, an optionally substituted alkyl group and an optionally substituted alkoxy group;

R¹ is a hydrogen atom, or an alkyl group substituted by a phenyl group that is substituted by 1 to 2 groups selected independently from an alkoxy group optionally substituted by 1 to 3 halogen atoms, an alkyl group optionally substituted by 1 to 3 halogen atoms and a cyano group;

R² is an amino group optionally substituted by 1 to 2 substituents, a halogen atom, an optionally substituted alkoxy group, an optionally substituted carbamoyl group, an oxy group substituted by optionally substituted heterocyclic group, a hydroxy group, an optionally substituted heterocyclic group, an optionally substituted homocyclic group, an oxy group substituted by optionally substituted homocyclic group, a hydroxyalkyl group or a nitro group, or a pharmaceutically acceptable derivative thereof.

6. The compound of the above embodiment 5 wherein the homocyclic group is a cycloalkyl group, a phenyl group or a naphthyl group;

the heterocyclic group is a thienyl, furyl, pyrrolyl, pyrrolinyl, oxazolyl, thiazolyl, pyrazolyl, imidazolyl, imidazolinyl, isoxazolyl, isothiazolyl, oxadiazolyl, furazanyl, thiadiazolyl, triazolyl, triazinyl, triazolidinyl, tetrazolyl, pyridyl, imidazopyridyl, pyrimidinyl, thiomorpholinyl, morpholinyl, triazinyl, pyrrolidinyl, piperidyl, pyranyl, tetrahydropyranyl, thiopyranyl, oxazinyl, thiazinyl, piperazinyl, triazinyl, oxatriazinyl, pyridazinyl, pyrazinyl, benzofuranyl, benzothiazolyl, benzoxazolyl, tetrazolopyridazinyl, triazolopyridazinyl, benzimidazolyl, quinolyl, isoquinolyl, dihydroisoquinolyl, cinnolinyl, phthalazinyl, quinazolinyl, quinoxalinyl, indolizinyl, dihydroindolyl, indolyl, quinolizinyl, naphthyridinyl, purinyl, pteridinyl, dibenzofuranyl, carbazolyl, acridinyl, phenanthridinyl, chromanyl, benzoxazinyl, phenazinyl, phenothiazinyl, phenoxazinyl, hexahydroazepinyl, imidazolidinyl, oxazolidinyl, tetrahydrofuranyl, dioxolanyl, oxiranyl, dihydropyrimidinyl, oxazolinyl, dihydrooxazinyl, dihydropyrazolyl, imidazopyridyl, dihydropyrazinyl, tetrahydroquinolyl, benzothienyl, dihydrooxazolyl, oxathiadiazolyl, dihydrooxazolyl or tetrahydroquinolyl group;

a substituent(s) for an optionally substituted alkyl group, an optionally substituted cycloalkyl group, an optionally substituted alkenyl group, an optionally substituted alkoxy group, an optionally substituted cycloalkoxy group, an optionally substituted alkoxycarbonyl group, an optionally substituted carbamoyl group, an optionally substituted carbamimidoyl group, an optionally substituted alkylsulfanyl group, an optionally substituted alkylsulfinyl group, an optionally substituted alkylsulfonyl group, an optionally substituted amino group, an optionally substituted sulfamoyl group, an optionally substituted alkanoyl group, an optionally substituted homocyclic group, an oxy group substituted by optionally substituted homocyclic group, a carbonyl group substituted by optionally substituted homocyclic group, an optionally substituted heterocyclic group, an oxy group substituted by optionally substituted heterocyclic group, a carbonyl group substituted by optionally substituted heterocyclic group, an optionally substituted phenyl group, an optionally substituted alkylsulfonyloxy group, an optionally substituted alkynyl group or an optionally substituted alkylene group is/are 1 to 5 groups selected independently from the following groups:

a halogen atom; a cyano group; a hydroxy group; a nitro group; a carboxyl group; an oxo group; a thioxo group; a sulfo group; a cycloalkyl group optionally substituted by hydroxy group, halogen atom, carboxyl group, alkoxycarbonyl group, mono- or di-alkylamino group, phenyl group or morpholinyl group; an alkoxycarbonyl group optionally substituted by hydroxy group, halogen atom, carboxyl group, alkoxycarbonyl group, mono- or di-alkylamino group, phenyl group or morpholinyl group; a carbamoyl group; a mono- or di-alkylcarbamoyl group optionally substituted by hydroxy group, halogen atom, carboxyl group, alkoxycarbonyl group, mono- or di-alkylamino group, phenyl group or morpholinyl group; an alkyl group optionally substituted by hydroxy group, halogen atom, carboxyl group, alkoxycarbonyl group, mono- or di-alkylamino group, phenyl group or morpholinyl group; an alkanoyl group optionally substituted by hydroxy group, halogen atom, carboxyl group, alkoxycarbonyl group, mono- or di-alkylamino group, phenyl group or morpholinyl group; an alkoxy group optionally substituted by hydroxy group, halogen atom, carboxyl group, alkoxycarbonyl group, mono- or di-alkylamino group, phenyl group or morpholinyl group; an alkanoyloxy group optionally substituted by hydroxy group, halogen atom, carboxyl group, alkoxycarbonyl group, mono- or di-alkylamino group, phenyl group or morpholinyl group; an alkylsulfanyl group optionally substituted by hydroxy group, halogen atom, carboxyl group, alkoxycarbonyl group, mono- or di-alkylamino group, phenyl group or morpholinyl group; an alkylsulfonyl group optionally substituted by hydroxy group, halogen atom, carboxyl group, alkoxycarbonyl group, mono- or di-alkylamino group, phenyl group or morpholinyl group; an alkylsulfinyl group optionally substituted by hydroxy group, halogen atom, carboxyl group, alkoxycarbonyl group, mono- or di-alkylamino group, phenyl group or morpholinyl group; a mono- or di-alkylsulfamoyl group optionally substituted by hydroxy group, halogen atom, carboxyl group, alkoxycarbonyl group, mono- or di-alkylamino group, phenyl group or morpholinyl group; an amino group; a mono- or di-alkylamino group optionally substituted by hydroxy group, halogen atom, carboxyl group, alkoxycarbonyl group, mono- or di-alkylamino group, phenyl group or morpholinyl group; a mono- or di-alkylsulfamoylamino group optionally substituted by hydroxy group, halogen atom, carboxyl group, alkoxycarbonyl group, mono- or di-alkylamino group, phenyl group or morpholinyl group; a mono- or di-alkylureido group optionally substituted by hydroxy group, halogen atom, carboxyl group, alkoxycarbonyl group, mono- or di-alkylamino group, phenyl group or morpholinyl group; a homocyclic group selected from a cycloalkyl group, a phenyl group and a naphthyl group; an oxy group substituted by the homocyclic group as defined above; a carbonyl group substituted by the homocyclic group as defined above; a heterocyclic group selected from a thienyl, furyl, pyrrolyl, pyrrolinyl, oxazolyl, thiazolyl, pyrazolyl, imidazolyl, imidazolinyl, isoxazolyl, isothiazolyl, oxadiazolyl, furanyl, thiadiazolyl, triazolyl, triazinyl, triazolidinyl, tetrazolyl, pyridyl, imidazopyridyl, pyrimidinyl, thiomorpholinyl, morpholinyl, triazinyl, pyrrolidinyl, piperidyl, pyranyl, tetrahydropyranyl, thiopyranyl, oxazinyl, thiazinyl, piperazinyl, triazinyl, oxatriazinyl, pyridazinyl, pyrazinyl, benzofuranyl, benzothiazolyl, benzoxazolyl, tetrazolopyridazinyl, triazolopyridazinyl, benzimidazolyl, quinolyl, isoquinolyl, dihydroisoquinolyl, cinnolinyl, phthalazinyl, quinazolinyl, quinoxalinyl, indolizinyl, dihydroindolyl, indolyl, quinolizinyl, naphthyridinyl, purinyl, pteridinyl, dibenzofuranyl, carbazolyl, acridinyl, phenanthridinyl, chromanyl, benzoxazinyl, phenazinyl, phenothiazinyl, phenoxazinyl, hexahydroazepinyl, imidazolidinyl, oxazolidinyl, tetrahydrofuranyl, dioxolanyl, oxiranyl, dihydropyrimidinyl, oxazolinyl, dihydrooxazinyl, dihydropyrazolyl, imidazopyridyl, dihydropyrazinyl, tetrahydroquinolyl, benzothienyl, dihydrooxazolyl, oxathiadiazolyl, dihydrooxazolyl and tetrahydroquinolyl groups; an oxy group substituted by the heterocyclic group as defined above; a carbonyl group substituted by the heterocyclic group as defined above; and a group of the formulae:

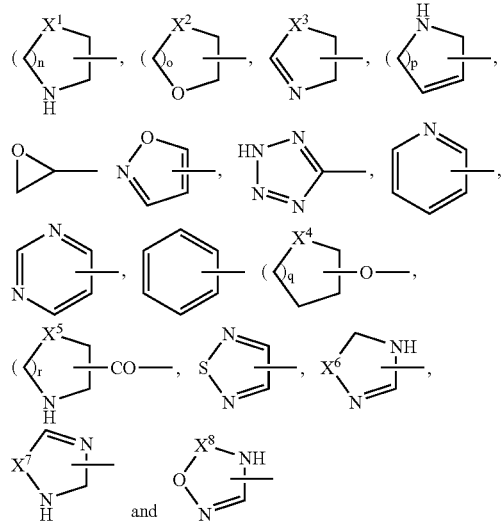

wherein $X^1$ and $X^3$ are each independently $CH_2$, NH, O, S, SO or $SO_2$; $X^2$ and $X^5$ are each independently $CH_2$, O, S, SO or $SO_2$; $X^4$ is NH, O, S, SO or $SO_2$; $X^6$ and $X^7$ are each independently O or S; $X^8$ is S or SO; and n, o, p, q and r are each independently an integer of 1 to 4, and further wherein each of the above groups may optionally be substituted by 1 to 3 substituents selected from the following groups: halogen atom, carboxyl group, hydroxy group, cyano group, oxo group, thioxo group, alkyl group, hydroxyalkyl group, alkoxycarbonylalkyl group, carboxyalkyl group, morpholinylalkyl group, phenylalkyl group, alkanoyl group, hydroxyalkanoyl group, alkoxyalkanoyl group, alkoxy group, phenylalkoxy group, alkoxycarbonyl group, benzyloxycarbonyl group, mono- or di-alkylamino group, mono- or di-alkylcarbamoyl group, mono- or di-alkylsulfamoyl group, alkylsulfonyl group and tetrazolyl group, or a pharmaceutically acceptable derivative thereof.

7. The compound of the above embodiment 6 wherein $A^1$ is a pyrimidinyl group or a pyridyl group;

$A^2$ is (a) a heterocyclic group selected from a piperidyl group and a morpholinyl group, respectively optionally substituted by a substituent(s) selected from a carboxyl group, a carboxyalkyl group and an alkyl group;

(b) an alkoxy group substituted by a group selected from a carboxyl group, a hydroxy group, an alkoxy group and a cyano group;

(c) a halogen atom;

(d) an amino group optionally substituted by 1 to 2 substituents independently selected from a carboxyalkyl group, a hydroxyalkyl group, an alkyl group, an alkoxyalkyl group and an aminoalkyl group optionally substituted by 1 to 2 alkyl groups;

(e) a hydrogen atom;

B is a phenyl group optionally substituted by 1 to 4 groups selected independently from halogen atom, hydroxy group, alkyl group optionally substituted by 1 to 3 halogen atoms and alkoxy group optionally substituted by 1 to 3 halogen atoms;

$R^1$ is a hydrogen atom, or a benzyl group substituted by 1 to 3 groups selected independently from an alkoxy group optionally substituted by 1 to 3 halogen atoms, an alkyl group optionally substituted by 1 to 3 halogen atoms and a cyano group;

$R^2$ is (a) an amino group optionally substituted by 1 to 2 groups independently selected from an alkyl group, an alkoxyalkyl group, a cycloalkylalkyl group, an alkoxycarbonyl group, an alkylcarbonyl group, an alkylcarbamoyl group, a carboxyalkyl group, a cycloalkylalkyl group substituted by carboxyalkyl group, a hydroxyalkyl group, a carboxyalkoxycarbonyl group, a carboxydihydrooxazolyl group, a carboxyalkylcarbonyl group, a phenylalkyl group, an alkoxyalkoxycarbonyl group, an alkoxyalkylcarbonyl group, an alkyl group substituted by piperidyl group, a piperidylalkyl group substituted by carboxyalkyl group, and an alkyl group substituted by phenyl that is optionally substituted by 1 to 2 alkyl groups (said alkyl group may optionally be substituted by 1 to 3 halogen atoms);

wherein said alkyl group or alkoxy group may further optionally be substituted by 1 to 5 groups selected independently from the following groups:

a halogen atom, a cyano group, a hydroxy group, a carboxyl group, an alkoxycarbonyl group, a tetrazolyl group, a carbamoyl group, a mono- or di-alkylcarbamoyl group (said mono- or di-alkylcarbamoyl group may optionally be substituted by carboxyl group, alkoxycarbonyl group or hydroxy group), an alkoxy group (said alkoxy group may optionally be substituted by carboxyl group, formyl group or hydroxy group), an alkanoyloxy group, an alkylsulfanyl group, an alkylsulfonyl group, an alkylsulfinyl group, an aminosulfonyl group, an amino group, a mono- or di-alkylamino group optionally substituted by carboxyl group or alkoxy group, a mono- or di-alkylsulfamoylamino group, a mono- or di-alkylureido group optionally substituted by morpholinyl group, a cycloalkyl group group optionally substituted by carboxymethyl group, an oxiranyl group, a phenyl group optionally substituted by alkoxy group or carboxyl group, a morpholinyl group, a pyrrolidinyl group optionally substituted by alkoxycarbonyl group or carboxyl group, a pyrrolidinyl group optionally substituted by alkoxycarbonylalkyl group or carboxyalkyl group, a pyrrolidinyl group optionally substituted by oxo group, a piperidyl group optionally substituted by alkoxycarbonyl group or carboxyl group, a piperidyl group optionally substituted by alkoxycarbonylalkyl group or carboxyalkyl group, a piperazinyl group optionally substituted by alkyl group, a hexahydroazepinyl group, a pyrimidinyl group, a pyridyl group, a dioxolanyl group optionally substituted by alkyl group, an oxadiazolyl group optionally substituted by oxo group, an oxathiadiazolyl group optionally substituted by oxo group, a pyrrolidinylcarbonyl group optionally substituted by carboxyl group, a piperidyloxy group optionally substituted by alkyl group and a morpholinylcarbonyl group;

(b) a halogen atom;

(c) an alkoxy optionally substituted by a group selected from carboxyl group, cycloalkyl group and alkoxy group; wherein said cycloalkyl group or alkoxy group may optionally be substituted by 1 to 5 groups selected independently from the following groups:

a halogen atom, a cyano group, a hydroxy group, a carboxyl group, an alkoxycarbonyl group, a tetrazolyl group, a carbamoyl group, a mono- or di-alkylcarbamoyl group (said mono- or di-alkylcarbamoyl group may optionally be substituted by carboxyl group, alkoxycarbonyl group or hydroxy group), an alkoxy group (said alkoxy group may optionally be substituted by carboxyl group, formyl group or hydroxy group), an alkanoyloxy group, an alkylsulfanyl group, an alkylsulfonyl group, an alkylsulfinyl group, an aminosulfonyl group, an amino group, a mono- or di-alkylamino group optionally substituted by carboxyl group or alkoxy group, a mono- or di-alkylsulfamoylamino group, a mono- or di-alkylureido group optionally substituted by morpholinyl group, a cycloalkyl group optionally substituted by carboxymethyl group, an oxiranyl group, a phenyl group optionally substituted by alkoxy group or carboxyl group, a morpholinyl group, a pyrrolidinyl group optionally substituted by alkoxycarbonyl group or carboxyl group, a pyrrolidinyl group optionally substituted by alkoxycarbonylalkyl group or carboxyalkyl group, a pyrrolidinyl group optionally substituted by oxo group, a piperidyl group optionally substituted by alkoxycarbonyl group or carboxyl group, a piperidyl group optionally substituted by alkoxycarbonylalkyl group or carboxyalkyl group, a piperazinyl group optionally substituted by alkyl group, a hexahydroazepinyl group, a pyrimidinyl group, a pyridyl group, a dioxolanyl group optionally substituted by alkyl group, an oxadiazolyl group optionally substituted by oxo group, an oxathiadiazolyl group optionally substituted by oxo group, a pyrrolidinylcarbonyl group optionally substituted by carboxyl group, a piperidyloxy group optionally substituted by alkyl group and a morpholinylcarbonyl group;

(d) a carbamoyl group optionally substituted by 1 to 2 substituents selected independently from alkyl group and carboxyalkyl group, wherein said alkyl group may optionally be substituted by 1 to 5 groups selected independently from the following groups:

a halogen atom, a cyano group, a hydroxy group, a carboxyl group, an alkoxycarbonyl group, a tetrazolyl group, a carbamoyl group, a mono- or di-alkylcarbamoyl group (said mono- or di-alkylcarbamoyl group may be substituted by carboxyl, alkoxycarbonyl or hydroxy group), an alkoxy group (said alkoxy group may be substituted by carboxyl, formyl or hydroxy group), an alkanoyloxy group, an alkylsulfanyl group, an alkylsulfonyl group, an alkylsulfinyl group, an aminosulfonyl group, an amino group, a mono- or di-alkylamino group optionally substituted by carboxyl or alkoxy group, a mono- or di-alkylsulfamoylamino group, a mono- or di-alkylureido group optionally substituted by morpholinyl group, a cycloalkyl group optionally substituted by carboxymethyl group, an oxiranyl group, a phenyl group optionally substituted by alkoxy or carboxyl group, a morpholinyl group, a pyrrolidinyl optionally substituted by alkoxycarbonyl or carboxyl group, a pyrrolidinyl optionally substituted by alkoxycarbonylalkyl or carboxyalkyl group, a pyrrolidinyl substituted by oxo group, a piperidyl optionally substituted by alkoxycarbonyl or carboxyl group, a piperidyl optionally substituted by alkoxycarbonylalkyl or carboxyalkyl group, a piperazinyl optionally substituted by alkyl group, a hexahydroazepinyl group, a pyrimidinyl group, a pyridyl group, a dioxolanyl group optionally substituted by alkyl group, an oxadiazolyl group optionally substituted by oxo group, an oxathiadiazolyl group optionally substituted by oxo group, a pyrrolidinylcarbonyl group optionally substituted by carboxyl group, a piperidyloxy group optionally substituted by alkyl group and a morpholinylcarbonyl group;

(e) a hydroxy group;

(f) an oxy group substituted by a heterocyclic group selected from pyrimidinyl group and tetrahydropyranyl group;

(g) a heterocyclic group selected from a morpholinyl, pyrimidinyl, piperidyl, piperazinyl, pyrazinyl, tetrazolyl, thienyl, furyl, dihydroisoquinolyl, pyridyl and pyrrolyl group, which are each optionally substituted by 1 to 3 substituents selected independently from pyrimidinyl group, alkyl group, halogen atom, cyano group, mono- or di-alkylamino group, alkoxy group, phenyl group, carboxyl group, carbamoyl group and carboxyalkyl group;

wherein said alkoxy group or alkyl group may optionally be substituted by 1 to 5 groups selected independently from the following groups:

a halogen atom, a cyano group, a hydroxy group, a carboxyl group, an alkoxycarbonyl group, a tetrazolyl group, a carbamoyl group, a mono- or di-alkylcarbamoyl group (said mono- or di-alkylcarbamoyl group may optionally be substituted by carboxyl group, alkoxycarbonyl group or hydroxy group), an alkoxy group (said alkoxy group may optionally be substituted by carboxyl group, formyl group or hydroxy group), an alkanoyloxy group, an alkylsulfanyl group, an alkylsulfonyl group, an alkylsulfinyl group, an aminosulfonyl group, an amino group, a mono- or di-alkylamino group optionally substituted by carboxyl group or alkoxy group, a mono- or di-alkylsulfamoylamino group, a mono- or di-alkylureido group optionally substituted by morpholinyl group, a cycloalkyl group optionally substituted by carboxymethyl group, an oxiranyl group, a phenyl group optionally substituted by alkoxy group or carboxyl group, a morpholinyl group, a pyrrolidinyl group optionally substituted by alkoxycarbonyl group or carboxyl group, a pyrrolidinyl group optionally substituted by alkoxycarbonylalkyl group or carboxyalkyl group, a pyrrolidinyl group substituted by oxo group, a piperidyl group optionally substituted by alkoxycarbonyl group or carboxyl group, a piperidyl group optionally substituted by alkoxycarbonylalkyl group or carboxyalkyl group, a piperazinyl group optionally substituted by alkyl group, a hexahydroazepinyl group, a pyrimidinyl group, a pyridyl group, a dioxolanyl group optionally substituted by alkyl group, an oxadiazolyl group optionally substituted by oxo group, an oxathiadiazolyl group optionally substituted by oxo group, a pyrrolidinylcarbonyl group optionally substituted by carboxyl group, a piperidyloxy group optionally substituted by alkyl group and a morpholinylcarbonyl group;

(h) a phenyl group optionally substituted by 1 to 3 substituents selected independently from halogen atom, alkyl group and alkoxy group; wherein said alkoxy group or alkyl group may further optionally be substituted by 1 to 5 groups selected independently from the following groups:

a halogen atom, a cyano group, a hydroxy group, a carboxyl group, an alkoxycarbonyl group, a tetrazolyl group, a carbamoyl group, a mono- or di-alkylcarbamoyl group (said mono- or di-alkylcarbamoyl group may optionally be substituted by carboxyl group, alkoxycarbonyl group or hydroxy group), an alkoxy group (said alkoxy group may optionally be substituted by carboxyl group, formyl group or hydroxy group), an alkanoyloxy group, an alkylsulfanyl group, an alkylsulfonyl group, an alkylsulfinyl group, an aminosulfonyl group, an amino group, a mono- or di-alkylamino group optionally substituted by carboxyl group or alkoxy group, a mono- or di-alkylsulfamoylamino group, a mono- or di-alkylureido group optionally substituted by morpholinyl group, a cycloalkyl group optionally substituted by carboxymethyl group, an oxiranyl group, a phenyl group optionally substituted by alkoxy group or carboxyl group, a morpholinyl group, a pyrrolidinyl group optionally substituted by alkoxycarbonyl group or carboxyl group or carboxyalkyl group, a pyrrolidinyl group optionally substituted by alkoxycarbonylalkyl group, a pyrrolidinyl group substituted by oxo group, a piperidyl group optionally substituted by alkoxycarbonyl group or carboxyl group, a piperidyl group optionally substituted by alkoxycarbonylalkyl group or carboxyalkyl group, a piperazinyl group optionally substituted by alkyl group, a hexahydroazepinyl group, a pyrimidinyl group, a pyridyl group, a dioxolanyl group optionally substituted by alkyl group, an oxadiazolyl group optionally substituted by oxo group, an oxathiadiazolyl group optionally substituted by oxo group, a pyrrolidinylcarbonyl group optionally substituted by carboxyl group, a piperidyloxy group optionally substituted by alkyl group and a morpholinylcarbonyl group;

(i) an oxy group substituted by cycloalkyl group;

(j) a hydroxyalkyl group; or (k) a nitro group, or a pharmaceutically acceptable derivative thereof.

8. The compound of the above embodiment 7 wherein $A^1$ is a pyrimidinyl group or a pyridyl group;

$A^2$ is (a) a heterocyclic group selected from piperidyl group and morpholinyl group, which are each optionally substituted by a substituent(s) selected from a carboxyl group, carboxyalkyl group or alkyl group;

(b) an alkoxy group substituted by a group selected from carboxyl group, hydroxy group, alkoxy group and cyano group;

(c) a halogen atom;

(d) an amino group optionally substituted by 1 to 2 substituents selected independently from carboxyalkyl group, hydroxyalkyl group, alkyl group, alkoxyalkyl group and aminoalkyl group optionally substituted by 1 to 2 alkyl groups;

(e) a hydrogen atom;

B is a phenyl group optionally substituted by 1 to 4 groups selected independently from alkyl group optionally substituted by 1 to 3 halogen atoms and alkoxy group optionally substituted by 1 to 3 halogen atoms;

$R^1$ is

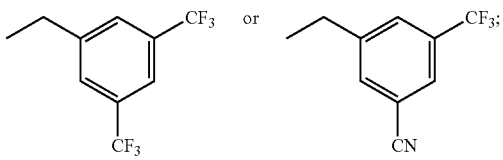

$R^2$ is (a) an amino group optionally substituted by 1 to 2 groups selected independently from an alkyl group, an alkoxyalkyl group, a cycloalkylalkyl group, an alkoxycarbonyl group, an alkylcarbonyl group, an alkylcarbamoyl group, a carboxyalkyl group, a cycloalkylalkyl group substituted by carboxyalkyl group, a hydroxyalkyl group, a carboxyalkoxycarbonyl group, a carboxydihydrooxazolyl group, a carboxyalkylcarbonyl group, a phenylalkyl group, an alkoxyalkoxycarbonyl group, an alkoxyalkylcarbonyl group, an alkyl group substituted by piperidyl group, a piperidylalkyl group substituted by carboxyalkyl group and an alkyl group substituted by phenyl group that is optionally substituted by 1 to 2 alkyl groups (said alkyl group may optionally be substituted by 1 to 3 halogen atoms);

(b) a halogen atom;

(c) an alkoxy group optionally substituted by a group selected from a carboxyl group, a cycloalkyl group and an alkoxy group;

(d) a carbamoyl group optionally substituted by 1 to 2 substituents selected independently from alkyl group and carboxyalkyl group;

(e) a hydroxy group;

(f) an oxy group substituted by a heterocyclic group selected from a pyrimidinyl group and a tetrahydropyranyl group;

(g) a heterocyclic group selected from a pyrimidinyl, pyridyl, morpholinyl, piperidyl, piperazinyl, tetrazolyl, dihydroisoquinolyl and pyrrolyl group, which are each optionally substituted by 1 to 2 substituents selected independently from alkyl group, alkoxy group, phenyl group, carboxyl group, carboxyalkoxy group and carboxyalkyl group;

(h) a phenyl group optionally substituted by 1 to 3 substituents selected independently from halogen atom, alkyl group and alkoxy group;

(i) an oxy group substituted by cycloalkyl group;

(j) a hydroxyalkyl group;

(k) a nitro group, or a pharmaceutically acceptable derivative thereof.

9. The compound of the above embodiment 8 wherein $A^2$ is an amino group substituted by 1 to 2 groups selected independently from a piperidyl group optionally substituted by carboxyl group; a morpholinyl group optionally substituted by carboxyl group; an alkoxy group substituted by a group selected from carboxyl group, hydroxy group, alkoxy group and cyano group; an amino group substituted by 1 to 2 groups selected independently from carboxyalkyl group and alkyl group;

B is a phenyl group optionally substituted by an alkyl group optionally substituted by 1 to 3 halogen atoms;

19

R¹ is

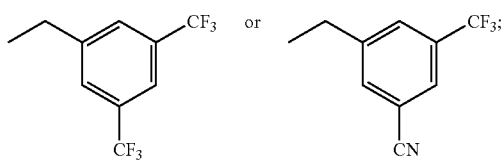

R² is (a) an amino group optionally substituted by 1 to 2 groups selected independently from an alkyl group, a cycloalkylalkyl group, an alkoxycarbonyl group, a carboxyalkyl group and a cycloalkylalkyl group substituted by carboxyalkyl group;
(b) an alkoxy group;
(c) a phenyl group optionally substituted by a group selected from a halogen atom, an alkyl group and an alkoxy group;
(d) a pyridyl group optionally substituted by a group selected from a halogen atom, an alkyl group and an alkoxy group,
or a pharmaceutically acceptable derivative thereof.

10. A compound described in any one of examples No. 7, 24, 75, 57, 13, 54, 12, 65, 63 and 64, or a pharmaceutically acceptable derivative thereof.

11. A compound of the formula (I-A):

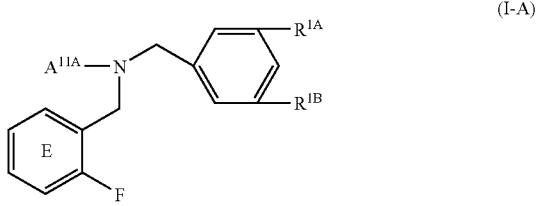

wherein
$A^{11A}$ is an optionally substituted pyrimidin-2-yl group or an optionally substituted pyridin-2-yl group;
$R^{1A}$ and $R^{1B}$ are independently a cyano group or an alkyl group optionally substituted by 1 to 3 halogen atoms;
Ring E is an optionally substituted phenyl group;
F is an optionally substituted cyclic group,
or a pharmaceutically acceptable derivative thereof.

12. A compound of the formula (I-B):

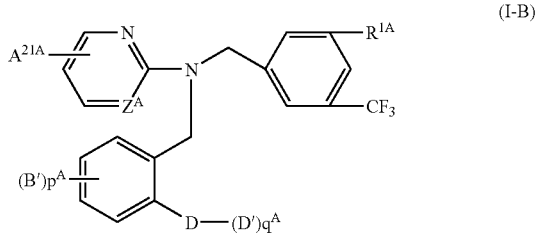

wherein
$Z^A$ is N or CH;
$A^{21A}$ is an optionally substituted homocyclic group, an optionally substituted alkylsulfanyl group, an optionally substituted alkylsulfinyl group, an optionally substituted alkylsulfonyl group, an optionally substituted alkyl group, a nitro group, a hydroxy group, a cyano group, an optionally substi-

20 tuted alkenyl group, an optionally substituted heterocyclic group, an optionally substituted alkoxy group, a halogen atom, an amino group optionally substituted by 1 to 2 substituents, a carbamoyl group optionally substituted by 1 to 2 substituents, a carboxyl group or a hydrogen atom;
$R^{1A}$ is a cyano group or an alkyl group optionally substituted by 1 to 3 halogen atoms;
B' is a group selected independently from an oxo group, a cyano group, a halogen atom, an optionally substituted alkylsulfanyl group, an optionally substituted alkylsulfinyl group, an optionally substituted alkylsulfonyl group, an amino group optionally substituted by 1 to 2 substituents, a hydroxy group, an optionally substituted heterocyclic group, an optionally substituted cycloalkoxy group, an optionally substituted cycloalkyl group, a carboxyl group, a carbamoyl group optionally substituted by 1 to 2 substituents, an optionally substituted alkyl group or an optionally substituted alkoxy group;
$p^A$ is an integer of 0 to 3;
D is a pyrimidinyl group, a pyridyl group, a phenyl group, a pyrimidinyloxy group, a tetrazolyl group or an oxazolidinyl group;
D' is a group selected independently from a halogen atom, an alkoxyalkyl group, an alkyl group substituted by 1 to 5 halogen atoms, an alkoxy group substituted by 1 to 5 halogen atoms, an alkenyl group, a carbamoyl group, a cycloalkyl group, a mono- or di-alkylaminoalkyl group, a mono- or di-alkylaminoalkoxy group, a carboxyl group, a hydroxy group, a cyano group, an oxo group, an alkyl group, a hydroxyalkyl group, an alkoxycarbonylalkyl group, a carboxyalkyl group, a morpholinylalkyl group, a phenylalkyl group, an alkanoyl group, a hydroxyalkanoyl group, an alkoxyalkanoyl group, an alkoxy group, a phenylalkoxy group, an alkoxycarbonyl group, a benzyloxycarbonyl group, a mono- or di-alkylamino group, a mono- or di-alkylcarbamoyl group, a mono- or di-alkylsulfamoyl group, an alkylsulfonyl group, a tetrazolyl group, a benzyloxyalkyl group, a cycloalkylalkyl group, a benzyloxy group, an alkoxyalkoxy group, a carboxyalkoxy group, a carboxyalkenyl group, an alkylcarbonylamino group, a carboxyalkoxyalkyl group, a morpholinyl group or a pyridylalkoxy group;
$q^A$ is an integer of 0 to 3,
or a pharmaceutically acceptable derivative thereof.

13. The compound of the above embodiment 12 wherein
$A^{21A}$ is selected from the following group:
(a) a heterocyclic group selected from a piperidyl group and a morpholinyl group, respectively optionally substituted by a substitutent(s) selected from a carboxyl group, an alkoxycarbonyl group, a carboxyalkyl group or an alkyl group;
(b) an alkoxy group optionally substituted by a group selected from a carboxyl group, an alkoxycarbonyl group, a halogen atom, an alkylsulfinyl group, a mono- or di-alkylamino group, a cyano group, a tetrazolyl group, an alkylsulfonyl group, an alkylsulfanyl group, a hydroxy group or an alkoxy group;
(c) a halogen atom;
(d) an amino group optionally substituted by 1 to 2 substituents independently selected from a carboxyalkyl group, an alkoxycarbonylalkyl group, an alkylsulfonylalkyl group, an alkylsulfinylalkyl group, a hydroxyalkyl group, an alkyl group, an alkoxyalkyl group or an aminoalkyl group optionally substituted by 1 to 2 alkyl groups;
(e) a hydrogen atom;
(f) an alkyl group optionally substituted by a group selected from a carboxyl group, an alkoxycarbonyl group, a halogen atom, an alkylsulfinyl group, a mono- or di-alkylamino group, a cyano group, a tetrazolyl group, an alkylsulfonyl group, an alkylsulfanyl group, a hydroxy group or an alkoxy group;

(g) a carboxyl group;

(h) a carbamoyl group optionally substituted by a carboxyalkyl group;

(i) an alkenyl group substituted by a group selected from a carboxyl group, an alkoxycarbonyl group, an alkylsulfinyl group, a cyano group, a tetrazolyl group, an alkylsulfonyl group, an alkylsulfanyl group, a hydroxy group or an alkoxy group;

(j) a morpholinyl group;

(k) a piperidinyl group optionally substituted by a carboxyl group or a carboxyalkyl group;

B' is a group selected independently from an oxo group, a halogen atom, an alkyl group optionally substituted by 1 to 3 halogen atoms, an alkoxy group optionally substituted by 1 to 3 halogen atoms, a cyano group, a hydroxy group, a cycloalkyl group, an alkoxyalkyl group, a cycloalkoxy group, an alkylsulfanyl group optionally substituted by 1 to 3 halogen atoms, an alkylsulfinyl group optionally substituted by 1 to 3 halogen atoms or an alkylsulfonyl group optionally substituted by 1 to 3 halogen atoms, or a pharmaceutically acceptable derivative thereof.

14. The compound of the above embodiment 13 wherein
$A^{21A}$ is an alkoxy group optionally substituted by 1 to 2 groups selected from a carboxyl group, a halogen atom, an alkoxycarbonyl group, an alkoxy group, a hydroxy group, a mono or di-alkylamino group, an alkylsulfinyl group, a cyano group, a tetrazolyl group, an alkylsulfonyl group and an alkylsulfanyl group; an alkyl group optionally substituted by 1 to 2 groups selected from a carboxyl group, a halogen atom, an alkoxycarbonyl group, an alkoxy group, a hydroxy group, a mono or di-alkylamino group, an alkylsulfinyl group, a cyano group, a tetrazolyl group, an alkylsulfonyl group and an alkylsulfanyl group; a morpholinyl group; a carboxyl group or a carboxypiperidinyl group;

B' is a group selected independently from a halogen atom, an alkyl group optionally substituted by 1 to 3 halogen atoms or an alkoxy group optionally substituted by 1 to 3 halogen atoms;

D' is a group selected independently from an alkoxy group optionally substituted by 1 to 3 halogen atoms, a halogen atom, a cyano group, an alkylsulfanyl group, a mono or di-alkylamino group, an alkenyl group, an alkyl group optionally substituted by 1 to 3 halogen atoms, a carboxyl group, a hydroxy group, a carboxyalkoxy group, a carboxyalkyl group, an alkoxycarbonylalkyl group, an oxo group, a cycloalkyl group, a hydroxyalkyl group, an alkoxyalkyl group, a carbamoyl group, a mono- or di-alkylcarbamoyl group, an alkylcarbonylamino group, a morpholinyl group or a carboxyalkoxyalkyl group, or a pharmaceutically acceptable derivative thereof.

15. The compound of the above embodiment 14, wherein $Z^A$ is N, or a pharmaceutically acceptable derivative thereof.

16. The compound of the above embodiment 14, wherein $R^{1A}$ is an alkyl group optionally substituted by 1 to 3 halogen atoms, or a pharmaceutically acceptable derivative thereof.

17. The compound of the above embodiment 14, wherein D is a phenyl group, or a pharmaceutically acceptable derivative thereof.

18. The compound of the above embodiment 14, wherein D' is a group selected independently from a halogen atom, an alkoxy group or an alkyl group, or a pharmaceutically acceptable derivative thereof.

19. The compound of the above embodiment 14, wherein $A^{21A}$ is a morpholinyl group or an alkoxy group substituted by a carboxyl group, or a pharmaceutically acceptable derivative thereof.

20. A compound described in any one of examples No. 91, 94, 96, 112, 114, 118 to 123, 131, 133, 136, 138 to 140, 142 to 153, 158 to 163, 165 to 169, 173 to 177, 179 to 182, 185, 186, 190 to 194, 198, 203, 208 to 216, 218 to 223, 231, 239, 240, 241, or a pharmaceutically acceptable derivative thereof.

21. A compound described in any one of examples No. 154 to 157, 164, 170 to 172, 178, 183, 184, 187 to 189, 195 to 197, 199 to 202, 204 to 207, 217, 224 to 230, 232 to 238, 242 to 252, or a pharmaceutically acceptable derivative thereof.

22. A pharmaceutical composition, which comprises as an active ingredient a compound according to any one of the above embodiments 1 to 21, or a pharmaceutically acceptable derivative thereof.

23. A method for prophylaxis or treatment of arteriosclerosis such as atherosclerosis, peripheral vascular disease, dyslipidemia, hyperbetalipoproteinemia, hypoalphalipoproteinemia, hypercholesterolemia, hypertriglyceridemia, familial-hypercholesterolemia, cardiovascular diseases, angina, ischemia, cardiac ischemia, stroke, myocardial infarction, reperfusion injury, restenosis after angioplasty, hypertension, cerebral infarction, cerebral stroke, diabetes, vascular complication of diabetes, thrombotic diseases, obesity, endotoxemia, metabolic syndrome, cerebrovascular disease, coronary artery disease, ventricular dysfunction, cardiac arrhythmia, pulmonary vascular disease, reno-vascular disease, renal disease, splanchnic vascular disease, vascular hemostatic disease, fatty liver disease, steatohepatitis, inflammatory disease, autoimmune disorders and other systemic disease indications, immune function modulation, pulmonary disease, anti-oxidant disease, sexual dysfunction, cognitive dysfunction, schistosomiasis, cancer, regression of xanthoma or Alzheimer's disease, which comprises administering an effective amount of a compound according to any one of the above embodiments 1 to 21, or a pharmaceutically acceptable derivative thereof, to a patient in need thereof.

24. Use of a compound according to any one of the above embodiments 1 to 21, or a pharmaceutically acceptable derivative thereof, for the manufacture of a medicament in treatment of patients suffering from arteriosclerosis such as atherosclerosis, peripheral vascular disease, dyslipidemia, hyperbetalipoproteinemia, hypoalphalipoproteinemia, hypercholesterolemia, hypertriglyceridemia, familial-hypercholesterolemia, cardiovascular diseases, angina, ischemia, cardiac ischemia, stroke, myocardial infarction, reperfusion injury, restenosis after angioplasty, hypertension, cerebral infarction, cerebral stroke, diabetes, vascular complication of diabetes, thrombotic diseases, obesity, endotoxemia, metabolic syndrome, cerebrovascular disease, coronary artery disease, ventricular dysfunction, cardiac arrhythmia, pulmonary vascular disease, reno-vascular disease, renal disease, splanchnic vascular disease, vascular hemostatic disease, fatty liver disease, steatohepatitis, inflammatory disease, autoimmune disorders and other systemic disease indications, immune function modulation, pulmonary disease, anti-oxidant disease, sexual dysfunction, cognitive dysfunction, schistosomiasis, cancer, regression of xanthoma or Alzheimer's disease.

25. A compound of a general formula (I-1):

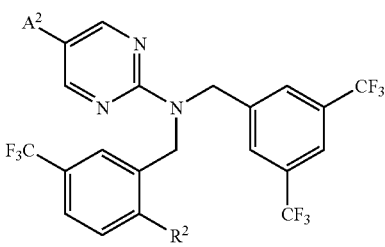

(1-1)

wherein the symbols have the same meanings as defined above, or a pharmaceutically acceptable derivative thereof.

When the compound (1) has one or more asymmetric carbon atoms, the compound (1) of the present invention encompasses racemate, racemic mixture, individual enantiomers or diastereomers. The present compounds also include all such isomers and a mixture thereof.

Also, when the present compound has an alkenyl or alkynyl group, cis (Z)- and trans (E)-forms may occur. In addition, the present compounds include individual stereoisomer of the compound and optionally, individual tautomeric forms thereof and a mixture thereof.

Separation of diastereomer or cis- and trans-isomers can be achieved by the conventional method such as fractional crystallization, chromatography and HPLC method, and the like. Also the drug containing the individual stereoisomer as needed can be prepared from a corresponding optically active intermediate or alternatively by resolving the corresponding racemate by using the suitable chiral support (e.g. HPLC) or by performing a fractional crystallization of diastereomeric salt formed by reacting a corresponding racemate and a suitable optically active acid or base. Alternatively, the resolution of the mixture of enantiomers can be done by forming on a novel covalently bounded species formed by means of reacting it with a suitable chiral compound. For example, at first, the coupling reaction between a racemic carboxylic acid and a chiral amine or a chiral alcohol gives a mixture of diastereoisomers (amide or ester, respectively) and then it is isolated by the conventional technique such as chromatography, HPLC or fractional crystallization, and the like. Thereafter, the resulting one diastereoisomer can be converted into one enantiomer of the desired compound by cleaving the new covalent binding with a suitable chemical reaction such as hydrolysis, and the like.

As used herein, the term "pharmaceutically acceptable derivative" represents a pharmaceutical acceptable salt, solvate or prodrug (e.g. ester) of the present compound, and which can provide (directly or indirectly) the compound of the present invention or an active metabolite or a residue thereof. Such derivatives can be obtained by a person skilled in the art without undue experimentation. See, for example, Burger's Medicinal Chemistry and Drug Discovery 5th ed., vol. 1st, "Principles and Practice". Preferred pharmaceutically acceptable derivative is a salt, a solvate, an ester, a carbaminic ester and a phosphoric ester. Especially preferred pharmaceutically acceptable derivative is a salt, a solvate and an ester. Most preferred pharmaceutically acceptable derivative is a salt and an ester.

A person skilled in the art of organic chemistry knows that many organic compounds can be formed a complex with a solvent of reaction system and which can be precipitated out or crystallized out from the solvent. These complexes are widely known as a "solvate". For example, the complex with water is known as a "hydrate". The solvate of the compound of the present invention falls within the scope of the invention.

As used herein, the "prodrug" represent a compound which convert to the active form having a pharmacological activity by a hydrolysis in vivo (such as in a blood). The example of the pharmaceutically acceptable prodrug is described in the literature: T. Higuchi and V. Stera, Prodrugs as Novel Delivery Systems, "Bioreversible Carriers in Drug Design", Edward B. Roche ed., American Pharmaceutical Association and Pergamon Press, A.C.S. Symposium Series, vol. 14th, (1987); and D. Freisher, S. Roman and H. Barbara, Improved oral drug delivery: solubility limitations overcome by the use of prodrugs, Advanced Drug Delivery Reviews (1996) 19(2): 115-130).

A prodrug is a carrier that releases the compound of the formula (1) which is bound covalently in vivo when administered to a patient. In general, the prodrug is prepared by the conventional method or by modifying a functional group such that the modified moiety is cleaved in vivo to give a parent compound. Examples of the prodrug include the compound wherein a hydroxy, amine or sulfhydryl group binds to an optional group such that provide a hydroxy, amine or sulfhydryl group by cleaving it when administered to a patient. Thus the representative examples of prodrug are the following ones, but not limited thereto; i.e. the derivatives with acetic ester, formic ester and benzoic ester at the functional groups such as alcohol, sulfhydryl or amine of the compound of the formula (1). In addition, when the functional group is a carboxylic acid, esters such as methyl ester, ethyl ester and double ester, and the like can be used. The esters exhibit inherently the activity in a human body and/or are hydrolyzed under in vivo condition to the active compound. The suitable pharmaceutically acceptable esters capable of hydrolyzing in vivo include those which are decomposed easily in the human body to release the parent acid compound or a salt thereof.

The compound of the present invention may be a pharmaceutically acceptable salt form thereof. The suitable salt is outlined in literature (Berge et. al., J. Pharm. Sci., 66: 1-19 (1977)).

In general, the pharmaceutically acceptable salts can be easily prepared with a desirable acid or base as needed. The resulting salts can be recovered by filtering after precipitating it out from the solution or distilling the solvent off.

The suitable additive salts may be formed with an acid forming a nontoxic salt. Examples of the salt include hydrochloride, hydrobromide, hydroiodide, sulfate, bisulfate, nitrate, phosphate, hydrogen phosphate, acetate, maleate, malate, fumarate, lactate, tartrate, citrate, formate, gluconate, succinate, pyruvate, oxalate, oxaloacetate, trifluoroacetate, saccharate, benzoate, methanesulfonate, ethanesulfonate, benzenesulfonate and p-toluenesulfonate.

Examples of the pharmaceutically acceptable salt with a base include alkaline metal salts including ammonium salt, sodium salt and potassium salt; alkaline earth metal salts including calcium salt and magnesium salt as well as salts with organic bases including a primary, secondary and tertiary amine (e.g. isopropylamine, diethylamine, ethanolamine, trimethylamine, dicyclohexylamine and N-methyl-D-glucamine).

The term "halogen" refers to fluorine, chlorine, bromine or iodine.

The term "alkyl group" or "alkyl" means a straight or branched saturated hydrocarbon chain having 1 to 10 carbon atoms and a cyclic saturated hydrocarbon chain having 3 to 10 carbon atoms. As a straight or branched hydrocarbon chain, those having 2 to 10 carbon atoms are preferred and those having 2 to 6 carbons are more preferred. More preferred examples are straight chain alkyl groups having 1 to 6 carbon atoms, especially those having 1 to 4 carbon atoms. Examples of alkyl group include methyl, ethyl, propyl, isopropyl, butyl, sec-butyl, tert-butyl, pentyl, isopentyl, neopentyl, tert-pentyl, 1-methylbutyl, 2-methylbutyl, 3-methylbutyl, hexyl and isohexyl groups, and the like.

The term "alkoxy group" or "alkoxy" means a straight or branched alkyloxy group having 1 to 10 carbon atoms and a cyclic alkyloxy group having 3 to 10 carbon atoms. As a straight or branched hydrocarbon chain, those having 2 to 10 carbon atoms are preferred and those having 2 to 6 carbons are more preferred. More preferred examples are straight chain alkoxy groups having 1 to 6 carbon atoms, especially those having 1 to 4 carbon atoms. Examples of alkoxy group include methoxy, ethoxy, propoxy, isopropoxy, butoxy, isobutoxy, tert-butoxy, pentyloxy, isopentyloxy, neopentyloxy, tert-pentyloxy, hexyloxy and isohexyloxy groups, and the like.

The term "alkylene group" or "alkylene" means a saturated hydrocarbon chain wherein a hydrogen atom is removed from each of the terminal carbons of a straight hydrocarbon chain. Preferred examples include an alkylene group having 1 to 6 carbon atoms, specifically, methylene, ethylene, trimethylene and tetramethylene groups, and the like. When an alkylene group herein used contains 1 to 3 heteroatoms selected independently from nitrogen, sulfur and oxygen atoms, the term "alkylene" includes a group of the formula: —O—$(CH_2)_m$—O—, —S—$(CH_2)_m$—S—, —NH—$(CH_2)_m$—NH—, or —O—$(CH_2)_m$—NH— (wherein m is an integer of 1 to 4), or the like.

The term "alkanoyl group" or "alkanoyl" means a straight or branched alkylcarbonyl group having 1 to 10 carbon atoms, preferably an alkylcarbonyl group having 1 to 6 carbon atoms, more preferably an alkylcarbonyl group having 1 to 4 carbon atoms. Examples of alkanoyl group include acetyl, propionyl, butyryl, valeryl and pivaloyl groups, and the like.

The term "alkenyl group" or "alkenyl" means a straight or branched hydrocarbon chain having 2 to 10 carbon atoms and containing at least one double bond, preferably an alkenyl group having 2 to 6 carbon atoms, more preferably an alkenyl group having 2 to 4 carbon atoms Examples of alkenyl group include vinyl, 1-propenyl, alkyl, isopropenyl, butenyl, butadienyl and pentenyl groups, and the like.

The term "alkynyl group" or "alkynyl" means a straight or branched hydrocarbon chain having 2 to 10 carbon atoms and containing at least one triple bond, preferably an alkynyl group having 2 to 6 carbon atoms, more preferably an alkynyl group having 2 to 4 carbon atoms Examples of alkynyl group include ethinyl, 1-propynyl, isopropynyl, and pentynyl groups, and the like.

As herein used throughout the claims and specification, when the term "mono- or di-alkyl" refers to di-alkyl, the alkyl moieties may be the same or independent from each other.

The cycloalkyl or cycloalkyl group as used herein is C3-10 cyclic hydrocarbon group and includes for example, cyclopropyl, cyclobutyl, cyclopentyl, cyclohexyl, cycloheptyl, cyclooctyl, cyclononyl groups, and the like and preferably C3-6 cyclic hydrocarbon group.

The cycloalkoxy and cycloalkoxy group as used herein is oxy group substituted by C3-10 cyclic hydrocarbon and includes, for example cyclopropyloxy, cyclobutyloxy, cyclopentyloxy, cyclohexyloxy, and the like and preferably oxy group substituted by C3-6 cyclic hydrocarbon group.

The heterocycle or heterocyclic group as used herein includes 5 to 8 membered heterocyclic group including 1 to 4 heteroatoms selected from oxygen, sulfur and nitrogen atoms and bicyclic or tricyclic fused heterocyclic group fused thereto. Specific examples of the heterocyclic group include, for example, a thienyl, furyl, pyrrolyl, pyrrolinyl, oxazolyl, thiazolyl, pyrazolyl, imidazolyl, imidazolinyl, isoxazolyl, isothiazolyl, oxadiazolyl, furazanyl, thiadiazolyl, triazolyl, triazinyl, triazolidinyl, tetrazolyl, pyridyl, imidazopyridyl, pyrimidinyl, thiomorpholinyl, morpholinyl, triazinyl, pyrrolidinyl, piperidyl, pyranyl, tetrahydropyranyl, thiopyranyl, oxazinyl, thiazinyl, piperazinyl, triazinyl, oxatriazinyl, pyridazinyl, pyrazinyl, benzofuranyl, benzothiazolyl, benzoxazolyl, tetrazolopyridazinyl, triazolopyridazinyl, benzimidazolyl, quinolyl, isoquinolyl, dihydroisoquinolyl, cinnolinyl, phthalazinyl, quinazolinyl, quinoxalinyl, indolizinyl, dihydroindolyl, indolyl, quinolizinyl, naphthyridinyl, purinyl, pteridinyl, dibenzofuranyl, carbazolyl, acridinyl, phenanthridinyl, chromanyl, benzoxazinyl, phenazinyl, phenothiazinyl, phenoxazinyl, hexahydroazepinyl, imidazolidinyl, oxazolidinyl, tetrahydrofuranyl, dioxolanyl, oxiranyl, dihydropyrimidinyl, oxazolinyl, dihydrooxazinyl, dihydropyrazolyl, imidazopyridyl, dihydropyrazinyl, tetrahydroquinolyl, benzothienyl, dihydrooxazolyl, oxathiadiazolyl, dihydrooxazolyl or tetrahydroquinolyl group, and the like.

The homocycle or homocyclic group as used herein includes, for example, 3 to 7 membered carbocyclic group optionally fused, such as C6-10 aryl group (e.g. phenyl and naphthyl group, and the like), C3-10 cycloalkyl group (e.g. cyclopropyl, cyclobutyl, cyclopentyl, cyclohexyl, cycloheptyl, and the like), C3-10 cycloalkenyl group (e.g., cyclopropenyl, cyclobutenyl, cyclopentenyl, cyclohexenyl, cycloheptenyl, and the like).

The cyclic group as used herein includes the heterocyclic group and the homocyclic group mentioned above.

EFFECT OF THE INVENTION

The compound (1) of the present invention has an inhibitory activity against CETP and shows the effects on increasing HDL cholesterol level and decreasing LDL cholesterol. Thus the compound is useful in a prophylaxis and a treatment of diseases such as arteriosclerosis and hyperlipidemia, and the like.

The present compound (1) can be administered either orally or parenterally, and can be formulated into a suitable pharmaceutical preparations with a conventional pharmaceutically acceptable carriers used therefor.

The pharmaceutically acceptable salts of the compound (1) include, for example, alkali metal salts such as lithium, sodium or potassium salt; alkali earth metal salts such as calcium or magnesium salt; salts with zinc or aluminum; salts with organic bases such as ammonium, choline, diethanolamine, lysine, ethylenediamine, tert-butylamine, tert-octylamine, tris(hydroxymethyl)aminomethane, N-methylglucosamine, triethanolamine or dehydroabiethylamine; salts with inorganic acids such as hydrochloric acid, hydrobromic acid, hydroiodic acid, sulfuric acid, nitric acid or phosphoric acid; salts with organic acids such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, benzenesulfonic acid or toluenesulfonic acid; or salts derived from acidic amino acids such as aspartic acid or glutamic acid.

Additionally, the pharmaceutically acceptable salts of the compound of the formula (1) include, for example, quaternary salts formed between a compound of the formula (1) and an alkyl halide or a phenylalkyl halide.

Preferred pharmaceutical preparations for oral administration of the present compound include solid formulations such as tablets, granules, capsules or powders; and liquid formulations such as solutions, suspensions or emulsions. Preferred pharmaceutical preparations for parenteral administration include injections or infusions formulated with injectable distilled-water, physiological saline or aqueous glucose solution; suppository; or inhalation preparation, and the like.

These pharmaceutical preparations comprise a compound (1) of the present invention or a pharmaceutically acceptable salt thereof and a pharmaceutically acceptable carrier which is usually used for oral or parenteral administration. The pharmaceutically acceptable carriers for oral administration include, for example, a binder (syrup, gum acacia, gelatin, sorbit, tragacanth, polyvinylpyrrolidone, and the like), an excipient (lactose, sugar, cornstarch, potassium phosphate, sorbit, glycine, and the like), a lubricant (magnesium stearate, talc, polyethylene glycol, silica, and the like), a disintegrant (potato starch, and the like), and a wetting agent (anhydrous sodium lauryl sulfate, and the like).

Also the pharmaceutically acceptable carriers for parenteral administration include, for example, injectable distilled-water, physiological saline and aqueous glucose solution.

The dose of a compound (1) of the present invention or a pharmaceutically acceptable salt thereof varies depending on the administration route, age, body weight, disease, and condition/severity, of the patient. It however can usually be in the range of about 0.001-1,000 mg/kg/day, preferably in the range of about 0.01-100 mg/kg/day, more preferably in the range of about 0.1-10 mg/kg/day.

The compounds (1) of the present invention have an inhibitory activity against CETP and show an activity of increasing HDL cholesterol level and an activity of lowering LDL cholesterol level. Accordingly, they are useful in the prophylaxis or treatment of a subject (particularly, mammal including human) suffering from arteriosclerosis such as atherosclerosis, peripheral vascular disease, dyslipidemia, hyperbetalipoproteinemia, hypoalphalipoproteinemia, hypercholesterolemia, hypertriglyceridemia, familial-hypercholesterolemia, cardiovascular diseases, angina, ischemia, cardiac ischemia, stroke, myocardial infarction, reperfusion injury, restenosis after angioplasty, hypertension, cerebral infarction, cerebral stroke, diabetes, vascular complication of diabetes, thrombotic diseases, obesity, endotoxemia, metabolic syndrome, cerebrovascular disease, coronary artery disease, ventricular dysfunction, cardiac arrhythmia, pulmonary vascular disease, reno-vascular disease, renal disease, splanchnic vascular disease, vascular hemostatic disease, fatty liver disease, steatohepatitis, inflammatory disease, autoimmune disorders and other systemic disease indications, immune function modulation, pulmonary disease, anti-oxidant disease, sexual dysfunction, cognitive dysfunction, schistosomiasis, cancer, regression of xanthoma, Alzheimer's disease, or the like.

In addition, the compounds of the present invention may be used in combination with other drugs useful for treatment of these diseases. For example, a compound of the present invention may be used in combination with an inhibitor of cholesterol synthesis such as HMG-CoA reductase inhibitor; an inhibitor of cholesterol absorption such as anion exchange resin; a triglyceride lowering agent such as fibrates, niacin and fish oil; an antihypertensive such as ACE inhibitor, angiotensin receptor blocker, calcium antagonist and beta blocker; an antiobesity agent such as central anorectic, lipase inhibitor and CB1 antagonist; an antidiabetic agent such as insulin sensitizer, D2 agonist, sulfonylurea, biguanide, α-glucosidase inhibitor, SGLT inhibitor and DPPIV inhibitor; or other cholesterol reducer such as ACAT inhibitor.

The compound (1) of the present invention may be prepared by the following methods, which should not be construed to be limited thereto.

In each process for preparing a compound of the formula (1) described above, when protection of a functional group contained in any compound is needed, the protection can be carried out in a conventional manner ad libitum. General statement related to protecting groups and their use is provided by Greene, Protective Groups in Organic Synthesis, John Wiley and Sons, New York, 1991.

Further in each process, the reaction can be carried out by the conventional method and a procedure for isolation and the purification may be selected from the conventional method such as crystallization, recrystallization and chromatography and preparative HPLC, and the like as appropriate, or may be combined with one another.

[Method I]

The compound (1) can be prepared by the following method I.

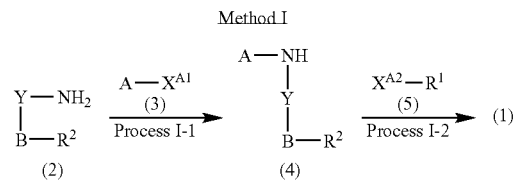

wherein the $X^{A1}$ and $X^{A2}$ are a leaving group and the other symbols have the same meanings as defined above (Process I-1)

The compound (4) can be prepared by reacting the compound (2) with the compound (3) in a solvent in the presence of a base.

Any solvent which dose not disturb the reaction can be preferably used as a solvent used, and include, for example, ethers including diethylether, tetrahydrofuran (THF), dioxane, 1,2-methoxyethane, diglyme; hydrocarbons including benzene, toluene, hexane, xylene; alcohols including methanol, ethanol, isopropyl alcohol, tert-butanol; esters including ethyl acetate, methyl acetate, butyl acetate; polar solvents including acetone, N,N-dimethylformamide, dimethyl sulfoxide, which can be used alone or in a combination thereof. Preferred solvents in this reaction include ethanol, dioxane, toluene and N,N-dimethylformamide.

A conventional base may be used as a base, and includes for example, alkaline metal hydride including sodium hydride and potassium hydride; alkaline metal alkoxide including sodium ethoxide, sodium methoxide, sodium tert-butoxide and potassium tert-butoxide; alkyl lithium including n-butyl lithium and sec-butyl lithium; alkaline metal amide including lithium diisopropylamide, sodium amide and lithium bis(trimethylsilyl)amide; alkaline metal carbonate including sodium carbonate, potassium carbonate, sodium bicarbonate and potassium bicarbonate; alkaline metal hydroxide including lithium hydroxide, sodium hydroxide and potassium hydroxide; alkaline metal phosphate including sodium phosphate and potassium phosphate; organic base including triethylamine, diisopropylethylamine, pyridine and N-methylmorpholine; preferably triethylamine, sodium bicarbonate, sodium tert-butoxide, diisopropylethylamine, sodium hydride and potassium tert-butoxide.

The leaving group includes a halogen atom including chlorine atom, bromine atom, iodine atom, and a substituted sulfonyloxy group including methanesulfonyloxy group, p-toluenesulfonyloxy group and trifluoro-methanesulfonyloxy group.

(Process I-2)

The compound (1) can be prepared by reacting the compound (4) with the compound (5) in a same manner as in process I-1 or 1'-1 described below.

(Process I'-1)

The process (I-1) may be replaced by the following process I'-1.

In the above process I-1, the compound (4) can also be prepared by reacting the compound (2) with the compound (3) in the presence or absence of a base or in the presence of a metal catalyst such as palladium catalyst in a suitable solvent.

A conventional palladium catalyst can be used as a palladium catalyst, and include palladium acetate, tetrakis(triphenylphosphine)-palladium, tris(dibenzylideneacetone)dipalladium, dichlorobis(triphenyl-phosphine)palladium, dichlorobis(tri-o-tolylphosphine)palladium, bis-(triphenylphosphine)palladium acetate, or the like.

As the base, alkaline metal hydroxide including sodium hydroxide, potassium hydroxide; alkaline earth metal hydroxide including barium hydroxide; alkaline metal alkoxide including sodium methoxide, sodium ethoxide, potassium ethoxide, sodium tert-butoxide, potassium tert-butoxide; alkaline metal carbonate including sodium carbonate, potassium carbonate, cesium carbonate; alkaline metal bicarbonate including sodium bicarbonate, potassium bicarbonate; alkaline metal phosphate including potassium phosphate; amines including triethylamine, diisopropyl-ethylamine, methylpiperidine, dicyclohexylmethylamine; and pyridines including pyridine, 4-dimethylaminopyridine can be preferably used.

Additionally, phosphines may be added in the present reaction. As the phosphines, triphenylphosphine, tributylphosphine, tri-tert-butylphosphonium tetrafluoroborate, 1,3-bis(diphenylphosphino)propane, 2,2'-bis(diphenylphosphino)-1,1'-binaphthyl, 1,1'-bis(diphenylphosphino)-ferrocene, 2-(di-tert-butylphosphino)biphenyl, 2-dicyclohexylphosphino-2'-(N,N-dimethylamino)biphenyl, 2-(dicyclohexylphosphino)biphenyl, and the like can be preferably used.

Any solvent which dose not disturb the reaction can be preferably used as a solvent used in the reaction, and include, for example, ethers including diethylether, tetrahydrofuran (THF), dioxane, 1,2-methoxyethane, diglyme; hydrocarbons including benzene, toluene, hexane, xylene; alcohols including methanol, ethanol, isopropyl alcohol, tert-butanol; esters including ethyl acetate, methyl acetate, butyl acetate; polar solvents including acetone, N,N-dimethylformamide, dimethyl sulfoxide, and which can be used alone or in a combination thereof.

(Process I'-2)

The compound (1) can be prepared by reacting the compound (4) with the compound (5) in a same manner as in process I'-1 or I-1.

[Method II]

The compound can be prepared by a method II.

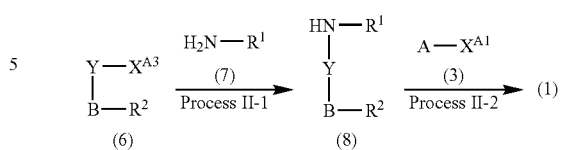

wherein the $X^{A3}$ is a leaving group and the other symbols have the same meanings as defined above (Process II-1)

The compound (8) can be prepared by reacting the compound (6) with the compound (7) in a same manner as process I-1.

(Process II-2)

The compound (1) can be prepared by reacting the compound (8) with the compound (3) in a same manner as in process I-1 or I'-1.

[Method III]

The compound (1) can be prepared by a method III.

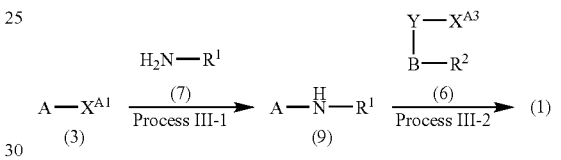

wherein the symbols have the same meanings as defined above (Process III-1)

The compound (9) can be prepared by reacting the compound (3) with the compound (7) in a same manner as in process I-1 or process I'-1.

(Process III-2)

The compound (1) can be prepared by reacting the compound (9) with the compound (6) in a same manner as in process I-1.

[Method IV]

The compound of the general formula (1-a):

wherein the symbols have the same meanings as defined above, that is, those wherein Y is a methylene group in the compound of the formula (1), can be prepared by a following method IV.

The compound (1-a) can be prepared by reducing the compound of a general formula (6'):

wherein the symbols have the same meanings as defined above, or its corresponding carboxylic acid or its corresponding carboxylic acid ester to provide the compound of a general formula (6"):

(6")

wherein the symbols have the same meanings as defined above, followed by halogenating the resulting compound and then reacting the resulting compound with the above compound (9) in a solvent in the presence of a base.

The reduction can be carried out by treating a starting compound with a reducing agent in a suitable solvent. Boron hydrides (sodium borohydride, and the like) and aluminum hydrides (lithium aluminum hydride, diisobutylaluminum hydride, and the like) can be preferably used as a reducing agent.

The hologenation can be carried out by treating a starting compound with a halogenating agent in a suitable solvent. As the halogenating agent, a conventional halogenating agent including thionyl chloride, phosphorus oxychloride, as well as carbon tetrahalide (e.g., carbon tetrachloride, carbon tetrabromide, and the like) and phosphines (e.g., triphenylphosphine, tritolylphosphine, triethylphosphine, and the like) can be preferably used.

A conventional base may be used as a base and include for example, alkaline metal hydride including sodium hydride and potassium hydride; alkaline metal alkoxide including sodium ethoxide, sodium methoxide, sodium tert-butoxide and potassium tert-butoxide; alkyl lithium including n-butyl lithium and sec-butyl lithium; alkaline metal amide including lithium diisopropylamide, sodium amide and lithium bis(trimethylsilyl)amide; alkaline metal carbonate including sodium carbonate, potassium carbonate, sodium bicarbonate and potassium bicarbonate; alkaline metal hydroxide including lithium hydroxide, sodium hydroxide and potassium hydroxide; alkaline metal phosphate including sodium phosphate and potassium phosphate; organic base including triethylamine, diisopropylethylamine, pyridine and N-methylmorpholine; preferably triethylamine, sodium bicarbonate, sodium tert-butoxide, diisopropylethylamine, sodium hydride and potassium tert-butoxide.

Any solvent which dose not disturb the reaction can be preferably used as a solvent used, and include, for example, ethers including diethylether, tetrahydrofuran (THF), dioxane, 1,2-methoxyethane, diglyme; hydrocarbons including benzene, toluene, hexane, xylene; alcohols including methanol, ethanol, isopropyl alcohol, tert-butanol; esters including ethyl acetate, methyl acetate, butyl acetate; polar solvents including acetone, N,N-dimethylformamide, dimethyl sulfoxide, which can be used alone or in a combination thereof. Preferred solvents in this reaction include ethanol, dioxane, toluene and N,N-dimethylformamide.

[Method IV']

The compound (1-a) can also be prepared by the following method IV'.

The compound (1-a) can also be prepared by halogenating the above compound (6") according to the above method IV, followed by reacting the resulting compound with the above compound (7) in a solvent in the presence of a base to provide the compound of a general formula (8')

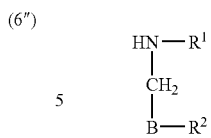

(8')

wherein the symbols have the same meanings as defined above, then reacting the resulting compound with the compound (3) according to the above process II-2.

[Method IV''']

In the above method IV', the compound (8') can be prepared by reacting the compound (6') with the compound (7) in a solvent in the presence of a reducing agent.

Any solvent which dose not disturb the reaction can be preferably used as a solvent used in the reaction, and include for example, halogenated solvents including 1,2-dichloroethane, dichloromethane, chloroform, ethers including diethylether, tetrahydrofuran (THF), dioxane, 1,2-methoxyethane, diglyme; hydrocarbons including benzene, toluene, hexane, xylene; alcohols including methanol, ethanol, isopropyl alcohol, tert-butanol; esters including ethyl acetate, methyl acetate, butyl acetate; polar solvents including acetone, N,N-dimethylformamide, dimethyl sulfoxide, and which can be used alone or in a combination thereof. Especially preferred solvent in this reaction includes 1,2-dichloroethane, dichloromethane and toluene. The reducing reagent includes sodium borohydrides including sodium triacetoxyborohydride, sodium cyanoborohydride; and aluminum hydrides including lithium aluminium hydride and diisobutylaluminium hydride.

[Method V]

The compound of a general formula (I-b):

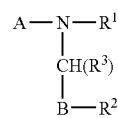

(1-b)

wherein $R^3$ is an alkyl group and the other symbols have the same meanings as defined above, those wherein Y is an alkyl group in the compound (1), can be prepared by undergoing a conventional Grignard reaction of the compound (6') with a reagent of a general formula: $R^3MgBr$ wherein the symbol has the same meaning as defined above, to provide the compound of a general formula (6'''):

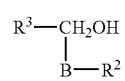

(6''')

wherein the symbols have the same meanings as defined above, followed by halogenating the resulting compound in a same manner as in the above method IV, then reacting the resulting compound with the above compound (9) in a solvent in the presence of a base.

[Method V']

The compound (1-b) can also be prepared by the following method V'.

The compound (1-b) can also be prepared by halogenating the above compound (6''') according to the above method V, followed by reacting the resulting compound with the above compound (7) in a solvent in the presence of a base, to provide a compound of a general formula (8''):

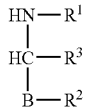
(8'''')

wherein the symbols have the same meanings as defined above, then reacting the resulting compound with the compound (3) according to the above process II-2.

[Method VI]

The compound of a general formula (1-c):

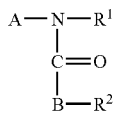
(1-c)

wherein the symbols have the same meanings as defined above, those wherein Y is an methylene group substituted by an oxo group in the compound (1), can be prepared by oxidizing the compound (6') to provide the compound of a general formula (6''''):

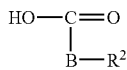
(6''')

wherein the symbols have the same meanings as defined above, followed by halogenating the resulting compound according to the above method IV, then reacting the resulting compound with the above compound (9) in a solvent in the presence of a base.

[Method VI']

The compound (1-c) can also be prepared by the following method VI'.

The compound (1-c) can be prepared by halogenating the above compound (6'''') according to the above method VI, followed by reacting the resulting compound with the above compound (7) in a solvent in the presence of a base, to provide a compound of a general formula (8'''):

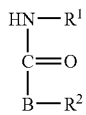
(8''')

wherein the symbols have the same meanings as defined above, then reacting the resulting compound with the compound (3) according to the above process II-2.

[Method VII]

The compound (1-a) can be prepared by the following method VII.

The compound (1-a) can also be prepared by reducing the compound of a general formula (6'''''):

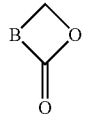
(6''''')

wherein the symbols have the same meanings as defined above, to provide the compound of a general formula (6''''''):

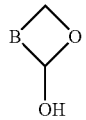
(6'''''')

wherein the symbols have the same meanings as defined above, then reacting the resulting compound with the above compound (9) in a same manner as in the method IV''', to provide the compound of a general formula (1-d):

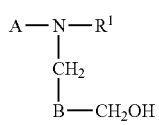
(1-d)

wherein the symbols have the same meanings as defined above, and interconverting on $R^2$ moiety.

[Method VII']

The compound (1-a) can also be prepared by reacting the above compound (6'''''') with the above compound (7) in a same manner as in the above method IV''' to provide the compound of a general formula (8''):

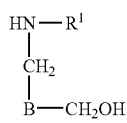
(8'')

wherein the symbols have the same meanings as defined above, followed by reacting the resulting compound with the compound (3) according to the above process II-2 to provide the compound (1-d), then interconverting on $R^2$ moiety.

In addition, substituents on the A, B, $R^1$ and $R^2$ may be further interconverted according to the known method after or before a synthesis of the compound (1).

$A^2$ can be interconverted by the following methods (EA) to (EL).

In the following each process, unless otherwise specified, a conventional base can be used as the base, and for example, alkaline metal hydride including sodium hydride, potassium hydride; alkaline metal hydroxide including sodium hydroxide, potassium hydroxide; alkaline earth metal hydroxide including barium hydroxide; alkaline metal alkoxide including sodium methoxide, sodium ethoxide, potassium ethoxide, potassium tert-butoxide; alkaline metal carbonate including sodium carbonate, potassium carbonate, cesium carbonate; alkaline metal bicarbonate including sodium bicarbonate, potassium bicarbonate; amines including triethylamine, diisopropylethylamine, methylpiperidine, dimethylaniline, 1,8-diazabicyclo[5.4.0]undecene, 1,4-diazabicyclo[2.2.2]octane, 1,5-diazabicyclo[4.3.0]nonene; pyridines including pyridine, dimethylaminopyridine can be preferably used.

Also in the following each process, a conventional acid can be used as the acid, and for example, unless otherwise specified, an inorganic acid (e.g. hydrochloric acid, nitric acid and sulfuric acid); organic acid represented by sulfonic acids (e.g. methanesulfonic acid, p-toluenesulfonic acid and trifluoromethanesulfonic acid, and the like) can be preferably used.

Also in the following each process, any solvent which dose not disturb the reaction can be used as the solvent and specifically include hydrocarbons including pentane, hexane; aromatic hydrocarbons including benzene, toluene, nitrobenzene; halogenated hydrocarbons including dichloromethane, chloroform; ethers including diethylether, tetrahydrofuran; amides including dimethylformamide, N-methylpyrrolidone, 1,3-dimethylimidazolidin-2-one; sulfoxides including dimethylsulfoxide; alcohols including methanol, ethanol; esters including ethyl acetate, butyl acetate; ketones including acetone, methyl ethyl ketone; nitriles including acetonitrile; water, or a mixed solvent thereof.

Also in the following each process, the leaving group includes a halogen atom including chlorine atom, bromine atom, iodine atom, and a substituted sulfonyloxy group including methanesulfonyloxy group, trifluoromethanesulfonyloxy group and toluenesulfonyloxy group.

(EA) The compound wherein $A^1$ is a tetrazolyl group and $A^2$ is an alkyl group or a substituted alkyl group can be prepared by alkylating a compound wherein $A^1$ is a tetrazolyl group and $A^2$ is a hydrogen atom.

The alkylation can be carried out by reacting with a compound of the formula:

$$A^{2A}\text{-}Z^2$$

wherein $A^{2A}$ is an alkyl group or a substituted alkyl group and $Z^2$ is a leaving group, in a suitable solvent in the presence or absence of a base, or by reacting with a compound of the formula:

$$A^{2A}\text{-OH}$$

wherein the symbol has the same meaning as defined above, in a suitable solvent in the presence of phosphines and azodicarboxylic esters.

N-alkylation of a compound wherein $A^1$ is a nitrogen-containing heterocyclic group can be carried out in a similar manner as above.

The reaction proceeds more preferably when a catalytic amount of an alkaline metal iodide (e.g., potassium iodide, and the like) is added.

Both phosphines and azodicarboxylic esters which usually employed in Mitsunobu reaction can be preferably used. Phosphines include, for example, triphenylphosphine, tributylphosphine, and the like, and azodicarboxylic esters include diethyl azodicarboxylate, diisopropyl azodiformate, and the like.

(EB) The compound wherein $A^1$ is 2-oxodihydropyrimidinyl group and $A^2$ is an alkyl group or a substituted alkyl group can be prepared by alkylating a compound of the formula (1) wherein $A^1$ is 2-hydroxypyrimidinyl group and $A^2$ is a hydrogen atom, with a compound of the formula:

$$A^{2A}\text{-}Z^2$$

wherein the symbols have the same meaning as defined above.

The reaction can be carried out in the same manner as in the above (EA).

(EC) The compound wherein $A^2$ is an optionally substituted amino group or a group of the formula:

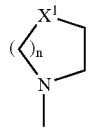

wherein the symbols have the same meaning as defined above, can be prepared by reacting a compound of the formula (1) wherein $A^2$ is a halogen atom, with a corresponding amine or a compound of the formula:

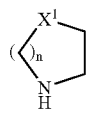

wherein the symbols have the same meanings as defined above.

The reaction can be carried out in the presence or absence of a base, and in the presence or absence of a palladium catalyst in a suitable solvent.

As the palladium catalyst, a conventional palladium catalyst including palladium acetate, tetrakis(triphenylphosphine)palladium, tris(dibenzylideneacetone)dipalladium, dichlorobis(triphenylphosphine)-palladium, dichlorobis(tri-o-tolylphosphine)palladium, bis-(triphenylphosphine)palladium acetate, or the like can be used.

As the base, alkaline metal hydroxide including sodium hydroxide, potassium hydroxide; alkaline earth metal hydroxide including barium hydroxide; alkaline metal alkoxide including sodium methoxide, sodium ethoxide, potassium ethoxide, potassium tert-butoxide; alkaline metal carbonate including sodium carbonate, potassium carbonate, cesium carbonate; alkaline metal bicarbonate including sodium bicarbonate, potassium bicarbonate; alkaline metal phosphate including potassium phosphate; amines including triethylamine, diisopropylethylamine, methylpiperidine, dicyclohexylmethylamine; and pyridines including pyridine, 4-dimethylaminopyridine can be preferably used.

Additionally, phosphines may be added in the present reaction. As the phosphines, triphenylphosphine, tributylphosphine, tri-tert-butylphosphonium tetrafluoroborate, 1,3-bis(diphenylphosphino)propane, 2,2'-bis(diphenylphosphino)-1,1'-binaphthyl, 1,1'-bis(diphenylphosphino)-ferrocene, 2-(di-tert-butylphosphino)biphenyl, 2-dicyclohexylphosphino-2'-(N,N-dimethylamino)biphenyl, 2-(dicyclohexylphosphino)biphenyl, and the like can be preferably used as the phosphines.

(ED) The compound wherein $A^2$ is an optionally substituted amino group can be prepared by coupling a compound of the formula (1) wherein $A^2$ is a halogen atom with a compound of the formula:

$$(R^{20})_3Sn\text{—}NR^{21}R^{22}$$

wherein $R^{20}$ is an alkyl group and $NR^{21}R^{22}$ is an optionally substituted amino group.

The coupling reaction can be carried out in the presence of a palladium catalyst in the presence or absence of a base in a suitable solvent.

The palladium catalysts, bases, and phosphines described in the above (EC) can be used in the same manner as in the above (EC).

(EE) The compound wherein $A^2$ is a cyano group can be prepared by cyanating a compound of the formula (1) wherein $A^2$ is a halogen atom.

The cyanation can be carried out by reacting a starting compound with a metal cyanide including sodium cyanide, potassium cyanide, or zinc cyanide in the presence of a palladium catalyst in a suitable solvent.

The same palladium catalyst as that described in the above (EC) can be preferably used.

(EF) The compound wherein $A^2$ is an optionally substituted alkoxycarbonyl group can be prepared by reacting a compound of the formula (1) wherein $A^2$ is a halogen atom, with a corresponding alkylalcohol under carbon monoxide atmosphere using a palladium catalyst in the presence of a base in a suitable solvent.

The same palladium catalyst and base as those described in the above (EC) can be preferably used.

Additionally, the reaction can be more preferably carried out by adding a ligand, and phosphines described in the above (EC) can be preferably used as the ligand.

(EG) The compound wherein $A^2$ is an optionally substituted alkenyl group can be prepared by coupling a compound of the formula (1) wherein $A^2$ is a halogen atom with a corresponding alkene.

The coupling reaction can be carried out in the presence of a palladium catalyst in the presence or absence of a base in a suitable solvent.

The same palladium catalyst as that described in the above (EC) can be preferably used.

The same base as that described in the above (EC) can be preferably used and silver carbonate can also be used.

Additionally, the reaction can be more preferably carried out by adding a ligand, and phosphines described in the above (EC) can be preferably used as the ligand.

(EG') The compound wherein $A^2$ is an optionally substituted alkenyl group can be prepared by dehydration reaction of a compound having a hydroxyalkyl group in a substituent $A^2$. The dehydration reaction can be carried out by treating a starting compound with acid.

As the acid, a conventional acid can be used. For example, an inorganic acid (e.g. hydrochloric acid, nitric acid and sulfuric acid) or an organic acid (e.g. methanesulfonic acid, p-toluenesulfonic acid, acetic acid, trifluoroacetic acid, trifluoromethanesulfonic acid, and the like) can be preferably used.

(EH) The compound wherein $A^2$ is a boronic acid ester can be prepared by reacting with the compound wherein $A^2$ is a leaving group with a trialkoxyborane (trimethoxyborane, triisopropoxyborane, and the like), a dialkoxyborane (pinacolborane, and the like) or a tetraalkoxydiboron (bis(pinacolato)diboron, and the like) in the presence of palladium catalyst. The leaving group includes a halogen atom including chlorine atom, bromine atom, iodine atom, and a substituted sulfonyloxy group including methanesulfonyloxy group, trifluoromethanesulfonyloxy group, and toluenesulfonyloxy group. The reaction can be carried out in the same manner as in the above (EC).

(EH') The compound wherein $A^2$ is a hydroxy group can be prepared by reacting the compound wherein $A^2$ is a boronic acid ester with the peroxide. Aqueous hydrogen peroxide, m-chloroperbenzoic acid and OXONE™ (DuPont Co. Ltd), and the like can be preferably used as the peroxide.

(EI) The compound wherein $A^2$ is an alkoxy group or a substituted alkoxy group can be prepared by alkoxylating the compound (1) wherein $A^2$ is a halogen atom.

The alkoxylation can be carried out by optionally adding a copper catalyst to react with a corresponding alcohol in a suitable solvent or solvent-free in the presence of a base.

The same base as described in the above (EC), in particular, cesium carbonate can be preferably used.

The copper catalyst including copper iodide, copper bromide, copper chloride, copper acetate, copper trifluoromethanesulfonate, and the like can be preferably used.

Additionally, this reaction proceeds more preferably when 1,10-phenanthroline, 2-aminopyridine, or the like is added.

(EJ) The compound wherein $A^2$ is an optionally substituted alkyl group, an optionally substituted heterocyclic group or an optionally substituted aryl group can be prepared by coupling a compound of the formula (1) wherein $A^2$ is a leaving group with a corresponding alkyl, aryl or heterocyclic boronic acid or a corresponding alkyl, aryl or heterocyclic boronic acid ester.

The coupling can be carried out in the presence of a palladium catalyst, and in the presence or absence of a base in a suitable solvent.

This reaction can be carried out in the same manner as in the above (EC).

The leaving group is the same as defined above (EH).

(EJ') The compound wherein $A^2$ is an optionally substituted alkyl group, an optionally substituted heterocyclic group or an optionally substituted aryl group can be prepared by coupling a compound of the formula (1) wherein $A^2$ is a boronic acid or a boronic acid ester with an alkyl, an aryl or a heterocyclic group which have a leaving group.

The coupling can be carried out in the presence of a palladium catalyst, and in the presence or absence of a base in a suitable solvent. The reaction can be carried out in the same manner as in the above (EC). The leaving group is the same as defined above (EH).

(EK) The compound wherein $A^2$ is an alkoxycarbonylalkylsulfonyl group can be prepared by reacting a compound of the formula (1) wherein $A^2$ is a halogen atom with an alkoxycarbonylalkylsulfinic acid alkaline metal salt.

The alkoxycarbonylalkylsulfinic acid alkaline metal salt can be prepared according to the method described, for example, in Baskin et. al., Tetrahedron Lett., 43, 8479 (2002).

Additionally, this reaction can be carried out in the presence of a copper catalyst in a suitable solvent according to the method described in the said literature.

The same copper catalyst as described in (EI) above can be used, and in particular, copper iodide can be preferably used.

(EL) The compound wherein $A^2$ is a group of the formula:

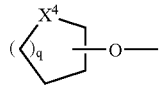

wherein the symbols have the same meaning as defined above, can be prepared by condensing a compound wherein $A^2$ is a hydroxy group with a compound of the formula:

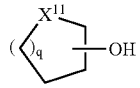

wherein $X^{11}$ is O, SO, $SO_2$ or $NR_P$ ($R_P$ is a protecting group) and q is an integer from 1 to 4, and as needed, removing the protecting group for amino group.

As a protecting group, a conventional protecting group including benzyloxycarbonyl group, tert-butoxycarbonyl group, and the like can be used.

The reaction can be carried out in a suitable solvent in the presence of phosphines and azodicarboxylic esters. The reaction can be carried out in the same manner as in the above (EA).

The removal of a protecting group can be carried out in a conventional manner including catalytic reduction, acid-treatment, and the like, depending on the type of a protecting group.

The same manner as in the above reactions (EA) to (EL) for conversions of $A^2$ can also be applied for conversion of the other substituent as needed.

Additionally, a substituent(s) of a compound (1) of the present invention can be converted into different one(s) within the scope of the compound (1) according to the following methods as appropriate.

In the following each process, a conventional base can be used as the base, and unless otherwise specified, the base described in the above (EA) can be preferably used.

Additionally, in the following each process, a conventional acid can be used as the acid, and unless otherwise specified, a mineral acid including hydrochloric acid, nitric acid, sulfuric acid, or an organic acid represented by sulfonic acids (e.g., methanesulfonic acid, p-toluenesulfonic acid, trifluoromethanesulfonic acid) or carboxylic acids (e.g., acetic acid, trifluoroacetic acid) can be preferably used.

Further additionally, in the following each process, any solvent which dose not disturb the reaction can be used, and as such, the solvent described in the above (EA) can be preferably used.

The leaving group includes a halogen atom including chlorine atom, bromine atom, iodine atom, and a substituted sulfonyloxy group including methanesulfonyloxy group, trifluoromethanesulfonyloxy group, and toluenesulfonyloxy group.

(E1) The compound wherein A is a heterocyclic group substituted by an optionally substituted amino group or a group of the formula:

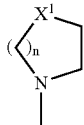

wherein the symbols have the same meanings as defined above, can be prepared by reacting a compound (1) wherein A is a heterocyclic group substituted by an optionally substituted alkylsulfonyloxy group, with a corresponding amine or a compound of the formula:

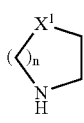

wherein the symbols have the same meaning as defined above in the presence of a palladium catalyst, and in the presence or absence of a base in a suitable solvent or solvent-free.

The reaction can be carried out in the same manner as in the above (EC).

(E2) The compound wherein A is a heterocyclic group substituted by an optionally substituted amino group or a group of the formula:

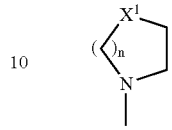

wherein the symbols have the same meanings as defined above, can also be prepared by reacting a compound wherein A is a heterocyclic group substituted by a halogen atom or an optionally substituted alkylsulfonyloxy group, with a corresponding amine or a compound of the formula:

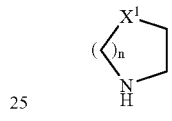

wherein the symbols have the same meanings as defined above.

The reaction can be carried out by optionally adding a copper catalyst in the presence or absence of a base in a suitable solvent.

Copper iodide, copper bromide, copper chloride, copper acetate, copper trifluoromethanesulfonate, and the like can be preferably used as the copper catalyst.

The same base as that described in the above (EC) can be preferably used.

Additionally, the reaction proceeds more preferably when N,N'-dimethylethylenediamine, 1,10-phenanthroline, ethylene glycol, phenylphenol, and the like is added.

(E3) The compound wherein A is a heterocyclic group substituted by an optionally substituted alkylsulfanyl group can be prepared by reacting a compound wherein A is a heterocyclic group substituted by a halogen atom or an optionally substituted alkylsulfonyloxy group with a corresponding alkylthiol.

The reaction can be carried out in the same manner as in that described in the above (EI) and more preferably facilitated by adding 1,10-phenanthroline or ethylene glycol.

(E4) The compound wherein A is a heterocyclic group substituted by an optionally substituted heterocyclic group can be prepared by coupling a compound wherein A is a heterocyclic group substituted by a halogen atom or an optionally substituted alkylsulfonyloxy group with a corresponding heterocyclic tin compound or a corresponding heterocyclic boron compound.

The reaction can be carried out in the same manner as in the above (ED) or (EI).

(E5) The compound wherein A is a heterocyclic group substituted by an alkoxy group can be prepared by reacting a compound wherein A is a heterocyclic group substituted by a halogen atom or an alkylsulfonyl group with a corresponding alkaline metal alkoxide in a suitable solvent. The corresponding alkaline metal alkoxide can be obtained by treating a corresponding alkylalcohol with alkaline metal hydride or alkaline metal in the said solvent.

(E6) The compound having an aminoalkyl group as a substituent on A can be prepared by catalytically reducing a compound having a cyano group or a cyanoalkyl group as a substituent on A.

The catalytic reduction can be carried out by using a catalyst under hydrogen atmosphere in a suitable solvent in a conventional manner. The catalyst includes a palladium catalyst including palladium-carbon, a nickel catalyst including Raney nickel, a platinum catalyst including platinum-carbon, and the like.

(E7) The compound having an optionally substituted mono- or di-alkylsulfamoylaminoalkyl group as a substituent on A can be prepared by reacting a compound having an aminoalkyl group as a substituent on A with a corresponding halogenated mono- or di-alkylsulfamoyl.

The reaction can be carried out in a suitable solvent in the presence of a base.

(E8) The compound having an optionally substituted mono-alkylcarbamoylaminoalkyl group as a substituent on A can be prepared by reacting a compound having an aminoalkyl group as a substituent on A with a corresponding alkyl isocyanate in a suitable solvent.

(E9) The compound having a group of the formula:

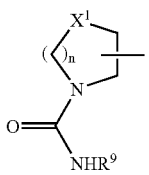

wherein $R^9$ is an alkyl group and the other symbols have the same meanings as defined above as a substituent on A can be prepared by reacting a compound having a group of the formula:

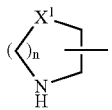

wherein the symbols have the same meanings as defined above as a substituent on A with a corresponding alkyl isocyanate ($R^9$NCO). The reaction can be carried out in the same manner as in the above (E8).

(E10) The compound having an optionally substituted mono- or di-alkylcarbamoylaminoalkyl group as a substituent on A can be prepared by condensing a compound having an aminoalkyl group as a substituent on A with an optionally substituted mono- or di-alkylamine using a carbonylating agent in a suitable solvent in the presence or absence of a base.

A conventional carbonylating agent such as carbonyldiimidazole, phosgene, triphosgene, and the like can be used.

(E11) The compound having a morpholinylcarbonylamino group as a substituent on A can be prepared by condensing a compound having an amino group as a substituent on A with morpholine using a carbonylating agent in a suitable solvent. The reaction can be carried out in the same manner as in the above (E10).

(E12) The compound having a group of the formula:

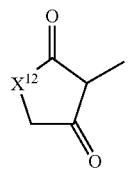

wherein $X^{12}$ is O or NH, as a substituent on A can be prepared by treating a compound having a group of the formula:

wherein the symbols have the same meanings as defined above as a substituent on A with a carbonylating agent in a suitable solvent.

The reaction can be carried out in the same manner as in the above (E10).

(E12') The compound having a group of the formula:

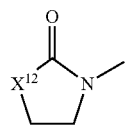

wherein $X^{12}$ is O or NH, as a substituent on A can be prepared by treating a compound having a group of the formula:

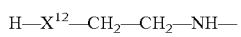

wherein the symbols have the same meanings as defined above as a substituent on A with a carbonylating agent in a suitable solvent.

The reaction can be carried out in the same manner as in the above (E10).

(E13) The compound having an optionally substituted carbamoyl group as a substituent on A can be prepared by condensing a compound having a carboxyl group as a substituent on A with a desirable amine.

The condensation can be carried out using a condensing agent in a suitable solvent. A conventional condensing agent such as dicyclohexylcarbodiimide, 1-ethyl-3-(3-dimethylaminopropyl)carbodiimide, carbonyldiimidazole, and the like can be preferably used.

Additionally, the condensation can be more preferably carried out by adding an activating agent including 1-hydroxybenzotriazole, 1-hydroxysuccinimide, and the like.

(E14) The compound having a group of the formula:

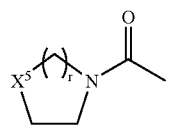

wherein the symbols have the same meanings as defined above as a substituent on A can be prepared by condensing a compound having a carboxyl group as a substituent on A with a compound of the formula:

wherein the symbols have the same meanings as defined above.

The reaction can be carried out in the same manner as in the above (E13).

(E15) The compound having a tetrazolyl group as a substituent on A can be prepared by reacting a compound having a cyano group as a substituent on A with an alkaline metal azide in the presence of an acid in a suitable solvent.

The alkaline metal azide includes sodium azide, lithium azide, and the like.

An ammonium salt of a halogenated hydrogen including ammonium chloride can be preferably used as the acid.

(E16) The compound having an optionally substituted alkyl tetrazolyl group as a substituent on A can be prepared by alkylating a compound having a tetrazolyl group as a substituent on A.

The alkylation can be carried out in the same manner as in the above (EA).

(E17) The compound having an optionally substituted amino group or a group of the formula:

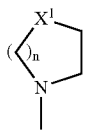

wherein the symbols have the same meanings as defined above as a substituent on A can be prepared by reacting a compound having a halogen atom or an optionally substituted alkylsulfonyloxy group as a substituent on A with a corresponding amine or a compound of the formula:

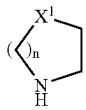

wherein the symbols have the same meanings as defined above.

The reaction can be preferably carried out in the presence or absence of a base in a suitable solvent.

(E18) The compound having an optionally substituted alkylamino group or a group of the formula:

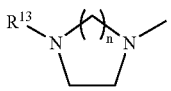

wherein $R^{13}$ is an alkyl group optionally substituted by a hydroxy group, an alkoxycarbonyl group, a morpholinyl group or a phenyl group, and n has the same meaning as defined above, as a substituent on A can be obtained by reacting a compound having an amino group or a group of the formula:

wherein the symbols have the same meanings as defined above as a substituent on A with a corresponding alkyl halide or a corresponding sulfonic acid alkyl esters.

The sulfonic acid alkyl esters including methanesulfonic acid ester, toluenesulfonic acid ester, trifluoromethanesulfonic acid ester, and the like can be preferably used.

The reaction can be preferably carried out in the presence or absence of a base in a suitable solvent.

(E19) The compound having a group of the formula:

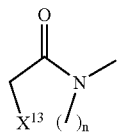

wherein $X^{13}$ is O or NH, and the other symbol has the same meaning as defined above as a substituent on A, can be prepared by ring-closing a compound having a group of the formula:

$$Z^3-(CH_2)_n-X^{13}-CH_2-CONH-$$

wherein $Z^3$ is a leaving group and the other symbols have the same meanings as defined above, as a substituent on A.

The reaction can be preferably carried out in the presence or absence of a base in a suitable solvent.

(E20) The compound having a carboxyl group as a substituent on A can be prepared by hydrolyzing a compound having an alkoxycarbonyl group as a substituent on A.

The hydrolysis can be carried out by treating a starting compound with a base or an acid in a suitable solvent according to a conventional manner. An alkaline metal hydroxide can be preferably used as the base.

(E21) The compound containing a carboxyl group as a substituent on A can be prepared by hydrolyzing a compound containing a cyano group as a substituent on A.

The hydrolysis can be carried out by treating a starting compound with an acid or a base in a suitable solvent.

(E22) The compound containing a carbamoyl group as a substituent on A can be prepared by hydrolyzing a compound containing a cyano group as a substituent on A.

The hydrolysis can be carried out by treating a starting compound with an acid or a base in a suitable solvent.

(E23) The compound having a carboxyalkyl group as a substituent on A can also be prepared by catalytically reducing a compound having a carboxyalkenyl group, a benzyloxycarbonylalkenyl group or a benzyloxycarbonylalkyl group as a substituent on A.

The catalytic reduction can be carried out in the same manner as in the above (E6).

(E24) The compound having a hydroxy group as a substituent on A can be prepared by hydrolyzing a compound wherein A has an alkanoyloxy group.

The hydrolysis can be carried out in the same manner as in the above (E20).

(E25) The compound containing sulfoxide (SO) or sulfone ($SO_2$) in a substituent on A can be prepared by oxidizing a compound having S in a substituent on A (e.g., a compound having a thiomorpholinyl group or an alkylsulfanylalkyl group as a substituent on A).

The oxidation can be carried out by treating a starting compound with an oxidizing agent in a suitable solvent.

Peroxides such as hydrogen peroxide, m-chloroperbenzoic acid, acetyl hydroperoxide, and the like can be preferably used as the oxidizing agent.

(E26) The compound containing N-oxide in a substituent on A can be prepared by oxidizing a compound having N in a substituent on A (e.g., a compound having a pyridyl group as a substituent on A).

The oxidation can be carried out in the same manner as in the above (E25).

(E27) The compound having a 1,2-dihydroxyalkyl group as a substituent on A can be prepared by treating a compound having an alkyl group substituted by mono- or di-alkyldioxolanyl group as a substituent on A with an acid in a suitable solvent.

A strongly acidic resin can also be preferably used as the acid, in addition to those previously described.

(E28) The compound having an alkyl group substituted by a hydroxy group and an optionally substituted alkoxy group as substituents on A can be prepared by reacting a compound having an oxiranylalkyl group as a substituent on A with an alkaline metal salt of the corresponding alcohol in a suitable solvent.

The alkaline metal salt of alcohol includes a lithium salt, a sodium salt, a potassium salt, and the like.

(E29) The compound having an alkyl group substituted by a hydroxy group and an amino group, or an alkyl group substituted by a hydroxy group and an optionally substituted mono- or di-alkylamino group as substituents on A can be prepared by reacting a compound having an oxiranylalkyl group as a substituent on A with ammonia or a corresponding mono- or di-alkylamines in a suitable solvent.

(E30) The compound having a hydroxycarbamimidoyl group as a substituent on A can be prepared by reacting a compound having a cyano group as a substituent on A with hydroxylamine or a salt thereof in a suitable solvent. Any solvent which does not disturb the reaction can be used, and as such, the solvent described in the above (EA) can be preferably used.

(E31) The compound having an oxodihydrooxadiazolyl group as a substituent on A can be prepared by reacting a compound having a hydroxycarbamimidoyl group as a substituent on A with a carbonylating agent in a suitable solvent in the presence or absence of a base.

The same carbonylating agent as that described in the above (E10) can be used.

(E32) The compound having a sulfo group as a substituent on A can be prepared by hydrolyzing a compound having an alkoxycarbonylalkylsulfonyl group as a substituent on A.

The hydrolysis can be carried out in the same manner as in the above (E20).

(E33) The compound having a sulfamoyl group as a substituent on A can be prepared by condensing a compound having a sulfo group as a substituent on A with a desirable amine.

The condensation can be carried out by treating a compound having a sulfo group as a substituent on A with a halogenating agent in a suitable solvent, followed by reacting the resulting compound with a desirable amine in the presence or absence of a base.

A conventional halogenating agent including thionyl halide, phosphorus oxyhalide, or the like can be used.

(E34) The compound having a hydroxyalkyl group as a substituent on A can be prepared by reducing a compound having a carboxyalkyl group as a substituent on A, or by converting the carboxyl group into an acid anhydride or an ester and then reducing the resulting compound.

A process for conversion into an acid anhydride can be carried out by reacting a starting compound with a halogenated alkyl formate in a suitable solvent in the presence of a base.

A process for conversion into an ester can be carried out by reacting a starting compound with an alcohol in the presence of a condensing agent in a suitable solvent. This process can be carried out in the same manner as in (E33) except that a desirable alcohol is used in place of amine.

The reduction can be carried out by treating the resulting compound with a reducing agent in a suitable solvent.

Boron hydrides (e.g. sodium borohydride), aluminum hydrides (lithium aluminum hydride, diisobutylaluminum hydride, and the like) can be preferably used as the reducing agent.

(E35) The compound having an aromatic group substituted by a cyano group as a substituent on $R^1$, optionally having one to three heteroatoms independently selected from oxygen atom, sulfur atom and nitrogen atom (hereinafter, referred to as "an aromatic group"), can also be prepared by cyanating a compound having an aromatic group substituted by a halogen atom as a substituent on $R^1$.

The cyanation can be carried out in the same manner as in the above (EE).

(E36) The compound wherein A is a hydrogen atom can be prepared by acid-treatment or reduction of a compound wherein A is a tert-butoxycarbonyl group or a benzyloxycarbonyl group.

The acid-treatment can be carried out in the same manner as in the above (E27) and the reduction can be carried out in the same manner as in the above (E23).

(E37) The compound wherein A is an optionally substituted alkoxycarbonyl group, or an optionally substituted carbamoyl group can be prepared by reacting a compound wherein A is a hydrogen atom with a carbonylating agent, or a desirable alcohol or a desirable amine in a suitable solvent.

The reaction can be carried out in the same manner as in the above (E10).

(E38) The compound having an amino group as a substituent on A can be prepared by undergoing a Curtius rearrangement reaction of a compound having a carboxyl group as a substituent on A.

Curtius rearrangement reaction can be carried out using a conventional azidating agent (e.g., diphenylphosphorylazide, and the like) in a suitable solvent in the presence of a base.

The reaction may also be carried out by adding alcohols to provide a compound having an optionally substituted alkoxycarbonylamino group as a substituent on A, followed by removing the alkoxycarbonyl group.

The removal of the alkoxycarbonyl group can be carried out in a conventional manner such as an acid-treatment or a reduction depending on the type of alkoxycarbonyl group to be removed. The acid-treatment can be carried out in the same manner as in the above (E27) and the reduction can be carried out in the same manner as in the above (E23).

(E39) The compound having a hydroxy group as a substituent on A can be prepared by catalytically reducing a compound having a benzyloxy group as a substituent on A. The reduction can be carried out in the same manner as in the above (E23).

(E40) The compound having an oxo group as a substituent on A can be prepared by oxidizing a compound having a hydroxy group as a substituent on A.

The oxidation can be carried out by using an oxidizing agent in a suitable solvent.

A conventional oxidizing agent can be used as the oxidizing agent, such as chromate-pyridine complex, pyridinium chlorochromate, pyridinium dichromate, Dess-Martin reagent (1,1,1-tris(acetoxy)-1,1-dihydro-1,2-benziodoxol-3-(1H)-one), dimethyl sulfoxide, and the like.

(E41) The compound containing an optionally substituted alkoxy group as a substituent on A can be prepared by alkylating a compound containing an oxo group or a hydroxy group as a substituent on A.

The alkylation can be carried out by using a corresponding compound in the same manner as in the above (EA).

(E41') The compound containing an optionally substituted heterocyclyloxy group or an optionally substituted aryloxy group as a substituent on A can be prepared by coupling a compound containing a hydroxy group as a substituent on A with a corresponding aryl compound or a heterocyclic compounds which have a leaving group.

The coupling can be carried out in the same manner as in the above (EC).

The leaving group have the same meaning as defined above (EH).

(E42) The compound having an optionally substituted alkanoylamino group as a substituent on A can be prepared by condensing a compound having an amino group as a substituent on A with a corresponding carboxylic acid or a reactive derivative thereof.

The condensation with the corresponding carboxylic acid can be preferably carried out in a suitable solvent in the presence of a condensing agent. The reaction can be carried out in the same manner as in the above (E13).

Additionally, the condensation with the reactive derivative of the corresponding carboxylic acid can be carried out in a suitable solvent or solvent-free in the presence or absence of a base.

The reactive derivative includes an acid halide, an acid anhydride, an activated ester, an activated amide, and the like.

(E43) The compound having a group of the formula:

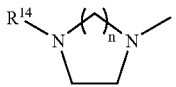

wherein $R^{14}$ is an alkanoyl group optionally substituted by a hydroxy group or an alkoxy group, and n has the same meaning as defined above, as a substituent on A can be prepared by condensing a compound of a group of the formula:

wherein the symbol has the same meaning as defined above, as a substituent on A with a corresponding carboxylic acid or a reactive derivative thereof.

The reaction can be carried out in the same manner as in the above (E42).

(E44) The compound having a maleimide group as a substituent on A can be prepared by reacting a compound having an amino group as a substituent on A with a maleic anhydride. The reaction can be carried out in a suitable solvent.

(E45) The compound having an alkyl group substituted by a pyridyl group and a hydroxy group as substituents on A can be prepared by reacting a compound having an alkyl group substituted by a pyridyl group of which nitrogen atom is oxidized as a substituent on A with a trifluoroacetic anhydride. The reaction can be carried out in a suitable solvent.

(E46) The compound having a halogen atom as a substituent on A can be prepared by treating a compound having a hydroxy group as a substituent on A with a halogenating agent.

As the halogenating agent, a conventional halogenating agent including thionyl chloride, phosphorus oxychloride, as well as carbon tetrahalide (e.g., carbon tetrachloride, carbon tetrabromide, and the like) and phosphines (e.g., triphenylphosphine, tritolylphosphine, triethylphosphine, and the like) can be preferably used.

(E46') The compound having a halogen atom as a substituent on A can be prepared by treating a compound with a halogenating agent. As the halogenating agent, a conventional halogenating agent such as bromine, N-bromosuccinimide, and the like can be preferably used.

(E47) The compound having a cyanoalkyl group as a substituent on A can be prepared by reducing a compound having a cyanoalkenyl group as a substituent on A.

The reduction can be carried out by treating a starting compound with a reducing agent or by catalytically reducing in a suitable solvent.

Any reducing agent can be used subject that it reduces only a double bond without affecting a cyano group. For example, sodium bis(2-methoxyethoxy)aluminum hydride in the presence of a copper bromide can be preferably used.

The catalytic reduction can be carried out in the same manner as in the above (E23).

(E48) The compound (1) having a hydroxyalkyl group as a substituent on A can be prepared by reducing a compound having a formyl group as a substituent on A.

The reduction can be carried out by treating a starting compound with a reducing agent in a suitable solvent.

The reaction can be carried out in the same manner as in the process for reducing in the above (E34).

(E49) The compound wherein a substituent on B is a hydroxy group can be prepared by demethylating a compound wherein the substituent on B is a methoxy group.

The demethylation can be carried out by treating a starting compound with a demethylating agent in a suitable solvent.

A conventional reagent including trimethylsilyl iodide, hydrogen bromide/acetic acid, boron tribromide, concentrated sulfuric acid, and the like can be used as the demethylating agent.

(E50) The compound wherein a substituent on B is an optionally substituted alkoxy group can be prepared by alkylating a compound wherein the substituent on B is a hydroxy group.

The alkylation can be carried out in the same manner as in the above (EA).

(E51) The compound wherein a substituent on B is an optionally substituted alkylsulfonyloxy group can be prepared by alkylsulfonylating a compound wherein the substituent on B is a hydroxy group.

The alkylsulfonylation can be carried out by reacting a corresponding alkylsulfonyl halide or a corresponding alkylsulfonic anhydride in a suitable solvent in the presence or absence of a base.

(E52) The compound wherein a substituent on B is a cyano group can be prepared by cyanating a compound wherein the substituent on B is an optionally substituted alkylsulfonyloxy group.

The cyanation can be carried out in the same manner as in the above (EE).

(E53) The compound wherein a substituent on B is an aminoalkyl group can be prepared by reducing a compound wherein the substituent on B is a cyano group.

The reduction can be carried out in the same manner as in the above (E6).

(E54) The compound wherein a substituent on B is an alkyl group can be prepared by alkylating a compound wherein the substituent on B is an optionally substituted alkylsulfonyloxy group.

The alkylation can be carried out by reacting alkyl aluminums in the presence of a palladium catalyst, a silver catalyst and a copper catalyst in a suitable solvent.

Tetrakis(triphenylphosphine)palladium as the palladium catalyst, silver carbonate as the silver catalyst, copper (I) chloride as the copper catalyst can be preferably used.

(E54') The compound wherein a substituent on B is an optionally substituted alkyl group can be prepared by catalytically reducing a compound wherein a substituent on B is an optionally substituted alkenyl group. The reaction can be carried out in the same manner as in the above (E6).

(E55) The compound having an imidazolinyl group or an oxazolinyl group as a substituent on A can be prepared by (i) reacting a compound containing a cyano group as a substituent on A with a desirable alcohol in the presence of an acid in a suitable solvent or solvent-free to provide a compound containing an alkoxycarbonimidoyl group as a substituent on A, and (ii) reacting the compound containing an alkoxycarbonimidoyl group as a substituent on A with 2-aminoethanol or ethylene diamine in a suitable solvent or solvent-free.

(E56) The compound having a carboxyl group as a substituent on A can be prepared by (i) oxidizing a compound containing a hydroxyalkyl group as a substituent on A in the same manner as in the above (E40) to provide a compound containing an oxo group as a substituent on A, and (ii) oxidizing the compound containing an oxo group as a substituent on A.

The oxidization for the second process can be carried out by using an oxidizing agent in a suitable solvent. Sodium chlorite, Silver(I) oxide, Sodium periodate and the like can be preferably used as the oxidizing agent.

(E57) The compound having a carboxyl group as a substituent on A can be directly prepared by oxidizing a compound containing a hydroxyalkyl group as a substituent on A.

The oxidization can be carried out by using Jones reagent, potassium permanganate, and the like as the oxidizing agent.

(E58) The compound wherein A is hydrogen atom can be prepared by treating a compound wherein A is ethoxycarbonyl group with a silyl halide or a base. Trimethylsilyl iodide can be preferably used as the silyl halide. Sodium hydroxide can be preferably used as the base.

In each process for preparing a compound (1) described above, when protection of a functional group contained in any compound is needed, the protection can be carried out in a conventional manner as appropriate. General statement related to protecting groups and their use is provided by Greene, Protective Groups in Organic Synthesis, John Wiley and Sons, New York, 1991.

When an amino group is protected by a benzyloxycarbonyl group, the protecting group can be removed by a catalytic reduction under hydrogen atmosphere in a suitable solvent.

When a hydroxy group is protected by a benzyl group, the protecting group can also be removed by a catalytic reduction in a similar manner as above.

When an amino group is protected by a tert-butoxycarbonyl group, the protecting group can be removed by treating a starting compound with an acid (e.g., hydrochloric acid, trifluoroacetic acid, toluenesulfonic acid, and the like) in a suitable solvent.

When a hydroxy group is protected by a tetrahydropyranyl group, the protecting group can also be removed by treating a starting compound with an acid in a similar manner as above.

Other substituents of the present compound (1) can also be converted in the same manner as in the reactions (E1) to (E58) for conversion of the above groups.

[Preparation of a Compound (6')]

The compound (6') can be prepared according to the following method (a) or (b).

(a) The compound (6') can be prepared by reacting the compound of a general formula (10):

(10)

wherein $X^{A4}$ is a leaving group and the other symbols have the same meanings as defined above, with the compound of a general formula (11):

$H—R^2$ (11)

wherein the symbol has the same meaning defined above, in the same manner as in the above process I-1 or process I'-1.

(b) The compound (6') can be prepared by reacting the compound of a general formula (12):

(12)

wherein P is a protecting group for a carboxyl group and the other symbols have the same meanings as defined above, with the compound (11) in the same manner as in the above process I-1 or process I'-1, followed by reducing the resulting compound to provide the compound (6") and further oxidizing the resulting compound.

The reduction and oxidation in the above methods can be carried out by the conventional method.

[Preparation of a Compound (2)]

The compound (2) can be prepared by oximating the compound (6') to provide the compound of a general formula (13):

(13)

wherein the symbols have the same meanings as defined above, followed by reducing the resulting compound.

The oximation can be carried out by the conventional oximation methods, for example, by treating the compound (6') with a salt of hydroxylamine in the presence of an acid or a base such as alkaline metal hydroxide, sodium acetate or pyridine in an alcohol, acetic acid or pyridine. Also any acidic material can be used as the agent for preparing a salt of hydroxylamine, for example, a mineral acid (e.g. sulfuric acid, phosphoric acid, hydrogen bromide and hydrogen iodide), and organic acid (e.g. acetic acid, oxalic acid, trichloroacetic acid, methanesulfonic acid, p-toluenesulfonic acid, 1,5-naphthalenedisulfonic acid).

The subsequent reduction reaction can be carried out in a conventional manner.

The compound (2) can also be prepared from the compound (6″) using the method of Gabriel synthesis, described in detail in Mitsunobu, O. Comp. Org. Syn. 1991, 6, 79-85.

[Preparation of a Compound (6″″)]

The compound (6″″) can be prepared from the compound of a general formula (14):

(14)

wherein $X^{A5}$ is a leaving group and the other symbols have the same meanings as defined above, by a conventional insertion reaction of carbon monoxide with a transition metal catalyst.

The reaction can be carried out in an aprotic solvent such as tetrahydrofuran or DMF, and the like. Preferred transition metal includes, for example, a salt form of palladium such as palladium (II)-acetate, and the like or a palladium (0) compound such as tetrakis(triphenylphosphine)palladium, and the like. This kind of an insertion reaction of carbon monoxide can be carried out by the method described in detail in J. Org. Chem. 1992, 57, 5979 or "Organometallic compound-Synthesis and Application-(Tokyo Kagaku Dozin Co., Ltd.), Metal-catalyzed Cross-coupling Reaction (WILLY-VCH), Handbook of Palladium-Catalyzed Organic Reactions (Academic Press)", and the like.

The compound (1-a) wherein $A^1$ is tetrazolyl group and $A^2$ is a hydrogen atom can be prepared by cyanidating the above compound (8') to provide the compound of a general formula (8″″):

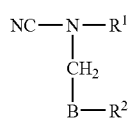

(8″″)

wherein the symbols have the same meanings as defined above, followed by reacting with an alkaline metal azide.

The cyanidation can be carried out by reacting a starting compound with cyanogen halide in the presence of a base in a suitable solvent.

The cyanogen halide is preferably cyanogen bromide.

The conventional base can be preferably used as a base, such as alkaline metal carbonate (e.g. potassium carbonate) or an alkaline metal bicarbonate (e.g. sodium bicarbonate).

Any solvent which dose not disturb the reaction can be used as a solvent and the solvent illustrated in the above method I can be preferably used.

The conversion of a cyano group into a tetrazolyl group can be achieved by reacting the compound having a cyano group with an alkaline metal azide in the presence of an acid in a suitable solvent.

The alkaline metal azide includes sodium azide and lithium azide, and the like.

The ammonium salt of halogenated hydrogen such as ammonium chloride can be preferably used as an acid.

In addition, for performing the above methods, there can be referred to PCT International Publication WO04/020393 pamphlet, WO05/100298 pamphlet and JP. 2003-221376 A.

The methods for preparation of the compound (1) are applicable to preparation of the corresponding compounds of formula (I-A), (I-B) and (1-1).

Many of starting materials and reagents for preparation of the aforementioned compound of the formula I are either commercially available or disclosed in literatures, or can be readily prepared by a method that is disclosed in literatures or used generally in the organic synthesis.

EXPERIMENT

The inhibitory activity of the compounds (1) of the present invention against CETP was tested in this experiment.

Preparation of Acceptor Microemulsion

A solution of 1-Palmitoyl-2-oleoyl-sn-glycero-3-phosphocholine (3.5 mg), cholesteryl oleate (3 mg) and triolein (0.7 mg) in chloroform was mixed and lipid was air-dried under nitrogen gas to remove solvent. 1,4-Dioxane (0.25 ml) was then added and the mixture was stirred for dissolution. The resultant lipid solution (0.2 ml) was slowly injected under the surface of Tris-saline-EDTA(TSE) buffer solution [10 mM Tris/HCl (pH 7.4), 0.15M NaCl, 2 mM EDTA] (10 ml) with Hamilton syringe, while sonicating in ice-bath. After 1-hour-sonication in ice-bath, the solution was stored at 4° C.

Preparation of Donor Microemulsion

A solution of egg PC (phosphatidylcholine) (0.33 mg) and BODIPY-CE™ (Invitrogen Corporation) (0.62 mg) in chloroform was mixed. After removing solvent by air-drying lipid under nitrogen gas, TSE buffer solution (3 ml) was added and the solution was sonicated in ice-bath. This solution was filtered to sterilize through 0.22 μm filter and stored at 4° C.

Inhibitory Activity Against CETP In Vitro

A test solution was prepared using dimethyl sulfoxide as a solvent. Plasma from a healthy volunteer was diluted to 0.64% with TSE buffer, and to the resultant plasma solution (187 μl) was added a test solution (3 μl) or the solvent alone followed by incubation at 37° C. for 24 hours. After addition of TSE buffer solution (10 μl) containing 5% donor microemulsion and 5% acceptor microemulsion, the mixture was incubated at 37° C. for 3 hours. Before and after the incubation, the fluorescence intensity was measured at Ex.550 nm/Em.600 nm. CETP activity was defined as the difference between the measurements obtained before incubation and after incubation. The decreasing rate of the difference in the sample was defined as the inhibition rate of CETP activity.

EXAMPLES

The present invention is illustrated in more detail by Examples and Reference Examples, but the present invention should not be construed to be limited thereto. Meanwhile, in the following Tables the symbol "Me" means methyl group and the symbol "TFA" means trifluoroacetic acid.

Example 1

(1) 2-Fluoro-5-trifluoromethyl-benzaldehyde (2.7 g) and ethyl-(2-methoxy-ethyl)-amine (2.18 g) are dissolved in toluene (20 ml), and thereto is added potassium carbonate (5.83 g) and the mixture is stirred at 120° C. overnight. The reaction solution is cooled to room temperature, and thereto are added ethyl acetate and a saturated brine and the mixture is separated, and the organic layer is washed with a saturated brine, and the mixture is dried over magnesium sulfate and concentrated under reduced pressure. The residue is purified by silica gel column chromatography (hexane:ethyl acetate=19:1→4:

1) to give 2-[ethyl-(2-methoxy-ethyl)-amino]-5-trifluoromethyl-benzaldehyde (3.75 g). MS (m/z): 276 [M+H]$^+$ (2) 2-[Ethyl-(2-methoxy-ethyl)-amino]-5-trifluoromethyl-benzaldehyde (3.7 g), 3,5-bis-trifluoromethyl-benzylamine (4.23 g), acetic acid (1.15 ml) are dissolved in 1,2-dichloroethane (30 ml), and thereto is added triacetoxy sodium borohydride (5.68 g) at room temperature and the mixture is stirred at room temperature overnight. To the reaction solution are added methylene chloride and a saturated aqueous sodium bicarbonate solution, and the mixture is separated, and the organic layer is washed with a saturated brine and the mixture is dried over magnesium sulfate and concentrated under reduced pressure. The resulting residue is purified by silica gel column chromatography (hexane:ethyl acetate=19:1→4:1) to give {2-[(3,5-bis-trifluoromethyl-benzylamino)-methyl]-4-trifluoromethyl-phenyl}-ethyl-(2-methoxy-ethyl)-amine (3.38 g). MS (m/z): 503 [M+H]$^+$.

(3) {2-[(3,5-Bis-trifluoromethyl-benzylamino)-methyl]-4-trifluoromethyl-phenyl}-ethyl-(2-methoxy-ethyl)-amine (3.37 g), 5-bromo-2-chloropyrimidine (2.6 g) and N-ethyldiisopropylamine (3.51 ml) are dissolved in toluene (50 ml) and the mixture is stirred at 120° C. overnight. The reaction solution is cooled to room temperature, and thereto are added ethyl acetate and water and the mixture is separated, and the organic layer is washed with a saturated brine, and the mixture is dried over magnesium sulfate and is concentrated under reduced pressure. The resulting residue is purified by silica gel column chromatography (hexane:ethyl acetate=1:0→19:1) to give (3,5-bis-trifluoromethyl-benzyl)-(5-bromopyrimidin-2-yl)-{2-[ethyl-(2-methoxy-ethyl)-amino]-5-trifluoromethyl-benzyl}-amine (4.06 g). MS (m/z): 659/661 [M+H]$^+$ (4) (3,5-Bis-trifluoromethyl-benzyl)-(5-bromo-pyrimidin-2-yl)-{2-[ethyl-(2-methoxy-ethyl)-amino]-5-trifluoromethyl-benzyl}-amine (350 mg) is dissolved in toluene (5 ml) and tris(dibenzylideneacetone)dipalladium (49 mg), sodium tert-butoxide (77 mg), 2-(di-tert-butylphosphino)biphenyl (63 mg) and ethyl piperidine-4-carboxylate (119 µl) and the mixture is stirred under nitrogen flow at room temperature overnight. To the reaction solution is added a saturated brine, and the mixture is extracted with ethyl acetate. The organic layer is washed with a saturated brine, dried over magnesium sulfate and concentrated under reduced pressure. The resulting residue is purified by silica gel column chromatography (hexane ethyl acetate=19:1→3:1) to give ethyl 1-[2-((3,5-bis-trifluoromethyl-benzyl)-{2-[ethyl-(2-methoxy-ethyl)-amino]-5-trifluoromethyl-benzyl}amino)-pyrimidin-5-yl]-piperidine-4-carboxylate (212 mg). MS (m/z): 7:36 [M+H]$^+$ (5) Ethyl 1-[2-((3,5-bis-trifluoromethyl-benzyl)-{2-[ethyl-(2-methoxy-ethyl)-amino]-5-trifluoromethyl-benzyl}-amino)-pyrimidin-5-yl]-piperidine-4-carboxylate (205 mg) is dissolved in ethanol (2 ml) and thereto is added 2N-aqueous sodium hydroxide solution (418 µl) and the mixture is stirred at room temperature overnight. Thereto are added ethyl acetate and a saturated aqueous citric acid solution, and the mixture is separated and the organic layer is washed with a saturated brine, dried over magnesium sulfate and concentrated under reduced pressure. The resulting residue is purified by silica gel column chromatography (hexane:ethyl acetate=1:1→0:1) to give 1-[2-((3,5-bis-trifluoromethyl-benzyl)-{2-[ethyl-(2-methoxy-ethyl)-amino]-5-trifluoromethyl-benzyl}-amino)-pyrimidin-5-yl]-piperidine-4-carboxylic acid (155 mg). The resulting carboxylic acid is dissolved in ethanol (1 ml) and thereto is added 2N-aqueous sodium hydroxide solution (110 µl) and the reaction solution is concentrated under reduced pressure to give 1-[2-((3,5-bis-trifluoromethyl-benzyl)-{2-[ethyl-(2-methoxy-ethyl)-amino]-5-trifluoromethyl-benzyl}-amino)-pyrimidin-5-yl]-piperidine-4-carboxylic acid sodium salt (159 mg). MS (m/z): 706 [M−Na]$^−$ Example 2

(1) 2-Fluoro-5-trifluoromethyl-benzaldehyde (5.0 g) and butyl-ethyl-amine (3.95 g) are dissolved in toluene (50 ml) and thereto is added potassium carbonate (10.78 g) and the mixture is heated under reflux overnight. The reaction solution is cooled to room temperature, and thereto are added water and diethyl ether, and the mixture is separated, and the organic layer is washed with a saturated brine, dried over magnesium sulfate, and concentrated under reduced pressure. The resulting residue is purified by silica gel column chromatography (hexane:ethyl acetate=19:1→4:1) to give 2-(butyl-ethyl-amino)-5-trifluoromethyl-benzaldehyde (6.54 g). MS (m/z): 274 [M+H]$^+$ (2) 2-(Butyl-ethyl-amino)-5-trifluoromethyl-benzaldehyde (6.5 g), 3,5-bis-trifluoromethyl-benzylamine (7.52 g), acetic acid (2.04 ml) are dissolved in 1,2-dichloroethane (50 ml), and thereto is added triacetoxy sodium borohydride (10.1 g) at room temperature and the mixture is stirred for 2 hours. To the reaction solution are added 1N-aqueous sodium hydroxide solution and methylene chloride, and the mixture is separated, and the organic layer is washed with a saturated brine and dried over magnesium sulfate, and concentrated under reduced pressure. The resulting residue is purified by silica gel column chromatography (hexane:ethyl acetate=19:1→4:1) to give {2-[(3,5-bis-trifluoromethyl-benzylamino)-methyl]-4-trifluoromethyl-phenyl}-butyl-ethyl-amine (10.48 g). MS (m/z): 501 [M+H]$^+$ (3) {2-[(3,5-Bis-trifluoromethyl-benzylamino)-methyl]-4-trifluoromethyl-phenyl}-butyl-ethyl-amine (4.6 g), 5-bromo-2-chloropyrimidine (3.56 g) and N-ethyldiisopropylethylamine (4.8 ml) are dissolved in toluene (100 ml) and the mixture is heated under reflux overnight. The reaction solution is cooled to room temperature, and thereto are added ethyl acetate and water, and the mixture is separated and the organic layer is washed with a saturated brine, dried over magnesium sulfate and concentrated under reduced pressure. The resulting residue is purified by silica gel column chromatography (hexane:ethyl acetate=19:1→9:1) to give (3,5-bis-trifluoromethyl-benzyl)-(5-bromo-pyrimidin-2-yl)-[2-(butyl-ethyl-amino)-5-trifluoromethyl-benzyl]-amine (5.24 g). MS (m/z): 657/659 [M+H]$^+$ (4) (3,5-Bis-trifluoromethyl-benzyl)-(5-bromopyrimidin-2-yl)-[2-(butyl-ethyl-amino)-5-trifluoromethyl-benzyl]-amine (3.0 g), [1,1'-bis(diphenylphosphino)ferrocene]dichloropalladium methylene chloride complex (112 mg), potassium acetate (1.34 g) and bis(pinacolato)diboron (1.74 g) are dissolved in dimethylsulfoxide (20 ml) and the mixture is heated to 80° C. under nitrogen atmosphere and stirred for 1 hour. The reaction solution is cooled to room temperature, and thereto are added water and ethyl acetate, and the mixture is separated, and the organic layer is washed with a saturated brine, dried over magnesium sulfate and concentrated under reduced pressure. The resulting residue is dissolved in tetrahydrofuran (70 ml) and thereto is added dropwise a 30% aqueous hydrogen peroxide solution (15 ml) under ice-cooling. One hour thereafter, thereto is added a saturated aqueous sodium thiosulfate solution under ice-cooling to consume the excess hydrogen peroxide, and thereto are added water and ethyl acetate, and the mixture is separated, and the organic layer is washed with a saturated brine, dried over magnesium sulfate and concentrated under reduced pressure. The resulting residue is purified by silica gel column chromatography (hexane:ethyl acetate=19:1→3:1) to give 2-{(3,5-bis-trifluoromethyl-benzyl)-[2-(butyl-ethyl-amino)-5-trifluoromethyl-benzyl]-amino}-pyrimidin-5-ol (263 mg). MS (m/z): 595 [M+H]$^+$ (5) 2-{(3,5-Bis-trifluoromethyl-benzyl)-[2-(butyl-ethyl-amino)-5-trifluoromethyl-benzyl]-amino}-pyrimidin-5-ol (150 mg) and ethyl 4-bromobutyrate (44 μl) are dissolved in N,N-dimethylformamide (3 ml) and thereto is added potassium carbonate (42 mg) and the mixture is stirred at room temperature overnight. Thereto are added ethyl acetate and a saturated brine, and the mixture is separated, and the organic layer is washed with a saturated brine, dried over magnesium sulfate and concentrated under reduced pressure. The resulting residue is purified by silica gel column chromatography (hexane:ethyl acetate=19:1→3:1) to give ethyl 4-(2-{(3,5-bis-trifluoromethyl-benzyl)-[2-(butyl-ethyl-amino)-5-trifluoromethyl-benzyl]-amino}-pyrimidin-5-yloxy)-butyrate (117 mg). MS (m/z): 709 [M+H]$^+$ (6) Ethyl 4-(2-{(3,5-bis-trifluoromethyl-benzyl)-[2-(butyl-ethyl-amino)-5-trifluoromethyl-benzyl]-amino}-pyrimidin-5-yloxy)-butyrate (110 mg) is dissolved in ethanol (2 ml) and thereto is added a 2N-aqueous sodium hydroxide solution (233 μl) and the mixture is stirred at room temperature overnight. Thereto are added ethyl acetate and a saturated aqueous citric acid solution, and the mixture is separated and the organic layer is washed with a saturated brine, dried over magnesium sulfate and concentrated under reduced pressure. The resulting residue is purified by silica gel column chromatography (hexane:ethyl acetate=9:1 to 7:3) to give 4-(2-{(3,5-bis-trifluoromethyl-benzyl)-[2-(butyl-ethyl-amino)-5-trifluoromethyl-benzyl]-amino}-pyrimidin-5-yloxy)-butyric acid (69 mg). The resulting carboxylic acid is dissolved in ethanol (0.2 mL) and thereto is added 2N-aqueous sodium hydroxide solution (50 μl) and the reaction solution is concentrated under reduced pressure to give 4-(2-{(3,5-bis-trifluoromethyl-benzyl)-[2-(butyl-ethyl-amino)-5-trifluoromethyl-benzyl]-amino}-pyrimidin-5-yloxy)-butyric acid sodium salt (70 mg). MS (m/z): 679 [M−Na]$^-$ Example 3

(1) 2-{(3,5-Bis-trifluoromethyl-benzyl)-[2-(cyclohexylmethyl-ethyl-amino)-5-trifluoromethyl-benzyl]-amino}-pyrimidin-5-ol (250 mg) and 3-bromo-1-propanol (43 μl) are dissolved in N,N-dimethylformamide (1 ml) and thereto is added potassium carbonate (65 mg) and the mixture is stirred at room temperature overnight. Thereto are added ethyl acetate and a saturated brine, and the mixture is separated and the organic layer is washed with a saturated brine, dried over magnesium sulfate and concentrated under reduced pressure. The resulting residue is purified by silica gel column chromatography (hexane:ethyl acetate=9:1→3:1) to give 3-(2-{(3,5-bis-trifluoromethyl-benzyl)-[2-(cyclohexylmethyl-ethyl-amino)-5-trifluoromethyl-benzyl]-amino}-pyrimidin-5-yloxy)-propan-1-ol (150 g). MS (m/z): 693 [M+H]$^+$ (2) 3-(2-{(3,5-Bis-trifluoromethyl-benzyl)-[2-(cyclohexylmethyl-ethyl-amino)-5-trifluoromethyl-benzyl]-amino}-pyrimidin-5-yloxy)-propan-1-ol (140 mg) is dissolved in methylene chloride (2 ml), and thereto is added 1,1,1-tris(acetyloxy)-1,1-dihydro-1,2-benziodoxol-3-(1H)-one (188 mg) at room temperature and the mixture is stirred at room temperature overnight. Thereto are added ethyl acetate and a saturated brine, and the mixture is separated and the organic layer is washed with a saturated brine, dried over magnesium sulfate and concentrated under reduced pressure. The resulting residue is dissolved in the mixed solvent of tert-butanol (4 ml) and water (1 ml) and thereto are added 2-methyl-2-butene (128 μl), sodium dihydrogenphosphate dihydrate (44 mg) and sodium chlorite (73 mg) and the mixture is stirred at room temperature for 30 minutes. Thereto are added ethyl acetate and a 1N-hydrochloric acid, and the mixture is separated, and the organic layer is washed with a saturated brine, dried over magnesium sulfate, and concentrated under reduced pressure. The resulting residue is purified by silica gel column chromatography (hexane:ethyl acetate=9:1→2:3) to give 3-(2-{(3,5-bis-trifluoromethyl-benzyl)-[2-(cyclohexylmethyl-ethyl-amino)-5-trifluoromethyl-benzyl]-amino}-pyrimidin-5-yloxy)-propionic acid (60 mg). The resulting carboxylic acid is dissolved in ethanol (0.5 ml), and thereto is added 1N-aqueous sodium hydroxide solution (85 μl) and the reaction solution is concentrated under reduced pressure to give 3-(2-{(3,5-bis-trifluoromethyl-benzyl)-[2-(cyclohexylmethyl-ethyl-amino)-5-trifluoromethyl-benzyl]-amino}-pyrimidin-5-yloxy)-propionic acid sodium salt (60 mg). MS (m/z): 705 [M−Na]$^-$.

Example 4

(1) Ethyl 4-{2-[[2-(benzyl-ethyl-amino)-5-trifluoromethyl-benzyl]-(3,5-bis-trifluoromethyl-benzyl)-amino]-pyrimidin-5-yloxy}-butyrate (4.07 g) is dissolved in ethanol (60 ml), and thereto is added 10% palladium-carbon (500 mg) and the mixture is stirred under hydrogen atmosphere at room temperature for 30 minutes. The catalyst is removed by filtration, and the filtrate is concentrated under reduced pressure. The resulting residue is purified by NH-silica gel column chromatography (hexane:ethyl acetate=19:1→17:3) to give ethyl 4-{2-[(3,5-bis-trifluoromethyl-benzyl)-(2-ethylamino-5-trifluoromethyl-benzyl)-amino]-pyrimidin-5-yloxy}-butyrate (3.1 g). MS (m/z): 653 [M+H]$^+$ (2) Ethyl 4-{2-[(3,5-bis-trifluoromethyl-benzyl)-(2-ethylamino-5-trifluoromethyl-benzyl)-amino]-pyrimidin-5-yloxy}-butyrate (200 mg) and pyridine (371 μl) are dissolved in methylene chloride (5 ml), and thereto is added ethyl chlorocarbonate (293 μl) under ice-cooling. The reaction solution is stirred at room temperature overnight and the organic solvent is concentrated under reduced pressure. To the residue are added ethyl acetate and an aqueous citric acid solution, and the mixture is separated. The organic layer is washed with a saturated brine, dried over magnesium sulfate, and concentrated under reduced pressure. The resulting residue is purified by silica gel column chromatography (hexane:ethyl acetate=19:1→4:1) to give ethyl 4-(2-{(3,5-bis-trifluoromethyl-benzyl)-[2-(ethoxycarbonyl-ethyl-amino)-5-trifluoromethyl-benzyl]-amino}-pyrimidin-5-yloxy)-butyrate (176 mg). MS (m/z): 725 [M+H]$^+$ (3) Ethyl 4-(2-{(3,5-bis-trifluoromethyl-benzyl)-[2-(ethoxycarbonyl-ethyl-amino)-5-trifluoromethyl-benzyl]-amino}-pyrimidin-5-yloxy)-butyrate (170 mg) is dissolved in ethanol (2 ml), and thereto is added 2N-aqueous sodium hydroxide solution (352 μl) and the mixture is stirred at room temperature for 1.5 hours and concentrated under reduced pressure. To the residue are added ethyl acetate and a 1N-hydrochloric acid, and the mixture is separated, and the organic layer is washed with a saturated brine, dried over magnesium sulfate and concentrated under reduced pressure to give 4-(2-{(3,5-bis-trifluoromethyl-benzyl)-[2-(ethoxycarbonyl-ethyl-amino)-5-trifluoromethyl-benzyl]-amino}-pyrimidin-5-yloxy)-butyric acid (147 mg). The resulting carboxylic acid is dissolved in ethanol (1 ml) and thereto is added 2N-aqueous sodium hydroxide solution (106 μl) and the reaction solution is concentrated under reduced pressure to give 4-(2-{(3,5-bis-trifluoromethyl-benzyl)-[2-(ethoxycarbonyl-ethyl-amino)-

5-trifluoromethyl-benzyl]-amino}-pyrimidin-5-yloxy)-butyric acid sodium salt (151 mg). MS (m/z): 695 [M−Na]⁻

Example 5

(1) Ethyl 4-{2-[(3,5-bis-trifluoromethyl-benzyl)-(2-ethylamino-5-trifluoromethyl-benzyl)-amino]-pyrimidin-5-yloxy}-butyrate (100 mg) and pyridine (19 μl) are dissolved in methylene chloride (1 ml) and thereto is added butyryl chloride (19 μl) at room temperature. The reaction solution is stirred at room temperature for 30 minutes, and thereto are added methylene chloride and 1N-hydrochloric acid, and the mixture is separated. The organic layer is washed with a saturated brine, dried over magnesium sulfate and concentrated under reduced pressure. The resulting residue is purified by silica gel column chromatography (hexane:ethyl acetate=19:1→4:1) to give ethyl 4-(2-{(3,5-bis-trifluoromethyl-benzyl)-[2-(butyryl-ethyl-amino)-5-trifluoromethyl-benzyl]-amino}-pyrimidin-5-yloxy)-butyrate (84 mg). MS (m/z): 723 [M+H]⁺

(2) Ethyl 4-(2-{(3,5-bis-trifluoromethyl-benzyl)-[2-(butyryl-ethyl-amino)-5-trifluoromethyl-benzyl]-amino}-pyrimidin-5-yloxy)-butyrate (78 mg) is dissolved in ethanol (1 ml) and thereto is added a 2N-aqueous sodium hydroxide solution (162 μl) and the mixture is stirred at room temperature for 3 hours. Thereto are added ethyl acetate and a 1N-hydrochloric acid, and the mixture is separated, and the organic layer is washed with a saturated brine, dried over magnesium sulfate, and concentrated under reduced pressure to give 4-(2-{(3,5-bis-trifluoromethyl-benzyl)-[2-(butyryl-ethyl-amino)-5-trifluoromethyl-benzyl]-amino}-pyrimidin-5-yloxy)-butyric acid (66 mg). The resulting carboxylic acid is dissolved in ethanol (0.5 ml), and thereto is added 2N-aqueous sodium hydroxide solution (47 μl) and the reaction solution is concentrated under reduced pressure to give 4-(2-{(3,5-bis-trifluoromethyl-benzyl)-[2-(butyryl-ethyl-amino)-5-trifluoromethyl-benzyl]-amino}-pyrimidin-5-yloxy)-butyric acid sodium salt (68 mg). MS (m/z): 693 [M−Na]⁻

Example 6

(1) Ethyl 4-{2-[(3,5-bis-trifluoromethyl-benzyl)-(2-ethylamino-5-trifluoromethyl-benzyl)-amino]-pyrimidin-5-yloxy}-butyrate (200 mg) and triethylamine (51 μl) are dissolved in methylene chloride (1 ml), and thereto is added triphosgene (36 mg) in a small amount at room temperature. The reaction solution is stirred at room temperature for 10 minutes and concentrated under reduced pressure. The residue is dissolved in tetrahydrofuran (1 ml) and therero is added a 2M ethylamine in tetrahydrofuran (1 ml) and the mixture is stirred at room temperature for 30 minutes. To the reaction solution are added ethyl acetate and a 1N-hydrochloric acid, and the mixture is separated, and the organic layer is washed with a saturated brine, dried over magnesium sulfate, and concentrated under reduced pressure. The resulting residue is purified by silica gel column chromatography (hexane:ethyl acetate=9:1→1:1) to give ethyl 4-(2-{(3,5-bis-trifluoromethyl-benzyl)-[2-(1,3-diethylureido)-5-trifluoromethyl-benzyl]-amino}-pyrimidin-5-yloxy)-butyrate (181 mg). MS (m/z): 724 [M+H]⁺

(2) Ethyl 4-(2-{(3,5-bis-trifluoromethyl-benzyl)-[2-(1,3-diethylureido)-5-trifluoromethyl-benzyl]-amino}-pyrimidin-5-yloxy)-butyrate (165 mg) is dissolved in ethanol (3 ml) and thereto is added 2N-aqueous sodium hydroxide solution (342 μl) and the mixture is stirred at room temperature overnight. To the reaction solution are added ethyl acetate and a 1N-hydrochloric acid, and the mixture is separated, and the organic layer is washed with a saturated brine, dried over magnesium sulfate, and concentrated under reduced pressure. The resulting residue is purified by silica gel column chromatography (chloroform:methanol=1:0→17:3) to give 4-(2-{(3,5-bis-trifluoromethyl-benzyl)-[2-(1,3-diethylureido)-5-trifluoromethyl-benzyl]-amino}-pyrimidin-5-yloxy)-butyric acid (68 mg). MS (m/z): 696 [M+H]⁺

Example 7

(1) 2-Fluoro-5-trifluoromethyl-benzaldehyde (1.3 g) and cyclopropylmethyl-propyl-amine (1.15 g) are dissolved in toluene (13 ml), and thereto is added potassium carbonate (2.81 g) and the mixture is stirred at 120° C. overnight. The reaction solution is cooled to room temperature, and thereto are added ethyl acetate and water, and the mixture is separated, and the organic layer is washed with a saturated brine, dried over magnesium sulfate, and concentrated under reduced pressure. The resulting residue is purified by silica gel column chromatography (hexane:ethyl acetate=1:0→97:3) to give 2-(cyclopropylmethyl-propyl-amino)-5-trifluoromethyl-benzaldehyde (1.7 g). MS (m/z): 286 [M+H]⁺

(2) 2-(Cyclopropylmethyl-propyl-amino)-5-trifluoromethyl-benzaldehyde (1.69 g) is dissolved in ethanol (10 ml) and thereto is added sodium borohydride (224 mg) and the mixture is stirred for 15 minutes. To the reaction solution are added a saturated aqueous ammonium chloride solution and ethyl acetate, and the mixture is separated, and the organic layer is washed with a saturated brine, dried over magnesium sulfate, and concentrated under reduced pressure. The resulting residue is dissolved in methylene chloride (10 ml) and thereto is added thionyl chloride (492 μl) under ice-cooling, and the mixture is stirred for 10 minutes. To the reaction solution are added a saturated aqueous sodium bicarbonate solution and ethyl acetate, and the mixture is separated, and the organic layer is washed with a saturated brine, dried over magnesium sulfate and concentrated under reduced pressure. (3,5-bis-trifluoromethyl-benzyl)-(5-bromopyrimidin-2-yl)-amine (2.7 g) is dissolved in N,N-dimethylformamide (10 ml) and thereto is added sodium hydride (62%) (343 mg) at room temperature and the mixture is stirred for 30 minutes. Thereto are added dropwise a solution of a residue obtained above in N,N-dimethylformamide (10 ml) and the mixture is stirred at room temperature for 30 minutes. To the reaction solution are added ethyl acetate and water, and the mixture is separated and the organic layer is washed with a saturated brine, dried over magnesium sulfate, and concentrated under reduced pressure. The resulting residue is purified by silica gel column chromatography (hexane ethyl acetate=19:1→9:1) to give (3,5-bis-trifluoromethyl-benzyl)-(5-bromo-pyrimidin-2-yl)-[2-(cyclopropylmethyl-propyl-amino)-5-trifluoromethyl-benzyl]-amine (3.38 g). MS (m/z): 669/671 [M+H]⁺

(3) (3,5-Bis-trifluoromethyl-benzyl)-(5-bromo-pyrimidin-2-yl)-[2-(cyclopropylmethyl-propyl-amino)-5-trifluoromethyl-benzyl]-amine (3.35 g) [1,1'-bis(diphenylphosphino)ferrocene]dichloropalladium dichloromethane complex (817 mg), potassium acetate (1.47 g), bis(pinacolato)diboron (2.54 g) are dissolved in dimethylsulfoxide (20 ml) and the mixture is heated to 80° C. under nitrogen atmosphere and stirred for 1 hour. The reaction solution is cooled to room temperature and thereto are added water and ethyl acetate, and the insoluble materials is removed by filtration through Celite™ and the mixture is separated, and the organic layer is washed with a saturated brine, dried over magnesium sulfate, and concentrated under reduced pressure. The resulting residue is dissolved in tetrahydrofuran (20 ml), and thereto is added dropwise a 30% aqueous hydrogen peroxide solution (10 ml) under ice-cooling. One hour thereafter, thereto is added a saturated aqueous sodium thiosulfate solution under ice-cooling to consume the excess hydrogen peroxide, and thereto are added water and ethyl acetate, and the mixture is separated. The organic layer is washed with a saturated brine, dried over magnesium sulfate, and concentrated under reduced pressure. The resulting residue is purified by silica gel column chromatography (hexane:ethyl acetate=9:1→4:1) to give 2-{(3,5-bis-trifluoromethyl-benzyl)-[2-(cyclopropylmethyl-propyl-amino)-5-trifluoromethyl-benzyl]-amino}-pyrimidin-5-ol (1.8 g). MS (m/z): 607 [M+H]$^+$ (4) 2-{(3,5-Bis-trifluoromethyl-benzyl)-[2-(cyclopropylmethyl-propyl-amino)-5-trifluoromethyl-benzyl]-amino}-pyrimidin-5-ol (300 mg) and ethyl 4-bromobutyrate (85%1) are dissolved in N,N-dimethylformamide (1 ml) and thereto is added potassium carbonate (82 mg) and the mixture is stirred at room temperature overnight. Thereto are added ethyl acetate and a saturated brine, and the mixture is separated, and the organic layer is washed with a saturated brine, dried over magnesium sulfate, and concentrated under reduced pressure. The resulting residue is purified by silica gel column chromatography (hexane:ethyl acetate=97:3% 17:3) to give ethyl 4-(2-{(3,5-bis-trifluoromethyl-benzyl)-[2-(cyclopropylmethyl-propyl-amino)-5-trifluoromethyl-benzyl]-amino}-pyrimidin-5-yloxy)-butyrate (296 mg). MS (m/z): 721 [M+H]$^+$ (5) Ethyl 4-(2-{(3,5-bis-trifluoromethyl-benzyl)-[2-(cyclopropylmethyl-propyl-amino)-5-trifluoromethyl-benzyl]-amino}-pyrimidin-5-yloxy)-butyrate (290 mg) is dissolved in ethanol (5 ml) and thereto is added a 2N-aqueous sodium hydroxide solution (604 µl) and the mixture is stirred at room temperature overnight. Thereto are added ethyl acetate and a 1N-hydrochloric acid, and the mixture is separated, and the organic layer is washed with a saturated brine, dried over magnesium sulfate, and concentrated under reduced pressure to give 4-(2-{(3,5-bis-trifluoromethyl-benzyl)-[2-(cyclopropylmethyl-propyl-amino)-5-trifluoromethyl-benzyl]-amino}-pyrimidin-5-yloxy)-butyric acid (277 mg). The resulting carboxylic acid is dissolved in ethanol (1 ml) and thereto is added 2N-aqueous sodium hydroxide solution (200 µl), and the reaction solution is concentrated under reduced pressure to give 4-(2-{(3,5-bis-trifluoromethyl-benzyl)-[2-(cyclopropylmethyl-propyl-amino)-5-trifluoromethyl-benzyl]-amino}-pyrimidin-5-yloxy)-butyric acid sodium salt (278 mg). MS (m/z): 691 [M−Na]$^-$ Example 8

(1) To toluene (5 ml) are added 2-fluoro-5-trifluoromethyl-benzaldehyde (650 mg) and dimethylamine hydrochloride (2.76 g), followed by addition of potassium carbonate (1.4 g), and the mixture is stirred at 120° C. overnight. The reaction solution is cooled to room temperature, and thereto are added ethyl acetate and water, and the mixture is separated, and the organic layer is washed with a saturated brine, dried over magnesium sulfate, and concentrated under reduced pressure. The resulting residue is purified by silica gel column chromatography (hexane:ethyl acetate=49:1→4:1) to give 2-dimethylamino-5-trifluoromethyl-benzaldehyde (529 mg). MS (m/z): 218 [M+H]$^+$ (2) 2-Dimethylamino-5-trifluoromethyl-benzaldehyde (144 mg) is dissolved in ethanol (10 ml) and thereto is added sodium borohydride (224 mg) at room temperature and the mixture is stirred for 15 minutes. To the reaction solution are added a saturated aqueous ammonium chloride solution and ethyl acetate, and the mixture is separated, and the organic layer is washed with a saturated brine, dried over magnesium sulfate, and concentrated under reduced pressure. The resulting residue is dissolved in methylene chloride (2 ml) and thereto is added thionyl chloride (58 µl) under ice-cooling and the mixture is stirred at room temperature for 10 minutes. To the reaction solution are added a saturated aqueous sodium bicarbonate solution and ethyl acetate, and the mixture is separated, and the organic layer is washed with a saturated brine, dried over magnesium sulfate, and concentrated under reduced pressure. Ethyl 4-[2-(3,5-bis-trifluoromethyl-benzylamino)-pyrimidin-5-yloxy]-butyrate (200 mg) is dissolved in N,N-dimethylformamide (1.5 ml) and thereto is added sodium hydride (62%) (26 mg) under ice-cooling, and the mixture is stirred for 15 minutes. Thereto is added a solution of a residue obtained above in N,N-dimethylformamide (1.5 ml), and the mixture is stirred at the same temperature for 15 minutes. To the reaction solution are added ethyl acetate and water, and the mixture is separated, and the organic layer is washed with a saturated brine, dried over magnesium sulfate, and concentrated under reduced pressure. The resulting residue is purified by silica gel column chromatography (hexane: ethyl acetate=19:1→9:1) to give ethyl 4-{2-[(3,5-bis-trifluoromethyl-benzyl)-(2-dimethylamino-5-trifluoromethyl-benzyl)-amino]-pyrimidin-5-yloxy}-butyrate (97 mg). MS (m/z): 653 [M+H]$^+$ (3) Ethyl 4-{2-[(3,5-bis-trifluoromethyl-benzyl)-(2-dimethylamino-5-trifluoromethyl-benzyl)-amino]-pyrimidin-5-yloxy}-butyrate (90 mg) is dissolved in ethanol (2 ml), and thereto is added a 2N-aqueous sodium hydroxide solution (207 µl), and the mixture is stirred at room temperature overnight. Thereto are added ethyl acetate and a 1N-hydrochloric acid, and the mixture is separated, and the organic layer is washed with a saturated brine, dried over magnesium sulfate, and concentrated under reduced pressure. The resulting residue is purified by silica gel column chromatography (hexane: ethyl acetate=9:1→1:4) to give 4-{2-[(3,5-bis-trifluoromethyl-benzyl)-(2-dimethylamino-5-trifluoromethyl-benzyl)-amino]-pyrimidin-5-yloxy}-butyric acid (29 mg). The resulting carboxylic acid is dissolved in ethanol (0.5 ml) and thereto is added a 2N-aqueous sodium hydroxide solution (23 µl) and the reaction solution is concentrated under reduced pressure to give 4-{2-[(3,5-bis-trifluoromethyl-benzyl)-(2-dimethylamino-5-trifluoromethyl-benzyl)-amino]-pyrimidin-5-yloxy}-butyric acid ethyl ester sodium salt (30 mg). MS (m/z): 623 [M−Na]$^-$ Example 9

(1) 2-Fluoro-5-trifluoromethyl-benzylamine (2.0 g) is dissolved in 1,4-dioxane (10 ml) and thereto are added N,N-diisopropylethylamine (2.7 ml) and 5-bromo-2-chloropyrimidine (3.02 g) and the mixture is heated under reflux overnight. The reaction solution is cooled to room temperature and concentrated under reduced pressure. The resulting residue is purified by silica gel column chromatography (hexane:ethyl acetate=9:1 to 7:3) to give (5-bromo-pyrimidin-2-yl)-(2-fluoro-5-trifluoromethyl-benzyl)-amine (1.69 g). MS (m/z): 350/352 [M+H]$^+$ (2) (5-Bromo-pyrimidin-2-yl)-(2-fluoro-5-trifluoromethyl-benzyl)-amine (2.10 g) is dissolved in N,N-dimethylformamide (10 ml) and thereto is added sodium hydride (62.7%) (345 mg) under ice-cooling and the mixture is stirred for 30 minutes, and thereto is added 1-bromomethyl-3,5-bis-trifluoromethyl-benzene (2.76 g) and the mixture is stirred at room temperature for 45 minutes. To the reaction solution are added a saturated aqueous sodium bicarbonate solution and ethyl acetate, and the mixture is separated, and the organic layer is washed with a saturated brine, dried over magnesium sulfate, and concentrated under reduced pressure. The resulting residue is purified by silica gel column chromatography (hexane:ethyl acetate=1:0→9:1) to give (3,5-bis-trifluoromethyl-benzyl)-(5-bromo-pyrimidin-2-yl)-(2-fluoro-5-trifluoromethyl-benzyl)-amine (3.30 g). MS (m/z): 576/578 [M+H]$^+$ (3) (3,5-Bis-trifluoromethyl-benzyl)-(5-bromo-pyrimidin-2-yl)-(2-fluoro-5-trifluoromethyl-benzyl)-amine (300 mg) is dissolved in toluene (5 ml) and tris(dibenzylideneacetone)dipalladium (48 mg), 2-(di-tert-butylphosphino)biphenyl (62 mg), sodium tert-butoxide (75 mg) and morpholine (68 µl) and the mixture is stirred under nitrogen atmosphere at room temperature overnight. To the reaction solution are added a saturated aqueous sodium bicarbonate solution and ethyl acetate, and the mixture is separated, and the organic layer is washed with a saturated brine, dried over magnesium sulfate, and concentrated under reduced pressure. The resulting residue is purified by NH-silica gel column chromatography (hexane:ethyl acetate=19:1→9:1) to give (3,5-bis-trifluoromethyl-benzyl)-(2-fluoro-5-trifluoromethyl-benzyl)-(5-morpholin-4-yl-pyrimidin-2-yl)-amine (176 mg). MS (m/z): 583 [M+H]$^+$ Example 10

(1) (3,5-Bis-trifluoromethyl-benzyl)-(5-bromo-pyrimidin-2-yl)-(2-fluoro-5-trifluoromethyl-benzyl)-amine (300 mg) is dissolved in toluene (5 ml) and thereto are added tris(dibenzylideneacetone)dipalladium (48 mg), 2-(di-tert-butylphosphino)biphenyl (62 mg), sodium tert-butoxide (75 mg) and ethyl piperidine-4-carboxylate (120 µl) and the mixture is stirred under nitrogen atmosphere at room temperature overnight. To the reaction solution are added a saturated aqueous sodium bicarbonate solution and ethyl acetate, and the mixture is separated, and the organic layer is washed with a saturated brine, dried over magnesium sulfate, and concentrated under reduced pressure. The resulting residue is purified by NH-silica gel column chromatography (hexane:ethyl acetate=19:1→9:1) to give 1-{2-[(3,5-bis-trifluoromethyl-benzyl)-(2-fluoro-5-trifluoromethyl-benzyl)-amino]-pyrimidin-5-yl}-ethyl piperidine-4-carboxylate (111 mg). MS (m/z): 653 [M+H]$^+$ (2) 1-{2-[(3,5-Bis-trifluoromethyl-benzyl)-(2-fluoro-5-trifluoromethyl-benzyl)-amino]-pyrimidin-5-yl}-ethyl piperidine-4-carboxylate (105 mg) is dissolved in ethanol (4 ml) and thereto is added a 1N-aqueous sodium hydroxide solution (2 ml), and the mixture is stirred at room temperature for 2 hours. To the reaction solution are added 1N-hydrochloric acid and ethyl acetate, and the mixture is separated, and the organic layer is washed with a saturated brine, dried over magnesium sulfate, and concentrated under reduced pressure. The resulting residue is purified by silica gel column chromatography (chloroform:methanol=1:0→9:1) to give 1-{2-[(3,5-bis-trifluoromethyl-benzyl)-(2-fluoro-5-trifluoromethyl-benzyl)-amino]-pyrimidin-5-yl}-piperidine-4-carboxylic acid (81 mg). MS (m/z): 625 [M+H]$^+$ Example 11

(1) (3,5-Bis-trifluoromethyl-benzyl)-(5-bromo-pyrimidin-2-yl)-(2-fluoro-5-trifluoromethyl-benzyl)-amine (300 mg) is dissolved in tetrahydrofuran (3 ml) and thereto are added ethyl-carbamic ethyl ester (67 mg) and sodium hydride (60%) (23 mg) and the mixture is stirred at 120° C. under a condition of 192 W by a microwave instrument for 1 hour and thereto are added ethyl-carbamic ethyl ester (134 mg) and sodium hydride (60%) (46 mg) and the mixture is stirred at 120° C. under a condition of 192 W by a microwave instrument for an additional 1 hour. To the reaction solution are added water and ethyl acetate, and the mixture is separated, and the organic layer is washed with a saturated brine, dried over magnesium sulfate, and concentrated under reduced pressure. The resulting residue is purified by silica gel column chromatography (hexane:ethyl acetate=1:0→9:1) to give (3,5-bis-trifluoromethyl-benzyl)-(5-bromo-pyrimidin-2-yl)-(2-ethoxy-5-trifluoromethyl-benzyl)-amine (220 mg). MS (m/z): 602/604 [M+H]$^+$ (2) (3,5-Bis-trifluoromethyl-benzyl)-(5-bromo-pyrimidin-2-yl)-(2-ethoxy-5-trifluoromethyl-benzyl)-amine (210 mg) is dissolved in toluene (5 ml) and thereto are added tris(dibenzylideneacetone)dipalladium (32 mg), 2-(di-tert-butylphosphino)biphenyl (42 mg), sodium tert-butoxide (50 mg) and ethyl piperidine-4-carboxylate (80 µl) and the mixture is stirred under nitrogen atmosphere at room temperature overnight. To the reaction solution are added a saturated aqueous sodium bicarbonate solution and ethyl acetate, and the mixture is separated, and the organic layer is washed with a saturated brine, dried over magnesium sulfate, and concentrated under reduced pressure. The resulting residue is purified by NH-silica gel column chromatography (hexane:ethyl acetate=1:0→17:3) to give ethyl 1-{2-[(3,5-bis-trifluoromethyl-benzyl)-(2-ethoxy-5-trifluoromethyl-benzyl)-amino]-pyrimidin-5-yl}-piperidine-4-carboxylate (121 mg). MS (m/z): 679 [M+H]$^+$ (3) Ethyl 1-{2-[(3,5-bis-trifluoromethyl-benzyl)-(2-ethoxy-5-trifluoromethyl-benzyl)-amino]-pyrimidin-5-yl}-piperidine-4-carboxylate (110 mg) is dissolved in ethanol (4 ml) and thereto is added a 1N-aqueous sodium hydroxide solution (1 ml) and the mixture is stirred at room temperature for 1 hour. To the reaction solution are added a 1N-hydrochloric acid and ethyl acetate, and the mixture is separated, and the organic layer is washed with a saturated brine, dried over magnesium sulfate, and concentrated under reduced pressure. The resulting residue is purified by silica gel column chromatography (chloroform:methanol=1:0→9:1) to give 1-{2-[(3,5-bis-trifluoromethyl-benzyl)-(2-ethoxy-5-trifluoromethyl-benzyl)-amino]-pyrimidin-5-yl}-piperidine-4-carboxylic acid (63 mg). MS (m/z): 651 [M+H]$^+$ Example 12

(1) 2-Fluoro-5-trifluoromethyl-benzaldehyde (1 g) is dissolved in toluene (5 ml) and thereto are added ethyl 7-ethylamino-heptanoate (3.98 g) and potassium carbonate (2.88 g) and the mixture is heated under reflux overnight. The reaction solution is cooled to room temperature, and thereto are added water and ethyl acetate, and the mixture is separated, and the organic layer is washed with a saturated brine, dried over magnesium sulfate, and concentrated under reduced pressure. The resulting residue is purified by silica gel column chromatography (hexane:ethyl acetate=97:3→83:17) to give ethyl 7-[ethyl-(2-formyl-4-trifluoromethyl-phenyl)-amino]-heptanoate (1.29 g). MS (m/z): 374 [M+H]$^+$ (2) Ethyl 7-[ethyl-(2-formyl-4-trifluoromethyl-phenyl)-amino]-heptanoate (1.29 g) is dissolved in a mixed solvent of toluene (5 ml) and ethanol (1 ml), and thereto is added sodium borohydride (156 mg) and the mixture is stirred for 2 hours and 30 minutes. To the reaction solution are added a saturated aqueous ammonium chloride solution and ethyl acetate, and the mixture is separated, and the organic layer is washed with a saturated brine, dried over magnesium sulfate, and concentrated under reduced pressure. The resulting residue is purified by silica gel column chromatography (hexane:ethyl acetate=9:1→3:1) to give ethyl 7-[ethyl-(2-hydroxymethyl-4-trifluoromethyl-phenyl)-amino]-heptanoate (589 mg). MS (m/z): 376 [M+H]$^+$ (3) Ethyl 7-[ethyl-(2-hydroxymethyl-4-trifluoromethyl-phenyl)-amino]-heptanoate (580 mg) is dissolved in toluene (10 ml) and thereto is added thionyl chloride (135 μl) under ice-cooling, and the mixture is stirred at room temperature for 1 hour. To the reaction solution are added water and ethyl acetate, and the mixture is separated, and the organic layer is washed with a saturated brine, dried over magnesium sulfate, and concentrated under reduced pressure. The resulting residue is dissolved in N,N-dimethylformamide (10 ml), and thereto are added (3,5-bis-trifluoromethyl-benzyl)-(5-bromo-pyrimidin-2-yl)-amine (740 mg) and sodium tert-butoxide (178 mg) and the mixture is stirred at room temperature overnight. To the reaction solution are added a saturated aqueous ammonium chloride solution and ethyl acetate, and the mixture is separated, and the organic layer is washed with a saturated brine, dried over magnesium sulfate, and concentrated under reduced pressure. The resulting residue is purified by silica gel column chromatography (hexane:ethyl acetate=23:2→41:9) to give ethyl 7-[(2-{[(3,5-bis-trifluoromethyl-benzyl)-(5-bromo-pyrimidin-2-yl)-amino]-methyl}-4-trifluoromethyl-phenyl)-ethyl-amino]-heptanoate (760 mg). MS (m/z): 757/759 [M+H]$^+$ (4) Ethyl 7-[(2-{[(3,5-bis-trifluoromethyl-benzyl)-(5-bromo-pyrimidin-2-yl)-amino]-methyl}-4-trifluoromethyl-phenyl)-ethyl-amino]-heptanoate (300 mg) is dissolved in toluene (5 ml) and thereto are added tris(dibenzylideneacetone)dipalladium (37 mg), 2-(di-tert-butylphosphino)biphenyl (48 mg), sodium tert-butoxide (58 mg), and morpholine (53 μl) and the mixture is stirred under nitrogen atmosphere at room temperature overnight. To the reaction solution are added a saturated aqueous sodium bicarbonate solution and ethyl acetate, and the mixture is separated, and the organic layer is washed with a saturated brine, dried over magnesium sulfate, and concentrated under reduced pressure. The resulting residue is purified by NH-silica gel column chromatography (hexane:ethyl acetate=9:1→4:1) to give ethyl 7-[(2-{[(3,5-bis-trifluoromethyl-benzyl)-(5-morpholin-4-yl-pyrimidin-2-yl)-amino]-methyl}-4-trifluoromethyl-phenyl)-ethyl-amino]-heptanoate (254 mg). MS (m/z): 764 [M+H]$^+$ (5) Ethyl 7-[(2-{[(3,5-bis-trifluoromethyl-benzyl)-(5-morpholin-4-yl-pyrimidin-2-yl)-amino]-methyl}-4-trifluoromethyl-phenyl)-ethyl-amino]-heptanoate (250 mg) is dissolved in ethanol (4 ml), and thereto is added a 1N-aqueous sodium hydroxide solution (1 ml) and the mixture is stirred at room temperature for 3 hours and 30 minutes. To the reaction solution are added a 1N-hydrochloric acid and ethyl acetate, and the mixture is separated, and the organic layer is washed with a saturated brine, dried over magnesium sulfate, and concentrated under reduced pressure. The resulting residue is purified by silica gel column chromatography (chloroform:methanol=1:0→19:1) to give 7-[(2-{[(3,5-bis-trifluoromethyl-benzyl)-(5-morpholin-4-yl-pyrimidin-2-yl)-amino]-methyl}-4-trifluoromethyl-phenyl)-ethylamino]-heptanoic acid (131 mg). The resulting 7-[(2-{[(3,5-bis-trifluoromethyl-benzyl)-(5-morpholin-4-yl-pyrimidin-2-yl)-amino]-methyl}-4-trifluoromethyl-phenyl)-ethyl-amino]-heptanoic acid (131 mg) is dissolved in ethanol (1 ml), and thereto is added a 1N-aqueous sodium hydroxide solution (178 μl), and concentrated under reduced pressure to give 7-[(2-{[(3,5-bis-trifluoromethyl-benzyl)-(5-morpholin-4-yl-pyrimidin-2-yl)-amino]-methyl}-4-trifluoromethyl-phenyl)-ethyl-amino]-heptanoic acid sodium salt (133 mg). MS (m/z): 734 [M−Na]$^-$ Example 13

(1) Ethyl trans-(4-{[(2-{[(3,5-bis-trifluoromethyl-benzyl)-(5-bromo-pyrimidin-2-yl)-amino]-methyl}-4-trifluoromethyl-phenyl)-ethyl-amino]-methyl}-cyclohexyl)-acetate (which is prepared by treating the corresponding starting compound in a same manner as in Example 12 (1)-(3)) (2.6 g) is dissolved dimethylsulfoxide (15 ml), and thereto are added [1,1'-bis(diphenylphosphino)ferrocene] dichloropalladium dichloromethane complex (73 mg), potassium acetate (977 mg) and bis(pinacolato)diboron (1.26 g), and the mixture is heated to 80° C. under nitrogen atmosphere and stirred for 2 hours. The reaction solution is cooled to room temperature and thereto are added a saturated brine and ethyl acetate, and the mixture is separated and the organic layer is washed with a saturated brine again, dried over magnesium sulfate, and concentrated under reduced pressure. The resulting residue is dissolved in tetrahydrofuran (30 ml) and thereto is added dropwise a 30% aqueous hydrogen peroxide solution (30 ml) under ice-cooling. The mixture is stirred for 1 hour, and thereto is added a saturated aqueous sodium thiosulfate solution to consume the excess hydrogen peroxide and thereto are added water and ethyl acetate, and the mixture is separated. The organic layer is washed with a saturated brine, dried over magnesium sulfate, and concentrated under reduced pressure. The resulting residue is purified by silica gel column chromatography (hexane:ethyl acetate=19:1 to 7:3) to give ethyl trans-(4-{[(2-{[(3,5-bis-trifluoromethyl-benzyl)-(5-hydroxy-pyrimidin-2-yl)-amino]-methyl}-4-trifluoromethyl-phenyl)-ethylamino]-methyl}-cyclohexyl)-acetate (1.29 g). MS (m/z): 721 [M+H]$^+$ (2) Ethyl trans-(4-{[(2-{[(3,5-bis-trifluoromethyl-benzyl)-(5-hydroxy-pyrimidin-2-yl)-amino]-methyl}-4-trifluoromethyl-phenyl)-ethyl-amino]-methyl}-cyclohexyl)-acetate (300 mg) is dissolved in N,N-dimethylformamide (4 ml), and thereto are added 2-bromoethanol (87 μl) and potassium carbonate (172 mg), and the mixture is stirred at 60° C. for 1 day. The reaction solution is cooled to room temperature, and thereto are added water and ethyl acetate, and the mixture is separated, and the organic layer is washed with a saturated brine, dried over magnesium sulfate, and concentrated under reduced pressure. The resulting residue is purified by silica gel column chromatography (hexane:ethyl acetate=7:3% 1:1) to give ethyl trans-[4-({[2-({(3,5-bis-trifluoromethyl-benzyl)-[5-(2-hydroxy-ethoxy)-pyrimidin-2-yl]-amino}-methyl)-4-trifluoromethyl-phenyl]-ethyl-amino}-methyl)-cyclohexyl]-acetate (138 mg). MS (m/z): 765 [M+H]$^+$ (3) Ethyl trans-[4-({[2-({(3,5-bis-trifluoromethyl-benzyl)-[5-(2-hydroxy-ethoxy)-pyrimidin-2-yl]-amino}-methyl)-4-trifluoromethyl-phenyl]-ethyl-amino}-methyl)-cyclohexyl]-acetate (122 mg) is dissolved in ethanol (4 ml), and thereto is added 1N-aqueous sodium hydroxide solution (1 ml) and the mixture is stirred at 60° C. for 2 hours. The reaction solution is cooled to room temperature, and thereto are added 1N-hydrochloric acid and ethyl acetate, and the mixture is separated, and the organic layer is washed with a saturated brine, dried over magnesium sulfate, and concentrated under reduced pressure. The resulting residue is purified by silica gel column chromatography (hexane:ethyl acetate=7:3→3:7) to give trans-[4-({[2-({(3,5-bis-trifluoromethyl-benzyl)-[5-(2-hydroxy-ethoxy)-pyrimidin-2-yl]-amino}-methyl)-4-trifluoromethyl-phenyl]-ethylamino}-methyl)-cyclohexyl]-acetic acid (50 mg). MS (m/z): 737 [M+H]$^+$ Example 14

Tert-butyl 3-[(2-{[(3,5-bis-trifluoromethyl-benzyl)-(5-morpholin-4-yl-pyrimidin-2-yl)-amino]-methyl}-4-trifluoromethyl-phenyl)-ethyl-amino]-propionate (which is prepared by treating the corresponding starting compound in a same manner as in Example 12(1)-(4)) (205 mg) is dissolved in a 4N-hydrochloric acid in ethyl acetate (5 ml) and the mixture is stirred at room temperature for 2 hours. To the reaction solution are added a saturated aqueous sodium bicarbonate solution and ethyl acetate, and the mixture is separated, and the organic layer is washed with a saturated brine, dried over magnesium sulfate, and concentrated under reduced pressure. The resulting residue is purified by silica gel column chromatography (hexane:ethyl acetate=1:1→0:1) to give 3-[(2-{[(3,5-bis-trifluoromethyl-benzyl)-(5-morpholin-4-yl-pyrimidin-2-yl)-amino]-methyl}-4-trifluoromethyl-phenyl)-ethyl-amino]-propionic acid (133 mg). MS (m/z): 680 [M+H]$^+$ Example 15

(1) Ethyl 7-[(2-{[(3,5-bis-trifluoromethyl-benzyl)-(5-morpholin-4-yl-pyrimidin-2-yl)-amino]-methyl}-4-trifluoromethyl-phenyl)-(2-tert-butoxy-ethyl)-amino]-heptanoate (which is prepared by treating the corresponding starting compound in a same manner as in Example 12(1)-(4)) (260 mg) is dissolved in a 4N-hydrochloric acid in ethyl acetate (4 ml) and the mixture is stirred at room temperature overnight. To the reaction solution are added a saturated aqueous sodium bicarbonate solution and ethyl acetate, and the mixture is separated, and the organic layer is washed with a saturated brine, dried over magnesium sulfate, and concentrated under reduced pressure. The resulting residue is purified by silica gel column chromatography (hexane:ethyl acetate=9:1→3:2) to give ethyl 7-[(2-acetoxy-ethyl)-(2-{[(3,5-bis-trifluoromethyl-benzyl)-(5-morpholin-4-yl-pyrimidin-2-yl)-amino]-methyl}-4-trifluoromethyl-phenyl)-amino]-heptanoate (162 mg). MS (m/z): 822 [M+H]$^+$ (2) Ethyl 7-[(2-acetoxy-ethyl)-(2-{[(3,5-bis-trifluoromethyl-benzyl)-(5-morpholin-4-yl-pyrimidin-2-yl)-amino]-methyl}-4-trifluoromethyl-phenyl)-1-amino]-heptanoate (156 mg) is dissolved in ethanol (4 ml), and thereto is added 1N-aqueous sodium hydroxide solution (1 ml), and the mixture is stirred at room temperature for 4 hours. To the reaction solution are added 1N-hydrochloric acid and ethyl acetate, and the mixture is separated, and the organic layer is washed with a saturated brine, dried over magnesium sulfate, and concentrated under reduced pressure. The resulting residue is purified by silica gel column chromatography (chloroform:methanol=1:0→19:1) to give 7-[(2-acetoxy-ethyl)-(2-{[(3,5-bis-trifluoromethyl-benzyl)-(5-morpholin-4-yl-pyrimidin-2-yl)-amino]-methyl}-4-trifluoromethyl-phenyl)-amino]-heptanoic acid (144 mg). The resulting 7-[(2-{[(3,5-bis-trifluoromethyl-benzyl)-(5-morpholin-4-yl-pyrimidin-2-yl)-amino]-methyl}-4-trifluoromethyl-phenyl)-(2-hydroxy-ethyl)-amino]-heptanoic acid (144 mg) is dissolved in ethanol (1 ml), and thereto is added a 1N-aqueous sodium hydroxide solution (172 μl), and concentrated under reduced pressure to give 7-[(2-{[(3,5-bis-trifluoromethyl-benzyl)-(5-morpholin-4-yl-pyrimidin-2-yl)-amino]-methyl}-4-trifluoromethyl-phenyl)-(2-hydroxy-ethyl)-amino]-heptanoic acid sodium salt (133 mg) MS (m/z): 750 [M–Na]$^-$ Example 16

(1) Ethyl 6-[(2-{[(3,5-bis-trifluoromethyl-benzyl)-(5-hydroxy-pyrimidin-2-yl)-amino]-methyl}-4-trifluoromethyl-phenyl)-ethyl-amino]-hexanoate (120 mg) is dissolved in tetrahydrofuran (1 ml), and thereto are added 2-methoxyethanol (21 μl) and triphenylphosphine (69 mg), and thereto is added dropwise 40% diethyl azodicarboxylate in toluene (115 μl) under water-cooling, and the mixture is stirred at room temperature for 1 hour. To the reaction mixture is added a saturated brine, and the mixture is extracted with ethyl acetate. The organic layer is washed with a saturated brine, dried over magnesium sulfate, and concentrated under reduced pressure. The resulting residue is purified by NH-silica gel column chromatography (hexane:ethyl acetate=6:1) to give ethyl 6-{[2-({(3,5-bis-trifluoromethyl-benzyl)-[5-(2-methoxy-ethoxy)-pyrimidin-2-yl]-amino}-methyl)-4-trifluoromethyl-phenyl]-ethyl-amino}-hexanoate (120 mg). MS (m/z): 739 [M+H]$^+$ (2) Ethyl 6-{[2-({(3,5-bis-trifluoromethyl-benzyl)-[5-(2-methoxy-ethoxy)-pyrimidin-2-yl]-amino}-methyl)-4-trifluoromethyl-phenyl]-ethyl-amino}-hexanoate (113 mg) is dissolved in a mixed solvent of ethanol (2 ml) and tetrahydrofuran (1 ml), and thereto is added 1M-aqueous sodium hydroxide solution (1 ml), and the mixture is stirred at room temperature for 2 hours. The reaction solution is made weakly acidic with a 10% aqueous citric acid solution, and the mixture is extracted with ethyl acetate, and the organic layer is washed with a saturated brine, dried over magnesium sulfate, and concentrated under reduced pressure. The resulting residue is purified by silica gel column chromatography (chloroform:methanol=1:0→49:1) to give 6-{[2-({(3,5-bis-trifluoromethyl-benzyl)-[5-(2-methoxy-ethoxy)-pyrimidin-2-yl]-amino}-methyl)-4-trifluoromethyl-phenyl]-ethyl-amino}-hexanoic acid (111 mg). MS (m/z): 711 [M+H]$^+$ (3) 6-{[2-({(3,5-Bis-trifluoromethyl-benzyl)-[5-(2-methoxy-ethoxy)-pyrimidin-2-yl]-amino}-methyl)-4-trifluoromethyl-phenyl]-ethyl-amino}-hexanoic acid (105 mg) is dissolved in ethanol (1 ml), and thereto is added a 2M-aqueous sodium hydroxide solution (74 μl), and the mixture is stirred at room temperature for 5 minutes. The reaction solution is concentrated under reduced pressure to give 6-{[2-({(3,5-bis-trifluoromethyl-benzyl)-[5-(2-methoxy-ethoxy)-pyrimidin-2-yl]-amino}-methyl)-4-trifluoromethyl-phenyl]-ethyl-amino}-hexanoic acid sodium salt (102 mg). MS (m/z): 709 [M–Na]$^-$ Example 17

(1) (2-Bromo-trifluoromethyl-phenyl)-methanol (5 g) is dissolved in N,N-dimethylformamide (45 ml) and thereto are added palladium acetate (440 mg), 1,1'-bis(diphenylphosphino)ferrocene (2.17 g) and triethylamine (2 (5 ml), and the mixture is stirred under carbon monooxide flow at room temperature for 5 minutes and at 90° C. for 1 day. The reaction solution is cooled to room temperature, and thereto are added a 1N-hydrochloric acid and ethyl acetate, and the mixture is separated, and the organic layer is washed with a saturated brine, dried over magnesium sulfate, and concentrated under reduced pressure. The resulting residue is purified by silica gel column chromatography (hexane:ethyl acetate=4:1→3:2) to give 6-trifluoromethyl-3H-isobenzofuran-1-one (2.77 g). MS (m/z): 203 [M+H]$^+$ (2) 6-Trifluoromethyl-3H-isobenzofuran-1-one (1.77 g) is dissolved in methylene chloride (20 ml) and the mixture is cooled to −78° C., and thereto is added a 1.0M diisobutylaluminum hydride in toluene (19.5 ml) and the mixture is stirred for 1 hour and 20 minutes. The reaction solution is cooled to room temperature, and thereto are added a saturated aqueous ammonium chloride solution and ethyl acetate, and the mixture is separated, and the organic layer is washed with a saturated brine, dried over magnesium sulfate, and concentrated under reduced pressure. The resulting residue is purified by silica gel column chromatography (hexane:ethyl acetate=4:1→3:2) to give 6-trifluoromethyl-1,3-dihydro-isobenzofuran-1-ol (1.36 g). MS (m/z): 187 [M+H—$H_2O$]$^+$ (3) 6-Trifluoromethyl-1,3-dihydro-isobenzofuran-1-ol (4.12 g) is dissolved in 1,2-dichloroethane (75 ml), and thereto are added 3,5-bis-trifluoromethyl-benzylamine (5.89 g), triacetoxy-sodium borohydride (9.0 g) and acetic acid (2.3 ml), and the mixture is stirred at room temperature for 1 hour. To the reaction solution are added a saturated aqueous sodium bicarbonate solution and ethyl acetate, and the mixture is separated, and the organic layer is washed with a saturated brine, dried over magnesium sulfate, and concentrated under reduced pressure. The resulting residue is purified by silica gel column chromatography (hexane:ethyl acetate=7:3→1:1) to give {2-[(3,5-bis-trifluoromethyl-benzylamino)-methyl]-4-trifluoromethyl-phenyl}-methanol (7.06 g). MS (m/z): 432 [M+H]$^+$ (4) {2-[(3,5-Bis-trifluoromethyl-benzylamino)-methyl]-4-trifluoromethyl-phenyl}-methanol (7.0 g) is dissolved in toluene (70 ml) and thereto are added 5-bromo-2-chloro-pyrimidine (4.7 g) and N,N-diisopropylethylamine (4.23 ml) and the mixture is heated under reflux for 3 days. The reaction solution is cooled to room temperature, and thereto are added water and ethyl acetate, and the mixture is separated, and the organic layer is washed with a saturated brine, dried over magnesium sulfate, and concentrated under reduced pressure. The resulting residue is purified by silica gel column chromatography (hexane:ethyl acetate=4:1→13:2) to give (2-{[(3,5-bis-trifluoromethyl-benzyl)-(5-bromo-pyrimidin-2-yl)-amino]-methyl}-4-trifluoromethyl-phenyl)-methanol (7.37 g). MS (m/z): 588/590 [M+H]$^+$ (5) (2-{[(3,5-Bis-trifluoromethyl-benzyl)-(5-bromo-pyrimidin-2-yl)-amino]-methyl}-4-trifluoromethyl-phenyl)-methanol (225 mg) is dissolved in acetone (5 ml), and thereto is added 1.94M Jones reagent (290 µl) under ice-cooling, and the mixture is stirred for 30 minutes. To the reaction solution are added sodium hydrogensulfite, water and ethyl acetate, and the mixture is separated, and the organic layer is washed with a saturated brine, dried over magnesium sulfate, and concentrated under reduced pressure. The resulting residue is purified by silica gel column chromatography (chloroform:methanol=1:0→9:1) to give 2-{[(3,5-bis-trifluoromethyl-benzyl)-(5-bromo-pyrimidin-2-yl)-amino]-methyl}-4-trifluoromethyl-benzoic acid (181 mg). MS (m/z): 602/604 [M+H]$^+$ (6) 2-{[(3,5-Bis-trifluoromethyl-benzyl)-(5-bromo-pyrimidin-2-yl)-amino]-methyl}-4-trifluoromethyl-benzoic acid (1 g) is dissolved in tetrahydrofuran (10 ml), and thereto are added diphenoxyphosphinylazide (540 µl), triethylamine (695 µl) and ethanol (6 ml) and the mixture is heated at 60° C. for 3 days with stirring. The reaction solution is cooled to room temperature, and thereto are added 1N-hydrochloric acid and ethyl acetate, and the mixture is separated, and the organic layer is washed with a saturated brine, dried over magnesium sulfate, and concentrated under reduced pressure. The resulting residue is purified by silica gel column chromatography (hexane:ethyl acetate=1:0→4:1→chloroform:methanol=4:1) to give ethyl (2-{[(3,5-bis-trifluoromethyl-benzyl)-(5-bromo-pyrimidin-2-yl)-amino]-methyl}-4-trifluoromethyl-phenyl)-carbamate (660 mg). MS (m/z): 645/647 [M+H]$^+$ (7) Ethyl (2-{[(3,5-bis-trifluoromethyl-benzyl)-(5-bromo-pyrimidin-2-yl)-amino]-methyl}-4-trifluoromethyl-phenyl)-carbamate (980 mg) is dissolved in N,N-dimethylformamide (10 ml), and thereto is added sodium hydride (60%) (91 mg) under ice-cooling, and the mixture is stirred for 30 minutes and thereto is added ethyl iodide (182 µl) and the mixture is stirred at room temperature overnight. Thereto are added water and ethyl acetate, and the mixture is separated, and the organic layer is washed with a saturated brine, dried over magnesium sulfate, and concentrated under reduced pressure. The resulting residue is purified by silica gel column chromatography (hexane:ethyl acetate=19:1→4:1) to give ethyl (2-{[(3,5-bis-trifluoromethyl-benzyl)-(5-bromo-pyrimidin-2-yl)-amino]-methyl}-4-trifluoromethyl-phenyl)-ethyl-carbamate (425 mg). MS (m/z): 673/675 [M+H]$^+$ (8) Ethyl (2-{[(3,5-bis-trifluoromethyl-benzyl)-(5-bromo-pyrimidin-2-yl)-amino]-methyl}-4-trifluoromethyl-phenyl)-carbamate (412 mg) is dissolved in toluene (5 ml), and thereto are added tris(dibenzylideneacetone)dipalladium (112 mg), 2-(di-tert-butylphosphino)biphenyl (146 mg), sodium tert-butoxide (176 mg) and ethyl piperidine-4-carboxylate (140 µl), and the mixture is stirred under nitrogen atmosphere at room temperature overnight. To the reaction solution are added a saturated aqueous sodium bicarbonate solution and ethyl acetate, and the mixture is separated, and the organic layer is washed with a saturated brine, dried over magnesium sulfate, and concentrated under reduced pressure. The resulting residue is purified by NH-silica gel column chromatography (hexane:ethyl acetate=19:1→4:1) to give 1-(2-{(3,5-bis-trifluoromethyl-benzyl)-[2-(ethoxycarbonyl-ethyl-amino)-5-trifluoromethyl-benzyl]-amino}-pyrimidin-5-yl)-ethyl piperidine-4-carboxylate (72 mg). MS (m/z): 750 [M+H]$^+$ (9) 1-(2-{(3,5-Bis-trifluoromethyl-benzyl)-[2-(ethoxycarbonyl-ethyl-amino)-5-trifluoromethyl-benzyl]-amino}-pyrimidin-5-yl)-ethyl piperidine-4-carboxylate (70 mg) is dissolved in ethanol (4 ml), and thereto is added 1N-aqueous sodium hydroxide solution (1 ml) and the mixture is stirred at room temperature for 2 hours. To the reaction solution are added a 1N-hydrochloric acid and ethyl acetate, and the mixture is separated, and the organic layer is washed with a saturated brine, dried over magnesium sulfate, and concentrated under reduced pressure. The resulting residue is purified by silica gel column chromatography (chloroform:methanol=1:0→9:1) to give 1-(2-{(3,5-bis-trifluoromethyl-benzyl)-[2-(ethoxycarbonyl-ethyl-amino)-5-trifluoromethyl-benzyl]-amino}-pyrimidin-5-yl)-piperidine-4-carboxylic acid (44 mg). The resulting 1-(2-{(3,5-bis-trifluoromethyl-benzyl)-[2-(ethoxycarbonyl-ethyl-amino)-5-trifluoromethyl-benzyl]-amino}-pyrimidin-5-yl)-piperidine-4-carboxylic acid (44 mg) is dissolved in ethanol (1 ml), and thereto is added 1N-aqueous sodium hydroxide solution (44 µl), and then the mixture is concentrated under reduced pressure to give 1-(2-{(3,5-bis-trifluoromethyl-benzyl)-[2-(ethoxycarbonyl-ethyl-amino)-5-trifluoromethyl-benzyl]-amino}-pyrimidin-5-yl)-piperidine-4-carboxylic acid sodium salt (45 mg). MS (m/z): 720 [M−Na]$^-$ Example 18

(1) Ethyl (2-{[(3,5-bis-trifluoromethyl-benzyl)-(5-bromo-pyrimidin-2-yl)-amino]-methyl}-4-trifluoromethyl-phenyl)-carbamate (614 mg) is dissolved in toluene (6.5 ml), and thereto are added tris(dibenzylideneacetone)dipalladium(0) (87 mg), 2-(di-tert-butylphosphino)biphenyl (114 mg), morpholine (166 µl) and sodium tert-butoxide (183 mg) and the mixture is stirred under nitrogen flow at 60° C. for 2 hours. To the reaction mixture is added a saturated brine, and the mixture is extracted with ethyl acetate. The organic layer is washed with a saturated brine, dried over magnesium sulfate, and concentrated under reduced pressure. The resulting residue is purified by NH-silica gel column chromatography (hexane:ethyl acetate=9:1→4:1) to give ethyl (2-{[(3,5-bistrifluoromethyl-benzyl)-(5-morpholin-4-yl-pyrimidin-2-yl)-amino]-methyl}-4-trifluoromethyl-phenyl)-carbamate (476 mg). MS (m/z): 652 [M+H]+

(2) Ethyl (2-{[(3,5-bis-trifluoromethyl-benzyl)-(5-morpholin-4-yl-pyrimidin-2-yl)-amino]-methyl}-4-trifluoromethyl-phenyl)-carbamate (140 mg) is dissolved in N,N-dimethylformamide (1 ml), and thereto is added sodium hydride (63%) (12 mg) under ice-cooling, and the mixture is stirred at the same temperature for 30 minutes. To the reaction mixture is added ethyl 5-bromo-pentanoate (68 µl), and the mixture is stirred at 0° C. to room temperature overnight. To the reaction mixture is added a saturated brine, and the mixture is extracted with ethyl acetate, and the organic layer is washed with a saturated brine, dried over magnesium sulfate, and concentrated under reduced pressure. The resulting residue is purified by silica gel column chromatography (hexane:ethyl acetate=2:1) to give ethyl 5-[(2-{[(3,5-bis-trifluoromethyl-benzyl)-(5-morpholin-4-yl-pyrimidin-2-yl)-amino]-methyl}-4-trifluoromethyl-phenyl)-ethoxycarbonyl-amino]-pentanoate (137 mg). MS (m/z): 780 [M+H]+

(3) Ethyl 5-[(2-{[(3,5-bis-trifluoromethyl-benzyl)-(5-morpholin-4-yl-pyrimidin-2-yl)-amino]-methyl}-4-trifluoromethyl-phenyl)-ethoxycarbonyl-amino]-pentanoate (134 mg) is dissolved in methanol (1 ml), and thereto is added 1M-aqueous sodium hydroxide solution (1 ml), and the mixture is stirred at room temperature for 1 hour and a half. The reaction solution is made weakly acidic with a 10% aqueous citric acid solution, and the mixture is extracted with ethyl acetate, and the organic layer is washed with a saturated brine, dried over magnesium sulfate, and concentrated under reduced pressure. The resulting residue is purified by silica gel column chromatography (chloroform:methanol=19:1) to give 5-[(2-{[(3,5-bis-trifluoromethyl-benzyl)-(5-morpholin-4-yl-pyrimidin-2-yl)-amino]-methyl}-4-trifluoromethyl-phenyl)-ethoxycarbonyl-amino]-pentanoic acid (123 mg). MS (m/z): 752 [M+H]+

Example 19

(1) 2-{[(3,5-Bis-trifluoromethyl-benzyl)-(5-bromo-pyrimidin-2-yl)-amino]-methyl}-4-trifluoromethyl-benzoic acid (2.5 g) is dissolved in tetrahydrofuran (25 ml), and thereto are added diphenoxyphosphinylazide (1.34 ml), triethylamine (174 ml) and benzyl alcohol (1.3 ml) and the mixture is heated at 60° C. overnight with stirring. The reaction solution is cooled to room temperature, and thereto are added a 1N-hydrochloric acid and ethyl acetate, and the mixture is separated, and the organic layer is washed with a saturated brine, dried over magnesium sulfate, and concentrated under reduced pressure. The resulting residue is purified by silica gel column chromatography (hexane:ethyl acetate=1:0→9:1→4:1) to give benzyl (2-{[(3,5-bis-trifluoromethyl-benzyl)-(5-bromo-pyrimidin-2-yl)-amino]-methyl}-4-trifluoromethyl-phenyl)-carbamate (2.66 g). MS (m/z): 707/709 [M+H]+

(2) Benzyl (2-{[(3,5-bis-trifluoromethyl-benzyl)-(5-bromo-pyrimidin-2-yl)-amino]-methyl}-4-trifluoromethyl-phenyl)-carbamate (1.5 g) is dissolved in N,N-dimethylformamide (15 ml), and thereto is sodium hydride (60%) (127 mg) under ice-cooling, and the mixture is stirred for 30 minutes and thereto is added ethyl iodide (255 µl), and the mixture is stirred at room temperature overnight. Thereto are added water and ethyl acetate, and the mixture is separated, and the organic layer is washed with a saturated brine, dried over magnesium sulfate, and concentrated under reduced pressure. The resulting residue is purified by silica gel column chromatography (hexane:ethyl acetate=1:0→17:3) to give benzyl (2-{[(3,5-bis-trifluoromethyl-benzyl)-(5-bromo-pyrimidin-2-yl)-amino]-methyl}-4-trifluoromethyl-phenyl)-ethyl-carbamate (1.30 g). MS (m/z): 735/737 [M+H]+

(3) Benzyl (2-{[(3,5-bis-trifluoromethyl-benzyl)-(5-bromo-pyrimidin-2-yl)-amino]-methyl}-4-trifluoromethyl-phenyl)-ethyl-carbamate (1.28 g) is dissolved in toluene (15 ml), and thereto are added tris(dibenzylideneacetone)dipalladium (159 mg), 2-(di-tert-butylphosphino)biphenyl (208 mg), sodium tert-butoxide (250 mg) and morpholine (230 µl) and the mixture is stirred under nitrogen atmosphere at room temperature overnight. To the reaction solution are added tris(dibenzylideneacetone)dipalladium (159 mg), 2-(di-tert-butylphosphino)biphenyl (208 mg) and sodium tert-butoxide (250 mg) and the mixture is stirred for 3 hours and a half. To the reaction solution are added a saturated aqueous sodium bicarbonate solution and ethyl acetate, and the mixture is separated, and the organic layer is washed with a saturated brine, dried over magnesium sulfate, and concentrated under reduced pressure. The resulting residue is purified by NH-silica gel column chromatography (hexane:ethyl acetate=19:1→4:1) to give benzyl (2-{[(3,5-bis-trifluoromethyl-benzyl)-(5-morpholin-4-yl-pyrimidin-2-yl)-amino]-methyl}-4-trifluoromethyl-phenyl)-ethyl-carbamate (724 mg). MS (m/z): 742 [M+H]+

(4) Benzyl (2-{[(3,5-bis-trifluoromethyl-benzyl)-(5-morpholin-4-yl-pyrimidin-2-yl)-amino]-methyl}-4-trifluoromethyl-phenyl)-ethyl-carbamate (720 mg) is dissolved in ethanol (10 ml), and thereto is added 10% palladium-carbon (200 mg), and the mixture is stirred under hydrogen atmosphere at room temperature for 2 hours. The catalyst is removed by filtration, and the filtrate is concentrated under reduced pressure. The resulting residue is purified by NH-silica gel column chromatography (hexane:ethyl acetate=9:1 to 7:3) to give (3,5-bis-trifluoromethyl-benzyl)-(2-ethylamino-5-trifluoromethyl-benzyl)-(5-morpholin-4-yl-pyrimidin-2-yl)-amine (569 mg). MS (m/z): 608 [M+H]+

(5) (3,5-Bis-trifluoromethyl-benzyl)-(2-ethylamino-5-trifluoromethyl-benzyl)-(5-morpholin-4-yl-pyrimidin-2-yl)-amine (200 mg) and triethylamine (55 µl) is dissolved in methylene chloride (5 ml), and thereto is added triphosgene (39 mg) under ice-cooling, and the mixture is stirred under nitrogen atmosphere at room temperature for 30 minutes. To the reaction solution are added a saturated aqueous sodium bicarbonate solution and chloroform, and the mixture is separated, and the organic layer is washed with a saturated brine, dried over magnesium sulfate, and concentrated under reduced pressure. The resulting residue is dissolved in tetrahydrofuran (5 ml), and thereto are added tert-butyl 3-hydroxy-propionate (73 µl) and sodium hydride (60%) (20 mg), and the mixture is stirred at room temperature overnight. To the reaction solution are added water and ethyl acetate, and the mixture is separated, and the organic layer is washed with a saturated brine, dried over magnesium sulfate, and concentrated under reduced pressure. The resulting residue is purified by silica gel column chromatography (hexane:ethyl acetate=9:1 to 7:3) to give tert-butyl 3-[(2-{[(3,5-bis-trifluoromethyl-benzyl)-(5-morpholin-4-yl-pyrimidin-2-yl)-amino]-methyl}-4-trifluoromethyl-phenyl)-ethyl-carbamoyloxy]-propionate (120 mg). MS (m/z): 780 [M+H]+

(6) Tert-butyl 3-[(2-{[(3,5-bis-trifluoromethyl-benzyl)-(5-morpholin-4-yl-pyrimidin-2-yl)-amino]-methyl}-4-trifluoromethyl-phenyl)-ethyl-carbamoyloxy]-propionate (114 mg) is dissolved in a 4N-hydrochloric acid in ethyl acetate (5 ml), and the mixture is stirred at room temperature for 1 hour and 30 minutes. Thereto are added a saturated aqueous sodium bicarbonate solution and ethyl acetate, and the mixture is separated, and the organic layer is washed with a saturated brine, dried over magnesium sulfate, and concentrated under reduced pressure. The resulting residue is purified by silica gel column chromatography (chloroform:methanol=1:0→19:1) to give 3-[(2-{[(3,5-bis-trifluoromethyl-benzyl)-(5-morpholin-4-yl-pyrimidin-2-yl)-amino]-methyl}-4-trifluoromethyl-phenyl)-ethyl-carbamoyloxy]-propionic acid (81 mg). The resulting 3-[(2-{[(3,5-bis-trifluoromethyl-benzyl)-(5-morpholin-4-yl-pyrimidin-2-yl)-amino]-methyl}-4-trifluoromethyl-phenyl)-ethyl-carbamoyloxy]-propionic acid (81 mg) is dissolved in ethanol (1 ml), and thereto is added 1N-aqueous sodium hydroxide solution (115 µl) and concentrated under reduced pressure to give 3-[(2-{[(3,5-bis-trifluoromethyl-benzyl)-(5-morpholin-4-yl-pyrimidin-2-yl)-amino]-methyl}-4-trifluoromethyl-phenyl)-ethylcarbamoyloxy]-propionic acid sodium salt (78 mg). MS (m/z): 722 [M−Na]⁻

Example 20

(1) (3,5-Bis-trifluoromethyl-benzyl)-(2-ethylamino-5-trifluoromethyl-benzyl)-(5-morpholin-4-yl-pyrimidin-2-yl)-amine (400 mg) is dissolved in methylene chloride (5 ml), and thereto is added triethylamine (110 µl) and triphosgene (78 mg) under ice-cooling, and the mixture is stirred under nitrogen atmosphere at room temperature for 2 hours. To the reaction solution are added a saturated aqueous sodium bicarbonate solution and chloroform, and the mixture is separated, and the organic layer is washed with a saturated brine, dried over magnesium sulfate, and concentrated under reduced pressure. The resulting residue is dissolved in tetrahydrofuran (5 ml), and thereto are added (S)-2-amino-3-tert-butoxy-propionic acid methyl ester hydrochloride (279 mg) and triethylamine (183 µl), and the mixture is stirred at room temperature for 1 day. To the reaction solution are added water and ethyl acetate, and the mixture is separated, and the organic layer is washed with a saturated brine, dried over magnesium sulfate, and concentrated under reduced pressure. The resulting residue is purified by silica gel column chromatography (hexane:ethyl acetate=1:1→3:7) to give methyl(S)-2-[3-(2-{[(3,5-bis-trifluoromethyl-benzyl)-(5-morpholin-4-yl-pyrimidin-2-yl)-amino]-methyl}-4-trifluoromethyl-phenyl)-3-ethyl-ureido]-3-tert-butoxy-propionate (462 mg). MS (m/z): 809 [M+H]⁺

(2) Methyl (S)-2-[3-(2-{[(3,5-bis-trifluoromethyl-benzyl)-(5-morpholin-4-yl-pyrimidin-2-yl)-amino]-methyl}-4-trifluoromethyl-phenyl)-3-ethyl-ureido]-3-tert-butoxy-propionate (455 mg) is dissolved in a 4N-hydrochloric acid in dioxane (5 ml), and the mixture is stirred at room temperature for 8 hours. To the reaction solution are added a saturated aqueous sodium bicarbonate solution and ethyl acetate, and the mixture is separated, and the organic layer is washed with a saturated brine, dried over magnesium sulfate, and concentrated under reduced pressure. The resulting residue is purified by silica gel column chromatography (hexane:ethyl acetate=1:1→0:1) to give methyl (S)-2-[3-(2-{[(3,5-bis-trifluoromethyl-benzyl)-(5-morpholin-4-yl-pyrimidin-2-yl)-amino]-methyl}-4-trifluoromethyl-phenyl)-3-ethyl-ureido]-3-hydroxy-propionate (285 mg). MS (m/z): 753 [M+H]⁺

(3) Methyl (S)-2-[3-(2-{[(3,5-bis-trifluoromethyl-benzyl)-(5-morpholin-4-yl-pyrimidin-2-yl)-amino]-methyl}-4-trifluoromethyl-phenyl)-3-ethyl-ureido]-3-hydroxy-propionate (280 mg) and pyridine (72 µl) is dissolved in methylene chloride (5 ml), and the mixture is cooled to −20° C., and thereto is added trifluoromethanesulfonic anhydride (150 µl) and the mixture is stirred at −20° C. for 1 hour and 30 minutes. To the reaction solution are added a saturated aqueous sodium bicarbonate solution and ethyl acetate, and the mixture is separated, and the organic layer is washed with a saturated brine, dried over magnesium sulfate, and concentrated under reduced pressure. The resulting residue is purified by NH-silica gel column chromatography (hexane:ethyl acetate=4:1→1:1) to give methyl (S)-2-[(2-{[(3,5-bis-trifluoromethyl-benzyl)-(5-morpholin-4-yl-pyrimidin-2-yl)-amino]-methyl}-4-trifluoromethyl-phenyl)-ethyl-amino]-4,5-dihydro-oxazole-4-carboxylate (197 mg). MS (m/z): 735 [M+H]⁺

(4) Methyl (S)-2-[(2-{[(3,5-bis-trifluoromethyl-benzyl)-(5-morpholin-4-yl-pyrimidin-2-yl)-amino]-methyl}-4-trifluoromethyl-phenyl)-ethyl-amino]-4,5-dihydro-oxazole-4-carboxylate (190 mg) is dissolved in methanol (4 ml) and thereto is added a 1N-aqueous sodium hydroxide solution (1 ml), and the mixture is stirred at room temperature for 1 hour. To the reaction solution are added a 1N-hydrochloric acid and ethyl acetate, and the mixture is separated, and the organic layer is washed with a saturated brine, dried over magnesium sulfate, and concentrated under reduced pressure. The resulting residue is purified by silica gel column chromatography (chloroform:methanol=1:0→4:1) to give (S)-2-[(2-{[(3,5-bis-trifluoromethyl-benzyl)-(5-morpholin-4-yl-pyrimidin-2-yl)-amino]-methyl}-4-trifluoromethyl-phenyl)-ethyl-amino]-4,5-dihydro-oxazole-4-carboxylic acid (130 mg). The resulting (S)-2-[(2-{[(3,5-bis-trifluoromethyl-benzyl)-(5-morpholin-4-yl-pyrimidin-2-yl)-amino]-methyl}-4-trifluoromethyl-phenyl)-ethyl-amino]-4,5-dihydro-oxazole-4-carboxylic acid (130 mg) is dissolved in ethanol (1 ml), and thereto is added 1N-aqueous sodium hydroxide solution (180 µl) and concentrated under reduced pressure to give (S)-2-[(2-{[(3,5-bis-trifluoromethyl-benzyl)-(5-morpholin-4-yl-pyrimidin-2-yl)-amino]-methyl}-4-trifluoromethyl-phenyl)-ethyl-amino]-4,5-dihydro-oxazole-4-carboxylic acid sodium salt (120 mg). MS (m/z): 729 [M−Na]⁻

Example 21

(1) (3,5-Bis-trifluoromethyl-benzyl)-(2-ethylamino-5-trifluoromethyl-benzyl)-(5-morpholin-4-yl-pyrimidin-2-yl)-amine (164 mg) is dissolved in methylene chloride (5 ml), and thereto are added ethyl 6-(chloroformyl)hexanoate (67 mg) and triethylamine (26 µl), and the mixture is stirred at room temperature for 1 hour. To the reaction solution are added a 1N-hydrochloric acid and ethyl acetate, and the mixture is separated, and the organic layer is washed with a saturated brine, dried over magnesium sulfate, and concentrated under reduced pressure. The resulting residue is purified by silica gel column chromatography (hexane:ethyl acetate=17:3→7:3) to give ethyl 6-[(2-{[(3,5-bis-trifluoromethyl-benzyl)-(5-morpholin-4-yl-pyrimidin-2-yl)-amino]-methyl}-4-trifluoromethyl-phenyl)-ethyl-carbamoyl]-hexanoate (147 mg). MS (m/z): 778 [M+H]⁺

(2) Ethyl 6-[(2-{[(3,5-bis-trifluoromethyl-benzyl)-(5-morpholin-4-yl-pyrimidin-2-yl)-amino]-methyl}-4-trifluoromethyl-phenyl)-ethyl-carbamoyl]-hexanoate (140 mg) is dissolved in ethanol (4 ml), and thereto is added 1N-aqueous sodium hydroxide solution (1 ml), and the mixture is stirred at room temperature for 2 hours. To the reaction solution are added a 1N-hydrochloric acid and ethyl acetate, and the mixture is separated, and the organic layer is washed with a saturated brine, dried over magnesium sulfate, and concentrated under reduced pressure. The resulting residue is purified by silica gel column chromatography (chloroform:methanol=1:0→9:1) to give 6-[(2-{[(3,5-bis-trifluoromethyl-benzyl)-(5-morpholin-4-yl-pyrimidin-2-yl)- amino]-methyl}-4-trifluoromethyl-phenyl)-ethyl-carbamoyl]-hexanoic acid (137 mg). MS (m/z): 750 [M+H]+

Example 22

(1) 2-{[(3,5-Bis-trifluoromethyl-benzyl)-(5-bromo-pyrimidin-2-yl)-amino]-methyl}-4-trifluoromethyl-benzoic acid (250 mg) is dissolved in tetrahydrofuran (5 ml), and thereto are added tert-butyl 3-ethylamino-propionate (103 mg), 1-hydroxybenzotriazole dihydrate (81 mg), 1-ethyl-3-(3-dimethylaminopropyl)carbodiimide hydrochloride (114 mg) and triethylamine (83 μl), and the mixture is stirred at room temperature overnight. To the reaction solution are added water and ethyl acetate, and the mixture is separated, and the organic layer is washed with a saturated brine, dried over magnesium sulfate, and concentrated under reduced pressure. The resulting residue is purified by silica gel column chromatography (hexane:ethyl acetate=19:1→4:1) to give tert-butyl 3-[(2-{[(3,5-bis-trifluoromethyl-benzyl)-(5-bromo-pyrimidin-2-yl)-amino]-methyl}-4-trifluoromethyl-benzoyl)-ethyl-amino]-propionate (310 mg). MS (m/z): 757/759 [M+H]+

(2) Tert-butyl 3-[(2-{[(3,5-bis-trifluoromethyl-benzyl)-(5-bromo-pyrimidin-2-yl)-amino]-methyl}-4-trifluoromethyl-benzoyl)-ethyl-amino]-propionate (300 mg) is dissolved in toluene (5 ml), and thereto are added tris(dibenzylideneacetone)dipalladium (36 mg), 2-(di-tert-butylphosphino)biphenyl (47 mg), sodium tert-butoxide (57 mg) and morpholine (52 μl), and the mixture is stirred under nitrogen atmosphere at room temperature overnight. To the reaction solution are added a saturated aqueous sodium bicarbonate solution and ethyl acetate, and the mixture is separated, and the organic layer is washed with a saturated brine, dried over magnesium sulfate, and concentrated under reduced pressure. The resulting residue is purified by NH-silica gel column chromatography (hexane:ethyl acetate=17:3→7:3) and further by silica gel column chromatography (hexane:ethyl acetate=4:1→3:2) to give tert-butyl 3-[(2-{[(3,5-bis-trifluoromethyl-benzyl)-(5-morpholin-4-yl-pyrimidin-2-yl)-amino]-methyl}-4-trifluoromethyl-benzoyl)-ethyl-amino]-propionate (13.3 mg). MS (m/z): 764 [M+H]+

(3) Tert-butyl 3-[(2-{[(3,5-bis-trifluoromethyl-benzyl)-(5-morpholin-4-yl-pyrimidin-2-yl)-amino]-methyl}-4-trifluoromethyl-benzoyl)-ethyl-amino]-propionate (13.3 mg) is dissolved in a 4N-hydrochloric acid in ethyl acetate (2 ml), and the mixture is stirred at room temperature for 4 hours. Thereto are added a saturated aqueous sodium bicarbonate solution and ethyl acetate, and the mixture is separated, and the organic layer is washed with a saturated brine, dried over magnesium sulfate, and concentrated under reduced pressure to give 3-[(2-{[(3,5-bis-trifluoromethyl-benzyl)-(5-morpholin-4-yl-pyrimidin-2-yl)-amino]-methyl}-4-trifluoromethyl-benzoyl)-ethyl-amino]-propionic acid (12 mg). MS (m/z): 780 [M+H]+

Example 23

(1) (3,5-Bis-trifluoromethyl-benzyl)-(5-bromo-pyrimidin-2-yl)-amine (8.55 g) is dissolved in N,N-dimethylformamide (20 ml), and thereto is added sodium hydride (60%) (855 mg) under ice-cooling, and the mixture is stirred for 15 minutes. To the reaction solution are added 2-bromomethyl-1-fluoro-4-trifluoromethyl-benzene (5 g), and the mixture is stirred at room temperature overnight. To the reaction solution are added water and ethyl acetate, and the mixture is separated, and the organic layer is washed with a saturated brine, dried over magnesium sulfate, and concentrated under reduced pressure. The resulting residue is purified by silica gel column chromatography (hexane:ethyl acetate=1:0→9:1) to give (3,5-bis-trifluoromethyl-benzyl)-(5-bromo-pyrimidin-2-yl)-(2-fluoro-5-trifluoromethyl-benzyl)-amine (11.1 g). MS (m/z): 576/578 [M+H]+

(2) (3,5-Bis-trifluoromethyl-benzyl)-(5-bromo-pyrimidin-2-yl)-(2-fluoro-5-trifluoromethyl-benzyl)-amine (11.1 g) is dissolved in tetrahydrofuran (20 ml), and thereto are added benzyl alcohol (6 ml) and sodium hydride (60%) (2.32 g), and the mixture is heated under reflux overnight. The reaction solution is cooled to room temperature, and thereto are added water and ethyl acetate, and the mixture is separated, and the organic layer is washed with a saturated brine, dried over magnesium sulfate, and concentrated under reduced pressure. The resulting residue is purified by silica gel column chromatography (hexane:ethyl acetate=97:3→9:1) to give (2-benzyloxy-5-trifluoromethyl-benzyl)-(3,5-bis-trifluoromethyl-benzyl)-(5-bromo-pyrimidin-2-yl)-amine (12.9 g). MS (m/z): 664/666 [M+H]+

(3) (2-Benzyloxy-5-trifluoromethyl-benzyl)-(3,5-bis-trifluoromethyl-benzyl)-(5-bromo-pyrimidin-2-yl)-amine (12.9 g) is dissolved in dimethylsulfoxide (150 ml), and thereto are added [1,1-bis(diphenylphosphino)ferrocene]dichloropalladium dichloromethane complex (3.17 g), potassium acetate (5.71 g) and bis(pinacolato)diboron (9.85 g), and the mixture is heated to 80° C. under nitrogen atmosphere for 1 hour and 30 minutes. The reaction solution is cooled to room temperature, and thereto are added a saturated brine and ethyl acetate, and the mixture is separated, dried over magnesium sulfate, and concentrated under reduced pressure. The resulting residue is dissolved in tetrahydrofuran (150 ml), and thereto is added dropwise a 30% aqueous hydrogen peroxide solution (40 ml) under ice-cooling. Two hours thereafter, thereto is added a saturated aqueous sodium thiosulfate solution to consume the excess hydrogen peroxide, and thereto is added ethyl acetate, and the mixture is separated. The organic layer is washed with a saturated brine, dried over magnesium sulfate, and concentrated under reduced pressure. The resulting residue is purified by silica gel column chromatography (hexane:ethyl acetate=9:1 to 7:3) to give 2-[(2-benzyloxy-5-trifluoromethyl-benzyl)-(3,5-bis-trifluoromethyl-benzyl)-amino]-pyrimidin-5-ol (7.68 g). MS (m/z): 602 [M+H]+

(4) 2-[(2-Benzyloxy-5-trifluoromethyl-benzyl)-(3,5-bis-trifluoromethyl-benzyl)-amino]-pyrimidin-5-ol (7.68 g) is dissolved in N,N-dimethylformamide (100 ml) and thereto are added ethyl 4-bromo-butyrate (2.3 ml) and potassium carbonate (2.22 g), and the mixture is stirred at room temperature overnight. To the reaction solution are added ethyl 4-bromo-butyrate (2.3 ml) and potassium carbonate (2.22 g), and the mixture is stirred at room temperature for 3 days. To the reaction solution are added water and ethyl acetate, and the mixture is separated, and the organic layer is washed with a saturated brine, dried over magnesium sulfate, and concentrated under reduced pressure. The resulting residue is purified by silica gel column chromatography (hexane:ethyl acetate=9:1→4:1) to give ethyl 4-{2-[(2-benzyloxy-5-trifluoromethyl-benzyl)-(3,5-bis-trifluoromethyl-benzyl)-amino]-pyrimidin-5-yloxy}-butyrate as crude product (11.3 g). MS (m/z): 716 [M+H]+

(5) Crude ethyl 4-{2-[(2-benzyloxy-5-trifluoromethyl-benzyl)-(3,5-bis-trifluoromethyl-benzyl)-amino]-pyrimidin-5-yloxy}-butyrate (11.3 g) is dissolved in ethanol (100 ml) and thereto is added 10% palladium-carbon (3 g), and the mixture is stirred under hydrogen atmosphere at room temperature for 2 hours. The catalyst is removed by filtration, and the filtrate is concentrated under reduced pressure. The resulting residue is purified by silica gel column chromatography (hexane:ethyl acetate=19:1→4:1) to give ethyl 4-{2-[(3,5-bis-trifluoromethyl-benzyl)-(2-hydroxy-5-trifluoromethyl-benzyl)-amino]-pyrimidin-5-yloxy}-butyrate (6.03 g). MS (m/z): 626 [M+H]$^+$ (6) Ethyl 4-{2-[(3,5-bis-trifluoromethyl-benzyl)-(2-hydroxy-5-trifluoromethyl-benzyl)-amino]-pyrimidin-5-yloxy}-butyrate (200 mg) is dissolved in ethanol (4 ml), and thereto is added 1N-aqueous sodium hydroxide solution (1 ml), and the mixture is stirred at room temperature for 3 hours. To the reaction solution are added a 1N-hydrochloric acid and ethyl acetate, and the mixture is separated, and the organic layer is washed with a saturated brine, dried over magnesium sulfate, and concentrated under reduced pressure. The resulting residue is purified by silica gel column chromatography (chloroform:methanol=1:0→19:1) to give 4-{2-[(3,5-bis-trifluoromethyl-benzyl)-(2-hydroxy-5-trifluoromethyl-benzyl)-amino]-pyrimidin-5-yloxy}-butyric acid (182 mg). The resulting 4-{2-[(3,5-bis-trifluoromethyl-benzyl)-(2-hydroxy-5-trifluoromethyl-benzyl)-amino]-pyrimidin-5-yloxy}-butyric acid (184 mg) is dissolved in ethanol (5 ml), and thereto is added 1N-aqueous sodium hydroxide solution (305 μl), and concentrated under reduced pressure to give 4-{2-[(3,5-bis-trifluoromethyl-benzyl)-(2-hydroxy-5-trifluoromethyl-benzyl)-amino]-pyrimidin-5-yloxy}-butyric acid sodium salt (184 mg). MS (m/z): 598 [M+H]$^+$ Example 24

(1) Ethyl 4-{2-[(3,5-bis-trifluoromethyl-benzyl)-(2-hydroxy-5-trifluoromethyl-benzyl)-amino]-pyrimidin-5-yloxy}-butyrate (300 mg) and 3-pentanol (63 mg) are dissolved in tetrahydrofuran (4 ml), and thereto are added dropwise triphenylphosphine (189 mg) and a 40% diethyl azodicarboxylate in toluene (130 μl) under ice-cooling, and the mixture is stirred at room temperature overnight. Thereto are added water and ethyl acetate, and the mixture is separated, and the organic layer is washed with a saturated brine, dried over magnesium sulfate, and concentrated under reduced pressure. The resulting residue is purified by silica gel column chromatography (hexane:ethyl acetate=1:0→9:1) to give ethyl 4-(2-{(3,5-bis-trifluoromethyl-benzyl)-[2-(1-ethyl-propoxy)-5-trifluoromethyl-benzyl]-amino}-pyrimidin-5-yloxy)-butyrate (195 mg). MS (m/z): 696 [M+H]$^+$ (2) Ethyl 4-(2-{(3,5-bis-trifluoromethyl-benzyl)-[2-(1-ethylpropoxy)-5-trifluoromethyl-benzyl]-amino}-pyrimidin-5-yloxy)-butyrate (190 mg) is dissolved in ethanol (5 ml), and thereto is added a 1N-aqueous sodium hydroxide solution (1 ml) and the mixture is stirred at room temperature for 3 hours and 30 minutes. To the reaction solution are added a 1N-hydrochloric acid and ethyl acetate, and the mixture is separated, and the organic layer is washed with a saturated brine, dried over magnesium sulfate, and concentrated under reduced pressure. The resulting residue is purified by silica gel column chromatography (chloroform:methanol=1:0→93:7) to give 4-(2-{(3,5-bis-trifluoromethyl-benzyl)-[2-(1-ethylpropoxy)-5-trifluoromethyl-benzyl]-amino}-pyrimidin-5-yloxy)-butyric acid (158 mg). The resulting 4-(2-{(3,5-bis-trifluoromethyl-benzyl)-[2-(1-ethylpropoxy)-5-trifluoromethyl-benzyl]-amino}-pyrimidin-5-yloxy)-butyric acid (158 mg) is dissolved in ethanol (1 ml), and thereto is added 1N-aqueous sodium hydroxide solution (237 μl) and concentrated under reduced pressure to give 4-(2-{(3,5-bis-trifluoromethyl-benzyl)-[2-(1-ethyl-propoxy)-5-trifluoromethyl-benzyl]-amino}-pyrimidin-5-yloxy)-butyric acid sodium salt (149 mg). MS (m/z): 666 [M−Na]$^-$ Example 25

(1) Ethyl 4-{2-[(3,5-bis-trifluoromethyl-benzyl)-(2-hydroxy-5-trifluoromethyl-benzyl)-amino]-pyrimidin-5-yloxy}-butyrate (200 mg) is dissolved in N,N-dimethylformamide (3 ml), and thereto are added 2-chloropyrimidine (45 mg) and potassium carbonate (55 mg), and the mixture is stirred at 85° C. overnight. The reaction solution is cooled to room temperature, and thereto are added water and ethyl acetate, and the mixture is separated, and the organic layer is washed with a saturated brine, dried over magnesium sulfate, and concentrated under reduced pressure. The resulting residue is purified by silica gel column chromatography (hexane:ethyl acetate=41:9→13:7) to give ethyl 4-(2-{(3,5-bis-trifluoromethyl-benzyl)-[2-(pyrimidin-2-yloxy)-5-trifluoromethyl-benzyl]-amino}-pyrimidin-5-yloxy)-butyrate (120 mg). MS (m/z): 704 [M+H]$^+$ (2) Ethyl 4-(2-{(3,5-bis-trifluoromethyl-benzyl)-[2-(pyrimidin-2-yloxy)-5-trifluoromethyl-benzyl]-amino}-pyrimidin-5-yloxy)-butyrate (115 mg) is dissolved in ethanol (4 ml), and thereto is added 1N-aqueous sodium hydroxide solution (1 ml) and the mixture is stirred at room temperature for 2 hours. To the reaction solution are added a 1N-hydrochloric acid and ethyl acetate, and the mixture is separated, and the organic layer is washed with a saturated brine, dried over magnesium sulfate, and concentrated under reduced pressure. The resulting residue is purified by silica gel column chromatography (chloroform:methanol=1:0→9:1) to give 4-(2-{(3,5-bis-trifluoromethyl-benzyl)-[2-(pyrimidin-2-yloxy)-5-trifluoromethyl-benzyl]-amino}-pyrimidin-5-yloxy)-butyric acid (96 mg). MS (m/z): 676 [M+H]$^+$ Example 26

(1) Ethyl 4-{2-[(3,5-bis-trifluoromethyl-benzyl)-(2-hydroxy-5-trifluoromethyl-benzyl)-amino]-pyrimidin-5-yloxy}-butyrate (3 g) and pyridine (580 μl) are dissolved in methylene chloride (45 ml), and thereto is added trifluoromethanesulfonic anhydride (1.2 ml) under ice-cooling, and the mixture is stirred under nitrogen atmosphere for 2 hours. The reaction solution is cooled to room temperature, and thereto are added a saturated aqueous sodium bicarbonate solution and ethyl acetate, and the mixture is separated, and the organic layer is washed with a saturated brine, dried over magnesium sulfate, and concentrated under reduced pressure. The resulting residue is purified by silica gel column chromatography (hexane:ethyl acetate=19:1→4:1) to give ethyl 4-{2-[(3,5-bis-trifluoromethyl-benzyl)-(2-trifluoromethanesulfonyloxy-5-trifluoromethyl-benzyl)-amino]-pyrimidin-5-yloxy}-butyrate (3.44 g). MS (m/z): 758 [M+H]$^+$ (2) Ethyl 4-{2-[(3,5-bis-trifluoromethyl-benzyl)-(2-trifluoromethanesulfonyloxy-5-trifluoromethyl-benzyl)-amino]-pyrimidin-5-yloxy}-butyrate (200 mg) is dissolved in 1,4-dioxane (3 ml), and thereto are added phenyl boronic acid (64 mg), [1,1'-bis(diphenylphosphino)ferrocene]dichloropalladium dichloromethane complex (22 mg) and cesium carbonate (172 mg), and the mixture is stirred under nitrogen atmosphere at 80° C. overnight. To the reaction solution are added water and ethyl acetate, and the mixture is separated, and the organic layer is washed with a saturated brine, dried over magnesium sulfate, and concentrated under reduced pressure. The resulting residue is purified by NH-silica gel column chromatography (hexane:ethyl acetate=19:1→17:3) to give ethyl 4-{2-[(3,5-bis-trifluoromethyl-benzyl)-(4-trifluoromethyl-biphenyl-2-ylmethyl)-amino]-pyrimidin-5-yloxy}-butyrate (192 mg). MS (m/z): 686 [M+H]$^+$ (3) Ethyl 4-{2-[(3,5-bis-trifluoromethyl-benzyl)-(4-trifluoromethyl-biphenyl-2-ylmethyl)-amino]-pyrimidin-2-ylmethyl}-amino]-pyrimidin-5-yloxy}-butyrate (185 mg) is dissolved in ethanol (4 ml), and thereto is added 1N-aqueous sodium hydroxide solution (1 ml), and the mixture is stirred at room temperature for 2 hours. To the reaction solution are added a 1N-hydrochloric acid and ethyl acetate, and the mixture is separated, and the organic layer is washed with a saturated brine, dried over magnesium sulfate, and concentrated under reduced pressure. The resulting residue is purified by silica gel column chromatography (chloroform: methanol=1:0→19:1) to give 4-{2-[(3,5-bis-trifluoromethyl-benzyl)-(4-trifluoromethyl-biphenyl-2-ylmethyl)-amino]-pyrimidin-5-yloxy}-butyric acid (160 mg). The resulting 4-{2-[(3,5-bis-trifluoromethyl-benzyl)-(4-trifluoromethyl-biphenyl-2-ylmethyl)-amino]-pyrimidin-5-yloxy}-butyric acid (160 mg) is dissolved in ethanol (1 ml) and thereto is added 1N-aqueous sodium hydroxide solution (245 µl) and concentrated under reduced pressure to give 4-{2-[(3,5-bis-trifluoromethyl-benzyl)-(4-trifluoromethyl-biphenyl-2-ylmethyl)-amino]-pyrimidin-5-yloxy}-butyric acid sodium salt (158 mg). MS (m/z): 656 [M−Na]−

Example 27

(1) (2-Benzyloxy-5-trifluoromethyl-benzyl)-(3,5-bis-trifluoromethyl-benzyl)-(5-bromo-pyrimidin-2-yl)-amine (3.75 g) is dissolved in toluene (50 ml) and thereto are added tris(dibenzylideneacetone)dipalladium (516 mg), 2-(di-tert-butylphosphino)biphenyl (673 mg), sodium tert-butoxide (813 mg) and morpholine (740 µl), and the mixture is stirred under nitrogen atmosphere at room temperature overnight. To the reaction solution are added a saturated aqueous sodium bicarbonate solution and ethyl acetate, and the mixture is separated, and the organic layer is washed with a saturated brine, dried over magnesium sulfate, and concentrated under reduced pressure. The resulting residue is purified by NH-silica gel column chromatography (hexane:ethyl acetate=9:1→4:1) to give (2-benzyloxy-5-trifluoromethyl-benzyl)-(3,5-bis-trifluoromethyl-benzyl)-(5-morpholin-4-yl-pyrimidin-2-yl)-amine (2.46 g). MS (m/z): 671 [M+H]+

(2) (2-Benzyloxy-5-trifluoromethyl-benzyl)-(3,5-bis-trifluoromethyl-benzyl)-(5-morpholin-4-yl-pyrimidin-2-yl)-amine (2.46 g) is dissolved in ethanol (35 ml), and thereto is added 10% palladium-carbon (750 mg) and the mixture is stirred under hydrogen atmosphere at room temperature for 1 hour and 30 minutes. The catalyst is removed by filtration, and the filtrate is concentrated under reduced pressure. The resulting residue is purified by silica gel column chromatography (hexane:ethyl acetate=4:1→3:2) to give 2-{[(3,5-bis-trifluoromethyl-benzyl)-(5-morpholin-4-yl-pyrimidin-2-yl)-amino]-methyl}-4-trifluoromethyl-phenol (1.53 g). MS (m/z): 581 [M+H]+

(3) 2-{[(3,5-Bis-trifluoromethyl-benzyl)-(5-morpholin-4-yl-pyrimidin-2-yl)-amino]-methyl}-4-trifluoromethyl-phenol (150 mg) is dissolved in N,N-dimethylformamide (4 ml), and thereto are added ethyl 4-bromo-butyrate (74 µl) and potassium carbonate (71 mg) and the mixture is stirred at 80° C. overnight. To the reaction solution are added water and ethyl acetate, and the mixture is separated, and the organic layer is washed with a saturated brine, dried over magnesium sulfate, and concentrated under reduced pressure. The resulting residue is purified by silica gel column chromatography (hexane:ethyl acetate=22:3→7:3) to give ethyl 4-(2-{[(3,5-bis-trifluoromethyl-benzyl)-(5-morpholin-4-yl-pyrimidin-2-yl)-amino]-methyl}-4-trifluoromethyl-phenoxy)-butyrate (123 mg). MS (m/z): 695 [M+H]+

(4) Ethyl 4-(2-{[(3,5-bis-trifluoromethyl-benzyl)-(5-morpholin-4-yl-pyrimidin-2-yl)-amino]-methyl}-4-trifluoromethyl-phenoxy)-butyrate (115 mg) is dissolved in ethanol (4 ml), and thereto is added 1N-aqueous sodium hydroxide solution (1 ml), and the mixture is stirred at room temperature for 4 hours. To the reaction solution are added a 1N-hydrochloric acid and ethyl acetate, and the mixture is separated, and the organic layer is washed with a saturated brine, dried over magnesium sulfate, and concentrated under reduced pressure. The resulting residue is purified by silica gel column chromatography (chloroform:methanol=1:0→19:1) to give 4-(2-{[(3,5-bis-trifluoromethyl-benzyl)-(5-morpholin-4-yl-pyrimidin-2-yl)-amino]-methyl}-4-trifluoromethyl-phenoxy)-butyric acid (108 mg). MS (m/z): 667 [M+H]+

Example 28

(1) 2-{[(3,5-Bis-trifluoromethyl-benzyl)-(5-morpholin-4-yl-pyrimidin-2-yl)-amino]-methyl}-4-trifluoromethyl-phenol (300 mg) and pyridine (50 µl) are dissolved in methylene chloride (5 ml) and thereto is added trifluoromethanesulfonic anhydride (104 µl) under ice-cooling, and the mixture is stirred under nitrogen atmosphere for 1 hour. The reaction solution is cooled to room temperature, and thereto are added a saturated aqueous sodium bicarbonate solution and ethyl acetate, and the mixture is separated, and the organic layer is washed with a saturated brine, dried over magnesium sulfate, and concentrated under reduced pressure. The resulting residue is purified by silica gel column chromatography (hexane:ethyl acetate=9:1 to 7:3) to give trifluoromethanesulfonic acid 2-{[(3,5-bis-trifluoromethyl-benzyl)-(5-morpholin-4-yl-pyrimidin-2-yl)-amino]-methyl}-4-trifluoromethyl-phenyl ester (330 mg). MS (m/z): 713 [M+H]+

(2) Trifluoromethanesulfonic acid 2-{[(3,5-bis-trifluoromethyl-benzyl)-(5-morpholin-4-yl-pyrimidin-2-yl)-amino]-methyl}-4-trifluoromethyl-phenyl ester (200 mg) is dissolved in 1,4-dioxane (3 ml), and thereto are added phenyl boronic acid (69 mg), [1,1'-bis(diphenylphosphino)ferrocene]dichloropalladium dichloromethane complex (23 mg) and cesium carbonate (183 mg), and the mixture is stirred under nitrogen atmosphere at 80° C. for 1 day. The reaction solution is cooled to room temperature, and thereto are added water and ethyl acetate, and the mixture is separated, and the organic layer is washed with a saturated brine, dried over magnesium sulfate, and concentrated under reduced pressure. The resulting residue is purified by NH-silica gel column chromatography (hexane:ethyl acetate=19:1→4:1) to give (3,5-bis-trifluoromethyl-benzyl)-(5-morpholin-4-yl-pyrimidin-2-yl)-(4-trifluoromethyl-biphenyl-2-ylmethyl)-amine (52 mg). MS (m/z): 641 [M+H]+

Examples 29 to 35

The corresponding starting compounds are treated in a similar manner to Example 1 to give the compounds as listed in Table 1.

Example 36

The corresponding starting compound is treated in a similar manner to Example 1(1)-(3) to give the compound as listed in Table 1.

Examples 37 to 46

The corresponding starting compounds are treated in a similar manner to Example 2 to give the compounds as listed in Table 1.

Examples 47 to 48

The corresponding starting compounds are treated in a similar manner to Example 4 to give the compounds as listed in Table 1.

Example 49

The corresponding starting compound is treated in a similar manner to Example 5 to give the compound as listed in Table 1.

Examples 50 to 53

The corresponding starting compounds are treated in a similar manner to Example 8 to give the compounds as listed in Table 1.

Examples 54 to 60

The corresponding starting compounds are treated in a similar manner to Example 12 to give the compounds as listed in Table 1.

Examples 61 to 62

The corresponding starting compounds are treated in a similar manner to Example 12(1)-(3) to give the compounds as listed in Table 1.

Examples 63 to 64

The corresponding starting compounds are treated in a similar manner to Example 13 to give the compounds as listed in Table 1.

Example 65

The corresponding starting compound is treated in a similar manner to Example 16 to give the compound as listed in Table 1.

Example 66

The corresponding starting compound is treated in a similar manner to Example 18 to give the compound as listed in Table 1.

Example 67

The corresponding starting compound is treated in a similar manner to Example 20 to give the compound as listed in Table 1.

Examples 68 to 71

The corresponding starting compounds are treated in a similar manner to Example 24 to give the compounds as listed in Table 1.

Examples 72 to 75

The corresponding starting compounds are treated in a similar manner to Example 26 to give the compounds as listed in Table 1.

TABLE 1

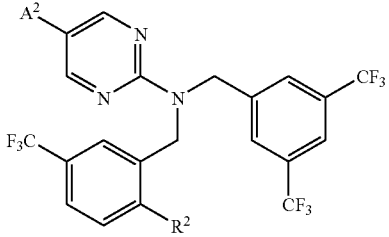

| Ex. No. | A²- | -R² | Physical properties etc. |
|---|---|---|---|
| 1 | Na⁺ ⁻O-C(=O)-(1-methylpiperidin-4-yl) | -N(Me)CH₂CH₂OMe with N-Me | MS(m/z): 706[M − Na]⁻ |
| 2 | Na⁺ ⁻O-C(=O)-CH₂CH₂CH₂-OMe | -N(Me)CH₂CH₂Me with N-Me | MS(m/z): 679[M − Na]⁻ |
| 3 | Na⁺ ⁻O-C(=O)-CH₂-O-Me | -N(Me)CH₂-cyclohexyl with N-Me | MS(m/z): 705[M − Na]⁻ |
| 4 | Na⁺ ⁻O-C(=O)-CH₂CH₂-O-Me | -N(Me)C(=O)-O-Me with N-Me | MS(m/z): 695[M − Na]⁻ |

TABLE 1-continued
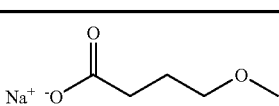
| Ex. No. | A²- | -R² | Physical properties etc. |
|---|---|---|---|
| 5 | 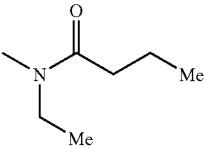 | 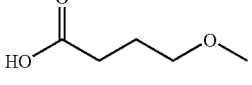 | MS(m/z): 693[M − Na]⁻ |
| 6 | 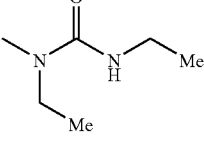 | 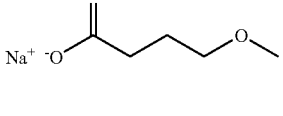 | MS(m/z): 696[M + H]⁻ |
| 7 | 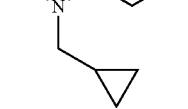 | 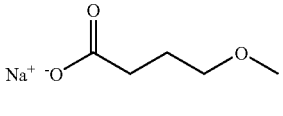 | MS(m/z): 691[M − Na]⁻ |
| 8 |  | 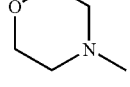 | MS(m/z): 623[M − Na]⁻ |
| 9 |  | 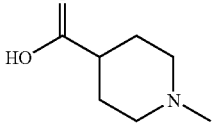 | MS(m/z): 583[M + H]⁺ |
| 10 |  | 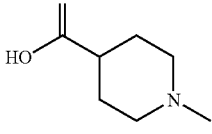 | MS(m/z): 625[M + H]⁺ |
| 11 |  | 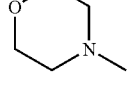 | MS(m/z): 651[M + H]⁺ |
| 12 | 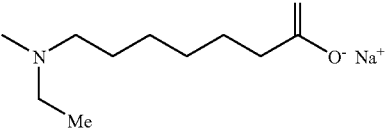 | 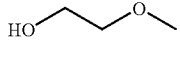 | MS(m/z): 734[M − Na]⁻ |
| 13 | 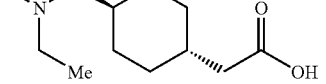 | | MS(m/z): 737[M + H]⁺ |

TABLE 1-continued

| Ex. No. | A²- | -R² | Physical properties etc. |
|---|---|---|---|
| 14 | morpholinyl | N(Me)(CH₂CH₂CO₂H) with Et branch | MS(m/z): 880[M + H]⁺ |
| 15 | morpholinyl | N(CH₂CH₂OH)(CH₂)₅CO₂⁻Na⁺ with Me | MS(m/z): 750[M − Na]⁻ |
| 16 | MeOCH₂CH₂OMe | N(Me)(CH₂)₄CO₂⁻Na⁺ with Et | MS(m/z): 709[M − Na]⁻ |
| 17 | Na⁺ ⁻O₂C-piperidinyl-Me | N(Et)(Me)C(O)OEt | MS(m/z): 720[M − Na]⁻ |
| 18 | morpholinyl | N(Me)(CH₂)₃CO₂H with C(O)OEt | MS(m/z): 752[M + H]⁺ |
| 19 | morpholinyl | N(Me)(Et)C(O)OCH₂CH₂CO₂⁻Na⁺ | MS(m/z): 722[M − Na]⁻ |
| 20 | morpholinyl | oxazoline (S) with N(Me)(Et), CO₂⁻Na⁺ | MS(m/z): 719[M − Na]⁻ |
| 21 | morpholinyl | N(Me)C(O)(CH₂)₄CO₂H with Et | MS(m/z): 750[M + H]⁺ |

TABLE 1-continued

| Ex. No. | A²- | -R² | Physical properties etc. |
|---|---|---|---|
| 22 | N-methylmorpholine | N-ethyl-N-acetyl-β-alanine | MS(m/z): 708[M + H]⁺ |
| 23 | Na⁺ ⁻O-C(O)-CH₂CH₂CH₂-O-Me | -OH | MS(m/z): 598[M + 2H − Na]⁺ |
| 24 | Na⁺ ⁻O-C(O)-CH₂CH₂CH₂-O-Me | -OCH(Me)CH₂Me (isobutyl ether) | MS(m/z): 666[M − Na]⁻ |
| 25 | HO-C(O)-CH₂CH₂CH₂-O-Me | 2-methoxypyrimidine | MS(m/z): 676[M + H]⁺ |
| 26 | Na⁺ ⁻O-C(O)-CH₂CH₂CH₂-O-Me | phenyl | MS(m/z): 656[M − Na]⁻ |
| 27 | N-methylmorpholine | MeO-CH₂CH₂CH₂-C(O)OH | MS(m/z): 667[M + H]⁺ |
| 28 | N-methylmorpholine | phenyl | MS(m/z): 641[M + H]⁺ |
| 29 | 1-methylpiperidine-4-carboxylic acid | N-methyl-N-ethyl-butyl amine | MS(m/z): 706[M + H]⁺ |
| 30 | 1-methylpiperidine-4-carboxylic acid | morpholine | MS(m/z): 692[M + H]⁺ |
| 31 | 2-(1-methylpiperidin-4-yl)acetic acid | morpholine | MS(m/z): 706[M + H]⁺ |

TABLE 1-continued

| Ex. No. | A²- | -R² | Physical properties etc. |
|---|---|---|---|
| 32 | 3-(carboxymethyl)-1-methylpiperidine | 4-methylmorpholine | MS(m/z): 706[M + H]⁺ |
| 33 | 1-methylpiperidine-4-carboxylic acid | N-methyl-N-ethyl-cyclohexylmethylamine | MS(m/z): 746[M + H]⁺ |
| 34 | 4-(carboxymethyl)-1-methylpiperidine | N-methyl-N-ethyl-cyclohexylmethylamine | MS(m/z): 760[M + H]⁺ |
| 35 | 3-(carboxymethyl)-1-methylpiperidine | N-methyl-N-ethyl-cyclohexylmethylamine | MS(m/z): 760[M + H]⁺ |
| 36 | Br— | 4-methylmorpholine | MS(m/z): 643/645 [M + H]⁺ |
| 37 | sodium 4-methoxybutanoate | N-methyl-N-ethyl-2-methoxyethylamine | MS(m/z): 681[M − Na]⁻ |
| 38 | methoxyacetic acid | N-methyl-N-ethyl-cyclohexylmethylamine | MS(m/z): 693[M + H]⁺ |
| 39 | sodium 4-methoxybutanoate | N-methyl-N-ethyl-cyclohexylmethylamine | MS(m/z): 719[M − Na]⁻ |
| 40 | sodium 5-methoxypentanoate | N-methyl-N-ethyl-cyclohexylmethylamine | MS(m/z): 733[M − Na]⁻ |
| 41 | sodium 6-methoxyhexanoate | N-methyl-N-ethyl-cyclohexylmethylamine | MS(m/z): 747[M − Na]⁻ |
| 42 | sodium 7-methoxyheptanoate | N-methyl-N-ethyl-cyclohexylmethylamine | MS(m/z): 761[M − Na]⁻ |

TABLE 1-continued
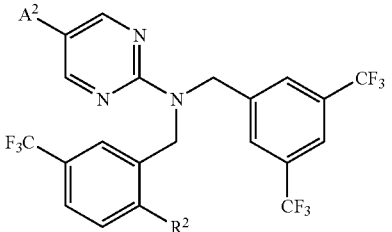
| Ex. No. | A²- | -R² | Physical properties etc. |
|---|---|---|---|
| 43 | 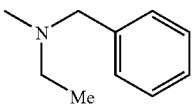 | 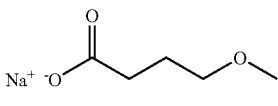 | MS(m/z): 713[M − Na]⁻ |
| 44 | 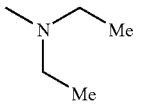 | 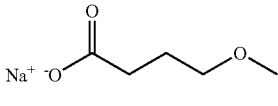 | MS(m/z): 651[M − Na]⁻ |
| 45 | 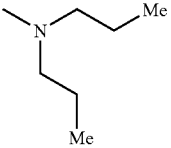 | 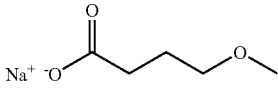 | MS(m/z): 679[M − Na]⁻ |
| 46 | 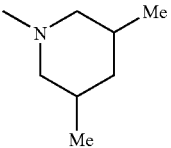 | 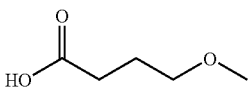 | MS(m/z): 691[M − Na]⁻ |
| 47 | 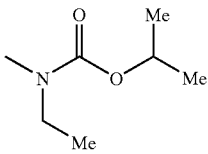 | 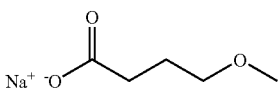 | MS(m/z): 711[M + H]⁺ |
| 48 | 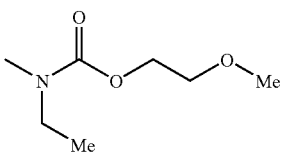 | 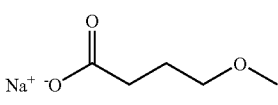 | MS(m/z): 725[M − Na]⁻ |
| 49 | 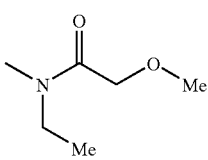 | 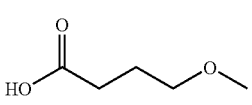 | MS(m/z): 695[M − Na]⁻ |
| 50 | 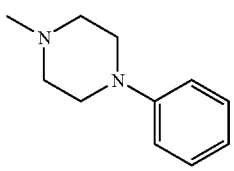 | 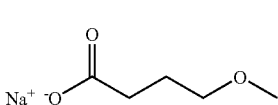 | MS(m/z): 742[M + H]⁺ |
| 51 | 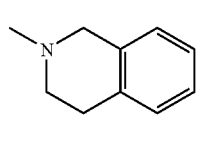 | | MS(m/z): 711[M − Na]⁻ |

TABLE 1-continued

| Ex. No. | A²- | -R² | Physical properties etc. |
|---|---|---|---|
| 52 | Na⁺ ⁻O-C(O)-CH₂CH₂-O-Me | -N(Me)-CH₂CH₂-(2-pyridyl) | MS(m/z): 714[M − Na]⁻ |
| 53 | Na⁺ ⁻O-C(O)-CH₂CH₂-O-Me | -N(Me)-CH₂CH₂CH₂-Me | MS(m/z): 665[M − Na]⁻ |
| 54 | morpholin-4-yl | -N(Me)-(CH₂)₅-C(O)O⁻ Na⁺ (with Et on N) | MS(m/z): 720[M − Na]⁻ |
| 55 | morpholin-4-yl | 1-methylpiperidine-4-carboxylic acid | MS(m/z): 692[M + H]⁺ |
| 56 | morpholin-4-yl | 1-methylpiperidin-4-yl-CH₂-COOH | MS(m/z): 706[M + H]⁺ |
| 57 | morpholin-4-yl | -N(Me)-CH₂-cyclohexyl-CH₂-COOH (with Et on N) | MS(m/z): 762[M + H]⁺ |
| 58 | morpholin-4-yl | -N(Et)-(CH₂)₄-C(O)O⁻ Na⁺ | MS(m/z): 734[M − Na]⁻ |
| 59 | morpholin-4-yl | -N(Me)-(CH₂)₄-C(O)O⁻ Na⁺ | MS(m/z): 706[M − Na]⁻ |
| 60 | morpholin-4-yl | -N(Et)-CH₂-(piperidin-4-yl)-N-CH₂-C(O)O⁻ Na⁺ | MS(m/z): 763[M + 2H − Na]⁺ |
| 61 | Br- | 1-methylpiperidine-4-carboxylic acid | MS(m/z): 685/637 [M + H]⁺ |

TABLE 1-continued
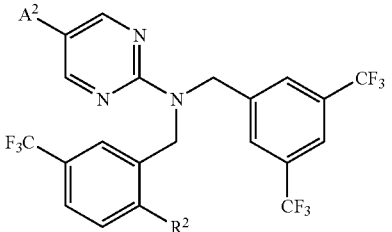
| Ex. No. | A²- | -R² | Physical properties etc. |
|---|---|---|---|
| 62 | 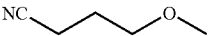 | 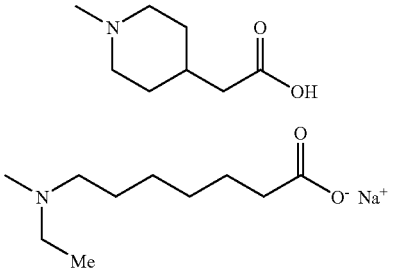 | MS(m/z): 699/701 [M + H]⁺ |
| 63 | 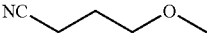 | 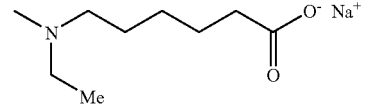 | MS(m/z): 732[M − Na]⁻ |
| 64 | 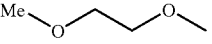 | 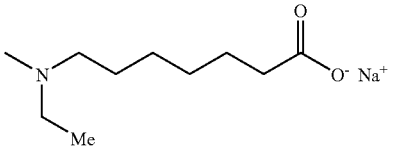 | MS(m/z): 718[M − Na]⁻ |
| 65 | 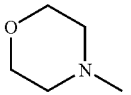 | 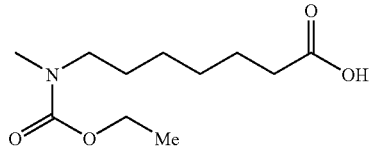 | MS(m/z): 723[M − Na]⁻ |
| 66 | 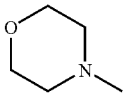 | 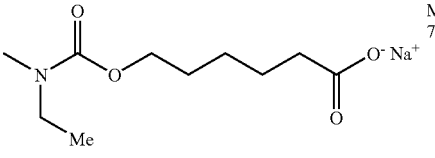 | MS(m/z): 780[M + H]⁺ |
| 67 | 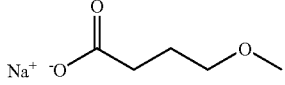 | 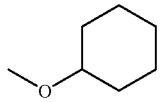 | MS(m/z): 764[M − Na]⁻ |
| 68 | 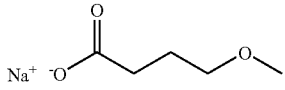 | 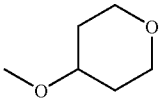 | MS(m/z): 678[M − Na]⁻ |
| 69 | 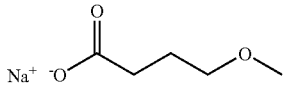 | 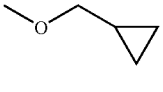 | MS(m/z): 680[M − Na]⁻ |
| 70 | 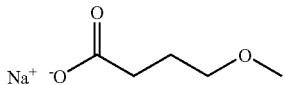 | 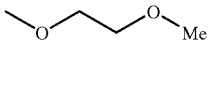 | MS(m/z): 650[M − Na]⁻ |
| 71 | | | MS(m/z): 654[M − Na]⁻ |

TABLE 1-continued

[Structure: pyrimidine with A² substituent at 5-position, N linked to CH₂-(3,5-bis-CF₃-phenyl) and CH₂-(2-R², 5-CF₃-phenyl)]

| Ex. No. | A²- | -R² | Physical properties etc. |
|---|---|---|---|
| 72 | HO-C(=O)-CH₂CH₂CH₂-O-CH₃ | 4-methylpyridin-yl | MS(m/z): 659[M + H]⁺ |
| 73 | Na⁺ ⁻O-C(=O)-CH₂CH₂CH₂-O-CH₃ | 3-methylpyridin-yl | MS(m/z): 657[M − Na]⁻ |
| 74 | HO-C(=O)-CH₂CH₂CH₂-O-CH₃ | 2-pyrrolyl (HN-) | MS(m/z): 647[M + H]⁺ |
| 75 | HO-C(=O)-CH₂CH₂CH₂-O-CH₃ | 4-(1-methylethyl)-3-methyl-2-methoxy-phenyl | MS(m/z): 730[M + H]⁺ |

Example 76

(1) 2-Fluoro-5-trifluoromethyl-benzaldehyde (5 g) and cyclopropylmethyl-propyl-amine (5.57 ml) is dissolved in toluene (50 ml), and thereto is added potassium carbonate (10.7 g) and the mixture is stirred at 120° C. overnight. The reaction solution is cooled to room temperature, and thereto are added ethyl acetate and water, and the mixture is separated, and the organic layer is washed with a saturated brine, dried over magnesium sulfate, and concentrated under reduced pressure. The resulting residue is purified by silica gel column chromatography (hexane:ethyl acetate=20:1) to give 2-(cyclopropylmethyl-propyl-amino)-5-trifluoromethyl-benzaldehyde (6.8 g). MS (m/z): 286 [M+H]⁺

(2) To ethanol (30 ml) are added 2-(cyclopropylmethyl-propyl-amino)-5-trifluoromethyl-benzaldehyde (6.8 g), hydroxylamine hydrochloride (1.66 g) and sodium acetate (1.95 g) and the mixture is stirred at room temperature overnight. Ethanol is removed by evaporating under reduced pressure and thereto is added chloroform and water, and the mixture is separated. The organic layer is washed with a saturated brine, dried over magnesium sulfate, and concentrated under reduced pressure. The resulting residue is purified by silica gel column chromatography (hexane:ethyl acetate=10:1→2:1) to give 2-(cyclopropylmethyl-propyl-amino)-5-trifluoromethyl-benzaldehyde oxime (5.78 g). MS (m/z): 301 [M+H]⁺

(3) Lithium aluminum hydride (1.4 g) is suspended in tetrahydrofuran (50 ml) and thereto is added dropwise a 2-(cyclopropylmethyl-propyl-amino)-5-trifluoromethyl-benzaldehyde oxime (5.7 g) in tetrahydrofuran (20 ml) under ice-cooling, and the mixture is stirred at room temperature overnight. To the reaction solution are added water (1.4 ml), a 2N-aqueous sodium hydroxide solution (2.8 ml) and water (2.8 ml) successively under ice-cooling, and the insoluble material is removed by filtration and the filtrate is concentrated under reduced pressure. The resulting residue is purified by NH-silica gel column chromatography (chloroform: ethyl acetate=10:1) to give (2-aminomethyl-4-trifluoromethyl-phenyl)-cyclopropylmethyl-propyl-amine as a crude product (5.1 g).

(4) The crude (2-aminomethyl-4-trifluoromethyl-phenyl)-cyclopropylmethyl-propyl-amine obtained in (3) (5.06 g) is dissolved in dioxane (25 ml), and thereto are added N-ethyl-diisopropylethylamine (9.19 ml) and 5-bromo-2-chloropyrimidine (8.48 g), and the mixture is heated under reflux for 4 hours and 20 minutes. The insoluble material is removed by filtration and the filtrate is concentrated under reduced pressure and the resulting residue is purified by silica gel column chromatography (hexane:ethyl acetate=15:1) to give (5-bromo-pyrimidin-2-yl)-[2-(cyclopropylmethyl-propyl-amino)-5-trifluoromethyl-benzyl]-amine (6.33 g). MS (m/z): 443/445 [M+H]⁺

(5) (5-Bromo-pyrimidin-2-yl)-[2-(cyclopropylmethyl-propyl-amino)-5-trifluoromethyl-benzyl]-amine (2.33 g) is dissolved in N,N-dimethylformamide (16.8 ml) and thereto is added sodium hydride (60%) (273 mg) under ice-cooling. Twenty minutes thereafter, thereto is added 3-bromomethyl-5-trifluoromethyl-benzonitrile (2.08 g) and the mixture is stirred at room temperature for 1 hour and 15 minutes. To the reaction solution are added acetic acid to consume the excess sodium hydride, and thereto are added ethyl acetate and water, and the mixture is separated. The organic layer is washed with a saturated brine, dried over magnesium sulfate, and concentrated under reduced pressure and the resulting residue is purified by silica gel column chromatography (hexane:ethyl acetate=10:1) to give 3-({(5-bromo-pyrimidin-2-yl)-[2-(cyclopropylmethyl-propyl-amino)-5-trifluoromethyl-benzyl]-amino}-methyl)-5-trifluoromethyl-benzonitrile (2.81 g). MS (m/z): 626/628 [M+H]$^+$ (6) 3-({(5-Bromo-pyrimidin-2-yl)-[2-(cyclopropylmethyl-propyl-amino)-5-trifluoromethyl-benzyl]-amino}-methyl)-5-trifluoromethyl-benzonitrile (2.81 g) is dissolved in dimethylsulfoxide (12.6 ml) and the mixture is degassed under reduced pressure and flushed with nitrogen gas. Thereto are added potassium acetate (1.32 g), bis(pinacolato) diboron (2.88 g) and [1,1'-bis(diphenylphosphino)ferrocene] dichloropalladium methylene chloride complex (732 mg) and the mixture is heated at 80° C. under nitrogen atmosphere and stirred for 1 hour and 40 minutes. The reaction solution is cooled to room temperature and thereto are added water and ethyl acetate, and the mixture is separated, and the organic layer is washed with a saturated brine, dried over sodium sulfate and concentrated under reduced pressure. The resulting residue is dissolved in tetrahydrofuran (26 ml) and thereto is added dropwise a 30% aqueous hydrogen peroxide solution (15.7 ml) under ice-cooling. Two hours thereafter, thereto is added a saturated aqueous sodium thiosulfate under ice-cooling to consume the excess hydrogen peroxide, and thereto are added water and ethyl acetate, and the mixture is separated. The organic layer is washed with a saturated brine, dried over sodium sulfate and concentrated under reduced pressure. The resulting residue is purified by silica gel column chromatography (hexane:ethyl acetate=4:1) to give 3-{[[2-(cyclopropylmethyl-propyl-amino)-5-trifluoromethyl-benzyl]-(5-hydroxy-pyrimidin-2-yl)-amino]-methyl}-5-trifluoromethyl-benzonitrile (1.94 g). MS (m/z): 564 [M+H]$^+$.

(7) Ethyl 3-{[[2-(cyclopropylmethyl-propyl-amino)-5-trifluoromethyl-benzyl]-(5-hydroxy-pyrimidin-2-yl)-amino]-methyl}-5-trifluoromethyl-benzonitrile (250 mg) and 4-bromobutyrate (76.9 µl) is dissolved in N,N-dimethylformamide (3.7 ml) and thereto is added potassium carbonate (74 mg) and the mixture is stirred at room temperature overnight. Thereto are added ethyl acetate and a saturated brine, and the mixture is separated, and the organic layer is washed with a saturated brine, dried and concentrated under reduced pressure. The resulting residue is purified by NH-silica gel column chromatography (hexane:ethyl acetate=8:1) to give ethyl 4-(2-{(3-cyano-5-trifluoromethyl-benzyl)-[2-(cyclopropylmethyl-propyl-amino)-5-trifluoromethyl-benzyl]-amino}-pyrimidin-5-yloxy)-butyrate (220 mg). MS (m/z): 678 [M+H]$^+$ (8) Ethyl 4-(2-{(3-cyano-5-trifluoromethyl-benzyl)-[2-(cyclopropylmethyl-propyl-amino)-5-trifluoromethyl-benzyl]-amino}-pyrimidin-5-yloxy)-butyrate (240 mg) is dissolved in tetrahydrofuran (2.6 ml), and thereto is added 1N-aqueous sodium hydroxide solution (2.6 ml) and the mixture is stirred at 40° C. for additional 30 minutes and warmed to 50° C. and stirred for 3 hours. Thereto is added a 2N-aqueous sodium hydroxide solution (650 µl) and the mixture is stirred at 60° C. for 20 minutes. The reaction solution is cooled to room temperature and thereto are added ethyl acetate and a 1N-hydrochloric acid, and the mixture is separated, and the organic layer is washed with a saturated brine, dried over sodium sulfate and concentrated under reduced pressure. The resulting residue is purified by silica gel column chromatography (chloroform:methanol=19:1) to give 4-(2-{(3-cyano-5-trifluoromethyl-benzyl)-[2-(cyclopropylmethyl-propyl-amino)-5-trifluoromethyl-benzyl]-amino}-pyrimidin-5-yloxy)-butyric acid (189 mg). MS (m/z): 650 [M+H]$^+$ Example 77

The corresponding starting compound is treated in a similar manner to Example 76 to give the compounds as listed in Table 2.

TABLE 2

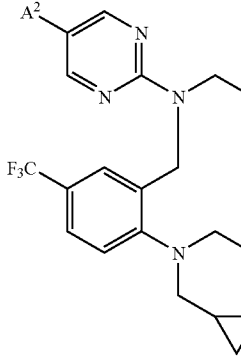

| Ex. No. | A$^2$- | Physical properties etc. |
|---|---|---|
| 76 | 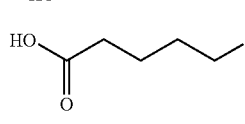 | MS(m/z): 650[M + H]$^+$ |
| 77 | | MS(m/z): 664[M + H]$^+$ |

Example 78

(1) {2-[(3,5-Bis-trifluoromethyl-benzylamino)-methyl]-4-trifluoromethyl-phenyl}-butyl-ethyl-amine (2.0 g), 4,6-dichloropyrimidine (1.19 g) and N-ethyldiisopropylamine (2.09 ml) are dissolved in toluene (10 ml) and the mixture is heated under reflux for 3 hours. The reaction solution is cooled to room temperature, and thereto are added ethyl acetate and water, and the mixture is separated, and the organic layer is washed with a saturated brine, dried over magnesium sulfate, and concentrated under reduced pressure. The resulting residue is purified by silica gel column chromatography (hexane:ethyl acetate=19:1→17:3) to give (3,5-bis-trifluoromethyl-benzyl)-[2-(butyl-ethyl-amino)-5-trifluoromethyl-benzyl]-(6-chloropyrimidin-4-yl)-amine (1.8 g). MS (m/z): 613 [M+H]$^+$ (2) (3,5-Bis-trifluoromethyl-benzyl)-[2-(butyl-ethyl-amino)-5-trifluoromethyl-benzyl]-(6-chloropyrimidin-4-yl)-amine (300 mg) is dissolved in toluene (5 ml), and thereto are added 3-aminopropionic acid tert-butyl ester hydrochloride (888 mg) and N-ethyldiisopropylamine (1.7 ml), and the mixture is stirred at 120° C. overnight. To the reaction solution are added ethyl acetate and a 1N-hydrochloric acid, and the mixture is separated. The organic layer is washed with a saturated brine, dried over magnesium sulfate, and concentrated under reduced pressure. The resulting residue is purified by column chromatography (hexane:ethyl acetate=9:1→3:1) to give tert-butyl 3-(6-{(3,5-bis-trifluoromethyl-benzyl)-[2-(butyl-ethyl-amino)-5-trifluoromethyl-benzyl]-amino}-pyrimidin-4-ylamino)-propionate (70 mg). MS (m/z): 722 [M+H]$^+$ (3) Tert-butyl 3-(6-{(3,5-bis-trifluoromethyl-benzyl)-[2-(butyl-ethyl-amino)-5-trifluoromethyl-benzyl]-amino}-pyrimidin-4-ylamino)-propionate (60 mg) is dissolved in a 4N-hydrochloric acid in ethyl acetate (0.5 ml) and the mixture is stirred at room temperature for 1.5 hours. To the reaction solution are added ethyl acetate and water, and followed by a further addition of a saturated aqueous sodium bicarbonate solution to make the pH of aqueous layer to be about 4, and the mixture is separated. The organic layer is washed with a saturated brine, dried over magnesium sulfate and the mixture is concentrated under reduced pressure to give 3-(6-{(3,5-bis-trifluoromethyl-benzyl)-[2-(butyl-ethyl-amino)-5-trifluoromethyl-benzyl]-amino}-pyrimidin-4-ylamino)-propionic acid (57 mg). MS (m/z): 666 [M+H]+

Examples 79 to 83

The corresponding starting compounds are treated in a similar manner to Example 78(2) to give the compounds as listed in Table 3.

TABLE 3

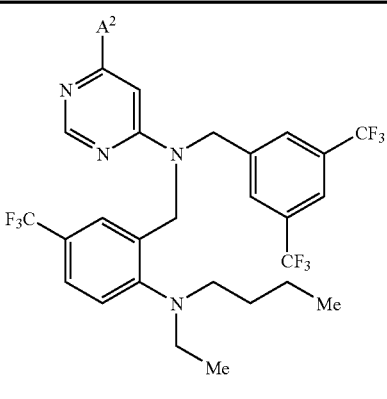

| Ex. No. | A²- | Physical properties etc. |
|---|---|---|
| 78 | HO-C(=O)-CH₂CH₂-NH-CH₂- | MS(m/z): 666[M + H]+ |
| 79 | HO-CH₂CH₂-NH-CH₂- | MS(m/z): 638[M + H]+ |
| 80 | HO-CH₂CH₂CH₂-NH-CH₂- | MS(m/z): 652[M + H]+ |
| 81 | HO-CH₂CH₂-N(Me)-CH₂- | MS(m/z): 652[M + H]+ |
| 82 | Me-O-CH₂CH₂-N(Mr)-CH₂- | MS(m/z): 666[M + H]+ |
| 83 | Me-N(Me)-CH₂CH₂-N(Me)-CH₂- | MS(m/z): 679[M + H]+ |

Example 84

(1) 3,5-Bis-trifluoromethylbenzaldehyde (3.00 g) is dissolved in 1,2-dichloroethane (50 ml), and thereto are added 70% aqueous ethylamine solution (0.80 ml) and acetic acid (2.1 ml), followed by an addition of triacetoxy-sodium borohydride (13.1 µg) at room temperature over 1 hour with stirring. The mixture is stirred at room temperature for additional 30 minutes, and to the reaction mixture is then added a saturated aqueous sodium bicarbonate solution, and the mixture is extracted with ethyl acetate. The organic layer is washed successively with a saturated aqueous sodium bicarbonate solution and a saturated brine, dried over magnesium sulfate, and concentrated under reduced pressure. The resulting residue is purified by silica gel column chromatography (hexane ethyl acetate=4:1) to give (3,5-bis-trifluoromethyl-benzyl)-ethyl-amine (1.52 g). MS (m/z): 272 [M+H]+

(2) (3,5-Bis-trifluoromethyl-benzyl)-ethyl-amine (1.03 g) is dissolved in N,N-dimethylformamide (10 ml), and thereto are added 2-fluoro-5-trifluoromethyl-benzaldehyde (1.45 g) and potassium carbonate (1.48 g), and the mixture is stirred under nitrogen atmosphere at 90° C. for 3 hours and at room temperature overnight. To reaction mixture is added a saturated brine and water, and the mixture is extracted five times with ethyl acetate and the organic layer is washed twice with a saturated brine, dried over magnesium sulfate, and concentrated under reduced pressure. The resulting residue is purified by silica gel column chromatography (hexane:ethyl acetate=10:1) to give 2-[(3,5-bis-trifluoromethyl-benzyl)-ethyl-amino]-5-trifluoromethyl-benzaldehyde (282 mg). MS (m/z): 444 [M+H]+

(3) 2-[(3,5-Bis-trifluoromethyl-benzyl)-ethyl-amino]-5-trifluoromethyl-benzaldehyde (275 mg) is dissolved in ethanol (2.5 ml) and thereto are added hydroxylammonium chloride (86 mg) and sodium acetate (102 mg), and the mixture is stirred at 60° C. under nitrogen atmosphere for 1 hour and a half. To the reaction solution are added a saturated brine and water, and the mixture is extracted with ethyl acetate, and the organic layer is washed with a saturated brine, dried over magnesium sulfate, and concentrated under reduced pressure. The resulting residue is purified by silica gel column chromatography (hexane:ethyl acetate=24:1→83:17) to give 2-[(3,5-bis-trifluoromethyl-benzyl)-ethyl-amino]-5-trifluoromethyl-benzaldehydeoxime (244 mg). MS (m/z): 459 [M+H]+

(4) 2-[(3,5-Bis-trifluoromethyl-benzyl)-ethyl-amino]-5-trifluoromethyl-benzaldehyde oxime (241 mg) is dissolved in methanol (10 ml) and thereto is added Raney nickel (0.5 g) and the mixture is stirred under hydrogen atmosphere at room temperature overnight. Raney nickel is removed by filtration and the filtrate is concentrated under reduced pressure. The resulting residue is purified by silica gel column chromatography (hexane:ethyl acetate=1:0→0:1) to give (2-aminomethyl-4-trifluoromethyl-phenyl)-(3,5-bis-trifluoromethyl-benzyl)-ethyl-amine (210 mg). MS (m/z): 445 [M+H]+

(5) (2-Aminomethyl-4-trifluoromethyl-phenyl)-(3,5-bis-trifluoromethyl-benzyl)-ethyl-amine (165 mg) is dissolved in toluene (3 ml) and thereto are added tert-butyl 4-(2-chloropyrimidin-5-yloxy)-butyrate (202 mg), tris(dibenzylideneacetone)dipalladium(0) (68 mg), (±)-2,2'-bis(diphenylphosphino)-1,1'-binaphthalene (92 mg) and sodium tert-butoxide (71 mg), and the mixture is stirred under nitrogen flow at 80° C. for 5 hours. To the reaction mixture is added a saturated brine, and the mixture is extracted with ethyl acetate. The organic layer is washed with a saturated brine, dried over magnesium sulfate, and concentrated under reduced pressure. The resulting residue is purified by NH-silica gel column chromatography (hexane:ethyl acetate=7:1) to give tert-butyl 4-(2-{2-[(3,5-bis-trifluoromethyl-benzyl)-ethyl-amino]-5-trifluoromethyl-benzylamino}-pyrimidin-5-yloxy)-butyrate (73 mg). MS (m/z): 681 [M+H]+

(6) To tert-butyl 4-(2-{2-[(3,5-bis-trifluoromethyl-benzyl)-ethyl-amino]-5-trifluoromethyl-benzylamino}-pyrimidin-5-yloxy)-butyrate (84 mg) is added a 4N-hydrochloric acid in dioxane (1.5 ml), and the mixture is stirred at room temperature for 1 hour. The reaction mixture is neutralized with a saturated aqueous sodium bicarbonate solution and made weakly acidic with 10% aqueous citric acid solution, and the mixture is extracted with ethyl acetate. The organic layer is washed with a saturated brine, dried over magnesium sulfate, and concentrated under reduced pressure. The resulting residue is purified by silica gel column chromatography (chloroform:methanol=19:1) to give 4-(2-{2-[(3,5-bis-trifluoromethyl-benzyl)-ethyl-amino]-5-trifluoromethyl-benzylamino}-pyrimidin-5-yloxy)-butyric acid (47 mg). MS (m/z): 625 [M+H]+ with diethylether. The organic layer is washed with a saturated brine, dried over magnesium sulfate, and concentrated under reduced pressure. The resulting residue is purified by silica gel column chromatography (hexane:ethyl acetate=4:1→3:2) to give 1-[2-(cyclopropylmethyl-propyl-amino)-5-trifluoromethyl-phenyl]-ethanol (5.43 g). MS (m/z): 302 [M+H]+

(3) 1-[2-(Cyclopropylmethyl-propyl-amino)-5-trifluoromethyl-phenyl]-ethanol (500 mg) is dissolved in methylene chloride (5 ml) and thereto is added thionyl chloride (133 µl) under ice-cooling and the mixture is stirred at room temperature for 15 minutes. To the reaction solution are added methylene chloride and a saturated aqueous sodium bicarbonate solution, and the mixture is separated, and the organic layer is washed with a saturated brine, dried over magnesium sulfate, and concentrated under reduced pressure. The resulting residue and ethyl 4-[2-(3,5-bis-trifluoromethyl-benzylamino)-pyrimidin-5-yloxy]-butyrate (749 mg) are dissolved in N,N-dimethylformamide (5 ml) and thereto is added sodium hydride (62%) (64 mg) under ice-cooling and the mixture is stirred for 1 hour. Thereto are added water and ethyl acetate, and the mixture is separated, and the organic layer is washed with a saturated brine, dried over magnesium sulfate, and

TABLE 4

| Ex. No. | Structural formula | Physical properties etc. |
| --- | --- | --- |
| 84 | 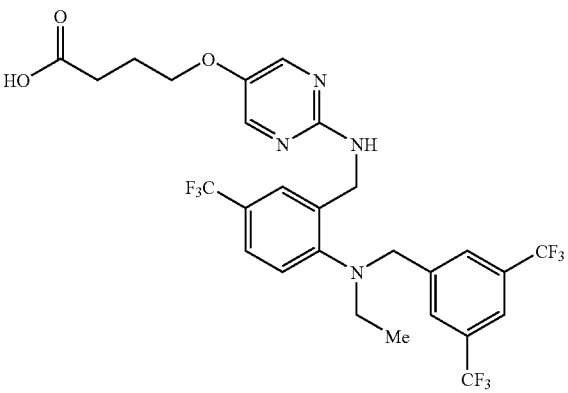 | MS(m/z):<br>625[M + H]+ |

Example 85

(1) 2-Fluoro-5-trifluoromethyl-benzaldehyde (5.38 g) and cyclopropylmethyl-propyl-amine (4.75 g) are dissolved in toluene (50 ml), and thereto is added potassium carbonate (11.6 g) and the mixture is stirred at 120° C. for 4 hours. The reaction solution is cooled to room temperature, and thereto is added water and the mixture is separated, and the organic layer is washed with a saturated brine, dried over magnesium sulfate, and concentrated under reduced pressure. The resulting residue is purified by silica gel column chromatography (hexane:ethyl acetate=19:1→4:1) to give 2-(cyclopropylmethyl-propyl-amino)-5-trifluoromethyl-benzaldehyde (8.0 g). MS (m/z): 286 [M+H]+

(2) 2-(Cyclopropylmethyl-propyl-amino)-5-trifluoromethyl-benzaldehyde (6.0 g) is dissolved in diethylether (50 ml) and thereto is added a 2M methyl magnesium bromide in diethylether (7.35 ml) under nitrogen flow at −70° C. The mixture is stirred at the same temperature for 30 minutes, and the reaction solution is quenched with a saturated aqueous ammonium chloride solution and the mixture is extracted concentrated under reduced pressure. The resulting residue is with a saturated brine, dried over magnesium sulfate, and purified by silica gel column chromatography (hexane:ethyl acetate=9:14:1) to give ethyl 4-[2-((3,5-bis-trifluoromethyl-benzyl)-{1-[2-(cyclopropylmethyl-propyl-amino)-5-trifluoromethyl-phenyl]-ethyl}-amino)-pyrimidin-5-yloxy]-butyrate (144 mg) as a crude product. The resulting ester is dissolved in ethanol (2 ml) and thereto is added a 2N-aqueous sodium hydroxide solution (500 µl) and the mixture is stirred at room temperature for 2 hours and concentrated under reduced pressure. To the residue is added ethyl acetate and a dilute hydrochloric acid and the mixture is separated, and the organic layer is washed with a saturated brine, dried over magnesium sulfate, and concentrated under reduced pressure. The resulting residue is purified by silica gel column chromatography (chloroform:methanol=1:0→24:1) to give 4-[2-((3,5-bis-trifluoromethyl-benzyl)-{1-[2-(cyclopropylmethyl-propyl-amino)-5-trifluoromethyl-phenyl]-ethyl}-amino)-pyrimidin-5-yloxy]-butyric acid (11 mg). MS (m/z): 707 [M+H]+

Example 86

1-[2-(Cyclopropylmethyl-propyl-amino)-5-trifluoromethyl-phenyl]-ethanol (1.0 g) is dissolved in methylene chloride (10 ml) and thereto is added thionyl chloride (266 µl) under ice-cooling, and the mixture is stirred for 30 minutes and concentrated under reduced pressure. (3,5-bis-trifluoromethyl-benzyl)-(5-bromo-pyrimidin-2-yl)-amine (1.33 g) is dissolved in N,N-dimethylformamide (5 ml) and thereto is added sodium hydride (62%) (142 mg) under ice-cooling, and the mixture is stirred for 15 minutes. Thereto are added a solution of a residue obtained above in N,N-dimethylformamide (5 ml) and the mixture is stirred at room temperature overnight. To the reaction solution are added water and diethyl ether, and the mixture is separated, and the organic layer is washed with a saturated brine, dried over magnesium sulfate, and concentrated under reduced pressure. The resulting residue is purified by silica gel column chromatography (hexane:ethyl acetate=1:0→49:1) to give (3,5-bis-trifluoromethyl-benzyl)-(5-bromo-pyrimidin-2-yl)-{1-[2-(cyclopropylmethyl-propyl-amino)-5-trifluoromethyl-phenyl]-ethyl}-amine (816 mg). MS (m/z): 683/685 [M+H]+

Example 87

(1) (3,5-Bis-trifluoromethyl-benzyl)-(5-bromo-pyrimidin-2-yl)-{1-[2-(cyclopropylmethyl-propyl-amino)-5-trifluoromethyl-phenyl]-ethyl}-amine (200 mg) is dissolved in toluene (3 ml), and thereto are added tris(dibenzylideneacetone)dipalladium (27 mg), sodium tert-butoxide (42 mg), 2-(di-tert-butylphosphino)biphenyl (35 mg) and ethyl piperidine-4-carboxylate (66 µl) and the mixture is stirred at room temperature under nitrogen flow overnight. To the reaction solution are added a saturated brine, and the mixture is extracted with ethyl acetate. The organic layer is washed with a saturated brine, dried over magnesium sulfate, and concentrated under reduced pressure. The resulting residue is purified by column chromatography (hexane:ethyl acetate=19:1→21:4) to give ethyl 1-[2-((3,5-bis-trifluoromethyl-benzyl)-{1-[2-(cyclopropylmethyl-propyl-amino)-5-trifluoromethyl-phenyl]-ethyl}-amino)-pyrimidin-5-yl]-piperidine-4-carboxylate (78 mg). MS (m/z): 760 [M+H]+

(2) Ethyl 1-[2-((3,5-bis-trifluoromethyl-benzyl)-{1-[2-(cyclopropylmethyl-propyl-amino)-5-trifluoromethyl-phenyl]-ethyl}-amino)-pyrimidin-5-yl]-piperidine-4-carboxylate (75 mg) is dissolved in ethanol (1 ml), and thereto is added a 2N-aqueous sodium hydroxide solution (148 µl), and the mixture is stirred at room temperature overnight. Thereto are added ethyl acetate and a dilute hydrochloric acid and the mixture is separated, and the organic layer is washed with a saturated brine, dried over magnesium sulfate, and concentrated under reduced pressure. The resulting residue is purified by silica gel column chromatography (chloroform:methanol=1:0→49:1) to give 1-[2-((3,5-bis-trifluoromethyl-benzyl)-{1-[2-(cyclopropylmethyl-propyl-amino)-5-trifluoromethyl-phenyl]-ethyl}-amino)-pyrimidin-5-yl]-piperidine-4-carboxylic acid (54 mg). MS (m/z): 732 [M+H]+

TABLE 5

| Ex. No. | A²- | Physical properties etc. |
|---|---|---|
| 85 | (structure: HO-C(=O)-CH2CH2-O-CH3) | MS(m/z): 707[M + H]+ |
| 86 | Br— | MS(m/z): 683/685 [M + H]+ |
| 87 | (structure: HO-C(=O)-piperidine-N-Me) | MS(m/z): 732[M + H]+ |

Example 88

(1) 2-(Butyl-ethyl-amino)-5-trifluoromethyl-benzaldehyde (1.72 g) is dissolved in a mixed solvent of tert-butanol (8 ml) and water (2 ml), and thereto are added 2-methyl-2-butene (4 ml), sodium dihydrogenphosphate dihydrate (1.37 g) and sodium chlorite (1.82 g) under ice-cooling, and the mixture is stirred for 2 hours. Thereto are added ethyl acetate and a 1N-hydrochloric acid and the mixture is separated, and the organic layer is washed with a saturated brine, dried over magnesium sulfate, and concentrated under reduced pressure. The resulting residue is purified by silica gel column chromatography (chloroform:methanol=1:0→9:1) to give 2-(butyl-ethyl-amino)-5-trifluoromethyl-benzoic acid (1.29 mg). MS (m/z): 290 [M+H]+

(2) 2-(Butyl-ethyl-amino)-5-trifluoromethyl-benzoic acid (1.28 g) is dissolved in methylene chloride (10 ml) and thereto are added oxalyl chloride (578 µl) and a catalytic amount of N,N-dimethylformamide under ice-cooling, and the mixture is stirred for 30 minutes and evaporated under reduced pressure to dryness. The resulting residue is dissolved in methylene chloride (10 ml) again and thereto are added dropwise a solution of (3,5-bis-trifluoromethyl-benzyl)-(5-bromopyrimidin-2-yl)-amine (1.77 g) and triethylamine (924 µl) under ice-cooling. The reaction solution is stirred at room temperature overnight and the mixture is washed with a 1N-hydrochloric acid and a saturated brine, dried over magnesium sulfate, and concentrated under reduced pressure. The resulting residue is purified by silica gel column chromatography (chloroform:methanol=1:0→9:1) to give N-(3,5-bis-trifluoromethyl-benzyl)-N-(5-bromo-pyrimidin-2-yl)-2-(butyl-ethyl-amino)-5-trifluoromethylbenzamide (842 mg). MS (m/z): 671/673 [M+H]$^+$

TABLE 6

| Ex. No. | Structural formula | Physical properties etc. |
|---|---|---|
| 88 | (structure) | MS(m/z): 671/673[M + H]$^+$ |

Examples 89 to 90

The corresponding starting compounds are treated in a similar manner to any of the above Examples to give the compounds as listed in Table 7.

TABLE 7

| Ex. No. | Structural formula | Physical properties etc. |
|---|---|---|
| 89 | (structure) | MS(m/z): 643/645 [M + H]$^+$ |
| 90 | (structure) | MS(m/z): 501[M + H]$^+$ |

Examples 91 to 102

The corresponding starting compounds are treated in a similar manner to Example 26 to give the compounds as listed in Table 8.

TABLE 8

| Ex. No. | A²- | -R² | Physical properties etc. |
|---|---|---|---|
| 91 | HOOC-CH2CH2CH2-OMe | 2-OMe-phenyl | MS(m/z): 688 [M + H]⁺ |
| 92 | HOOC-CH2CH2CH2-OMe | 5-Me-2,4-dimethoxypyrimidin-? | MS(m/z): 720 [M + H]⁺ |
| 93 | HOOC-CH2CH2CH2-OMe | 2-Cl-3-Me-pyridin-? | MS(m/z): 693/695 [M + H]⁺ |
| 94 | Na⁺ ⁻OOC-CH2CH2CH2-OMe | 3-(1-methylethyl)phenyl | MS(m/z): 698 [M − Na]⁻ |
| 95 | Na⁺ ⁻OOC-CH2CH2CH2-OMe | 3-Me-2,6-dimethoxypyridin-? | MS(m/z): 717 [M − Na]⁻ |
| 96 | HOOC-CH2CH2CH2-OMe | 2,5-dimethoxy-3-methylphenyl | MS(m/z): 718 [M + H]⁺ |
| 97 | HOOC-CH2CH2CH2-OMe | 3,5-dimethylphenyl | MS(m/z): 686 [M + H]⁺ |
| 98 | HOOC-CH2CH2CH2-OMe | 3-CN-phenyl | MS(m/z): 683 [M + H]⁺ |
| 99 | Na⁺ ⁻OOC-CH2CH2CH2-OMe | 3-(N,N-dimethylamino)phenyl | MS(m/z): 699 [M − Na]⁻ |

TABLE 8-continued

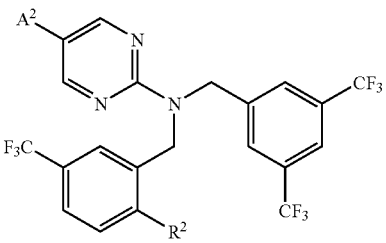

| Ex. No. | A²- | -R² | Physical properties etc. |
|---|---|---|---|
| 100 | HO-C(O)-CH₂CH₂CH₂-O-CH₃ | 5-methyl-2-(OMe)-pyrimidin-yl | MS(m/z): 690 [M + H]⁺ |
| 101 | Na⁺ ⁻O-C(O)-CH₂CH₂CH₂-O-CH₃ | 2-methyl-3,6-dimethoxyphenyl (OMe, MeO) | MS(m/z): 716 [M − Na]⁻ |
| 102 | Na⁺ ⁻O-C(O)-CH₂CH₂CH₂-O-CH₃ | 3-methyl-2-methoxy-pyridinyl (MeO, N) | MS(m/z): 687 [M − Na]⁻ |

Example 103

(1) Ethyl 4-{2-[(3,5-bis-trifluoromethyl-benzyl)-(2-trifluoro-methanesulfonyloxy-5-trifluoromethyl-benzyl)-amino]-pyrimidin-5-yloxy}-butyrate (1.0 g) is dissolved in 1,4-dioxane (10 ml) and thereto are added [1,1'-bis(diphenylphosphino)ferrocene]dichloropalladium dichloromethane complex (216 mg), bis(pinacolato)diboron (670 mg) and potassium acetate (389 mg), and the mixture is stirred under nitrogen atmosphere at 80° C. overnight. The reaction solution is cooled to room temperature, and thereto are added ethyl acetate and water, and the mixture is separated, and the organic layer is washed with a saturated brine, dried over magnesium sulfate, and concentrated under reduced pressure. The resulting residue is purified by silica gel column chromatography (hexane:ethyl acetate=19:1→4:1) to give ethyl 4-(2-{(3,5-bis-trifluoromethyl-benzyl)-[2-(4,4,5,5-tetramethyl-[1,3,2]dioxaborolan-2-yl)-5-trifluoromethyl-benzyl]-amino}-pyrimidin-5-yloxy)-butyrate (805 mg). MS (m/z): 736[M+H]⁺

(2) Ethyl 4-(2-{(3,5-bis-trifluoromethyl-benzyl)-[2-(4,4,5,5-tetramethyl-[1,3,2]dioxaborolan-2-yl)-5-trifluoromethyl-benzyl]-amino}-pyrimidin-5-yloxy)-butyrate (200 mg) is dissolved in 1,4-dioxane (4 ml) and thereto are added 2-bromo-4-methyl-pyridine (70 mg), [1,1'-bis(diphenylphosphino)ferrocene]dichloropalladium dichloromethane complex (22 mg) and cesium carbonate (133 mg), and the mixture is stirred under nitrogen atmosphere at 80° C. for 5 days. The reaction solution is cooled to room temperature, and thereto are added ethyl acetate and water, and the mixture is separated, and the organic layer is washed with a saturated brine, dried over magnesium sulfate, and concentrated under reduced pressure. The resulting residue is purified by NH- silica gel column chromatography (hexane:ethyl acetate=19:1→14:1) to give ethyl 4-(2-{(3,5-bis-trifluoromethyl-benzyl)-[2-(4-methyl-pyridin-2-yl)-5-trifluoromethyl-benzyl]-amino}-pyrimidin-5-yloxy)-butyrate (85 mg). MS (m/z): 701 [M+H]⁺

(3) Ethyl 4-(2-{(3,5-bis-trifluoromethyl-benzyl)-[2-(4-methyl-pyridin-2-yl)-5-trifluoromethyl-benzyl]-amino}-pyrimidin-5-yloxy)-butyrate (85 mg) is dissolved in ethanol (4 ml), and thereto is added 1N-aqueous sodium hydroxide solution (1 ml) and the mixture is stirred at room temperature for 45 minutes. To the reaction solution are added a 1N-hydrochloric acid and ethyl acetate, and the mixture is separated, and the organic layer is washed with a saturated brine, dried over magnesium sulfate, and concentrated under reduced pressure. The resulting residue is purified by silica gel column chromatography (chloroform:methanol=1:0→23:2) to give 4-(2-{(3,5-bis-trifluoromethyl-benzyl)-[2-(4-methylpyridin-2-yl)-5-trifluoromethyl-benzyl]-amino}-pyrimidin-5-yloxy)-butyric acid (68 mg). The resulting carboxylic acid is dissolved in ethanol (1 ml), and thereto is added 1N-aqueous sodium hydroxide solution (101 µl), and the reaction solution is concentrated under reduced pressure to give 4-(2-{(3,5-bis-trifluoromethyl-benzyl)-[2-(4-methyl-pyridin-2-yl)-5-trifluoromethyl-benzyl]-amino}-pyrimidin-5-yloxy)-butyric acid sodium salt (69 mg). MS (m/z): 671 [M−Na]⁻

Examples 104 to 112

The corresponding starting compounds are treated in a similar manner to Example 103 to give the compounds as listed in Table 9.

TABLE 9

| Ex. No. | A² - | -R² | Physical properties etc. |
|---|---|---|---|
| 103 | Na⁺ ⁻O-C(=O)-CH₂CH₂CH₂-O-Me | 2,4-dimethylpyridinyl (Me, Me on pyridine) | MS(m/z): 671 [M − Na]⁻ |
| 104 | Na⁺ ⁻O-C(=O)-CH₂CH₂CH₂-O-Me | 3-OMe-phenyl (Me) | MS(m/z): 686 [M − Na]⁻ |
| 105 | Na⁺ ⁻O-C(=O)-CH₂CH₂CH₂-O-Me | 2,6-dimethylpyridinyl | MS(m/z): 671 [M − Na]⁻ |
| 106 | Na⁺ ⁻O-C(=O)-CH₂CH₂CH₂-O-Me | 4-Me-5-OMe-2-SMe-pyrimidinyl | MS(m/z): 734 [M − Na]⁻ |
| 107 | Na⁺ ⁻O-C(=O)-CH₂CH₂CH₂-O-Me | 4,6-dimethyl-2-isopropyl-pyrimidinyl | MS(m/z): 714 [M − Na]⁻ |
| 108 | Na⁺ ⁻O-C(=O)-CH₂CH₂CH₂-O-Me | 4-Me-2,6-diOMe-pyrimidinyl | MS(m/z): 718 [M − Na]⁻ |
| 109 | Na⁺ ⁻O-C(=O)-CH₂CH₂CH₂-O-Me | 2-Me-4,6-diOMe-pyrimidinyl | MS(m/z): 718 [M − Na]⁻ |
| 110 | HO-C(=O)-CH₂CH₂CH₂-O-Me | 5-Me-4,6-diOMe-pyrimidinyl | MS(m/z): 720 [M + H]⁺ |
| 111 | Na⁺ ⁻O-C(=O)-CH₂CH₂CH₂-O-Me | 3,5-diOMe-phenyl (Me) | MS(m/z): 716 [M − Na]⁻ |

TABLE 9-continued

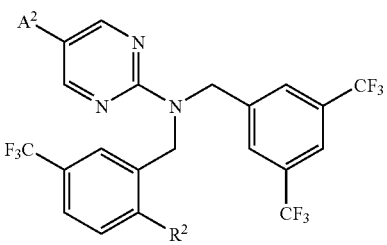

| Ex. No. | A²- | -R² | Physical properties etc. |
|---|---|---|---|
| 112 | Na⁺ ⁻O−C(O)−CH₂CH₂CH₂−O−CH₃ (sodium 4-methoxybutanoate) | CH₂ group attached to 6-methyl-3-methoxy-pyridin-2-yl with =CH₂ (methylidene) at Me position | MS(m/z): 727 [M − Na]⁻ |

Example 113

(1) Trifluoromethanesulfonic acid 2-{[(3,5-bis-trifluoromethyl-benzyl)-(5-morpholin-4-yl-pyrimidin-2-yl)-amino]-methyl}-4-trifluoromethyl-phenyl ester (1.19 g) is dissolved in 1,4-dioxane (10 ml) and thereto are added [1,1'-bis(diphenylphosphino)ferrocene]dichloropalladium dichloromethane complex (273 mg), bis(pinacolato)diboron (848 mg) and potassium acetate (492 mg), and the mixture is stirred under nitrogen atmosphere at 80° C. overnight. The reaction solution is cooled to room temperature, and thereto are added water and ethyl acetate and the insoluble materials are removed by filtration through Celite™. The filtrate is separated, and the organic layer is washed with a saturated brine, dried over magnesium sulfate, and concentrated under reduced pressure. The resulting residue is purified by silica gel column chromatography (hexane:ethyl acetate=9:1→7:3) to give (3,5-bis-trifluoromethyl-benzyl)-(5-morpholin-4-yl-pyrimidin-2-yl)-[2-(4,4,5,5-tetramethyl-[1,3,2]dioxaborolan-2-yl)-5-trifluoromethyl-benzyl]-amine (648 mg). MS (m/z): 691 [M+H]⁺

(2) (3,5-Bis-trifluoromethyl-benzyl)-(5-morpholin-4-yl-pyrimidin-2-yl)-[2-(4,4,5,5-tetramethyl-[1,3,2]dioxaborolan-2-yl)-5-trifluoromethyl-benzyl]-amine (250 mg) is dissolved in 1,4-dioxane (5 ml) and thereto are added ethyl 4-chloro-2-trifluoromethyl-pyrimidine-5-carboxylate (140 mg), [1,1'-bis(diphenylphosphino)ferrocene]dichloropalladium dichloromethane complex (30 mg) and cesium carbonate (177 mg), and the mixture is stirred under nitrogen atmosphere at 80° C. overnight. The reaction solution is cooled to room temperature, and thereto are added water and ethyl acetate and the insoluble materials are removed by filtration through Celite™. The filtrate is separated, and the organic layer is washed with a saturated brine, dried over magnesium sulfate, and concentrated under reduced pressure. The resulting residue is purified by silica gel column chromatography (hexane:ethyl acetate=9:1→4:1) to give ethyl 4-(2-{[(3,5-bis-trifluoromethyl-benzyl)-(5-morpholin-4-yl-pyrimidin-2-yl)-amino]-methyl}-4-trifluoromethyl-phenyl)-2-trifluoromethyl-pyrimidine-5-carboxylate (199 mg). MS (m/z): 783 [M+H]⁺

(3) Ethyl 4-(2-{[(3,5-bis-trifluoromethyl-benzyl)-(5-morpholin-4-yl-pyrimidin-2-yl)-amino]-methyl}-4-trifluoromethyl-phenyl)-2-trifluoromethyl-pyrimidine-5-carboxylate (194 mg) is dissolved in ethanol (4 ml), and thereto is added 1N-aqueous sodium hydroxide solution (1 ml) and the mixture is stirred at room temperature for 2 hours. To the reaction solution are added a 1N-hydrochloric acid and ethyl acetate, and the mixture is separated, and the organic layer is washed with a saturated brine, dried over magnesium sulfate, and concentrated under reduced pressure. The resulting residue is purified by silica gel column chromatography (chloroform:methanol=1:0→7:3) to give 4-(2-{[(3,5-bis-trifluoromethyl-benzyl)-(5-morpholin-4-yl-pyrimidin-2-yl)-amino]-methyl}-4-trifluoromethyl-phenyl)-2-trifluoromethyl-pyrimidine-5-carboxylic acid (165 mg). MS (m/z): 755 [M+H]⁺

Example 114

(1) Ethyl 4-(2-{(3,5-bis-trifluoromethyl-benzyl)-[2-(4,4,5,5-tetramethyl-[1,3,2]dioxaborolan-2-yl)-5-trifluoromethyl-benzyl]-amino}-pyrimidin-5-yloxy)-butyrate (300 mg) is dissolved in 1,4-dioxane (5 ml) and thereto are added 4-chloro-5-methoxy-2-methylsulfanyl-pyrimidine (117 mg), [1,1'-bis(diphenylphosphino)ferrocene]dichloropalladium dichloromethane complex (33 mg) and cesium carbonate (199 mg), and the mixture is stirred under nitrogen atmosphere at 80° C. overnight. The reaction solution is cooled to room temperature, and thereto are added chloroform and water, and the insoluble materials are removed by filtration through Celite™. The filtrate is separated, and the organic layer is dried and concentrated under reduced pressure. The resulting residue is purified by silica gel column chromatography (hexane:ethyl acetate=9:1→7:3) to give ethyl 4-(2-{(3,5-bis-trifluoromethyl-benzyl)-[2-(5-methoxy-2-methylsulfanyl-pyrimidin-4-yl)-5-trifluoromethyl-benzyl]-amino}-pyrimidin-5-yloxy)-butyrate (165 mg). MS (m/z): 764 [M+H]⁺

(2) Ethyl 4-(2-{(3,5-bis-trifluoromethyl-benzyl)-[2-(5-methoxy-2-methylsulfanyl-pyrimidin-4-yl)-5-trifluoromethyl-benzyl]-amino}-pyrimidin-5-yloxy)-butyrate (162 mg) is dissolved in chloroform (5 ml) and thereto is added m-chloroperbenzoic acid (70%) (63 mg) and the mixture is stirred at room temperature for 30 minutes. To the reaction solution are added saturated aqueous sodium thiosulfate solution and chloroform, and the mixture is separated, and the organic layer is washed with a saturated brine, dried over magnesium sulfate and concentrated under reduced pressure. The resulting residue is purified by silica gel column chromatography (hexane:ethyl acetate=1:0→19:1) to give ethyl 4-(2-{(3,5-bis-trifluoromethyl-benzyl)-[2-(2-methanesulfinyl-5-methoxy-pyrimidin-4-yl)-5-trifluoromethyl-benzyl]-amino}-pyrimidin-5-yloxy)-butyrate (143 mg). MS (m/z): 780 [M+H]$^+$ (3) Ethyl 4-(2-{(3,5-bis-trifluoromethyl-benzyl)-[2-(2-methanesulfinyl-5-methoxy-pyrimidin-4-yl)-5-trifluoromethyl-benzyl]-amino}-pyrimidin-5-yloxy)-butyrate (139 mg) is dissolved in methanol (5 ml) and thereto is added sodium methoxide (48 mg) and the mixture is stirred at room temperature overnight and further thereto is added sodium methoxide (48 mg), and the mixture is stirred overnight. The reaction solution is concentrated under reduced pressure, and to the residue is added water and ethyl acetate, and the mixture is separated, and the organic layer is washed with a saturated brine, dried over magnesium sulfate, and concentrated under reduced pressure. The resulting residue is purified by silica gel column chromatography (hexane:ethyl acetate=7:3→1:1) to give methyl 4-(2-{(3,5-bis-trifluoromethyl-benzyl)-[2-(2,5-dimethoxy-pyrimidin-4-yl)-5-trifluoromethyl-benzyl]-amino}-pyrimidin-5-yloxy)-butyrate (54 mg). MS (m/z): 734 [M+H]$^+$ (4) Methyl 4-(2-{(3,5-bis-trifluoromethyl-benzyl)-[2-(2,5-dimethoxy-pyrimidin-4-yl)-5-trifluoromethyl-benzyl]-amino}-pyrimidin-5-yloxy)-butyrate (52 mg) is dissolved in methanol (4 ml), and thereto is added 1N-aqueous sodium hydroxide solution (1 ml) and the mixture is stirred at room temperature for 3 hours. To the reaction solution are added a 1N-hydrochloric acid and ethyl acetate, and the mixture is separated, and the organic layer is washed with a saturated brine, dried over magnesium sulfate, and concentrated under reduced pressure. The resulting residue is purified by silica gel column chromatography (chloroform:methanol=1:0→9:1) to give 4-(2-{(3,5-bis-trifluoromethyl-benzyl)-[2-(2,5-dimethoxy-pyrimidin-4-yl)-5-trifluoromethyl-benzyl]-amino}-pyrimidin-5-yloxy)-butyric acid (49 mg). MS (m/z): 720 [M+H]$^+$ Example 115

(1) Trifluoromethanesulfonic acid 2-{[(3,5-bis-trifluoromethyl-benzyl)-(5-morpholin-4-yl-pyrimidin-2-yl)-amino]-methyl}-4'-trifluoromethyl-phenyl ester (620 mg) is dissolved in 1,4-dioxane (10 ml) and thereto are added 2-benzyloxyphenyl boronic acid (398 mg), [1,1'-bis(diphenylphosphino)ferrocene]dichloropalladium dichloromethane complex (142 mg) and cesium carbonate (567 mg), and the mixture is stirred under nitrogen atmosphere at 80° C. overnight. The reaction solution is cooled to room temperature, and thereto are added water and ethyl acetate, and the insoluble materials are removed by filtration through Celite™. The filtrate is separated, and the organic layer is washed with a saturated brine, dried over magnesium sulfate, and concentrated under reduced pressure. The resulting residue is purified by silica gel column chromatography (hexane:ethyl acetate=19:1→4:1) to give (2'-benzyloxy-4-trifluoromethyl-biphenyl-2-ylmethyl)-(3,5-bis-trifluoromethyl-benzyl)-(5-morpholin-4-yl-pyrimidin-2-yl)-amine (617 mg). MS (m/z): 747 [M+H]$^+$ (2) (2'-Benzyloxy-4-trifluoromethyl-biphenyl-2-ylmethyl)-(3,5-bis-trifluoromethyl-benzyl)-(5-morpholin-4-yl-pyrimidin-2-yl)-amine (606 mg) is dissolved in ethanol (10 ml), and thereto is added 10% palladium-carbon (100 mg) and the mixture is stirred under hydrogen atmosphere at room temperature for 3.5 hours. The catalyst is removed by filtration, and the filtrate is concentrated under reduced pressure. The resulting residue is purified by silica gel column chromatography (hexane:ethyl acetate=9:1→7:3) to give 2'-{[(3,5-bis-trifluoromethyl-benzyl)-(5-morpholin-4-yl-pyrimidin-2-yl)-amino]-methyl}-4'-trifluoromethyl-biphenyl-2-ol (374 mg). MS (m/z): 657 [M+H]$^+$ Example 116

(1) 2'-{[(3,5-Bis-trifluoromethyl-benzyl)-(5-morpholin-4-yl-pyrimidin-2-yl)-amino]-methyl}-4'-trifluoromethyl-biphenyl-2-ol (150 mg) is dissolved in N,N-dimethylformamide (3 ml) and thereto are added ethyl 4-bromobutyrate (50 µl) and potassium carbonate (47 mg), and the mixture is stirred at room temperature for 2 hours and at 80° C. for 2 hours. The reaction solution is cooled to room temperature, and thereto are added water and ethyl acetate, and the mixture is separated, and the organic layer is washed with a saturated brine, dried over magnesium sulfate, and concentrated under reduced pressure. The resulting residue is purified by NH-silica gel column chromatography (hexane:ethyl acetate=19:1→4:1) to give ethyl 4-(2'-{[(3,5-bis-trifluoromethyl-benzyl)-(5-morpholin-4-yl-pyrimidin-2-yl)-amino]-methyl}-4'-trifluoromethyl-biphenyl-2-yloxy)-butyrate (163 mg). MS (m/z): 771 [M+H]$^+$ (2) Ethyl 4-(2'-{[(3,5-bis-trifluoromethyl-benzyl)-(5-morpholin-4-yl-pyrimidin-2-yl)-amino]-methyl}-4'-trifluoromethyl-biphenyl-2-yloxy)-butyrate (157 mg) is dissolved in ethanol (4 ml), and thereto is added 1N-aqueous sodium hydroxide solution (1 ml), and the mixture is stirred at room temperature for 2 hours. To the reaction solution are added a 1N-hydrochloric acid and ethyl acetate and the mixture is separated, and the organic layer is washed with a saturated brine, dried over magnesium sulfate, and concentrated under reduced pressure. The resulting residue is purified by silica gel column chromatography (chloroform:methanol=1:0→9:1) to give 4-(2'-{[(3,5-bis-trifluoromethyl-benzyl)-(5-morpholin-4-yl-pyrimidin-2-yl)-amino]-methyl}-4'-trifluoromethyl-biphenyl-2-yloxy)-butyric acid (146 mg). The resulting carboxylic acid is dissolved in ethanol (1 ml), and thereto is added 1N-aqueous sodium hydroxide solution (197 µl) and the reaction solution is concentrated under reduced pressure to give 4-(2'-{[(3,5-bis-trifluoromethyl-benzyl)-(5-morpholin-4-yl-pyrimidin-2-yl)-amino]-methyl}-4'-trifluoromethyl-biphenyl-2-yloxy)-butyric acid sodium salt (146 mg). MS (m/z): 741 [M−Na]$^-$ Example 117

(1) 2-Chloro-5-(trifluoromethyl)benzaldehyde (12.00 g) is dissolved in toluene (200 ml) and the mixture is degassed under reduced pressure. To this solution are added tetrakis(triphenylphosphine)palladium (13.29 g), 5-isopropyl-2-methoxybenzene boronic acid (14.51 g), ethanol (26 ml), distilled water (13 ml) and a 2M-aqueous sodium carbonate solution (57.5 ml), and the mixture is degassed under reduced pressure and heated at 85° C. under nitrogen atmosphere and stirred overnight. The reaction solution is allowed to cool to room temperature, and thereto is added a saturated brine and the mixture is extracted with ethyl acetate. The organic layer is washed with a saturated brine, dried over magnesium sulfate, and concentrated under reduced pressure. The resulting residue is purified by silica gel column chromatography (hexane:ethyl acetate=99:1→19:1) to give 5'-isopropyl-2'-methoxy-4-trifluoromethyl-biphenyl-2-carbaldehyde (14.25 g). MS (m/z): 323 [M+H]$^+$ (2) 5'-Isopropyl-2'-methoxy-4-trifluoromethyl-biphenyl-2-carbaldehyde (5.0 g) is dissolved in 1,2-dichloroethane (20 ml) and thereto are added 3,5-bis-(trifluoromethyl)benzylamine (3.8 g), acetic acid (1.1 ml) and triacetoxy-sodium borohydride (4.0 g), and the mixture is stirred at room temperature overnight. To the reaction mixture is added a saturated aqueous sodium bicarbonate solution and the mixture is extracted with chloroform. The organic layer is washed with a saturated brine, dried over magnesium sulfate, and concentrated under reduced pressure. The resulting residue is purified by NH-silica gel column chromatography (hexane:ethyl acetate=10:1) to give (3,5-bis-trifluoromethyl-benzyl)-(5'-isopropyl-2'-methoxy-4-trifluoromethyl-biphenyl-2-ylmethyl)-amine (7.2 g). MS (m/z): 550 [M+H]$^+$ (3) (3,5-Bis-trifluoromethyl-benzyl)-(5'-isopropyl-2'-methoxy-4-trifluoromethyl-biphenyl-2-ylmethyl)-amine (3.0 g) is dissolved in toluene (20 ml) and thereto are added 5-bromo-2-chloropyrimidine (1.6 g) and N,N-diisopropyl-ethylamine (1.4 ml) and the mixture is heated under reflux overnight. The reaction solution is allowed to cool to room temperature, and thereto is added water and the mixture is extracted with ethyl acetate. The organic layer is washed with a saturated brine, dried over magnesium sulfate, and concentrated under reduced pressure. The resulting residue is purified by silica gel column chromatography (hexane:ethyl acetate=40:1) to give (3,5-bis-trifluoromethyl-benzyl)-(5-bromo-pyrimidin-2-yl)-(5'-isopropyl-2'-methoxy-4-trifluoromethyl-biphenyl-2-ylmethyl)-amine (2.6 g). MS (m/z): 708/706 [M+H]$^+$ (4) (3,5-Bis-trifluoromethyl-benzyl)-(5-bromo-pyrimidin-2-yl)-(5'-isopropyl-2'-methoxy-4-trifluoromethyl-biphenyl-2-ylmethyl)-amine (1.2 g) is dissolved in N,N-dimethylformamide (6 ml) and thereto are added palladium acetate (II) (76 mg), 1,1'-bis(diphenylphosphino)ferrocene (376 mg), ethanol (4.0 ml) and triethylamine (4.8 ml), and the mixture is stirred under carbon monoxide at 90° C. overnight. The reaction solution is allowed to cool to room temperature, and thereto is added water and the mixture is extracted with ethyl acetate. The organic layer is washed with a saturated brine, dried over magnesium sulfate, and concentrated under reduced pressure. The resulting residue is purified by silica gel column chromatography (hexane:ethyl acetate=20:1→10:1) to give ethyl 2-[(3,5-bis-trifluoromethyl-benzyl)-(5'-isopropyl-2'-methoxy-4-trifluoromethyl-biphenyl-2-ylmethyl)-amino]-pyrimidine-5-carboxylate (1.1 g). MS (m/z): 700 [M+H]$^+$ (5) Ethyl 2-[(3,5-bis-trifluoromethyl-benzyl)-(5'-isopropyl-2'-methoxy-4-trifluoromethyl-biphenyl-2-ylmethyl)-amino]-pyrimidine-5-carboxylate (1.1 g) is dissolved in a mixed solvent of ethanol (18 ml) and tetrahydrofuran (20 ml) and thereto is added a 2M-aqueous sodium hydroxide solution (3 ml), and the mixture is stirred at 50° C. for 1 hour and a half. The reaction solution is concentrated under reduced pressure and thereto is added a 1N-hydrochloric acid and the mixture is extracted with ethyl acetate. The organic layer is washed with a saturated brine, dried over magnesium sulfate, and concentrated under reduced pressure. The resulting residue is purified by silica gel column chromatography (chloroform:methanol=25:1) to give 2-[(3,5-bis-trifluoromethyl-benzyl)-(5'-isopropyl-2'-methoxy-4-trifluoromethyl-biphenyl-2-ylmethyl)-amino]-pyrimidine-5-carboxylic acid (700 mg). MS (m/z): 672 [M+H]$^+$ Example 118

(1) 2-[(3,5-Bis-trifluoromethyl-benzyl)-(5'-isopropyl-2'-methoxy-4-trifluoromethyl-biphenyl-2-ylmethyl)-amino]-pyrimidine-5-carboxylic acid (200 mg) is dissolved in N,N-dimethylformamide (5 ml) and thereto are added 1-(3-dimethylaminopropyl)-3-ethylcarbodiimide hydrochloride (86 mg), 1-hydroxy-benzotriazole (60 mg), triethylamine (125 µl) and 4-aminobutyric acid ethyl ester hydrochloride (75 mg), and the mixture is stirred at room temperature overnight. To reaction mixture is added a saturated aqueous sodium bicarbonate solution and the mixture is extracted with ethyl acetate. The organic layer is washed with a saturated brine, dried over magnesium sulfate, and concentrated under reduced pressure. The resulting residue is purified by silica gel column chromatography (hexane:ethyl acetate=5:2) to give ethyl 4-({2-[(3,5-bis-trifluoromethyl-benzyl)-(5'-isopropyl-2'-methoxy-4-trifluoromethyl-biphenyl-2-ylmethyl)-amino]-pyrimidine-5-carbonyl}-amino)-butyrate (230 mg). MS (m/z): 785 [M+H]$^+$ (2) Ethyl 4-({2-[(3,5-bis-trifluoromethyl-benzyl)-(5'-isopropyl-2'-methoxy-4-trifluoromethyl-biphenyl-2-ylmethyl)-amino]-pyrimidine-5-carbonyl}-amino)-butyrate (230 mg) is dissolved in ethanol (5 ml) and thereto is added a 2M-aqueous sodium hydroxide solution (1 ml) and the mixture is stirred at room temperature for 1 hour and a half. To reaction mixture is added a 2N-hydrochloric acid and the mixture is extracted with ethyl acetate. The organic layer is washed with a saturated brine, dried over magnesium sulfate, and concentrated under reduced pressure. The resulting residue is purified by silica gel column chromatography (chloroform:methanol=25:1) to give 4-({2-[(3,5-bis-trifluoromethyl-benzyl)-(5'-isopropyl-2'-methoxy-4-trifluoromethyl-biphenyl-2-ylmethyl)-amino]-pyrimidine-5-carbonyl}-amino)-butyric acid (220 mg). MS (m/z): 757 [M+H]$^+$ Example 119

(1) (3,5-Bis-trifluoromethyl-benzyl)-(5-bromo-pyrimidin-2-yl)-(5'-isopropyl-2'-methoxy-4-trifluoromethyl-biphenyl-2-ylmethyl)-amine (1.06 g) is dissolved in dimethylsulfoxide (5 ml), and the mixture is degassed and thereto are added [1,1'-bis(diphenylphosphino)ferrocene]palladium (II) dichloride (61 mg), potassium acetate (442 mg) and bis(pinacolato)diboron (571 mg). The mixture is degassed and heated to 80° C. under nitrogen flow and stirred for 45 minutes. The reaction solution is allowed to cool to room temperature, and thereto is added a saturated brine, and the mixture is extracted with ethyl acetate. The organic layer is washed twice with a saturated brine, dried over magnesium sulfate, and concentrated under reduced pressure. The resulting residue is dissolved in tetrahydrofuran (5 ml), and thereto is added dropwise a 30% aqueous hydrogen peroxide solution (1.5 ml) under ice-cooling and stirred at the same temperature for 1 hour and a half. To the reaction mixture is added dropwise saturated aqueous sodium thiosulfate solution under ice-cooling, and thereto is added a saturated brine, and the mixture is extracted with ethyl acetate. The organic layer is washed with a saturated brine, dried over magnesium sulfate, and concentrated under reduced pressure. The resulting residue is purified by silica gel column chromatography (hexane:ethyl acetate=4:1→3:1) to give 2-[(3,5-bis-trifluoromethyl-benzyl)-(5'-isopropyl-2'-methoxy-4-trifluoromethyl-biphenyl-2-ylmethyl)-amino]-pyrimidin-5-ol (866 mg). MS (m/z): 644 [M+H]$^+$ (2) 2-{(3,5-Bis-trifluoromethyl-benzyl)-[4-(cyclopropyl-methyl-propyl-amino)-2-methoxy-pyrimidin-5-ylmethyl]-amino}-pyrimidin-5-ol (300 mg) is dissolved in N,N-dimethylformamide (2 ml) and thereto are added potassium carbonate (193 mg) and 4-bromo-butyronitrile (139 μl), and the mixture is stirred at room temperature for 2 hours. To the reaction mixture is added a saturated brine, and the mixture is extracted with ethyl acetate. The organic layer is washed twice with a saturated brine, dried over magnesium sulfate, and concentrated under reduced pressure. The resulting residue is purified by silica gel column chromatography (hexane:ethyl acetate=17:3→3:1) to give 4-{2-[(3,5-bis-trifluoromethyl-benzyl)-(5'-isopropyl-2'-methoxy-4-trifluoromethyl-biphenyl-2-ylmethyl)-amino]-pyrimidin-5-yloxy}-butyronitrile (308 mg). MS (m/z): 711 [M+H]$^+$ Example 120

4-{2-[(3,5-Bis-trifluoromethyl-benzyl)-(5'-isopropyl-2'-methoxy-4-trifluoromethyl-biphenyl-2-ylmethyl)-amino]-pyrimidin-5-yloxy}-butyronitrile (240 mg) is dissolved in N,N-dimethylformamide (7.5 ml), and the mixture is degassed and thereto are added sodium azide (220 mg) and ammonium chloride (181 mg) and the mixture is heated to 110° C. and stirred overnight. The reaction solution is allowed to cool to room temperature, and thereto are added a saturated brine and 10% aqueous citric acid solution, and the mixture is extracted with ethyl acetate. The organic layer is washed twice with a saturated brine, dried over magnesium sulfate, and concentrated under reduced pressure. The resulting residue is purified by silica gel column chromatography (chloroform:methanol=99:1→19:1) to give (3,5-bis-trifluoromethyl-benzyl)-(5'-isopropyl-2'-methoxy-4-trifluoromethyl-biphenyl-2-ylmethyl)-{5-[3-(1H-tetrazol-5-yl)-propoxy]-pyrimidin-2-yl}-amine (127 mg). MS (m/z): 754 [M+H]$^+$ Example 121

(1) 2-[(2-Benzyloxy-5-trifluoromethyl-benzyl)-(3,5-bis-trifluoromethyl-benzyl)-amino]-pyrimidin-5-ol (1.33 g) is dissolved in tetrahydrofuran (20 ml), and thereto are added 2-methylsulfanyl-ethanol (290 μl), triphenylphosphine (870 mg) and 40% diethyl azodicarboxylate/toluene solution (1.5 ml) and the mixture is stirred at room temperature for 45 minutes. To the reaction solution are added water and ethyl acetate, and the mixture is separated, and the organic layer is washed with a saturated brine, dried over magnesium sulfate, and concentrated under reduced pressure. The resulting residue is purified by NH-silica gel column chromatography (hexane:ethyl acetate=99:1→19:1) to give (2-benzyloxy-5-trifluoromethyl-benzyl)-(3,5-bis-trifluoromethyl-benzyl)-[5-(2-methylsulfanyl-ethoxy)-pyrimidin-2-yl]-amine (1.21 g). MS (m/z): 676 [M+H]$^+$ (2) (2-Benzyloxy-5-trifluoromethyl-benzyl)-(3,5-bis-trifluoromethyl-benzyl)-[5-(2-methylsulfanyl-ethoxy)-pyrimidin-2-yl]-amine (1.21 g) is dissolved in chloroform (15 ml) and thereto is added m-chloroperbenzoic acid (75%) (906 mg) and the mixture is stirred at room temperature for 2 hours. To the reaction solution are added saturated aqueous sodium thiosulfate solution and chloroform, and the mixture is separated, and the organic layer is washed with a saturated brine, dried over magnesium sulfate, and concentrated under reduced pressure. The resulting residue is purified by silica gel column chromatography (hexane:ethyl acetate=19:1→7:3) to give (2-benzyloxy-5-trifluoromethyl-benzyl)-(3,5-bis-trifluoromethyl-benzyl)-[5-(2-methanesulfonyl-ethoxy)-pyrimidin-2-yl]-amine (1.09 g). MS (m/z): 708 [M+H]$^+$ (3) (2-Benzyloxy-5-trifluoromethyl-benzyl)-(3,5-bis-trifluoromethyl-benzyl)-[5-(2-methanesulfonyl-ethoxy)-pyrimidin-2-yl]-amine (1.07 g) is dissolved in ethanol (15 ml) and thereto is added 10% palladium-carbon (320 mg) and the mixture is stirred under hydrogen atmosphere at room temperature for 7 hours. The catalyst is removed by filtration, and the filtrate is concentrated under reduced pressure. The resulting residue is purified by silica gel column chromatography (hexane:ethyl acetate=2:1) to give 2-({(3,5-bis-trifluoromethyl-benzyl)-[5-(2-methanesulfonyl-ethoxy)-pyrimidin-2-yl]-amino}-methyl)-4-trifluoromethyl-phenol (400 mg). MS (m/z): 618 [M+H]$^+$ (4) 2-({(3,5-Bis-trifluoromethyl-benzyl)-[5-(2-methanesulfonyl-ethoxy)-pyrimidin-2-yl]-amino}-methyl)-4-trifluoromethyl-phenol (400 mg) and pyridine (79 μl) are dissolved in methylene chloride (10 ml) and thereto is added trifluoromethanesulfonic anhydride (163 μl) under ice-cooling and the mixture is stirred under nitrogen atmosphere at 0° C. for 30 minutes. The reaction solution is cooled to room temperature and stirred for 50 minutes, and thereto is added trifluoromethanesulfonic anhydride (81 μl) and the mixture is stirred for 10 minutes. Thereto are added a saturated aqueous sodium bicarbonate solution and chloroform, and the mixture is separated, and the organic layer is washed with a saturated brine, dried over magnesium sulfate, and concentrated under reduced pressure. The residue is purified by silica gel column chromatography (hexane:ethyl acetate=4:1→2:1) to give trifluoromethanesulfonic acid 2-({(3,5-bis-trifluoromethyl-benzyl)-[5-(2-methanesulfonyl-ethoxy)-pyrimidin-2-yl]-amino}-methyl)-4-trifluoromethyl-phenyl ester (386 mg). MS (m/z): 750 [M+H]$^+$ (5) Trifluoromethanesulfonic acid 2-({(3,5-bis-trifluoromethyl-benzyl)-[5-(2-methanesulfonyl-ethoxy)-pyrimidin-2-yl]-amino}-methyl)-4-trifluoromethyl-phenyl ester (110 mg) is dissolved in 1,4-dioxane (2 ml) and thereto are added 2,4-dimethoxy-pyrimidine-5-boronic acid (70 mg), palladium acetate (13.2 mg), 1,1'-bis(di-tert-butylphosphino)ferrocene (28 mg) and tripotassium phosphate (62 mg) and the mixture is stirred under nitrogen atmosphere at 80° C. for 4 hours. The reaction solution is cooled to room temperature, and thereto are added ethyl acetate and water, and the mixture is separated, and the organic layer is washed with a saturated brine, dried over magnesium sulfate, and concentrated under reduced pressure. The resulting residue is purified by silica gel column chromatography (hexane:ethyl acetate=2:1) to give (3,5-bis-trifluoromethyl-benzyl)-[2-(2,4-dimethoxy-pyrimidin-5-yl)-5-trifluoromethyl-benzyl]-[5-(2-methanesulfonyl-ethoxy)-pyrimidin-2-yl]-amine (34 mg). MS (m/z): 740 [M+H]$^+$ Example 122

The corresponding starting compound is treated in a similar manner to Example 121 to give the compound as listed in Table 10.

TABLE 10
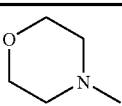
| Ex. No. | A²- | -R² | Physical properties etc. |
|---|---|---|---|
| 113 | 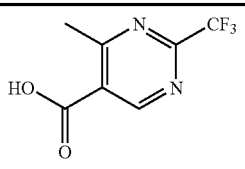 | 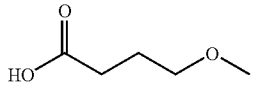 | MS(m/z): 755 [M + H]⁺ |
| 114 | 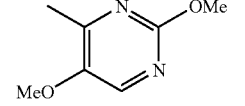 | 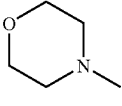 | MS(m/z): 720 [M + H]⁺ |
| 115 | 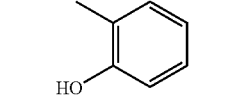 | 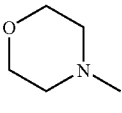 | MS(m/z): 657 [M + H]⁺ |
| 116 | 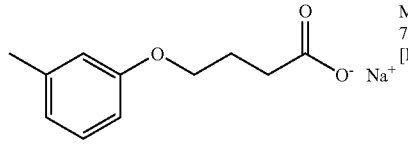 | 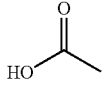 | MS(m/z): 741 [M − Na]⁻ |
| 117 | 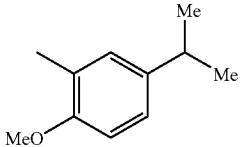 | 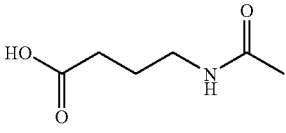 | MS(m/z): 672 [M + H]⁺ |
| 118 | 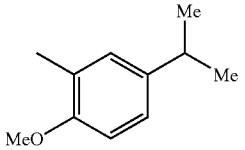 | 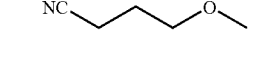 | MS(m/z): 757 [M + H]⁺ |
| 119 | 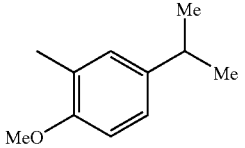 | 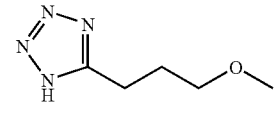 | MS(m/z): 711 [M + H]⁺ |
| 120 | 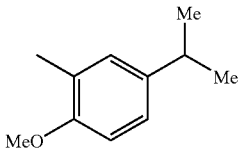 | 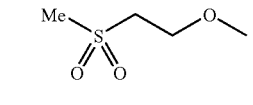 | MS(m/z): 754 [M + H]⁺ |
| 121 | 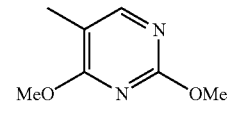 |  | MS(m/z): 740 [M + H]⁺ |

TABLE 10-continued

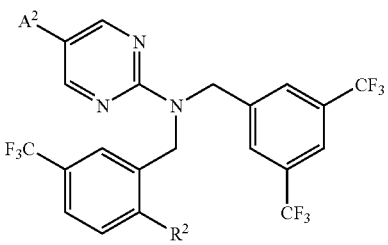

| Ex. No. | A²- | -R² | Physical properties etc. |
|---|---|---|---|
| 122 | Me-S(=O)₂-CH₂CH₂-O- | 2-methyl-4-methoxy, with MeO at position | MS(m/z): 738 [M + H]⁺ |

Example 123

(1) Ethyl 4-(2-{(3,5-bis-trifluoromethyl-benzyl)-[2-(6-isopropenyl-3-methoxy-pyridin-2-yl)-5-trifluoromethyl-benzyl]-amino}-pyrimidin-5-yloxy)-butyrate (76 mg) is dissolved in ethanol (5 ml), and thereto is added 10% palladium-carbon (15 mg) and the mixture is stirred under hydrogen atmosphere for 1.5 hours. The catalyst is removed by filtration, and the filtrate is concentrated under reduced pressure to give ethyl 4-(2-{(3,5-bis-trifluoromethyl-benzyl)-[2-(6-isopropyl-3-methoxy-pyridin-2-yl)-5-trifluoromethyl-benzyl]-amino}-pyrimidin-5-yloxy)-butyrate (70 mg). MS (m/z): 759 [M+H]⁺

(2) Ethyl 4-(2-{(3,5-bis-trifluoromethyl-benzyl)-[2-(6-isopropyl-3-methoxy-pyridin-2-yl)-5-trifluoromethyl-benzyl]-amino}-pyrimidin-5-yloxy)-butyrate (70 mg) is dissolved in ethanol (2 ml), and thereto is added 1N-aqueous sodium hydroxide solution (0.5 ml) and the mixture is stirred at room temperature for 1 hour. To the reaction solution are added a 1N-hydrochloric acid and ethyl acetate, and the mixture is separated, and the organic layer is washed with a saturated brine, dried over magnesium sulfate, and concentrated under reduced pressure. The resulting residue is purified by silica gel column chromatography (chloroform:methanol=1:0→9:1) to give 4-(2-{(3,5-bis-trifluoromethyl-benzyl)-[2-(6-isopropyl-3-methoxy-pyridin-2-yl)-5-trifluoromethyl-benzyl]-amino}-pyrimidin-5-yloxy)-butyric acid (62 mg). The resulting carboxylic acid is dissolved in ethanol (1 ml), and thereto is added 1N-aqueous sodium hydroxide solution (85 µl) and the reaction solution is concentrated under reduced pressure to give 4-(2-{(3,5-bis-trifluoromethyl-benzyl)-[2-(6-isopropyl-3-methoxy-pyridin-2-yl)-5-trifluoromethyl-benzyl]-amino}-pyrimidin-5-yloxy)-butyric acid sodium salt (729 mg). MS (m/z): 729 [M–Na]⁻

Example 124

(1) Ethyl 4-{2-[(3,5-bis-trifluoromethyl-benzyl)-(2-hydroxy-5-trifluoromethyl-benzyl)-amino]-pyrimidin-5-yloxy}-butyrate (300 mg) is dissolved in N,N-dimethylformamide (5 ml) and thereto are added sodium hydride (60%) (29 mg) and 4,6-dichloro-pyrimidine (107 mg) under ice-cooling, and the mixture is stirred for 30 minutes, and the reaction solution is cooled to room temperature, and thereto is added 4,6-dichloro-pyrimidine (107 mg), and the mixture is stirred for 30 minutes. To the reaction solution are added water and ethyl acetate, and the mixture is separated, and the organic layer is washed with a saturated brine, dried over magnesium sulfate, and concentrated under reduced pressure. The resulting residue is purified by silica gel column chromatography (hexane:ethyl acetate=49:1→17:1) to give ethyl 4-(2-{(3,5-bis-trifluoromethyl-benzyl)-[2-(6-chloro-pyrimidin-4-yloxy)-5-trifluoromethyl-benzyl]-amino}-pyrimidin-5-yloxy)-butyrate (244 mg). MS (m/z): 738/740 [M+H]⁺

(2) Ethyl 4-(2-{(3,5-bis-trifluoromethyl-benzyl)-[2-(6-chloro-pyrimidin-4-yloxy)-5-trifluoromethyl-benzyl]-amino}-pyrimidin-5-yloxy)-butyrate (170 mg) is dissolved in toluene (5 ml), and thereto are added diisopropylethylamine (136 µl), 2.0M-dimethylamine/tetrahydrofuran solution (0.4 ml) and the mixture is stirred at 50° C. for 1 day. The reaction solution is cooled to room temperature, and thereto are added aqueous citric acid solution and ethyl acetate, and the mixture is separated. The organic layer is washed with a saturated brine, dried over magnesium sulfate, and concentrated under reduced pressure. The resulting residue is purified by silica gel column chromatography (hexane:ethyl acetate=4:1→2:1) to give ethyl 4-(2-{(3,5-bis-trifluoromethyl-benzyl)-[2-(6-dimethylamino-pyrimidin-4-yloxy)-5-trifluoromethyl-benzyl]-amino}-pyrimidin-5-yloxy)-butyrate (115 mg). MS (m/z): 747 [M+H]⁺

(3) Ethyl 4-(2-{(3,5-bis-trifluoromethyl-benzyl)-[2-(6-dimethylamino-pyrimidin-4-yloxy)-5-trifluoromethyl-benzyl]-amino}-pyrimidin-5-yloxy)-butyrate (110 mg) is dissolved in ethanol (5 ml) and thereto is added 1N-aqueous sodium hydroxide solution (1 ml) and the mixture is stirred at room temperature for 2 hours. To the reaction solution are added a 1N-hydrochloric acid and ethyl acetate, and the mixture is separated, and the organic layer is washed with a saturated brine, dried over magnesium sulfate, and concentrated under reduced pressure. The resulting residue is purified by silica gel column chromatography (chloroform:methanol=1:0→9:1) to give 4-(2-{(3,5-bis-trifluoromethyl-benzyl)-[2-(6-dimethylamino-pyrimidin-4-yloxy)-5-trifluoromethyl-benzyl]-amino}-pyrimidin-5-yloxy)-butyric acid (107 mg). MS (m/z): 719 [M+H]⁺

Example 125

The corresponding starting compound is treated in a similar manner to Example 124 to give the compound as listed in Table 11.

TABLE 11

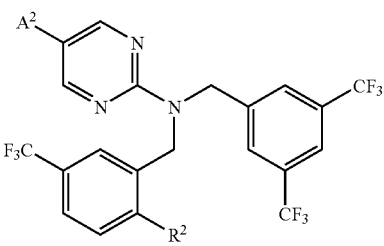

| Ex. No. | A²— | —R² | Physical properties etc. |
|---|---|---|---|
| 123 | Na⁺O-C(O)-CH₂CH₂CH₂-O-Me | 2-methyl-3-methoxy-6-(1-methylethyl)pyridine | MS (m/z): 729 [M − Na]⁻ |
| 124 | HO-C(O)-CH₂CH₂CH₂-O-Me | 6-methoxy-N,N-dimethylpyrimidin-4-amine | MS (m/z): 719 [M + H]⁺ |
| 125 | HO-C(O)-CH₂CH₂CH₂-O-Me | 6-methoxy-2-methyl-N,N-dimethylpyrimidin-4-amine | MS (m/z): 733 [M + H]⁺ |

Example 126

(1) Ethyl 4-{2-[(3,5-bis-trifluoromethyl-benzyl)-(2-trifluoro-methanesulfonyloxy-5-trifluoromethyl-benzyl)-amino]-pyrimidin-5-yloxy}-butyrate (260 mg) is dissolved in 1,2-dimethoxyethane (1 ml) and thereto are added (S)-1-(tert-butyl-dimethyl-silanyloxymethyl)-propylamine (140 mg), tris(dibenzylideneacetone)dipalladium (31 mg), 2-(di-tert-butylphosphino)biphenyl (41 mg) and tripotassium phosphate (146 mg), and the mixture is degassed under reduced pressure and stirred under nitrogen atmosphere at 80° C. overnight. The reaction solution is allowed to cool to room temperature, and thereto is added a saturated brine, and the mixture is extracted with ethyl acetate. The organic layer is washed with a saturated brine, dried over magnesium sulfate, and concentrated under reduced pressure. The resulting residue is purified by column chromatography (hexane:ethyl acetate=1:0→10:1) to give ethyl 4-[2-((3,5-bis-trifluoromethyl-benzyl)-{2-[(S)-1-(tert-butyl-dimethyl-silanyloxymethyl)-propylamino]-5-trifluoromethyl-benzyl}-amino)-pyrimidin-5-yloxy]-butyrate (186 mg). MS (m/z): 811 [M+H]⁺

(2) Ethyl 4-[2-((3,5-bis-trifluoromethyl-benzyl)-{2-[(S)-1-(tert-butyl-dimethyl-silanyloxymethyl)-propylamino]-5-trifluoromethyl-benzyl}-amino)-pyrimidin-5-yloxy]-butyrate (183 mg) is dissolved in tetrahydrofuran (3 mL) and thereto is added 1M-tetrabutylammonium fluoride/tetrahydrofuran solution (1 ml) and the mixture is stirred at room temperature for 20 minutes. The reaction solution is concentrated under reduced pressure and thereto is added a saturated brine, and the mixture is extracted with ethyl acetate. The organic layer is washed twice with a saturated brine, dried over magnesium sulfate, and concentrated under reduced pressure. The resulting residue is purified by silica gel column chromatography (hexane:ethyl acetate=4:1→2:1) to give ethyl 4-(2-{(3,5-bis-trifluoromethyl-benzyl)-[2-((S)-1-hydroxymethyl-propylamino)-5-trifluoromethyl-benzyl]-amino}-pyrimidin-5-yloxy)-butyrate (93 mg). MS (m/z): 697 [M+H]⁺

(3) Ethyl 4-(2-{(3,5-bis-trifluoromethyl-benzyl)-[2-((S)-1-hydroxymethyl-propylamino)-5-trifluoromethyl-benzyl]-amino}-pyrimidin-5-yloxy)-butyrate (40 mg) is dissolved in a mixed solvent of methanol (0.3 ml) and tetrahydrofuran (1 ml) and thereto is added a 1M-aqueous sodium hydroxide solution (0.5 ml), and the mixture is stirred at room temperature for 30 minutes. To reaction mixture are added a 10% aqueous citric acid solution and a saturated brine, and the mixture is extracted with ethyl acetate. The organic layer is washed with a saturated brine, dried over magnesium sulfate, and concentrated under reduced pressure to give 4-(2-{(3,5-bis-trifluoromethyl-benzyl)-[2-((S)-1-hydroxymethyl-propylamino)-5-trifluoromethyl-benzyl]-amino}-pyrimidin-5-yloxy)-butyric acid (41 mg). MS (m/z): 669 [M+H]⁺

Example 127

(1) Ethyl 4-(2-{(3,5-bis-trifluoromethyl-benzyl)-[2-((S)-1-hydroxymethyl-propyl-amino)-5-trifluoromethyl-benzyl]- amino}-pyrimidin-5-yloxy)-butyrate (102 mg) is dissolved in methylene chloride (1.5 ml) and thereto is added triethylamine (31 µl), followed by an addition of triphosgene (17 mg) under water-cooling, and the mixture is stirred at room temperature overnight. To the reaction mixture is added a saturated brine, and the mixture is extracted with ethyl acetate. The organic layer is washed with a saturated brine, dried over magnesium sulfate, and concentrated under reduced pressure. The resulting residue is purified by column chromatography (hexane:ethyl acetate=9:1→7:3) to give ethyl 4-(2-{(3,5-bis-trifluoromethyl-benzyl)-[2-((S)-4-ethyl-2-oxo-oxazolidin-3-yl)-5-trifluoromethyl-benzyl]-amino}-pyrimidin-5-yloxy)-butyrate (94 mg). MS (m/z): 723 [M+H]$^+$ (2) Ethyl 4-(2-{(3,5-bis-trifluoromethyl-benzyl)-[2-((S)-4-ethyl-2-oxo-oxazolidin-3-yl)-5-trifluoromethyl-benzyl]-amino}-pyrimidin-5-yloxy)-butyrate (90 mg) is dissolved in a mixed solvent of a methanol (0.5 mL) and tetrahydrofuran (1 ml) and thereto is added 1M-aqueous sodium hydroxide solution (0.5 mL) and the mixture is stirred at room temperature for 1 hour. The reaction mixture is made acidic with 10% aqueous citric acid solution and the mixture is extracted with ethyl acetate. The organic layer is washed with a saturated brine, dried over magnesium sulfate, and concentrated under reduced pressure. The resulting residue is purified by silica gel column chromatography (chloroform:methanol=1:0→97:3) to give 4-(2-{(3,5-bis-trifluoromethyl-benzyl)-[2-((S)-4-ethyl-2-oxazolidin-3-yl)-5-trifluoromethyl-benzyl]-amino}-pyrimidin-5-yloxy)-butyric acid (64 mg). MS (m/z): 695 [M+H]$^+$ wise a 40% diethyl azodicarboxylate/toluene solution (424 µl) under water-cooling, and the mixture is stirred at 50° C. overnight. Further thereto are added 2-(methylthio)ethanol (243 µl) and triphenylphosphine (244 mg), and thereto is added dropwise diisopropyl azodicarboxylate (361 µl) under water-cooling, and the mixture is stirred at 60° C. for 2 hours. To the reaction mixture is added a saturated brine, and the mixture is extracted with ethyl acetate. The organic layer is washed with a saturated brine, dried over magnesium sulfate, and concentrated under reduced pressure. The resulting residue is purified by silica gel column chromatography (hexane:ethyl acetate=99:1→9:1) to give (3,5-bis-trifluoromethyl-benzyl)-(5'-isopropyl-2'-methoxy-4-trifluoromethyl-biphenyl-2-ylmethyl)-[5-(2-methylsulfanyl-ethoxy)-pyrimidin-2-yl]-amine (300 mg). MS (m/z): 718 [M+H]$^+$ (2) (3,5-Bis-trifluoromethyl-benzyl)-(5'-isopropyl-2'-methoxy-4-trifluoromethyl-biphenyl-2-ylmethyl)-[5-(2-methylsulfanyl-ethoxy)-pyrimidin-2-yl]-amine (296 mg) is dissolved in chloroform (3 ml) and thereto is added m-chloroperbenzoic acid (152 mg), and the mixture is stirred at room temperature for 1 hour. To the reaction solution is added a saturated aqueous sodium bicarbonate solution and the mixture is stirred at room temperature for 10 minutes and extracted with chloroform, and the organic layer is washed successively a saturated aqueous sodium bicarbonate solution and a brine, dried over magnesium sulfate, and concentrated under reduced pressure. The resulting residue is purified by silica gel column chromatography (hexane:ethyl acetate=19:1→2:1, and chloroform:methanol=97:3→19:1)

TABLE 12

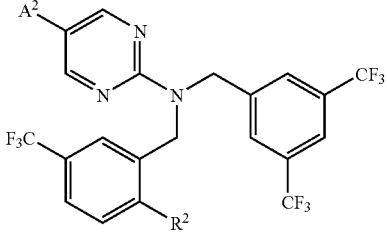

| Ex. No. | A$^2$— | —R$^2$ | Physical properties etc. |
|---|---|---|---|
| 126 | 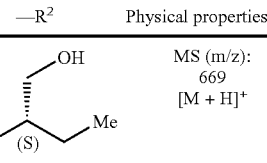 | | MS (m/z): 669 [M + H]$^+$ |
| 127 | 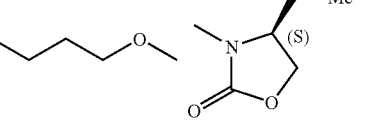 | | MS (m/z): 695 [M + H]$^+$ |

Example 128

(1) 2-[(3,5-Bis-trifluoromethyl-benzyl)-(5'-isopropyl-2'-methoxy-4-trifluoromethyl-biphenyl-2-ylmethyl)-amino]-pyrimidin-5-ol (300 mg) is dissolved in tetrahydrofuran (2 mL), and thereto are added 2-(methylthio)ethanol (162 µl) and triphenylphosphine (488 mg), and thereto is added dropto give (3,5-bis-trifluoromethyl-benzyl)-(5'-isopropyl-2'-methoxy-4-trifluoromethyl-biphenyl-2-ylmethyl)-[5-(2-methanesulfonyl-ethoxy)-pyrimidin-2-yl]-amine (203 mg) (MS (m/z): 750 [M+H]$^+$), and (3,5-bis-trifluoromethyl-benzyl)-(5'-isopropyl-2'-methoxy-4-trifluoromethyl-biphenyl-2-ylmethyl)-[5-(2-methanesulfinyl-ethoxy)-pyrimidin-2-yl]-amine (65 mg) (MS (m/z): 734 [M+H]$^+$).

TABLE 13

| Ex. No. | | Physical properties etc. |
|---|---|---|
| 128 | 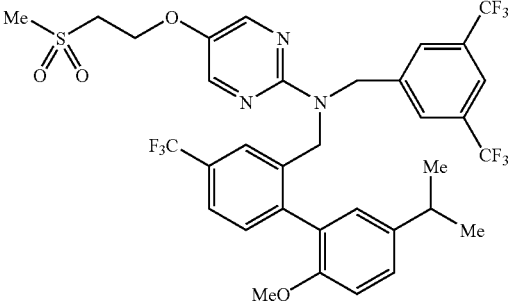 | MS (m/z): 750 [M + H]+ |
| | 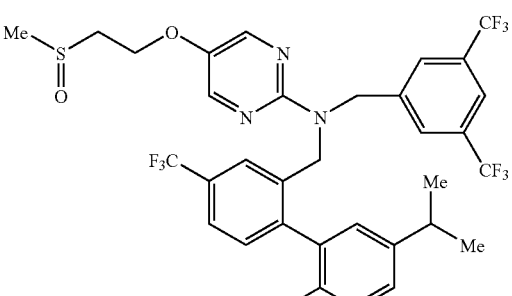 | MS (m/z): 734 [M + H]+ |

Example 129

(1) (3,5-Bis-trifluoromethyl-benzyl)-(5'-isopropyl-2'-methoxy-4-trifluoromethyl-biphenyl-2-ylmethyl)-amine (2.0 g) is dissolved in ethanol (20 ml), and thereto are added cyanogen bromide (578 mg) and sodium bicarbonate (928 mg) and the mixture is stirred at room temperature for 2 hours. To reaction mixture is added a saturated aqueous sodium bicarbonate solution and the mixture is extracted with ethyl acetate. The organic layer is washed with a saturated brine, dried over magnesium sulfate, and concentrated under reduced pressure. The resulting residue is purified by silica gel column chromatography (hexane:ethyl acetate=10:1→5:1) to give (3,5-bis-trifluoromethyl-benzyl)-(5'-isopropyl-2'-methoxy-4-trifluoromethyl-biphenyl-2-ylmethyl)-cyanamide (1.8 g). MS (m/z): 575 [M+H]+

(2) (3,5-Bis-trifluoromethyl-benzyl)-(5'-isopropyl-2'-methoxy-4-trifluoromethyl-biphenyl-2-ylmethyl)-cyanamide (1.8 g) is dissolved in N,N-dimethylformamide (10 ml), and thereto are added sodium azide (407 mg) and ammonium chloride (335 mg), and the mixture is heated to 100° C. and stirred for 6 hours. The reaction solution is allowed to cool to room temperature, and thereto is added a 10% aqueous citric acid solution and the mixture is extracted with ethyl acetate. The organic layer is washed with a saturated brine, dried over magnesium sulfate, and concentrated under reduced pressure. The resulting residue is purified by silica gel column chromatography (chloroform:methanol=30:1) to give (3,5-bis-trifluoromethyl-benzyl)-(5'-isopropyl-2'-methoxy-4-trifluoromethyl-biphenyl-2-ylmethyl)-(2H-tetrazol-5-yl)-amine (1.9 g). MS (m/z): 618 [M+H]+

(3) (3,5-Bis-trifluoromethyl-benzyl)-(5'-isopropyl-2'-methoxy-4-trifluoromethyl-biphenyl-2-ylmethyl)-(2H-tetrazol-5-yl)-amine (400 mg) is dissolved in N,N-dimethylformamide (3 ml) and thereto are added triethylamine (2 ml) and ethyl 4-bromobutyrate (278 μl) and the mixture is stirred at 50° C. for 3 hours. To reaction mixture is added water, and extracted with ethyl acetate, and the organic layer is washed with a saturated brine, dried over magnesium sulfate, and concentrated under reduced pressure. The resulting residue is purified by silica gel column chromatography (hexane:ethyl acetate=10:1) to give ethyl 4-{5-[(3,5-bis-trifluoromethyl-benzyl)-(5'-isopropyl-2'-methoxy-4-trifluoromethyl-biphenyl-2-ylmethyl)-amino]-tetrazol-2-yl}-butyrate (360 mg) MS (m/z): 732 [M+H]+

(4) Ethyl 4-{5-[(3,5-bis-trifluoromethyl-benzyl)-(5'-isopropyl-2'-methoxy-4-trifluoromethyl-biphenyl-2-ylmethyl)-amino]-tetrazol-2-yl}-butyrate (180 mg) is dissolved in ethanol (3 ml), and thereto is added a 2M-aqueous sodium hydroxide solution (0.5 mL) and the mixture is stirred at room temperature for 1 hour and a half. The reaction mixture is made acidic with a 1N-hydrochloric acid and extracted with ethyl acetate. The organic layer is washed with a saturated brine, dried over magnesium sulfate, and concentrated under reduced pressure. The resulting residue is purified by silica gel column chromatography (chloroform:methanol=20:1) to give 4-{5-[(3,5-bis-trifluoromethyl-benzyl)-(5'-isopropyl-2'-methoxy-4-trifluoromethyl-biphenyl-2-ylmethyl)-amino]-tetrazol-2-yl}-butyric acid (160 mg). MS (m/z): 704 [M+H]+

(5) 4-{5-[(3,5-Bis-trifluoromethyl-benzyl)-(5'-isopropyl-2'-methoxy-4-trifluoromethyl-biphenyl-2-ylmethyl)-amino]-tetrazol-2-yl}-butyric acid (154 mg) is dissolved in ethanol (3 ml), and thereto is added 1M-aqueous sodium hydroxide solution (225 μl), and concentrated under reduced pressure to give 4-{5-[(3,5-bis-trifluoromethyl-benzyl)-(5'-isopropyl-2'-methoxy-4-trifluoromethyl-biphenyl-2-ylmethyl)-amino]-tetrazol-2-yl}-butyric acid sodium salt (153 mg). MS (m/z): 702 [M−Na]+

Example 130

(1) (3,5-Bis-trifluoromethyl-benzyl)-(5'-isopropyl-2'-methoxy-4-trifluoromethyl-biphenyl-2-ylmethyl)-(2H-tetrazol-5-yl)-amine (300 mg) is dissolved in tetrahydrofuran (5 ml) and thereto are added triphenylphosphine (191 mg), 2-(methylthio)ethanol (63 μl), a 40% diethyl azodicarboxylate/toluene solution (332 μl) and the mixture is stirred at room temperature for 2 hours and a half. To reaction mixture is added water and the mixture is extracted with diethylether. The organic layer is washed with a saturated brine, dried over magnesium sulfate, and concentrated under reduced pressure. The resulting residue is purified by silica gel column chromatography (hexane:ethyl acetate=12:1) to give (3,5-bis-trifluoromethyl-benzyl)-(5'-isopropyl-2'-methoxy-4-trifluoromethyl-biphenyl-2-ylmethyl)-[2-(2-methylsulfanyl-ethyl)-2H-tetrazol-5-yl]-amine (270 mg). MS (m/z): 692 [M+H]$^+$ (2) (3,5-Bis-trifluoromethyl-benzyl)-(5'-isopropyl-2'-methoxy-4-trifluoromethyl-biphenyl-2-ylmethyl)-[2-(2-methylsulfanyl-ethyl)-2H-tetrazol-5-yl]-amine (270 mg) is dissolved in chloroform (3 ml), and thereto is added m-chloroperbenzoic acid (168 mg), and the mixture is stirred at room temperature for 3 hours. To the reaction solution is added a saturated aqueous sodium bicarbonate solution and the mixture is extracted with ethyl acetate, and the organic layer is washed with a brine, dried over magnesium sulfate, and concentrated under reduced pressure. The resulting residue is purified by silica gel column chromatography (chloroform:methanol=40:1) to give (3,5-bis-trifluoromethyl-benzyl)-(5'-isopropyl-2'-methoxy-4-trifluoromethyl-biphenyl-2-ylmethyl)-[2-(2-methanesulfinyl-ethyl)-2H-tetrazol-5-yl]-amine (157 mg). MS (m/z): 708 [M+H]$^+$

TABLE 14

| Ex. No. | A$^2$— | Physical properties etc. |
|---|---|---|
| 129 | Na$^+$O-C(=O)-CH$_2$CH$_2$CH$_2$CH$_3$ | MS (m/z): 702 [M − Na]$^-$ |
| 130 | Me-S(=O)-CH$_2$CH$_2$CH$_2$- | MS (m/z): 708 [M + H]$^+$ |

Example 131

(1) 5'-Isopropyl-2'-methoxy-4-trifluoromethyl-biphenyl-2-carbaldehyde (3.00 g) is dissolved in ethanol (40 ml) and thereto are added hydroxyl ammonium chloride (1.29 g) and sodium acetate (1.53 g), and the mixture is stirred under nitrogen atmosphere at 60° C. for 1 hour and a half. The reaction solution is concentrated under reduced pressure, and thereto is added a saturated brine, and the mixture is extracted with ethyl acetate. The organic layer is washed with a saturated brine, dried over magnesium sulfate, and concentrated under reduced pressure. The resulting residue (3.3 g) is dissolved in methanol (40 ml), and thereto is added Raney nickel (5 g) and the mixture is stirred under hydrogen atmosphere at room temperature overnight. Raney nickel is removed by filtration and the filtrate is concentrated under reduced pressure. The resulting residue is purified by silica gel column chromatography (chloroform:methanol=1:0→19:1) to give C-(5'-isopropyl-2'-methoxy-4-trifluoromethyl-biphenyl-2-yl)-methylamine (1.57 g). MS (m/z): 324 [M+H]$^+$ (2) C-(5'-isopropyl-2'-methoxy-4-trifluoromethyl-biphenyl-2-yl)-methylamine (1.54 g) is dissolved in toluene (25 ml), and thereto are added tert-butyl 4-(2-chloro-pyrimidin-5-yloxy)-butyrate (1.96 g), palladium acetate (II) (195 mg), (±)-2,2'-bis(diphenylphosphino)-1,1'-binaphthalene (543 mg), tetra-n-butyl ammonium iodide (359 mg) and sodium tert-butoxide (560 mg), and the mixture is stirred under nitrogen flow at 85° C. overnight. The reaction solution is allowed to cool to room temperature, and thereto is added a saturated brine, and the mixture is extracted with ethyl acetate, and the organic layer is dried over magnesium sulfate, and concentrated under reduced pressure. The resulting residue is purified by silica gel column chromatography (hexane:ethyl acetate=47:3→3:1) to give tert-butyl 4-{2-[(5'-isopropyl-2'-methoxy-4-trifluoromethyl-biphenyl-2-ylmethyl)-amino]-pyrimidin-5-yloxy}-butyrate (895 mg). MS (m/z): 560 [M+H]$^+$ (3) Tert-butyl 4-{2-[(5'-isopropyl-2'-methoxy-4-trifluoromethyl-biphenyl-2-ylmethyl)-amino]-pyrimidin-5-yloxy}-butyrate (180 mg) is dissolved in N,N-dimethylformamide (1.0 ml), and thereto is added 1,3-dichloro-5-chloromethyl-benzene (252 mg), followed by an addition of sodium hydride (60%) (34 mg) under ice-cooling and the mixture is stirred at room temperature for 3 hours. To the reaction solution are added a saturated brine, and the mixture is extracted with ethyl acetate, and the organic layer is dried over magnesium sulfate, and concentrated under reduced pressure. The resulting residue is purified by silica gel column chromatography (hexane:ethyl acetate=19:1→9:1) to give tert-butyl 4-{2-[(3,5-dichloro-benzyl)-(5'-isopropyl-2'-methoxy-4-trifluoromethyl-biphenyl-2-ylmethyl)-amino]-pyrimidin-5-yloxy}-butyrate (184 mg). MS (m/z): 720/718 [M+H]$^+$ (4) To tert-butyl 4-{2-[(3,5-dichloro-benzyl)-(5'-isopropyl-2'-methoxy-4-trifluoromethyl-biphenyl-2-ylmethyl)-amino]-pyrimidin-5-yloxy}-butyrate (180 mg) is added 4N-hydrochloric acid/dioxane solution (2 ml) and the mixture is stirred at room temperature for 4 hours. To the reaction mixture is added a saturated brine, and the mixture is extracted with ethyl acetate. The organic layer is washed with a saturated brine, dried over magnesium sulfate, and concentrated under reduced pressure. The resulting residue is purified by silica gel column chromatography (chloroform:methanol=1:0→19:1) to give 4-{2-[(3,5-dichlorobenzyl)-(5'-isopropyl-2'-methoxy-4-trifluoromethyl-biphenyl-2-ylmethyl)-amino]-pyrimidin-5-yloxy}-butyric acid (136 mg). MS (m/z): 664/662 [M+H]$^+$ Examples 132 to 133

The corresponding starting compounds are treated in a similar manner to Example 131 to give the compounds as listed in Table 15.

TABLE 15

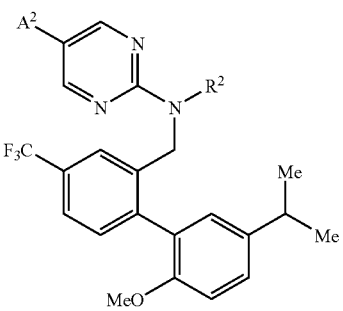

| Ex. No. | A²— | —R² | Physical properties etc. |
|---|---|---|---|
| 131 | HO-C(=O)-CH₂CH₂CH₂-O-Me | CH₂-(3,5-dichlorophenyl) | MS (m/z): 662/664 [M + H]⁺ |
| 132 | HO-C(=O)-CH₂CH₂CH₂-O- | CH₂-(2-ethyl-4,6-dimethoxypyrimidinyl) | MS (m/z): 656 [M + H]⁺ |
| 133 | Na⁺⁻O-C(=O)-CH₂CH₂CH₂-O-Me | CH₂-(3-CF₃-5-CN-phenyl) | MS (m/z): 685 [M − Na]⁻ |

Example 134

(1) To toluene (1 ml) are added 4,5-bis(diphenylphosphino)-9,9-dimethylxanthene (62 mg) and palladium acetate (II) (16 mg) and the mixture is stirred under nitrogen atmosphere at room temperature for 5 minutes. To the mixed solvent is added the mixed solution of tert-butyl 4-{2-[(5'-isopropyl-2'-methoxy-4-trifluoromethyl-biphenyl-2-ylmethyl)-amino]-pyrimidin-5-yloxy}-butyrate (200 mg), 1-bromo-3,5-bis-trifluoromethyl-benzene (126 mg) and toluene (1.5 ml), and the mixture is degassed under reduced pressure and thereto is added sodium tert-butoxide (51 mg) and the mixture is stirred under nitrogen flow at 80° C. overnight. The reaction solution is allowed to cool to room temperature, and thereto is added a saturated brine, and the mixture is extracted with ethyl acetate, and the organic layer is washed with a saturated brine, dried over magnesium sulfate, and concentrated under reduced pressure. The resulting residue is purified by NH-silica gel column chromatography (hexane:ethyl acetate=10:1) to give tert-butyl 4-{2-[(3,5-bis-trifluoromethyl-phenyl)-(5'-isopropyl-2'-methoxy-4-trifluoromethyl-biphenyl-2-ylmethyl)-amino]-pyrimidin-5-yloxy}-butyrate (204 mg). MS (m/z): 772 [M+H]⁺

(2) To tert-butyl 4-{2-[(3,5-bis-trifluoromethyl-phenyl)-(5'-isopropyl-2'-methoxy-4-trifluoromethyl-biphenyl-2-ylmethyl)-amino]-pyrimidin-5-yloxy}-butyrate (197 mg) is added a 4N-hydrochloric acid in dioxane (2.5 ml) and the mixture is stirred at room temperature for 3 hours. To the reaction mixture is added a saturated brine, and the mixture is extracted with ethyl acetate, and the organic layer is washed with a saturated brine, dried over magnesium sulfate, and concentrated under reduced pressure. The resulting residue is purified by silica gel column chromatography (chloroform:methanol=1:0→19:1) to give 4-{2-[(3,5-bis-trifluoromethyl-phenyl)-(5'-isopropyl-2'-methoxy-4-trifluoromethyl-biphenyl-2-ylmethyl)-amino]-pyrimidin-5-yloxy}-butyric acid (104 mg). MS (m/z): 716 [M+H]⁺

Example 135

(1) C-(5'-isopropyl-2'-methoxy-4-trifluoromethyl-biphenyl-2-yl)-methylamine (3.47 g) is dissolved in dioxane (50 ml), and thereto are added 5-bromo-2-chloropyrimidine (5.30 g) and N,N-diisopropylethylamine (5.74 ml) and the mixture is stirred at 100° C. for 2 hours and a half. The reaction solution is allowed to cool to room temperature, and concentrated under reduced pressure. The resulting residue is purified by silica gel column chromatography (hexane:ethyl acetate=50:1→22:3) to give (5-bromo-pyrimidin-2-yl)-(5'-isopropyl-2'-methoxy-4-trifluoromethyl-biphenyl-2-ylmethyl)-amine (4.82 g). MS (m/z): 482/480 [M+H]+

(2) (5-Bromo-pyrimidin-2-yl)-(5'-isopropyl-2'-methoxy-4-trifluoromethyl-biphenyl-2-ylmethyl)-amine (3.30 g) is dissolved in toluene (30 ml), and thereto are added tris(dibenzylideneacetone)dipalladium (1.26 g), 2-(di-tert-butylphosphino)biphenyl (1.23 g), morpholine (2.4 ml) and sodium tert-butoxide (1.32 g) and the mixture is degassed under reduced pressure and stirred under nitrogen flow at 50° C. overnight. To the reaction mixture is added a saturated brine, and extracted with ethyl acetate. The organic layer is washed with a saturated brine, dried over magnesium sulfate, and concentrated under reduced pressure. The resulting residue is purified by silica gel column chromatography (hexane:ethyl acetate=19:1→3:1) to give (5'-isopropyl-2'-methoxy-4-trifluoromethyl-biphenyl-2-ylmethyl)-(5-morpholin-4-yl-pyrimidin-2-yl)-amine (1.11 g). MS (m/z): 487 [M+H]+

(3) (5'-Isopropyl-2'-methoxy-4-trifluoromethyl-biphenyl-2-ylmethyl)-(5-morpholin-4-yl-pyrimidin-2-yl)-amine (500 mg) is dissolved in N,N-dimethylformamide (3 ml), and thereto is added 3-fluoro-5-(trifluoromethyl)benzylbromide (528 mg) and thereto is added sodium hydride (60%) (82 mg) under ice-cooling, and the mixture is stirred at room temperature for 2 hours and a half. To the reaction solution are added a saturated brine, and the mixture is extracted with ethyl acetate. The organic layer is washed with a saturated brine, dried over magnesium sulfate, and concentrated under reduced pressure. The resulting residue is purified by silica gel column chromatography (hexane:ethyl acetate=49:1→22:3) to give (3-fluoro-5-trifluoromethyl-benzyl)-(5'-isopropyl-2'-methoxy-4-trifluoromethyl-biphenyl-2-ylmethyl)-(5-morpholin-4-yl-pyrimidin-2-yl)-amine (440 mg). MS (m/z): 663 [M+H]+

(4) To tetrahydrofuran (6 ml) is added sodium hydride (60%) (390 mg) under nitrogen atmosphere, followed by an addition dropwise of benzyl alcohol (1.01 ml) under water-cooling, and the mixture is stirred at the same temperature for 30 minutes. To this reaction mixture is added a mixture of (3-fluoro-5-trifluoromethyl-benzyl)-(5'-isopropyl-2'-methoxy-4-trifluoromethyl-biphenyl-2-ylmethyl)-(5-morpholin-4-yl-pyrimidin-2-yl)-amine (430 mg) and tetrahydrofuran (4 ml) and the mixture is stirred under nitrogen atmosphere at 70° C. overnight. To the reaction solution are added a saturated brine, and the mixture is extracted with ethyl acetate. The organic layer is washed with a saturated brine, dried over magnesium sulfate, and concentrated under reduced pressure. The resulting residue is purified by NH-silica gel column chromatography (hexane:ethyl acetate=97:3→17:3) to give (3-benzyloxy-5-trifluoromethyl-benzyl)-(5'-isopropyl-2'-methoxy-4-trifluoromethyl-biphenyl-2-ylmethyl)-(5-morpholin-4-yl-pyrimidin-2-yl)-amine (221 mg). MS (m/z): 751 [M+H]+

(5) (3-Benzyloxy-5-trifluoromethyl-benzyl)-(5'-isopropyl-2'-methoxy-4-trifluoromethyl-biphenyl-2-ylmethyl)-(5-morpholin-4-yl-pyrimidin-2-yl)-amine (215 mg) is dissolved in methanol (10.5 ml), and thereto is added 10% palladium-carbon and the mixture is stirred under hydrogen atmosphere at room temperature for 1 hour. The catalyst is removed by filtration, and the filtrate is concentrated under reduced pressure. The resulting residue is purified by NH-silica gel column chromatography (hexane:ethyl acetate=4:1→1:2, and chloroform:methanol 19:1→9:1) to give 3-{[(5'-isopropyl-2'-methoxy-4-trifluoromethyl-biphenyl-2-ylmethyl)-(5-morpholin-4-yl-pyrimidin-2-yl)-amino]-methyl}-5-trifluoromethyl-phenol (98 mg). MS (m/z): 661 [M+H]+

(6) 3-{[(5'-Isopropyl-2'-methoxy-4-trifluoromethyl-biphenyl-2-ylmethyl)-(5-morpholin-4-yl-pyrimidin-2-yl)-amino]-methyl}-5-trifluoromethyl-phenol (95 mg) is dissolved in N,N-dimethylformamide (1 ml), and thereto are added potassium carbonate (90 mg) and ethyl 4-bromobutyrate (93 μl) and the mixture is stirred at room temperature for 4 hours. To the reaction mixture is added a saturated brine, and the mixture is extracted with ethyl acetate, and the organic layer is washed with a saturated brine, dried over magnesium sulfate, and concentrated under reduced pressure. The resulting residue is purified by silica gel column chromatography (hexane:ethyl acetate=10:1→4:1) to give ethyl 4-(3-{[(5'-isopropyl-2'-methoxy-4-trifluoromethyl-biphenyl-2-ylmethyl)-(5-morpholin-4-yl-pyrimidin-2-yl)-amino]-methyl}-5-trifluoromethyl-phenoxy)butyrate (92 mg). MS (m/z): 775 [M+H]+

(7) Ethyl 4-(3-{[(5'-isopropyl-2'-methoxy-4-trifluoromethyl-biphenyl-2-ylmethyl)-(5-morpholin-4-yl-pyrimidin-2-yl)-amino]-methyl}-5-trifluoromethyl-phenoxy)butyrate (88 mg) is dissolved in a mixed solvent of ethanol (1 ml) and tetrahydrofuran (1 ml) and thereto is added a 1M-aqueous sodium hydroxide solution (1 ml), and the mixture is stirred at room temperature for 1 hour. The reaction mixture is made acidic with 10% aqueous citric, and the mixture is extracted with ethyl acetate. The organic layer is washed with a saturated brine, dried over magnesium sulfate, and concentrated under reduced pressure. The resulting residue is purified by silica gel column chromatography (hexane:ethyl acetate=4:1→1:1) to give 4-(3-{[(5'-isopropyl-2'-methoxy-4-trifluoromethyl-biphenyl-2-ylmethyl)-(5-morpholin-4-yl-pyrimidin-2-yl)-amino]-methyl}-5-trifluoromethyl-phenoxy)butyric acid (71 mg). MS (m/z): 747 [M+H]+

(8) 4-(3-{[(5'-Isopropyl-2'-methoxy-4-trifluoromethyl-biphenyl-2-ylmethyl)-(5-morpholin-4-yl-pyrimidin-2-yl)-amino]-methyl}-5-trifluoromethyl-phenoxy)butyric acid (69 mg) is dissolved in ethanol (1 ml) and thereto is added a 1M-aqueous sodium hydroxide solution (92 μl) and the mixture is stirred at room temperature for 3 minutes, and concentrated under reduced pressure to give 4-(3-{[(5'-isopropyl-2'-methoxy-4-trifluoromethyl-biphenyl-2-ylmethyl)-(5-morpholin-4-yl-pyrimidin-2-yl)-amino]-methyl}-5-trifluoromethyl-phenoxy)butyric acid sodium salt (66 mg). MS (m/z): 745 [M−Na]+

TABLE 16

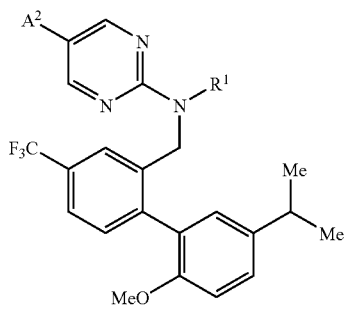

| Ex. No. | A²— | —R¹ | Physical properties etc. |
|---|---|---|---|
| 134 | HO-C(=O)-CH₂CH₂CH₂-O-CH₃ | 3,5-bis(CF₃)-phenyl (with Me) | MS (m/z): 716 [M + H]⁺ |
| 135 | morpholin-4-yl-methyl | 3-ethyl-5-CF₃-phenyl with -O-CH₂CH₂CH₂-C(=O)-O⁻Na⁺ | MS (m/z): 745 [M − Na]⁻ |

Example 136

(1) (2-Benzyloxy-3-chloro-5-trifluoromethyl-benzyl)-(3,5-bis-trifluoromethyl-benzyl)-(5-bromo-pyrimidin-2-yl)-amine (which is prepared by treating the corresponding starting compound in a same manner as in Example 23 (1)-(2)) (700 mg) is treated in a similar manner to Example 87

(1) to give 1-{2-[(2-benzyloxy-3-chloro-5-trifluoromethyl-benzyl)-(3,5-bis-trifluoromethyl-benzyl)-amino]-pyrimidin-5-yl}-ethyl piperidine-4-carboxylate (422 mg). MS (m/z): 775/777 [M+H]⁺

(2) Ethyl 1-{2-[(2-benzyloxy-3-chloro-5-trifluoromethyl-benzyl)-(3,5-bis-trifluoromethyl-benzyl)-amino]-pyrimidin-5-yl}-piperidine-4-carboxylate (412 mg) is treated in a similar manner to Example 23(5) to give ethyl 1-{2-[(3,5-bis-trifluoromethyl-benzyl)-(3-chloro2-hydroxy-5-trifluoromethyl-benzyl)-amino]-pyrimidin-5-yl}-piperidine-4-carboxylate (277 mg). MS (m/z): 685/687 [M+H]⁺

(3) Ethyl 1-{2-[(3,5-bis-trifluoromethyl-benzyl)-(3-chloro-2-hydroxy-5-trifluoromethyl-benzyl)-amino]-pyrimidin-5-yl}-piperidine-4-carboxylate (274 mg) is treated with the corresponding starting compound in a similar manner to Example 26 to give 1-{2-[(3,5-bis-trifluoromethyl-benzyl)-(6-chloro-3'-isopropyl-4-trifluoromethyl-biphenyl-2-ylmethyl)-amino]-pyrimidin-5-yl}-piperidine-4-carboxylic acid (180 mg). MS (m/z): 759/761 [M+H]⁺

Example 137

The corresponding starting compound is treated in a similar manner to Example 136 to give the compound as listed in Table 17.

татBLE 17

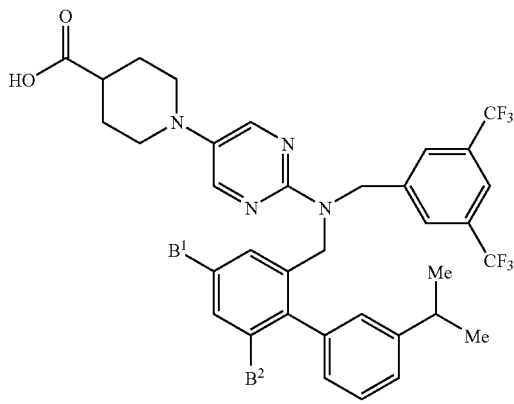

| Ex. No. | B¹— | B²— | Physical properties etc. |
|---|---|---|---|
| 136 | F₃C— | Cl— | MS (m/z): 759/761 [M + H]⁺ |
| 137 | H— | F₃C— | MS (m/z): 725 [M + H]⁺ |

Example 138

(1) (2-Benzyloxy-3-chloro-5-trifluoromethyl-benzyl)-(3,5-bis-trifluoromethyl-benzyl)-(5-bromo-pyrimidin-2-yl)-amine (2.11 g) is treated in a similar manner to Example 23(3)-(5) to give ethyl 4-{2-[(3,5-bis-trifluoromethyl-benzyl)-(3-chloro-2-hydroxy-5-trifluoromethyl-benzyl)-amino]-pyrimidin-5-yloxy}-butyrate (163 mg). MS (m/z): 660/662 [M+H]⁺

(2) Ethyl 4-{2-[(3,5-bis-trifluoromethyl-benzyl)-(3-chloro-2-hydroxy-5-trifluoromethyl-benzyl)-amino]-pyrimidin-5-yloxy}-butyrate (160 mg) is treated with the corresponding starting compound in a similar manner to Example 26 to give 4-{2-[(3,5-bis-trifluoromethyl-benzyl)-(6-chloro-3'-isopropyl-4-trifluoromethyl-biphenyl-2-ylmethyl)-amino]-pyrimidin-5-yloxy}-butyric acid sodium salt (87 mg). MS (m/z): 762/764 [M−Na]$^{-}$ Example 139

(1) (3,5-Bis-trifluoromethyl-benzyl)-(5-bromo-pyrimidin-2-yl)-(5'-isopropyl-4,5,2'-trimethoxy-biphenyl-2-ylmethyl)-amine (which is prepared in a similar manner to Example 117(1)-(3)) (532 mg) is treated with the corresponding starting compound in a similar manner to Example 2(4) to give 2-[(3,5-bis-trifluoromethyl-benzyl)-(5'-isopropyl-4,5,2'-trimethoxy-biphenyl-2-ylmethyl)-amino]-pyrimidin-5-ol (371 mg). MS (m/z): 636 [M+H]$^{+}$ (2) 2-[(3,5-Bis-trifluoromethyl-benzyl)-(5'-isopropyl-4,5,2'-trimethoxy-biphenyl-2-ylmethyl)-amino]-pyrimidin-5-ol (160 mg) is treated in a similar manner to Example 2(5)-(6) to give 4-{2-[(3,5-bis-trifluoromethyl-benzyl)-(5'-isopropyl-4,5,2'-trimethoxy-biphenyl-2-ylmethyl)-amino]-pyrimidin-5-yloxy}-butyric acid sodium salt (128 mg). MS (m/z): 720 [M−Na]$^{-}$ Example 140

(1) Ethyl 4-{2-[(3,5-bis-trifluoromethyl-benzyl)-(2-hydroxy-5-trifluoromethyl-benzyl)-amino]-pyrimidin-5-yloxy}-butyrate (1.39 g) is dissolved in chloroform (20 ml) and thereto is added N-bromosuccinimide (475 mg) and the mixture is stirred at room temperature for 2 hours and the reaction solution is concentrated under reduced pressure. The resulting residue is purified by silica gel column chromatography (hexane:ethyl acetate=19:1→4:1) to give ethyl 4-{2-[(3,5-bis-trifluoromethyl-benzyl)-(3-bromo-2-hydroxy-5-trifluoromethyl-benzyl)-amino]-pyrimidin-5-yloxy}-butyrate (1.29 g). MS (m/z): 704/706 [M+H]$^{+}$ (2) Ethyl 4-{2-[(3,5-bis-trifluoromethyl-benzyl)-(3-bromo-2-hydroxy-5-trifluoromethyl-benzyl)-amino]-pyrimidin-5-yloxy}-butyrate (1.29 g) and pyridine (220 µl) are dissolved in methylene chloride (15 ml) and thereto is added trifluoromethanesulfonic anhydride (460 µl) under ice-cooling, and the mixture is stirred under nitrogen atmosphere at 0° C. for 45 minutes. To the reaction solution are added a saturated aqueous sodium bicarbonate solution and chloroform, and the mixture is separated, and the organic layer is washed with a saturated brine, dried over magnesium sulfate, and concentrated under reduced pressure. The resulting residue is purified by silica gel column chromatography (hexane:ethyl acetate=19:1→4:1) to give ethyl 4-{2-[(3,5-bis-trifluoromethyl-benzyl)-(3-bromo-2-trifluoromethanesulfonyloxy-5-trifluoromethyl-benzyl)-amino]-pyrimidin-5-yloxy}-butyrate (907 mg). MS (m/z): 836/838 [M+H]$^{+}$ (3) Ethyl 4-{2-[(3,5-bis-trifluoromethyl-benzyl)-(3-bromo-2-trifluoro-methanesulfonyloxy-5-trifluoromethyl-benzyl)-amino]-pyrimidin-5-yloxy}-butyrate (300 mg) is dissolved in 1,4-dioxane (4 ml) and thereto are added [1,1'-bis(diphenylphosphino)ferrocene]dichloropalladium dichloromethane complex (58 mg), trimethyl borate (32 mg) and cesium carbonate (175 mg) and the mixture is stirred under nitrogen atmosphere at 80° C. for 3 days. The reaction solution is cooled to room temperature, and thereto are added ethyl acetate and a saturated aqueous sodium bicarbonate solution, and the mixture is separated, and the organic layer is washed with a saturated brine, dried over magnesium sulfate, and concentrated under reduced pressure. The resulting residue is purified by silica gel column chromatography (hexane:ethyl acetate=19:1→17:3) to give the crude product containing ethyl 4-{2-[(3,5-bis-trifluoromethyl-benzyl)-(3-methyl-2-trifluoro-methanesulfonyloxy-5-trifluoromethyl-benzyl)-amino]-pyrimidin-5-yloxy}-butyrate (207 mg). The resulting crude product (200 mg) is dissolved in 1,4-dioxane (4 ml) and thereto are added [1,1'-bis(diphenylphosphino)ferrocene]dichloropalladium dichloromethane complex (42 mg), 5-isopropyl-2-methoxyphenylboronic acid (150 mg) and cesium carbonate (127 mg) and the mixture is stirred under nitrogen atmosphere at 80° C. overnight. The reaction solution is cooled to room temperature, and thereto are added ethyl acetate and a saturated aqueous sodium bicarbonate solution, and the mixture is separated, and the organic layer is washed with a saturated brine, dried over magnesium sulfate, and concentrated under reduced pressure. The resulting residue is purified by NH-silica gel column chromatography (hexane:ethyl acetate=49:1→17:3), followed by Gel Permeation Chromatography (JAIGEL; chloroform) to give ethyl 4-{2-[(3,5-bis-trifluoromethyl-benzyl)-(5'-isopropyl-2'-methoxy-6-methyl-4-trifluoromethyl-biphenyl-2-ylmethyl)-amino]-pyrimidin-5-yloxy}-butyrate (20 mg). MS (m/z): 772 [M+H]$^{+}$ (4) Ethyl 4-{2-[(3,5-bis-trifluoromethyl-benzyl)-(5'-isopropyl-2'-methoxy-6-methyl-4-trifluoromethyl-biphenyl-2-ylmethyl)-amino]-pyrimidin-5-yloxy}-butyrate (20 mg) is dissolved in ethanol (2 ml), and thereto is added a 1N-aqueous sodium hydroxide solution (0.5 ml) and the mixture is stirred at room temperature for 1 hour. To the reaction solution are added a 1N-hydrochloric acid and ethyl acetate, and the mixture is separated, and the organic layer is washed with a saturated brine, dried over magnesium sulfate, and concentrated under reduced pressure. The resulting residue is purified by silica gel column chromatography (chloroform:methanol=1:0→9:1) to give 4-{2-[(3,5-bis-trifluoromethyl-benzyl)-(5'-isopropyl-2'-methoxy-6-methyl-4-trifluoromethyl-biphenyl-2-ylmethyl)-amino]-pyrimidin-5-yloxy}-butyric acid (21 mg). The resulting carboxylic acid is dissolved in ethanol (1 ml) and thereto is added 1N-aqueous sodium hydroxide solution (28 µl) and the reaction solution is concentrated under reduced pressure to give 4-{2-[(3,5-bis-trifluoromethyl-benzyl)-(5'-isopropyl-2'-methoxy-6-methyl-4-trifluoromethyl-biphenyl-2-ylmethyl)-amino]-pyrimidin-5-yloxy}-butyric acid sodium salt (19 mg). MS (m/z): 742 [M−Na]$^{-}$

TABLE 18

| Ex. No. | B$^3$— | B$^4$— | B$^5$— | Physical properties etc. |
|---|---|---|---|---|
| 138 | F$_3$C— | H— | Cl— | MS (m/z): 762/764 [M − Na]$^-$ |

TABLE 18-continued

[Structure: Na⁺⁻O-C(=O)-CH₂CH₂CH₂-O-pyrimidine-N(CH₂-3,5-bis-CF₃-phenyl)-CH₂-biphenyl with B³, B⁴, B⁵ substituents and MeO, Me, Me groups]

| Ex. No. | B³— | B⁴— | B⁵— | Physical properties etc. |
|---|---|---|---|---|
| 139 | MeO— | MeO— | H— | MS (m/z): 720 [M – Na]⁻ |
| 140 | F₃C— | H— | Me— | MS (m/z): 742 [M – Na]⁻ |

Example 141

(3,5-Bis-trifluoromethyl-benzyl)-(5'-isopropyl-2'-methoxy-4-trifluoromethyl-biphenyl-2-ylmethyl)-[2-(2-methanesulfinyl-ethyl)-2H-tetrazol-5-yl]-amine (129 mg) is dissolved in chloroform (2 ml), and thereto is added m-chloroperbenzoic acid (50 mg) and the mixture is stirred at room temperature overnight. To the reaction solution is added a saturated aqueous sodium bicarbonate solution, and the mixture is extracted with ethyl acetate, and the organic layer is washed with a brine, dried over magnesium sulfate, and concentrated under reduced pressure. The resulting residue is purified by silica gel column chromatography (hexane:ethyl acetate=2:1) to give (3,5-bis-trifluoromethyl-benzyl)-(5'-isopropyl-2'-methoxy-4-trifluoromethyl-biphenyl-2-ylmethyl)-[2-(2-methanesulfonyl-ethyl)-2H-tetrazol-5-yl]-amine (81 mg). MS (m/z): 724 [M+H]⁺

TABLE 19

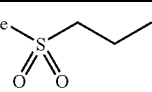

| Ex. No. | A²— | Physical properties etc. |
|---|---|---|
| 141 | Me-S(=O)(=O)-CH₂CH₂- | MS (m/z): 724 [M + H]⁺ |

Example 142

(1) Tert-butyl 4-(2-chloropyrimidin-5-yloxy)-butyrate (5.0 g) is dissolved in toluene (100 ml) and thereto are added palladium acetate (412 mg) and 2,2'-bis(diphenylphosphino)-1,1'-binaphthyl (1.26 g), and the mixture is stirred under nitrogen atmosphere at 50° C. for 1 hour. The reaction solution is cooled to room temperature, and thereto are added 3,5-bis-trifluoromethyl-benzylamine (5.35 g) and sodium tert-butoxide (3.88 g) and the mixture is stirred at 35° C. for 2 hours. Thereto are added ethyl acetate and water, and the mixture is separated, and the organic layer is washed with a saturated brine, dried over magnesium sulfate, and concentrated under reduced pressure. The residue is purified by silica gel column chromatography (hexane:ethyl acetate=9:1→2:1) and NH-silica gel column chromatography (hexane:ethyl acetate=4:1→2:1) to give tert-butyl 4-[2-(3,5-bis-trifluoromethyl-benzylamino)-pyrimidin-5-yloxy]-butyrate (5.59 g). MS (m/z): 480 [M+H]⁺

(2) (2-Bromo-4,5-dimethoxy-phenyl)-methanol (2.47 g) is dissolved in methylene chloride (30 ml) and thereto is added thionyl chloride (875 µl), and the mixture is stirred at room temperature for 30 minutes. The reaction solution is concentrated under reduced pressure, and thereto is added hexane and the resulting crystal is filtered to give 1-bromo-2-chloromethyl-4,5-dimethoxy-benzene (2.25 g). MS (m/z): 229/231

(3) Tert-butyl 4-[2-(3,5-bis-trifluoromethyl-benzyl-amino)-pyrimidin-5-yloxy]-butyrate (100 mg) is dissolved in DMF (1 ml) and thereto is added sodium hydride (60%) (10.8 mg) under ice-cooling, and the mixture is stirred under ice-cooling for 15 minutes. Thereto is added 1-bromo-2-chloromethyl-4,5-dimethoxybenzene (83.1 mg) and the mixture is stirred under ice-cooling for 1 hour. To the reaction solution are added aqueous ammonium chloride solution and ethyl acetate, and the mixture is separated, and the organic layer is washed with a saturated brine, dried over magnesium sulfate, and concentrated under reduced pressure. The residue is purified by silica gel column chromatography (hexane:ethyl acetate=10:1→14:1) to give tert-butyl 4-{2-[(3,5-bis-trifluoromethyl-benzyl)-(2-bromo-4,5-dimethoxy-benzyl)-amino]-pyrimidin-5-yloxy}-butyrate (116 mg). MS (m/z): 708/710 [M+H]⁺

(4) Tert-butyl 4-{2-[(3,5-bis-trifluoromethyl-benzyl)-(2-bromo-4,5-dimethoxy-benzyl)-amino]-pyrimidin-5-yloxy}-butyrate (150 mg) is dissolved in 1,4-dioxane (3 ml) and thereto are added (4-fluoro-5-isopropyl-2-methoxyphenyl)boronic acid (128 mg), [1,1'-bis(diphenylphosphino)ferrocene]dichloropalladium dichloromethane complex (32 mg) and cesium carbonate (196 mg), and the mixture is stirred under nitrogen atmosphere at 80° C. overnight. The reaction solution is cooled to room temperature, and thereto are added ethyl acetate and water, and the mixture is separated, and the organic layer is washed with a saturated brine, dried over magnesium sulfate, and concentrated under reduced pressure. The residue is purified by NH-silica gel column chromatography (hexane:ethyl acetate=19:1→17:3) to give tert-butyl 4-{2-[(3,5-bis-trifluoromethyl-benzyl)-(4'-fluoro-5'-isopropyl-4,5,2'-trimethoxy-biphenyl-2-ylmethyl)-amino]-pyrimidin-5-yloxy}-butyrate (140 mg). MS (m/z): 796 [M+H]⁺

(5) To tert-butyl 4-{2-[(3,5-bis-trifluoromethyl-benzyl)-(4'-fluoro-5'-isopropyl-4,5,2'-trimethoxy-biphenyl-2-ylmethyl)-amino]-pyrimidin-5-yloxy}-butyrate (129 mg) is added a 4N-hydrogen chloride/dioxane solution (3 ml) and the mixture is stirred at room temperature for 7 hours. To the reaction solution are added a saturated aqueous sodium hydroxide solution and ethyl acetate, and the mixture is separated, and the organic layer is washed with a saturated brine, dried over magnesium sulfate, and concentrated under reduced pressure. The resulting residue is purified by silica gel column chromatography (chloroform:methanol=1:0→9:

1) to give 4-{2-[(3,5-bis-trifluoromethyl-benzyl)-(4'-fluoro-5'-isopropyl-4,5,2'-trimethoxy-biphenyl-2-ylmethyl)-amino]-pyrimidin-5-yloxy}-butyric acid (100 mg). MS (m/z): 740 [M+H]+

(6) The resulting carboxylic acid obtained in the above (5) is dissolved in ethanol (1 ml) and thereto is added 1N-aqueous sodium hydroxide solution (128 µl), and the reaction solution is concentrated under reduced pressure to give 4-{2-[(3,5-bis-trifluoromethyl-benzyl)-(4'-fluoro-5'-isopropyl-4,5,2'-trimethoxy-biphenyl-2-ylmethyl)-amino]-pyrimidin-5-yloxy}-butyric acid sodium salt (100 mg). MS (m/z): 738 [M−Na]−

Examples 143 to 152

The corresponding starting compounds are treated in a similar manner to Example 142 to give the compounds as listed in Table 20.

Example 153

The corresponding starting compound is treated in a similar manner to Example 169 to give the compound as listed in Table 20.

Examples 154 to 157

The corresponding starting compounds are treated in a similar manner to Example 160 to give the compounds as listed in Table 20.

TABLE 20

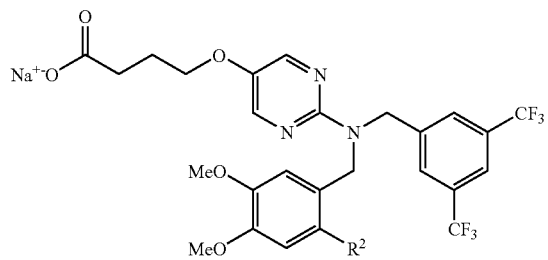

| Ex. No. | —R² | Physical properties, etc. |
|---|---|---|
| 142 | Me, MeO, F (phenyl with Me, F substituents) | MS (m/z): 738 [M − Na]− |
| 143 | Me, Me, Me, MeO (phenyl with gem-dimethyl) | MS (m/z): 734 [M − Na]− |
| 144 | Me, Me, MeO, Me (phenyl) | MS (m/z): 734 [M − Na]− |
| 145 | Me, Me, Me, Me-CH(O) (phenyl with isopropoxy) | MS (m/z): 748 [M − Na]− |
| 146 | Me, Me, Me, Me, MeCH₂O (phenyl) | MS (m/z): 748 [M − Na]− |
| 147 | Me, Me, Me, MeO (phenyl) | MS (m/z): 734 [M − Na]− |
| 148 | Me, Me, Me, MeCH₂O (phenyl) | MS (m/z): 734 [M − Na]− |
| 149 | Me, CF₃, MeO (phenyl) | MS (m/z): 746 [M − Na]− |
| 150 | Me, Me, MeCH₂O (phenyl) | MS (m/z): 706 [M − Na]− |
| 151 | Me, Me, Me-CH(O)-Me (phenyl with isopropoxy) | MS (m/z): 720 [M − Na]− |
| 152 | cyclopentyl, Me, MeO (phenyl) | MS (m/z): 746 [M − Na]− |

TABLE 20-continued

[Core structure: Na+ −O−C(=O)−CH2CH2CH2−O−(pyrimidin-5-yl)−N(−CH2−C6H3(CF3)2)−CH2−C6H2(OMe)2(R2)]

| Ex. No. | —R² | Physical properties, etc. |
|---|---|---|
| 153 | 1-(5-methoxy-6-methylpyridin-2-yl)ethyl | MS (m/z): 721 [M − Na]⁻ |
| 154 | 2-(2-fluoro-4-methoxy-5-methylphenyl)propan-2-ol (C(Me)₂OH on phenyl with Me, F, OMe) | |
| 155 | 2-(4-methoxy-3-methylphenyl)propan-2-ol | |
| 156 | 2-(5-methoxy-6-methylpyridin-2-yl)propan-2-ol | |
| 157 | 1-(5-ethoxymethoxy-6-methylpyridin-2-yl)ethyl (MeCH₂O on pyridine) | MS (m/z): 735 [M − Na]⁻ |

Example 158

The corresponding starting compound is treated in a similar manner to Example 117(1) and Example 131 to give the compound as listed in Table 21.

Example 159

(1) Tert-butyl 4-{2-[(2-bromo-4,5-dimethoxy-benzyl)-(3-cyano-5-trifluoromethyl-benzyl)-amino]-pyrimidin-5-yloxy}-butyric acid (which is prepared by treating the corresponding starting compound in a similar manner to Example 142(1)-(3)) (1.0 g) is dissolved in 1,4-dioxane (10 ml) and thereto are added [1,1'-bis(diphenylphosphino)ferrocene]dichloropalladium dichloromethane complex (252 mg), bis(pinacolato)diboron (782 mg) and potassium acetate (453 mg) and the mixture is stirred under nitrogen atmosphere at 80° C. overnight. The reaction solution is cooled to room temperature, and thereto are added ethyl acetate and water, and the mixture is separated, and the organic layer is washed with a saturated brine, dried over magnesium sulfate, and concentrated under reduced pressure. The resulting residue is purified by silica gel column chromatography (hexane:ethyl acetate=80:20→70:30) to give tert-butyl 4-(2-{(3-cyano-5-trifluoromethyl-benzyl)-[4,5-dimethoxy-2-(4,4,5,5-tetramethyl-[1,3,2]dioxaborolan-2-yl)-benzyl]-amino}-pyrimidin-5-yloxy)-butyrate (769 mg). MS (m/z): 713 [M+H]⁺

(2) Tert-butyl 4-(2-{(3-cyano-5-trifluoromethyl-benzyl)-[4,5-dimethoxy-2-(4,4,5,5-tetramethyl-[1,3,2]dioxaborolan-2-yl)-benzyl]-amino}-pyrimidin-5-yloxy)-butyrate (60 mg) is dissolved in 1,4-dioxane (1.5 ml) and thereto are added 2-bromo-6-isopropenyl-3-methoxy-pyridine (38 mg), [1,1'-bis(diphenylphosphino)ferrocene]dichloropalladium dichloromethane complex (7 mg) and cesium carbonate (55 mg), and the mixture is stirred under nitrogen atmosphere at 80° C. overnight. The reaction solution is cooled to room temperature, and thereto are added ethyl acetate and water, and the mixture is separated and the organic layer is filtered by NH—silica gel and the mixture is extracted with ethyl acetate and concentrated under reduced pressure. The resulting residue is purified by silica gel column chromatography (hexane:ethyl acetate=85:15→70:30) to give tert-butyl 4-(2-{(3-cyano-5-trifluoromethyl-benzyl)-[2-(6-isopropenyl-3-methoxy-pyridin-2-yl)-4,5-dimethoxy-benzyl]-amino}-pyrimidin-5-yloxy)-butyrate (17 mg). MS (m/z): 734 [M+H]⁺

(3) Tert-butyl 4-(2-{(3-cyano-5-trifluoromethyl-benzyl)-[2-(6-isopropenyl-3-methoxy-pyridin-2-yl)-4,5-dimethoxy-benzyl]-amino}-pyrimidin-5-yloxy)-butyrate (36 mg) is treated in a similar manner to Example 142(5) to give 4-(2-{(3-cyano-5-trifluoromethyl-benzyl)-[2-(6-isopropenyl-3-methoxy-pyridin-2-yl)-4,5-dimethoxy-benzyl]-amino}-pyrimidin-5-yloxy)-butyric acid (24.5 mg). MS (m/z): 678 [M+H]⁺

(4) 4-(2-{(3-Cyano-5-trifluoromethyl-benzyl)-[2-(6-isopropenyl-3-methoxy-pyridin-2-yl)-4,5-dimethoxy-benzyl]-amino}-pyrimidin-5-yloxy)-butyric acid (24.5 mg) is dissolved in methanol (2 ml), and thereto is added 10% palladium-carbon (10 mg) and the mixture is stirred under hydrogen atmosphere at room temperature for 1 hour. The insoluble material is removed by filtration and the filtrate is concentrated under reduced pressure. The residue is purified by silica gel column chromatography (chloroform:methanol=100:0→85:15) to give 4-(2-{(3-cyano-5-trifluoromethyl-benzyl)-[2-(6-isopropyl-3-methoxy-pyridin-2-yl)-4,5-dimethoxy-benzyl]-amino}-pyrimidin-5-yloxy)-butyric acid (21 mg). MS (m/z): 680 [M+H]⁺

(5) 4-(2-{(3-Cyano-5-trifluoromethyl-benzyl)-[2-(6-isopropyl-3-methoxy-pyridin-2-yl)-4,5-dimethoxy-benzyl]-amino}-pyrimidin-5-yloxy)-butyric acid (21 mg) is treated in a similar manner to Example 142(6) to give 4-(2-{(3-cyano-5-trifluoromethyl-benzyl)-[2-(6-isopropyl-3-methoxy-pyridin-2-yl)-4,5-dimethoxy-benzyl]-amino}-pyrimidin-5-yloxy)-butyric acid sodium salt (22 mg). MS (m/z): 678 [M−Na]⁻

Example 160

Tert-butyl 4-(2-{(3-cyano-5-trifluoromethyl-benzyl)-[4,5-dimethoxy-2-(4,4,5,5-tetramethyl-[1,3,2]dioxaborolan-2-yl)-benzyl]-amino}-pyrimidin-5-yloxy)-butyrate (195 mg) and 1-bromo-5-isopropyl-2-methoxy-4-methyl-benzene (130 mg) is treated in a similar manner to Examples 159(2), (3) and (5) to give 4-{2-[(3-cyano-5-trifluoromethyl-benzyl)-(5'-isopropyl-4,5,2'-trimethoxy-4'-methyl-biphenyl-2-ylmethyl)-amino]-pyrimidin-5-yloxy}-butyric acid sodium salt (66 mg). MS (m/z): 691 [M−Na]⁻

Examples 161 to 162

The corresponding starting compounds are treated in a similar manner to Example 160 to give the compounds as listed in Table 21.

TABLE 21

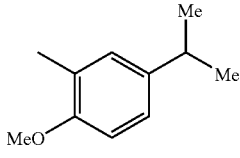

| Ex. No. | —R² | Physical properties, etc. |
|---|---|---|
| 158 | 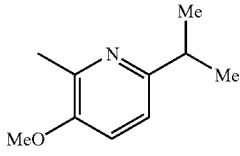 | MS (m/z): 677 [M − Na]⁻ |
| 159 | 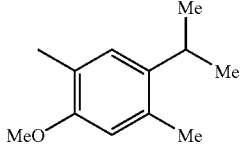 | MS (m/z): 678 [M − Na]⁻ |
| 160 | 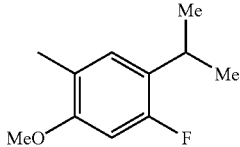 | MS (m/z): 691 [M − Na]⁻ |
| 161 | 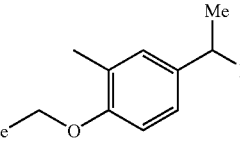 | MS (m/z): 695 [M − Na]⁻ |
| 162 | 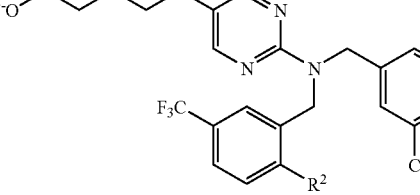 | MS (m/z): 691 [M − Na]⁻ |

Examples 163 to 168

The corresponding starting compounds are treated in a similar manner to Example 142 to give the compounds as listed in Table 22.

Example 169

(1) Tert-butyl 4-(2-{(3-cyano-5-trifluoromethyl-benzyl)-[2-(6-isopropenyl-3-methoxy-pyridine-2-yl)-5-trifluoromethyl-benzyl]-amino}-pyrimidine-5-yloxy)-butyrate (which is prepared in a similar manner to Example 142(2)-(3) and Example 159(1)-(2)) (73 mg) is treated in a similar manner to Example 159(4) to give tert-butyl 4-(2-{(3-cyano-5-trifluoromethyl-benzyl)-[2-(6-isopropyl-3-methoxy-pyridine-2-yl)-5-trifluoromethyl-benzyl]-amino}-pyrimidin-5-yloxy)-butyrate (70 mg). MS (m/z): 744 [M+H]⁺

(2) Tert-butyl 4-(2-{(3-cyano-5-trifluoromethyl-benzyl)-[2-(6-isopropyl-3-methoxy-pyridin-2-yl)-5-trifluoromethyl-benzyl]-amino}-pyrimidine-5-yloxy)-butyrate (70 mg) is treated in a similar manner to Example 142(5)-(6) to give 4-(2-{(3-cyano-5-trifluoromethyl-benzyl)-[2-(6-isopropyl-3-methoxy-pyridine-2-yl)-5-trifluoromethyl-benzyl]-amino}-pyrimidine-5-yloxy)-butyric acid sodium salt (40 mg). MS (m/z): 686 [M−Na]⁻.

Examples 170 to 172

The corresponding starting compounds are treated in a similar manner to Example 160 to give the compounds as listed in Table 22.

TABLE 22

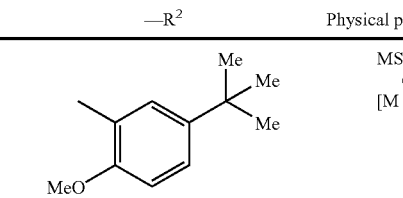

| Ex. No. | —R² | Physical properties, etc. |
|---|---|---|
| 163 | 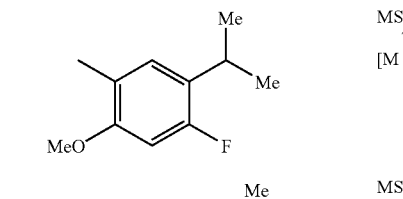 | MS (m/z): 699 [M − Na]⁻ |
| 164 | 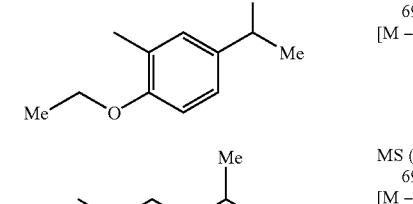 | MS (m/z): 703 [M − Na]⁻ |
| 165 | 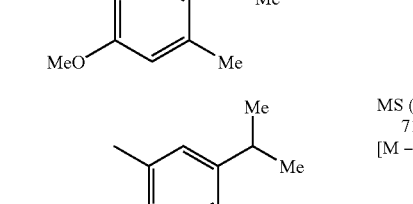 | MS (m/z): 699 [M − Na]⁻ |
| 166 | 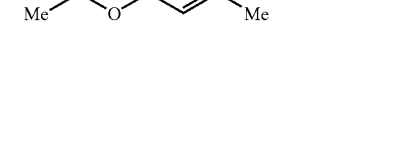 | MS (m/z): 699 [M − Na]⁻ |
| 167 | | MS (m/z): 713 [M − Na]⁻ |

TABLE 22-continued

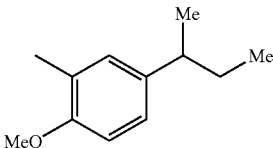

| Ex. No. | —R² | Physical properties, etc. |
|---|---|---|
| 168 | 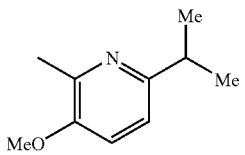 | MS (m/z): 699 [M − Na]⁻ |
| 169 | 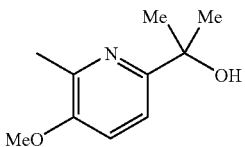 | MS (m/z): 686 [M − Na]⁻ |
| 170 | 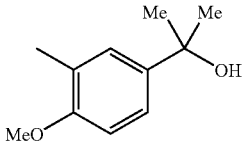 | |
| 171 | 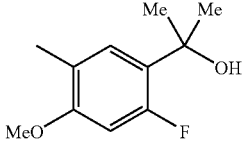 | |
| 172 | 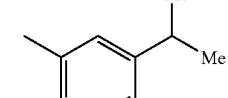 | |

Examples 173 to 177

The corresponding starting compounds are treated in a similar manner to Example 142 to give the compounds as listed in Table 23.

Example 178

The corresponding starting compound is treated in a similar manner to Example 169 to give the compound as listed in Table 23.

TABLE 23

| Ex. No. | —R² | Physical properties, etc. |
|---|---|---|
| 173 | 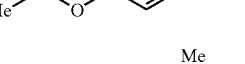 | MS (m/z): 690 [M − Na]⁻ |
| 174 | 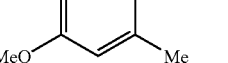 | MS (m/z): 704 [M − Na]⁻ |
| 175 | 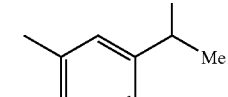 | MS (m/z): 704 [M − Na]⁻ |
| 176 | | MS (m/z): 708 [M − Na]⁻ |
| 177 | | MS (m/z): 704 [M − Na]⁻ |
| 178 | 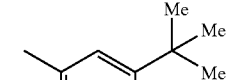 | MS (m/z): 691 [M − Na]⁻ |

Example 179

(1) 1-Methoxy-5-methyl-4-nitro-2-trifluoromethyl-benzene (10 g) is dissolved in methanol (100 ml), and thereto is added 10% palladium-carbon (1 g) and the mixture is stirred under hydrogen atmosphere at room temperature for 1 day. The catalyst is removed by filtration, and the filtrate is concentrated under reduced pressure to give 4-methoxy-2-methyl-5-trifluoromethyl-phenylamine (9.07 g). MS (m/z): 206 [M+H]⁺

(2) To copper (II) bromide (11.8 g) is added acetonitrile (50 ml) and followed by addition dropwise of tert-butyl nitrite (8.5 ml) under ice-cooling and the mixture is stirred under nitrogen atmosphere for 5 minutes. To the reaction mixture is added dropwise a solution of 4-methoxy-5-trifluoromethyl-phenylamine (9.07 g) in acetonitrile (20 ml) under ice-cooling over 20 minutes and the mixture is stirred at room temperature under nitrogen atmosphere overnight. Reaction mixture is concentrated under reduced pressure. To the resulting residue is added a 1N-hydrochloric acid and the mixture is extracted with ethyl acetate. The organic layer is washed successively with water and a saturated brine, dried over magnesium sulfate, and concentrated under reduced pressure. The resulting residue is purified by silica gel column chromatography (hexane:ethyl acetate=49:1→0:1) and NH-silica gel column chromatography (hexane:ethyl acetate=1:0→9:1) to give 1-bromo-4-methoxy-2-methyl-5-trifluoromethyl-benzene (3.61 g).

(3) 1-Bromo-4-methoxy-2-methyl-5-trifluoromethyl-benzene (1.0 g), 2,2'-azobisisobutyronitrile (61 mg) and N-bromosuccinimide (795 mg) are dissolved in carbon tetrachloride (15 ml) and the mixture is heated under reflux overnight. The reaction solution is cooled to room temperature and concentrated under reduced pressure. The resulting residue is purified by silica gel column chromatography (hexane:ethyl acetate=1:0→9:1) to give 1-bromo-2-bromomethyl-4-methoxy-5-trifluoromethyl-benzene (732 mg).

(4) Tert-butyl 4-[2-(3,5-bis-trifluoromethyl-benzylamino)-pyrimidin-5-yloxy]-butyrate (300 mg) is dissolved in N,N-dimethylformamide (4 ml) and thereto is added sodium hydride (60%) (33 mg) under ice-cooling, and the mixture is stirred for 15 minutes and thereto is added 1-bromo-2-bromomethyl-4-methoxy-5-trifluoromethyl-benzene (327 mg) and the mixture is stirred at room temperature overnight. Thereto are added water and ethyl acetate, and the mixture is separated, and the organic layer is washed with a saturated brine, dried over magnesium sulfate, and concentrated under reduced pressure. The resulting residue is purified by silica gel column chromatography (hexane:ethyl acetate=19:1→17:3) to give tert-butyl 4-{2-[(3,5-bis-trifluoromethyl-benzyl)-(2-bromo-5-methoxy-4-trifluoromethyl-benzyl)-amino]-pyrimidin-5-yloxy}-butyrate (256 mg). MS (m/z): 746/748 [M+H]$^+$ (5) Tert-butyl 4-{2-[(3,5-bis-trifluoromethyl-benzyl)-(2-bromo-5-methoxy-4-trifluoromethyl-benzyl)-amino]-pyrimidin-5-yloxy}-butyrate (120 mg) is treated in a similar manner to Example 142(4)-(6) to give 4-{2-[(3,5-bis-trifluoromethyl-benzyl)-(4'-fluoro-5'-isopropyl-4,2'-dimethoxy-5-trifluoromethyl-biphenyl-2-ylmethyl)-amino]-pyrimidin-5-yloxy}-butyric acid sodium salt (53 mg). MS (m/z): 776 [M−Na]$^-$

Example 180

The corresponding starting compound is treated in a similar manner to Example 179 to give the compound as listed in Table 24.

Example 181

The corresponding starting compound is treated in a similar manner to Example 169 to give the compound as listed in Table 24.

Examples 182 to 184

The corresponding starting compounds are treated in a similar manner to Example 160 to give the compounds as listed in Table 24.

TABLE 24

| Ex. No. | —R² | Physical properties etc. |
|---|---|---|
| 179 | (4-MeO, 5-Me phenyl with F, CH(Me)-) | MS (m/z): 776 [M − Na]$^-$ |
| 180 | (4-MeO, 3-Me phenyl, CH(Me)-) | MS (m/z): 758 [M − Na]$^-$ |
| 181 | (5-MeO, 2-Me pyridin-6-yl, CH(Me)-) | MS (m/z): 759 [M − Na]$^-$ |
| 182 | (5-MeO, 2-Me pyridin-6-yl, C(Me)₂OH) | MS (m/z): 775 [M − Na]$^-$ |
| 183 | (4-MeO, 3-Me phenyl, C(Me)₂OH) | |
| 184 | (4-MeO, 3-Me phenyl with F, C(Me)₂OH) | |

Examples 185 to 186

The corresponding starting compounds are treated in a similar manner to Example 179 to give the compounds as listed in Table 25.

Example 187

The corresponding starting compound is treated in a similar manner to Example 169 to give the compound as listed in Table 25.

Examples 188 to 189

The corresponding starting compounds are treated in a similar manner to Example 160 to give the compounds as listed in Table 25.

TABLE 25

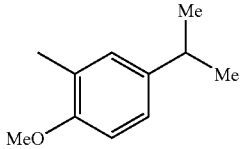

| Ex. No. | —R² | Physical properties etc. |
|---|---|---|
| 185 | 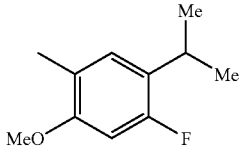 | MS (m/z): 715 [M − Na]⁻ |
| 186 | 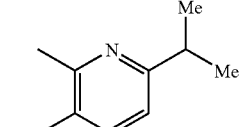 | MS (m/z): 733 [M − Na]⁻ |
| 187 | 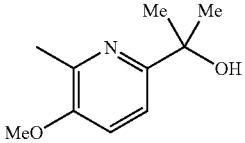 | |
| 188 | 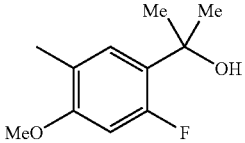 | |
| 189 | | |

Example 190

(1) 5-Methoxy-2-nitro-4-trifluoromethyl-phenol (5 g) and pyridine (2.6 ml) are dissolved in methylene chloride (150 ml), and the mixture is cooled to 0° C., and thereto is added trifluoromethane sulfonic anhydride (5.3 ml) and the mixture is stirred at room temperature overnight. To the reaction solution are added a saturated aqueous sodium bicarbonate solution and chloroform, and the mixture is separated, and the organic layer is washed with a saturated brine, dried over magnesium sulfate, and concentrated under reduced pressure. The resulting residue is purified by silica gel column chromatography (hexane:ethyl acetate=19:1→4:1) to give trifluoromethanesulfonic acid 5-methoxy-2-nitro-4-trifluoromethyl-phenyl ester (5.3 g).

(2) Trifluoromethanesulfonic acid 5-methoxy-2-nitro-4-trifluoromethyl-phenyl ester (2.6 g) is dissolved in 1,4-dioxane (20 ml) and thereto is added 5-isopropyl-2-methoxybenzene boronic acid (1.5 g), [1,1-bis(diphenylphosphino)ferrocene]dichloropalladium dichloromethane complex (575 mg) and cesium carbonate (3.44 g), and the mixture is stirred under nitrogen atmosphere at 80° C. overnight. The reaction solution is cooled to room temperature, and thereto are added ethyl acetate and a saturated aqueous sodium bicarbonate solution, and the mixture is separated, and the organic layer is washed with a saturated brine, dried over magnesium sulfate, and concentrated under reduced pressure. The resulting residue is purified by silica gel column chromatography (hexane:ethyl acetate=49:1→17:3) to give 5'-isopropyl-5,2'-dimethoxy-2-nitro-4-trifluoromethyl-biphenyl (2.35 g). MS (m/z): 370 [M+H]⁺

(3) 5'-Isopropyl-5,2'-dimethoxy-2-nitro-4-trifluoromethyl-biphenyl (2.35 g) is dissolved in a mixed solvent of tetrahydrofuran (20 ml) and methanol (30 ml), and thereto is added 10% palladium-carbon (500 mg) and the mixture is stirred under hydrogen atmosphere at room temperature for 1 day. The catalyst is removed by filtration, and the filtrate is concentrated under reduced pressure. The resulting residue is purified by silica gel column chromatography (hexane:ethyl acetate=9:1→4:1) to give 5'-isopropyl-5,2'-dimethoxy-4-trifluoromethyl-biphenyl-2-ylamine (1.88 g). MS (m/z): 340 [M+H]⁺

(4) To copper (II) bromide (1.17 g) is added acetonitrile (5 ml) and followed by addition dropwise of tert-butyl nitrite (0.835 ml) under ice-cooling and the mixture is stirred under nitrogen atmosphere for 5 minutes. To the reaction mixture is added dropwise a solution of 5'-isopropyl-5,2'-dimethoxy-4-trifluoromethyl-biphenyl-2-ylamine (1.48 g) in acetonitrile (2 ml) under ice-cooling and the mixture is stirred at room temperature under nitrogen atmosphere overnight. Reaction mixture is concentrated under reduced pressure. To the resulting residue is added a 1N-hydrochloric acid and the mixture is extracted with ethyl acetate. The organic layer is washed with a saturated brine, dried over magnesium sulfate, and concentrated under reduced pressure. The resulting residue is purified by silica gel column chromatography (hexane:ethyl acetate=1:0→9:1) to give 2-bromo-5'-isopropyl-5,2'-dimethoxy-4-trifluoromethyl-biphenyl (1.29 g).

(5) 2-Bromo-5'-isopropyl-5,2'-dimethoxy-4-trifluoromethyl-biphenyl (1.29 g) is dissolved in dry tetrahydrofuran (30 ml) and thereto is added dropwise 1.6M n-butyllithium in hexane at −78° C., and the mixture is stirred for 1 hour and thereto is added N,N-dimethylformamide (1.2 ml), and the mixture is stirred for 1.5 hours. To the reaction solution are added a saturated aqueous ammonium chloride solution and ethyl acetate, and the mixture is separated, and the organic layer is washed with a saturated brine, dried over magnesium sulfate, and concentrated under reduced pressure. The resulting residue is purified by silica gel column chromatography (hexane:ethyl acetate=49:1→17:3) to give 5'-isopropyl-5,2'-dimethoxy-4-trifluoromethyl-biphenyl-2-carbaldehyde (733 mg). MS (m/z): 353 [M+H]⁺

(6) 5'-Isopropyl-5,2'-dimethoxy-4-trifluoromethyl-biphenyl-2-carbaldehyde (692 mg) is dissolved in a mixed solvent of tetrahydrofuran (12 ml), ethanol (3.5 ml) and methylene chloride (1 ml), and thereto is added sodium borohydride (82 mg) and the mixture is stirred at room temperature for 40 minutes. The reaction solution is concentrated under reduced pressure and thereto are added ethyl acetate and water, and the mixture is separated, and the organic layer is washed with a saturated brine, dried over magnesium sulfate, and concentrated under reduced pressure. The resulting residue is purified by silica gel column chromatography (hexane:ethyl acetate=19:1→4:1) to give (5'-isopropyl-5,2'-dimethoxy-4-trifluoromethyl-biphenyl-2-yl)-methanol (566 mg). MS (m/z): 337 [M+H−H₂O]⁺

(7) (5'-Isopropyl-5,2'-dimethoxy-4-trifluoromethyl-biphenyl-2-yl)-methanol (200 mg) is dissolved in toluene (5 ml) and thereto is added thionyl chloride (60 μl) under ice-cooling, and the mixture is stirred for 3 hours. To the reaction solution are added water and ethyl acetate, and the mixture is separated, and the organic layer is washed with a saturated brine, dried over magnesium sulfate, and concentrated under reduced pressure. 4-[2-(3,5-Bis-trifluoromethyl-benzylamino)-pyrimidin-5-yloxy]-butyric acid tert-butyl ester (246 mg) is dissolved in N,N-dimethylformamide (5 ml) and thereto is added sodium hydride (60%) (23 mg) under ice-cooling, and the mixture is stirred for 20 minutes. Thereto is added a solution of a residue obtained above in N,N-dimethylformamide (3 ml) and the mixture is stirred at room temperature for 3 hours and 20 minutes. To the reaction solution are added water and ethyl acetate, and the mixture is separated, and the organic layer is washed with a saturated brine, dried over magnesium sulfate, and concentrated under reduced pressure. The resulting residue is purified by silica gel column chromatography (hexane:ethyl acetate=19: 1→17:3) to give tert-butyl 4-{2-[(3,5-bis-trifluoromethyl-benzyl)-(5'-isopropyl-5,2'-dimethoxy-4-trifluoromethyl-biphenyl-2-ylmethyl)-amino]-pyrimidin-5-yloxy}-butyrate (74 mg). MS (m/z): 816 [M+H]$^+$ (8) Tert-butyl 4-{2-[(3,5-bis-trifluoromethyl-benzyl)-(5'-isopropyl-5,2'-dimethoxy-4-trifluoromethyl-biphenyl-2-ylmethyl)-amino]-pyrimidin-5-yloxy}-butyrate (68 mg) is treated in a similar manner to Example 142(5)-(6) to give 4-{2-[(3,5-bis-trifluoromethyl-benzyl)-(5'-isopropyl-5,2'-dimethoxy-4-trifluoromethyl-biphenyl-2-ylmethyl)-amino]-pyrimidin-5-yloxy}-butyric acid sodium salt (23 mg). MS (m/z): 758 [M−Na]$^-$

Example 191

The corresponding starting compound is treated in a similar manner to Example 190 to give the compound as listed in Table 26.

TABLE 26

| Ex. No. | —R$^1$ | Physical properties etc. |
|---|---|---|
| 190 | 3-ethyl-5-CF$_3$ substituted phenyl with CF$_3$ | MS(m/z): 758[M − Na]$^-$ |

TABLE 26-continued

| Ex. No. | —R$^1$ | Physical properties etc. |
|---|---|---|
| 191 | 3-ethyl-5-CN substituted phenyl with CF$_3$ | MS(m/z): 715[M − Na]$^-$ |

Examples 192 to 200

The corresponding starting compounds are treated in a similar manner to Example 142 to give the compounds as listed in Table 27.

Examples 201 to 205

The corresponding starting compounds are treated in a similar manner to Example 160 to give the compounds as listed in Table 27.

Examples 206 to 207

The corresponding starting compounds are treated in a similar manner to any of the above Examples to give the compounds as listed in Table 27.

TABLE 27

| Ex. No. | —R$^2$ | Physical properties etc. |
|---|---|---|
| 192 | 1-(4-methoxy-2-fluoro-5-methylphenyl)ethyl | MS(m/z): 746[M − Na]$^-$ |

TABLE 27-continued

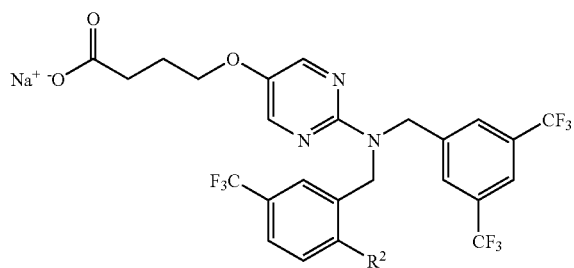

| Ex. No. | —R² | Physical properties etc. |
|---|---|---|
| 193 | 2,5-dimethyl-4-methoxy-1-isopropylphenyl | MS(m/z): 742[M − Na]⁻ |
| 194 | 3-methyl-4-ethoxy-1-isopropylphenyl | MS(m/s): 742[M − Na]⁻ |
| 195 | 3-methyl-4-methoxyphenyl-CH(Me)OMe | |
| 196 | 3-methyl-4-methoxyphenyl-CH(Me)OEt | |
| 197 | 3-methyl-4-methoxyphenyl-CH₂OH | |
| 198 | 3-methyl-4-methoxy-benzamide | MS(m/z): 729[M − Na]⁻ |
| 199 | 3-methyl-4-methoxy-N-methylbenzamide | |
| 200 | 3-methyl-4-methoxy-N-acetylaniline | |

TABLE 27-continued

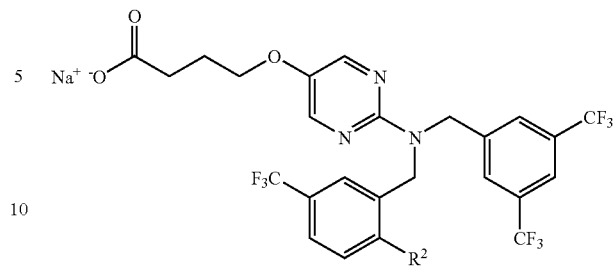

| Ex. No. | —R² | Physical properties etc. |
|---|---|---|
| 201 | 2-methyl-5-ethoxy-6-isopropylpyridine | MS(m/z): 743[M − Na]⁻ |
| 202 | 5-methyl-4-methoxy-2-fluoro-phenyl-C(Me)₂OH | |
| 203 | 2-methyl-5-methoxy-pyridin-6-yl-C(Me)₂OH | MS(m/z): 745[M − Na]⁻ |
| 204 | 3-methyl-4-methoxyphenyl-C(Me)₂OH | |
| 205 | 3-methoxy-2,4-dimethyl-pyridin-6-yl-CH(Me)₂ | |
| 206 | 3-methyl-2-methoxy-5-(CH(Me))-phenyl-CH₂OH | MS(m/z): 758[M − Na]⁻ |
| 207 | 3-methyl-4-methoxyphenyl-morpholine | MS(m/z): 771[M − Na]⁻ |

Example 208

(1) 2-[(3,5-Bis-trifluoromethyl-benzyl)-(5'-isopropyl-4,5,2'-trimethoxy-biphenyl-2-ylmethyl)-amino]-pyrimidin-5-ol (60 mg) is dissolved in tetrahydrofuran (1 ml) and thereto are added tert-butyl 3-hydroxy-propionate (336 mg) and triphenylphosphine (592 mg), and thereto is added dropwise diisopropyl azodicarboxylate (447 µl) and the mixture is stirred at 60° C. overnight. To the reaction mixture is added a saturated brine, and the mixture is extracted with ethyl acetate. The organic layer is washed with a saturated brine, dried over magnesium sulfate, and concentrated under reduced pressure. To the resulting residue is added isopropylether and the insoluble material is filtered and the filtrate is concentrated under reduced pressure. The resulting residue is purified by silica gel column chromatography (hexane:ethyl acetate=9:1→2:1) and NH-silica gel column chromatography (hexane:ethyl acetate=9:1→4:1) to give tert-butyl 3-{2-[(3,5-bis-trifluoromethyl-benzyl)-(5'-isopropyl-4,5,2'-trimethoxy-biphenyl-2-ylmethyl)-amino]-pyrimidin-5-yloxy}-propionate (43 mg). MS (m/z): 764 [M+H]$^+$ (2) To tert-butyl 3-{2-[(3,5-bis-trifluoromethyl-benzyl)-(5'-isopropyl-4,5,2'-trimethoxy-biphenyl-2-ylmethyl)-amino]-pyrimidin-5-yloxy}-propionate (41 mg) is added a 4N-hydrochloric acid/dioxane (4 ml) and the mixture is stirred at room temperature for 9 hours. The reaction mixture is neutralized with a saturated aqueous sodium bicarbonate solution and the mixture is made weakly acidic with a 10% aqueous citric acid solution, and extracted with ethyl acetate. The organic layer is washed with a saturated brine, dried over magnesium sulfate, and concentrated under reduced pressure. The resulting residue is purified by silica gel column chromatography (hexane:ethyl acetate=4:1→1:3) and the resulting purified product is dissolved in ethanol (0.5 ml) and thereto is added 1M-aqueous sodium hydroxide solution (24 µl) and the mixture is concentrated under reduced pressure to give 3-{2-[(3,5-bis-trifluoromethyl-benzyl)-(5'-isopropyl-4,5,2'-trimethoxy-biphenyl-2-ylmethyl)-amino]-pyrimidin-5-yloxy}-propionic acid sodium salt (18 mg). MS (m/z): 706 [M−Na]$^-$

Example 209

Methyl 3-{2-[(3,5-bis-trifluoromethyl-benzyl)-(5'-isopropyl-4,5,2'-trimethoxy-biphenyl-2-ylmethyl)-amino]-pyrimidin-5-yloxy}-2,2-dimethyl-propionate (which is prepared by treating the corresponding starting compound in a similar manner to Example 208(1)) (85 mg) is treated in a similar manner to Example 103(3) to give 3-{2-[(3,5-bis-trifluoromethyl-benzyl)-(5'-isopropyl-4,5,2'-trimethoxy-biphenyl-2-ylmethyl)-amino]-pyrimidin-5-yloxy}-2,2-dimethyl-propionic acid sodium salt (52 mg). MS (m/z): 734 [M−Na]$^-$

Example 210

The corresponding starting compound is treated in a similar manner to Example 139(2) to give the compound as listed in Table 28.

TABLE 28

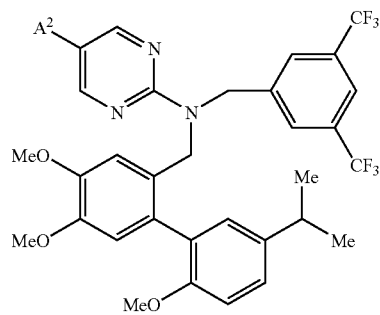

| Ex. No. | A$^2$— | Physical properties, etc. |
|---|---|---|
| 208 | Na$^+$ $^-$O-CH$_2$CH$_2$-C(=O)-O-CH$_3$ | MS(m/z): 706[M − Na]$^-$ |
| 209 | Na$^+$ $^-$O-C(CH$_3$)$_2$-C(=O)-O-CH$_3$ | MS(m/z): 734[M − Na]$^-$ |
| 210 | Na$^+$ $^-$O-(CH$_2$)$_3$-C(=O)-O-CH$_3$ | MS(m/z): 734[M − Na]$^-$ |

Example 211

The corresponding starting compound is treated in a similar manner to Example 208 to give the compound as listed in Table 29.

Example 212

The corresponding starting compound is treated in a similar manner to Example 209 to give the compound as listed in Table 29.

Example 213

The corresponding starting compound is treated in a similar manner to Example 139(2) to give the compound as listed in Table 29.

TABLE 29

[Structure shown with A² substituent, pyrimidine-N, CN-substituted benzyl, F₃C-biphenyl-CF₃, MeO, Me groups]

| Ex. No. | A²— | Physical properties, etc. |
|---|---|---|
| 211 | Na⁺ ⁻O-C(=O)-CH₂CH₂-O-CH₃ | MS(m/s): 671[M − Na]⁻ |
| 212 | Na⁺ ⁻O-C(=O)-C(Me)(Me)-CH₂-O-CH₃ | MS(m/z): 699[M − Na]⁻ |
| 213 | Na⁺ ⁻O-C(=O)-CH₂CH₂CH₂CH₂-O-CH₃ | MS(m/z): 699[M − Na]⁻ |

Example 214

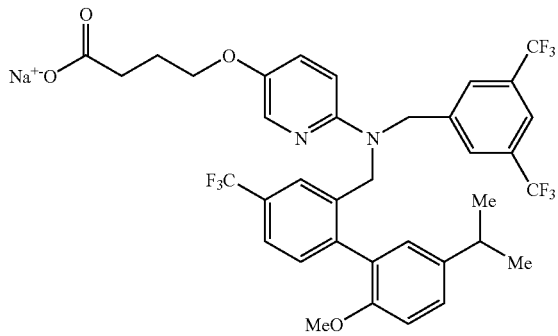

(1) 5'-Isopropenyl-2'-methoxy-4-trifluoromethyl-biphenyl-2-carbaldehyde (5.0 g) is dissolved in a mixed solvent of tetrahydrofuran (100 ml), ethanol (30 ml) and methylene chloride (10 ml), and thereto is added sodium borohydride (646 mg) and the mixture is stirred at room temperature for 10 minutes. The reaction solution is concentrated under reduced pressure and thereto are added ethyl acetate and water, and the mixture is separated, and the organic layer is washed with a saturated brine, dried over magnesium sulfate, and concentrated under reduced pressure. The resulting residue is purified by silica gel column chromatography (hexane:ethyl acetate=49:1→4:1) to give (5'-isopropenyl-2'-methoxy-4-trifluoromethyl-biphenyl-2-yl)-methanol (4.73 g). MS (m/z): 307 [M+H]⁺

(2) (5'-Isopropenyl-2'-methoxy-4-trifluoromethyl-biphenyl-2-yl)-methanol (500 mg) is dissolved in methylene chloride (3 ml), and thereto is added dropwise thionyl chloride (248 μl) under nitrogen atmosphere under ice-cooling and the mixture is stirred at room temperature for 15 minutes and the reaction solution is ice-cooled and thereto is added dropwise triethylamine (647 μl). To the reaction solution are added diethylether and a saturated brine, and the mixture is separated, and the organic layer is dried over magnesium sulfate, and concentrated under reduced pressure. The residue and (3,5-bis-trifluoromethyl-benzyl)-(5-bromo-pyridin-2-yl)-amine (799 mg) is dissolved in N,N-dimethylformamide and thereto is added sodium hydride (123 mg) and the mixture is stirred at 50° C. for 2 hours and a half. The reaction solution is cooled to room temperature, and thereto are added diethylether and water, and the mixture is separated and the organic layer is washed successively with water and a saturated brine, dried over magnesium sulfate, and concentrated under reduced pressure. The residue is purified by silica gel column chromatography (hexane:ethyl acetate=49:1→19:1) to give (3,5-bis-trifluoromethyl-benzyl)-(5-bromopyridin-2-yl)-(5'-isopropyl-2'-methoxy-4-trifluoromethyl-biphenyl-2-ylmethyl)-amine (481 mg). MS (m/z): 705/707 [M+H]⁺

(3) (3,5-Bis-trifluoromethyl-benzyl)-(5-bromo-pyridin-2-yl)-(5'-isopropyl-2'-methoxy-4-trifluoromethyl-biphenyl-2-ylmethyl)-amine (475 mg), [1,1'-bis(diphenylphosphino)ferrocene]dichloropalladium methylene chloride complex (55 mg), potassium acetate (198 mg) and bis(pinacolato)diboron (256 mg) are dissolved in dimethylsulfoxide (2 ml), and the mixture is heated to 80° C. under nitrogen atmosphere and stirred for 1 hour. The reaction solution is cooled to room temperature and thereto are added water and ethyl acetate, and the mixture is separated, and the organic layer is washed twice with a saturated brine, dried over magnesium sulfate, and concentrated under reduced pressure. The resulting residue is dissolved in tetrahydrofuran (10 ml), and thereto is added dropwise a 30% aqueous hydrogen peroxide solution (0.75 ml) under ice-cooling. The reaction solution is stirred at room temperature overnight, and thereto is added a saturated aqueous sodium thiosulfate solution under ice-cooling to consume the excess hydrogen peroxide, followed by an addition of water and diethylether, and the mixture is separated. The organic layer is washed successively with water and a saturated brine, dried over magnesium sulfate, and concentrated under reduced pressure. The resulting residue is purified by silica gel column chromatography (hexane:ethyl acetate=19:1→4:1) to give 6-[(3,5-bis-trifluoromethyl-benzyl)-(5'-isopropyl-2'-methoxy-4-trifluoromethyl-biphenyl-2-ylmethyl)-amino]-pyridin-3-ol (141 mg). MS (m/z): 643 [M+H]⁺

(4) 6-[(3,5-Bis-trifluoromethyl-benzyl)-(5'-isopropyl-2'-methoxy-4-trifluoromethyl-biphenyl-2-ylmethyl)-amino]-pyridin-3-ol (141 mg) is dissolved in N,N-dimethylformamide (1 ml), and thereto is added 60% sodium hydride (10 mg) under ice-cooling and the mixture is stirred for 5 minutes and thereto is added ethyl 4-bromobutyrate (48 μl), and the mixture is stirred at room temperature for 1 hour. To the reaction solution is added water under ice-cooling, and the mixture is extracted with methylene chloride, and the organic layer is concentrated under reduced pressure. The resulting residue is purified by silica gel column chromatography (hexane:ethyl acetate=19:1→4:1) to give ethyl 4-{6-[(3,5-bis-trifluoromethyl-benzyl)-(5'-isopropyl-2'-methoxy-4-trifluoromethyl-biphenyl-2-ylmethyl)-amino]-pyridin-3-yloxy}-butyrate (154.1 mg). MS (m/z): 757 [M+H]⁺

(5) Ethyl 4-{6-[(3,5-bis-trifluoromethyl-benzyl)-(5'-isopropyl-2'-methoxy-4-trifluoromethyl-biphenyl-2-ylmethyl)-amino]-pyridin-3-yloxy}-butyrate (150 mg) is dissolved in a mixed solvent of ethanol (1 ml) and tetrahydrofuran (2 ml) and thereto is added a 2N-aqueous sodium hydroxide solution (0.3 ml) and the mixture is stirred at 50° C. for 3 hours and 20 minutes. The reaction solution is cooled to room temperature and neutralized with a 2N-hydrochloric acid (0.3 ml), and thereto are added methylene chloride and a saturated brine and the mixture is separated, and the organic layer is concentrated under reduced pressure. The resulting residue is purified by LCMS (column: CAPCELPACK MG2 C18, eluate: a 10 µM aqueous carbonic acid solution/acetonitrile=55/45→40/60) to give 4-{6-[(3,5-bis-trifluoromethyl-benzyl)-(5'-isopropyl-2'-methoxy-4-trifluoromethyl-biphenyl-2-ylmethyl)-amino]-pyridin-3-yloxy}-butyric acid (31.4 mg). The resulting carboxylic acid is dissolved in ethanol (1 ml) and thereto is added a 2N-aqueous sodium hydroxide solution (42 µl) and the reaction solution is concentrated under reduced pressure to give 4-{6-[(3,5-bis-trifluoromethyl-benzyl)-(5'-isopropyl-2'-methoxy-4-trifluoromethyl-biphenyl-2-ylmethyl)-amino]-pyridin-3-yloxy}-butyric acid sodium salt (30.6 mg). MS (m/z): 727 [M−Na]⁻

Example 215

The corresponding starting compound is treated in a similar manner to Example 214 to give the compound as listed in Table 30.

tion is cooled to room temperature, and thereto are added ethyl acetate and a 1N-hydrochloric acid, and the mixture is separated, and the organic layer is washed with a saturated sodium carbonate, water and a saturated brine, and the mixture is dried over magnesium sulfate and concentrated under reduced pressure. Thereto are added ethyl acetate and a 1N-hydrochloric acid, and the mixture is separated, and the organic layer is washed with a 1N-hydrochloric acid, a saturated sodium carbonate, water and a saturated brine, and the mixture is dried over magnesium sulfate and concentrated under reduced pressure. The residue is dissolved in methanol (100 ml), and thereto is added Raney nickel, and the mixture is stirred under hydrogen atmosphere at room temperature for 30 minutes and at 50° C. overnight. The reaction solution is cooled to room temperature, and Raney nickel is removed by filtration, and the filtrate is concentrated under reduced pressure. The residue is purified by silica gel column chromatography (chloroform:methanol=1:0→23:2) to give C-(5'-isopropyl-2'-methoxy-4-trifluoromethyl-biphenyl-2-yl)-methylamine (5.50 g). MS (m/z): 324 [M+H]⁺

(2) C-(5'-isopropyl-2'-methoxy-4-trifluoromethyl-biphenyl-2-yl)-methylamine (107 mg) is dissolved in toluene (3 ml), and thereto are added tris(dibenzylideneacetone)dipal-

TABLE 30

| Ex. No. | Structural formula | Physical properties, etc. |
|---|---|---|
| 215 | 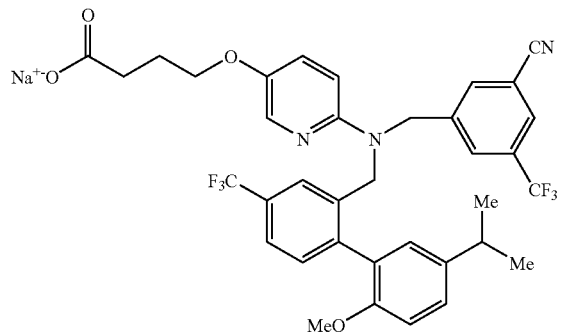 | MS(m/z): 719 [M − Na]⁻ |

Example 216

(1) 5'-Isopropyl-2'-methoxy-4-trifluoromethyl-biphenyl-2-carbaldehyde (8.0 g), hydroxylamine hydrochloride (3.45 g) and pyridine (28 ml) are dissolved in ethanol (140 ml), and the mixture is stirred at 80° C. for 1 hour. The reaction soluladium (30 mg), 1,3-bis(diphenylphosphino)propane (27 mg) and sodium tert-butoxide (44 mg), and the mixture is stirred under nitrogen atmosphere at 80° C. overnight. The reaction solution is cooled to room temperature, and to the reaction solution are added methylene chloride and a saturated aqueous sodium bicarbonate solution, and the mixture is separated, and the organic layer is concentrated under reduced pressure. The resulting residue is purified by silica gel column chromatography (hexane:ethyl acetate=49:1→4:1) to give (5-bromo-pyridin-2-yl)-(5'-isopropyl-2'-methoxy-4-trifluoromethyl-biphenyl-2-ylmethyl)-amine (41.3 mg). MS (m/z): 479/481 [M+H]⁺.

(3) (5-Bromo-pyridin-2-yl)-(5'-isopropyl-2'-methoxy-4-trifluoromethyl-biphenyl-2-ylmethyl)-amine (700 mg) is dissolved in N,N-dimethylformamide (5 ml), and thereto is added sodium hydride (60%) (88 mg) under nitrogen atmosphere at −10° C., and the mixture is stirred at the same temperature for 5 minutes, and thereto is added 3-bromomethyl-5-trifluoromethyl-benzonitrile (771 mg), and the mixture is stirred under ice-cooling for 1 hour and 40 minutes. To the reaction solution are added ethyl acetate and a saturated aqueous citric acid solution, and the mixture is separated, and the organic layer is washed twice with a saturated brine, and the mixture is dried over magnesium sulfate and is concentrated under reduced pressure. The resulting residue is purified by silica gel column chromatography (hexane:ethyl acetate=19:1→17:3) and (hexane:ethyl acetate=49:1→9:1). The residue is dissolved in diethyl ether, and filtered. The filtrate is concentrated under reduced pressure, and the residue obtained above (630 mg) is dissolved in tetrahydrofuran (3 ml), and thereto are added morpholine (119 µl) and triethylamine (190 µl), and the mixture is stirred at 50° C. for 4 hours, and the reaction solution is cooled to room temperature, and stirred at same temperature overnight. To the reaction solution are added ethyl acetate and water, and the mixture is separated, and the organic layer is washed with water and a saturated brine, and the mixture is dried over magnesium sulfate and is concentrated under reduced pressure. The resulting residue is purified by silica gel column chromatography (hexane:ethyl acetate=19:1→17:3) to give 3-{[(5-bromo-pyridin-2-yl)-(5'-isopropyl-2'-methoxy-4-trifluoromethyl-biphenyl-2-ylmethyl)-amino]-methyl}-5-trifluoromethyl-benzonitrile (440 mg). MS (m/z): 662/664 [M+H]+

(4) 3-{[(5-Bromo-pyridin-2-yl)-(5'-isopropyl-2'-methoxy-4-trifluoromethyl-biphenyl-2-ylmethyl)-amino]-methyl}-5-trifluoromethyl-benzonitrile (435 mg) is treated in a similar manner to Example 214(3) to give 3-{[(5-hydroxy-pyridin-2-yl)-(5'-isopropyl-2'-methoxy-4-trifluoromethyl-biphenyl-2-ylmethyl)-amino]-methyl}-5-trifluoromethyl-benzonitrile (251 mg). MS (m/z): 600 [M+H]+

(5) 3-{[(5-Hydroxy-pyridin-2-yl)-(5'-isopropyl-2'-methoxy-4-trifluoromethyl-biphenyl-2-ylmethyl)-amino]-methyl}-5-trifluoromethyl-benzonitrile (150 mg) is dissolved in N,N-dimethylformamide (2.5 ml), and thereto is added 60% sodium hydride (12 mg) under ice-cooling and the mixture is stirred for 30 minutes and thereto is added tert-butyl 4-bromobutyrate (85 mg), and the mixture is stirred at room temperature for 6 hours. To the reaction solution is added water under ice-cooling, and the mixture is extracted with methylene chloride, and the organic layer is washed with a saturated brine, and the mixture is dried over magnesium sulfate and is concentrated under reduced pressure. The resulting residue is purified by silica gel column chromatography (hexane:ethyl acetate=9:1→3:1) to give tert-butyl 4-{6-[(3-cyano-5-trifluoromethyl-benzyl)-(5'-isopropyl-2'-methoxy-4-trifluoromethyl-biphenyl-2-ylmethyl)-amino]-pyridin-3-yloxy}-butyrate (169 mg). MS (m/z): 742 [M+H]+

(6) Tert-butyl 4-{6-[(3-cyano-5-trifluoromethyl-benzyl)-(5'-isopropyl-2'-methoxy-4-trifluoromethyl-biphenyl-2-ylmethyl)-amino]-pyridin-3-yloxy}-butyrate (165 mg) is treated in a similar manner to Example 142(5)-(6) to give 4-{6-[(3-cyano-5-trifluoromethyl-benzyl)-(5'-isopropyl-2'-methoxy-4-trifluoromethyl-biphenyl-2-ylmethyl)-amino]-pyridin-3-yloxy}-butyric acid sodium salt (113.5 mg). MS (m/z): 684 [M−Na]−

Example 217

The corresponding starting compound is treated in a similar manner to any of the above Examples to give the compound as listed in Table 31.

TABLE 31

| Ex. No. | Structural formula | Physical properties, etc. |
|---|---|---|
| 217 | 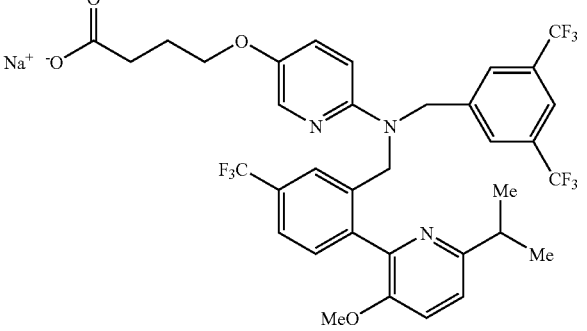 | |

Example 218 to 219

The corresponding starting compounds are treated in a similar manner to Example 142 to give the compounds as listed in Table 32.

Example 220

(1) 5-Benzyloxy-2-bromo-benzaldehyde (1.0 g) is dissolved in 1,4-dioxane (30 ml) and thereto are added [1,1'-bis(diphenylphosphino)ferrocene]-dichloropalladium dichloromethane complex (280 mg), (5-isopropyl-2-methoxyphenyl)boronic acid (800 mg) and cesium carbonate (1.68 g) and the mixture is stirred under nitrogen atmosphere at 80° C. for 6 hours. The reaction mixture is cooled to room temperature, and thereto are added ethyl acetate and a saturated aqueous sodium bicarbonate solution, and the mixture is separated, and the organic layer is washed with a saturated brine, dried over magnesium sulfate, and concentrated under reduced pressure. The resulting residue is purified by silica gel column chromatography (hexane:ethyl acetate=9:1→4:1) to give 4-benzyloxy-5'-isopropyl-2'-methoxy-biphenyl-2-carbaldehyde (1.19 g). MS (m/z): 361 [M+H]+.

(2) 4-Benzyloxy-5'-isopropyl-2'-methoxy-biphenyl-2-carbaldehyde (1.16 g) is dissolved in ethanol (15 ml) and thereto is added sodium borohydride (122 mg) and the mixture is stirred at room temperature for 10 minutes. Thereto are added a saturated aqueous ammonium chloride solution and ethyl acetate, and the mixture is separated, and the organic layer is washed with a saturated brine, dried over magnesium sulfate, and concentrated under reduced pressure to give (4-benzyloxy-5'-isopropyl-2'-methoxy-biphenyl-2-yl)-methanol (1.26 g). MS (m/z): 345

(3) (4-Benzyloxy-5'-isopropyl-2'-methoxy-biphenyl-2-yl)-methanol (1.10 g) is dissolved in methylene chloride (10 ml), and thereto is added thionyl chloride (332 µl) and the mixture is stirred at room temperature for 30 minutes. The reaction solution is concentrated under reduced pressure, and the residue is purified by silica gel column chromatography (hexane:ethyl acetate=1:0→9:1) to give 4-benzyloxy-2-chloromethyl-5'-isopropyl-2'-methoxy-biphenyl (1.15 g). MS (m/z): 345

(4) Tert-butyl 4-[2-(3,5-bis-trifluoromethyl-benzylamino)-pyrimidin-5-yloxy]-butyrate (1.11 g) and 4-benzyloxy-2-chloromethyl-5'-isopropyl-2'-methoxy-biphenyl (805 mg) are dissolved in N,N-dimethylformamide (10 ml) and thereto is added sodium hydride (60%) (120 mg) under ice-cooling, and the mixture is stirred under ice-cooling for 2 hours, and then is stirred at room temperature for 30 minutes. Thereto are added a saturated aqueous ammonium chloride solution and ethyl acetate, and the mixture is separated, and the organic layer is washed with a saturated brine, dried over magnesium sulfate, and concentrated under reduced pressure. The resulting residue is purified by silica gel column chromatography (hexane:ethyl acetate=1:0→4:1) to give tert-butyl 4-{2-[(4-benzyloxy-5'-isopropyl-2'-methoxy-biphenyl-2-ylmethyl)-(3,5-bis-trifluoromethyl-benzyl)-amino]-pyrimidin-5-yloxy}-butyrate (1.14 g). MS (m/z): 824 [M+H]⁺.

(5) Tert-butyl 4-{2-[(4-benzyloxy-5'-isopropyl-2'-methoxy-biphenyl-2-ylmethyl)-(3,5-bis-trifluoromethyl-benzyl)-amino]-pyrimidin-5-yloxy}-butyrate (80 mg) is treated in a similar manner to Example 142(5)-(6) to give 4-{2-[(4-benzyloxy-5'-isopropyl-2'-methoxy-biphenyl-2-ylmethyl)-(3,5-bis-trifluoromethyl-benzyl)-amino]-pyrimidin-5-yloxy}-butyric acid sodium salt (59.5 mg). MS (m/z): 766 [M–Na]⁻

Example 221

(1) Tert-butyl 4-{2-[(4-benzyloxy-5'-isopropyl-2'-methoxy-biphenyl-2-ylmethyl)-(3,5-bis-trifluoromethyl-benzyl)-amino]-pyrimidin-5-yloxy}-butyrate (1.0 g) is dissolved in ethanol (20 ml), and thereto is added 10% palladium-carbon (200 mg), and the mixture is stirred under hydrogen atmosphere at room temperature for 4 hours. The catalyst is removed by filtration, and the filtrate is concentrated under reduced pressure, and thereto is added hexane and the resulting crystal is filtered to give tert-butyl 4-{2-[(3,5-bis-trifluoromethyl-benzyl)-(4-hydroxy-5'-isopropyl-2'-methoxy-biphenyl-2-ylmethyl)-amino]-pyrimidin-5-yloxy}-butyrate (835 mg). MS (m/z): 734 [M+H]⁺

(2) Tert-butyl 4-{2-[(3,5-bis-trifluoromethyl-benzyl)-(4-hydroxy-5'-isopropyl-2'-methoxy-biphenyl-2-ylmethyl)-amino]-pyrimidin-5-yloxy}-butyrate (70 mg) is treated in a similar manner to Example 142(5)-(6) to give 4-{2-[(3,5-bis-trifluoromethyl-benzyl)-(4-hydroxy-5'-isopropyl-2'-methoxy-biphenyl-2-ylmethyl)-amino]-pyrimidin-5-yloxy}-butyric acid sodium salt (55.4 mg). MS (m/z): 676 [M–Na]⁻

Example 222

(1) Tert-butyl 4-{2-[(3,5-bis-trifluoromethyl-benzyl)-(4-hydroxy-5'-isopropyl-2'-methoxy-biphenyl-2-ylmethyl)-amino]-pyrimidin-5-yloxy}-butyrate (70 mg) is dissolved in N,N-dimethylformamide (3 ml) and thereto are added potassium carbonate (26.4 mg) and iodoethane (29.8 mg) and the mixture is stirred at 50° C. for 8 hours. Thereto are added ethyl acetate and a water, and the mixture is separated, and the organic layer is washed with a saturated brine, dried over magnesium sulfate and concentrated under reduced pressure. The resulting residue is purified by NH-silica gel column chromatography (hexane:ethyl acetate=1:0→9:1) to give tert-butyl 4-{2-[(3,5-bis-trifluoromethyl-benzyl)-(4-ethoxy-5'-isopropyl-2'-methoxy-biphenyl-2-ylmethyl)-amino]-pyrimidin-5-yloxy}-butyrate (60.5 mg). MS (m/z): 762 [M+H]⁺

(2) Tert-butyl 4-{2-[(3,5-bis-trifluoromethyl-benzyl)-(4-ethoxy-5'-isopropyl-2'-methoxy-biphenyl-2-ylmethyl)-amino]-pyrimidin-5-yloxy}-butyrate (59 mg) is treated in a similar manner to Example 142(5)-(6) to give 4-{2-[(3,5-bis-trifluoromethyl-benzyl)-(4-ethoxy-5'-isopropyl-2'-methoxy-biphenyl-2-ylmethyl)-amino]-pyrimidin-5-yloxy}-butyric acid sodium salt (48.2 mg). MS (m/z): 704 [M–Na]⁻

Example 223

The corresponding starting compound is treated in a similar manner to Example 222 to give the compound as listed in Table 32.

Example 224

(1) 2-Hydroxy-5-trifluoromethoxy-benzaldehyde (2.5 mg) is dissolved in DMF (30 ml) and thereto are added potassium carbonate (2.51 g) and benzyl bromide (2.07 g) and the mixture is stirred at room temperature overnight. Thereto are added ethyl acetate and water, and the mixture is separated, and the organic layer is washed with a saturated brine, dried over magnesium sulfate and concentrated under reduced pressure. The residue is purified by silica gel column chromatography (hexane:ethyl acetate=19:1→4:1) to give 2-benzyloxy-5-trifluoromethoxy-benzaldehyde (3.28 g). ¹H-NMR (CDCl₃): δ 5.20 (1H, t), 7.07 (1H, d), 7.35-7.45 (6H, m), 7.71 (1H, s), 10.5 (1H, s)

(2) 2-Benzyloxy-5-trifluoromethoxy-benzaldehyde (1.40 g) is dissolved in ethanol (30 ml) and thereto is added sodium borohydride (189 mg) and the mixture is stirred at room temperature for 30 minutes. To the reaction solution are added aqueous ammonium chloride solution and ethyl acetate and the mixture is separated, and the organic layer is washed with a saturated brine, dried over magnesium sulfate and concentrated under reduced pressure. The residue is purified by silica gel column chromatography (hexane:ethyl acetate=9:1→4:1) to give (2-benzyloxy-5-trifluoromethoxy-phenyl)methanol (1.10 g).

(3) (2-Benzyloxy-5-trifluoromethoxy-phenyl)-methanol (510 mg) is dissolved in methylene chloride (5 ml) and thereto is added thionyl chloride (198 µl) and the mixture is stirred at room temperature for 2 hours. The reaction solution is concentrated under reduced pressure and the residue is purified by silica gel column chromatography (hexane:ethyl acetate=1:0→4:1) to give 1-benzyloxy-2-chloromethyl-4-trifluoromethoxy-benzene (360 mg). ¹H-NMR (CDCl₃): δ 4.67 (2H, s), 5.14 (2H, s), 6.91 (1H, d), 7.10-7.45 (7H, m)

(4) Tert-butyl 4-[2-[(3,5-bis-trifluoromethyl-benzylamino)-pyrimidin-5-yloxy]-butyrate (558 mg), 1-benzyloxy-2-chloromethyl-4-trifluoromethoxy-benzene (350 mg) are dissolved in DMF (8 ml) and thereto is added sodium hydride (60%) under ice-cooling, and the mixture is stirred under ice-cooling for 15 minutes and at room temperature for 40 minutes. To the reaction solution are added aqueous ammonium chloride solution and ethyl acetate and the mixture is separated, and the organic layer is washed with a saturated brine, dried over magnesium sulfate and concentrated under reduced pressure. The residue is purified by silica gel column chromatography (hexane:ethyl acetate=9:1→4:1) to give tert-butyl 4-{2-[2-benzyloxy-5-trifluoromethoxy-benzyl)-

(3,5-bis-trifluoromethyl-benzyl)-amino]-pyrimidin-5-yloxy)-butyrate (440 mg). MS (m/z): 760 [M+Na]$^+$ (5) Tert-butyl 4-{2-[2-benzyloxy-5-trifluoromethoxy-benzyl)-(3,5-bis-trifluoromethyl-benzyl)-amino]-pyrimidin-5-yloxy)-butyrate (435 mg) is dissolved in ethanol (10 ml) and thereto is added 10% palladium-carbon (100 mg) and the mixture is stirred at room temperature for 2 hours. The insoluble material is filtered and the resultant solution is concentrated under reduced pressure to give tert-butyl 4-{2-[(3,5-bis-trifluoromethyl-benzyl)-(2-hydroxy-5-trifluoromethoxy-benzyl)-amino]-pyrimidin-5-yloxy}-butyrate (384 mg). MS (m/z): 670 [M+H]$^+$ (6) Tert-butyl 4-{2-[(3,5-bis-trifluoromethyl-benzyl)-(2-hydroxy-5-trifluoromethoxy-benzyl)-amino]-pyrimidin-5-yloxy}-butyrate (382 mg) is dissolved in methylene chloride (4 ml) and thereto are added pyridine (2 μl) and trifluoromethanesulfonic anhydride (144 μl) and the mixture is stirred under ice-cooling for 1 hour. Thereto is added an aqueous sodium bicarbonate solution and the mixture is separated and the organic layer is washed with a saturated brine, dried over magnesium sulphate and concentrated under reduced pressure. The residue is purified by silica gel column chromatography (hexane:ethyl acetate=9:1→4:1) to give tert-butyl 4-{2-[(3,5-bis-trifluoromethyl-benzyl)-(2-trifluoromethanesulfonyloxy-5-trifluoromethoxy-benzyl)-amino]-pyrimidin-5-yloxy}-butyrate (384 mg). MS (m/z): 802 [M+H]$^+$ (7) Tert-butyl 4-{2-[(3,5-bis-trifluoromethyl-benzyl)-(2-trifluoromethane-sulfonyloxy-5-trifluoromethoxy-benzyl)-amino]-pyrimidin-5-yloxy}-butyrate (100 mg) is dissolved in 1,4-dioxane (2 ml) and thereto are added (5-isopropyl-2-methoxy-phenyl)-boronic acid (72.6 mg), [1,1'-bis(diphenylphosphino)ferrocene]-dichloropalladium dichloromethane complex (20.4 mg) and cesium carbonate (122 mg) and the mixture is stirred at 80° C. overnight. The reaction mixture is cooled to room temperature, and thereto are added ethyl acetate and water, and the mixture is separated, and the organic layer is washed with a saturated brine, dried over magnesium sulfate, and concentrated under reduced pressure. The resulting residue is purified by NH-silica gel column chromatography (hexane:ethyl acetate=9:1→4:1) to give tert-butyl 4-{2-[(3,5-bis-trifluoromethyl-benzyl)-(5'-isopropyl-2'-methoxy-4-trifluoromethoxy-biphenyl-2-ylmethyl)-amino]-pyrimidin-5-yloxy}-butyrate (57.7 mg). MS (m/z): 802 [M+H]$^+$ (8) To tert-butyl 4-{2-[(3,5-bis-trifluoromethyl-benzyl)-(5'-isopropyl-2'-methoxy-4-trifluoromethoxy-biphenyl-2-ylmethyl)-amino]-pyrimidin-5-yloxy}-butyrate (57 mg) is added 4N-hydrogen chloride/dioxane solution (2 ml) and the mixture is stirred at room temperature overnight. To the reaction solution are added an aqueous saturated sodium hydroxide solution and chloroform, and the mixture is separated, dried over magnesium sulphate and concentrated under reduced pressure. The resulting residue is purified by silica gel column chromatography (chloroform:methanol=1:0→23:2) to give 4-{2-[(3,5-bis-trifluoromethyl-benzyl)-(5'-isopropyl-2'-methoxy-4-trifluoromethoxy-biphenyl-2-ylmethyl)-amino]-pyrimidin-5-yloxy}-butanoic acid (46.6 mg). MS (m/z): 746 [M+H]$^+$ (9) 4-{2-[(3,5-Bis-trifluoromethyl-benzyl)-(5'-isopropyl-2'-methoxy-4-trifluoromethoxy-biphenyl-2-ylmethyl)-amino]-pyrimidin-5-yloxy}-butanoic acid (46 mg) is dissolved in ethanol (1 ml) and thereto is added 1N-aqueous sodium hydroxide solution (60 μl) and the reaction solution is concentrated under reduced pressure to give 4-{2-[(3,5-bis-trifluoromethyl-benzyl)-(5'-isopropyl-2'-methoxy-4-trifluoromethoxy-biphenyl-2-ylmethyl)-amino]-pyrimidin-5-yloxy}-butanoic acid sodium salt (46 mg). MS (m/z): 744 [M−Na]$^-$ Examples 225 to 230

The corresponding starting compounds are treated in a similar manner to any of the above Examples to give the compounds as listed in Table 32.

TABLE 32

| Ex. No. | B$^1$ / B$^2$ structure | Physical properties, etc. |
|---|---|---|
| 218 | 4-CF$_3$, 2-Me phenyl (B$^1$=1, B$^2$=2) | MS(m/z): 728[M − Na]$^-$ |

TABLE 32-continued

[Structure: Sodium carboxylate-butoxy-pyrimidine with N-substituent bearing 3,5-bis(trifluoromethyl)benzyl and a CH₂ group labeled 1 connected to position labeled 2 on 2-methoxy-5-isopropylphenyl ring]

| Ex. No. | [B¹/B² substituent] | Physical properties, etc. |
|---|---|---|
| 219 | 4,5-bis(ethoxy)phenyl (1,2-positions) | MS(m/z): 748[M − Na]⁻ |
| 220 | 4-(benzyloxy)phenyl (1,2-positions) | MS(m/z): 766[M − Na]⁻ |
| 221 | 4-hydroxyphenyl (1,2-positions) | MS(m/z): 676[M − Na]⁻ |
| 222 | 4-ethoxyphenyl (1,2-positions) | MS(m/z): 704[M − Na]⁻ |
| 223 | 4-isopropoxyphenyl (1,2-positions) | MS(m/z): 718[M − Na]⁻ |
| 224 | 4-(trifluoromethoxy)phenyl (1,2-positions) | MS(m/z): 744[M − Na]⁻ |
| 225 | 2,3-dihydro-1,4-benzodioxin-6,7-diyl | |
| 226 | 4-(cyclopentyloxy)phenyl (1,2-positions) | MS(m/z): 744[M − Na]⁻ |

TABLE 32-continued
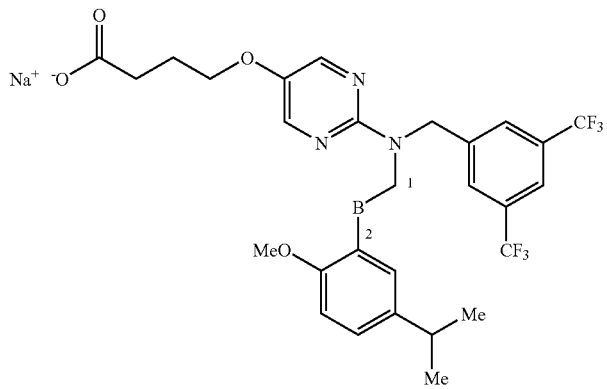
| Ex. No. | 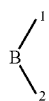 | Physical properties, etc. |
|---|---|---|
| 227 | 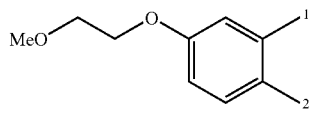 | MS(m/z): 734[M − Na]⁻ |
| 228 | 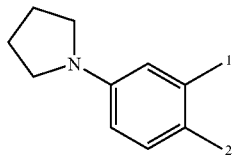 | |
| 230 | 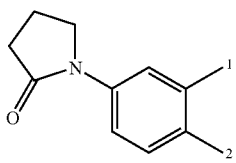 | |
| 229 | 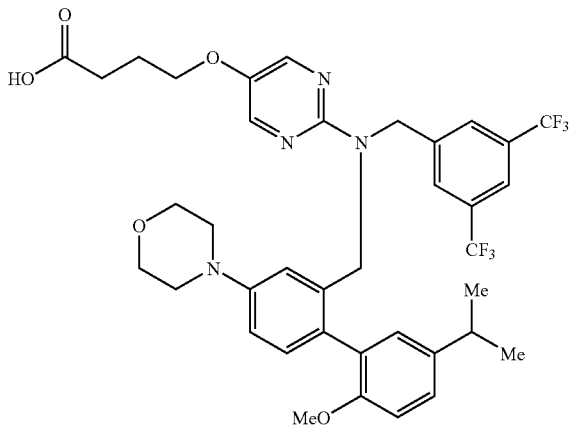 | MS(m/z): 747[M + H]⁺ |

Example 231

(1) (3,5-Bis-trifluoromethyl-benzyl)-(5-bromo-pyrimidin-2-yl)-amine (315 mg) and 4-benzyloxy-2-chloromethyl-5'-isopropyl-2'-methoxy-biphenyl (300 mg) are dissolved in N,N-dimethylformamide (5 ml) and thereto is added sodium hydride (60%) (40.9 mg) under ice-cooling, and the mixture is stirred at room temperature overnight. Thereto are added a saturated aqueous ammonium chloride solution and ethyl acetate, and the mixture is separated, and the organic layer is washed with a saturated brine, dried over magnesium sulfate, and concentrated under reduced pressure. The resulting residue is purified by silica gel column chromatography (hexane: ethyl acetate=1:0→97:3) to give (4-benzyloxy-5'-isopropyl-2'-methoxy-biphenyl-2-ylmethyl)-(3,5-bis-trifluoromethyl-benzyl)-(5-bromo-pyrimidin-2-yl)-amine (458 mg). MS (m/z): 744/746 [M+H]$^+$ (2) (4-Benzyloxy-5'-isopropyl-2'-methoxy-biphenyl-2-ylmethyl)-(3,5-bis-trifluoromethyl-benzyl)-(5-bromo-pyrimidin-2-yl)-amine (433 mg) is dissolved in toluene (5 ml) and thereto are added tris(dibenzylideneacetone)dipalladium (107 mg), sodium tert-butoxide (168 mg), 2-(di-tert-butylphosphino)biphenyl (69.4 mg) and morpholine (152 mg) and the mixture is stirred under nitrogen atmosphere at room temperature overnight. To the reaction solution is added a saturated brine, and the mixture is extracted with ethyl acetate. The organic layer is washed with a saturated brine, dried over magnesium sulfate and concentrated under reduced pressure. The resulting residue is purified by silica gel column chromatography (hexane:ethyl acetate=9:1→2:1) to give (4-benzyloxy-5'-isopropyl-2'-methoxy-biphenyl-2-ylmethyl)-(3,5-bis-trifluoromethyl-benzyl)-(5-morpholin-4-yl-pyrimidin-2-yl)-amine (384 mg). MS (m/z): 751 [M+H]$^+$ (3) (4-Benzyloxy-5'-isopropyl-2'-methoxy-biphenyl-2-ylmethyl)-(3,5-bis-trifluoromethyl-benzyl)-(5-morpholin-4-yl-pyrimidin-2-yl)-amine is treated in a similar manner to Example 221 and 222 to give 4-(2-{[(3,5-bis-trifluoromethyl-benzyl)-(5-morpholin-4-yl-pyrimidin-2-yl)-amino]-methyl}-5'-isopropyl-2'-methoxy-biphenyl-4-yloxy)-butyric acid sodium salt. MS (m/z): 745 [M−Na]$^-$

Example 232

The corresponding starting compound is treated in a similar manner to Example 231 to give the compound as listed in Table 33.

Examples 233 to 234

The corresponding starting compounds are treated in a similar manner to any of the above Examples to give the compounds as listed in Table 33.

TABLE 33

| Ex. No. | Structure | Physical properties, etc. |
|---|---|---|
| 231 | Na$^+$ $^-$O-C(=O)-CH$_2$CH$_2$CH$_2$-O-[aryl] | MS(m/z): 745[M−Na]$^-$ |
| 232 | Na$^+$ $^-$O-C(=O)-CH$_2$CH$_2$CH$_2$CH$_2$-O-[aryl] | MS(m/z): 759[M−Na]$^-$ |
| 233 | Na$^+$ $^-$O-C(=O)-CH$_2$CH$_2$CH$_2$-O-[aryl-OMe] | MS(m/z): 775[M−Na]$^-$ |
| 234 | Na$^+$ $^-$O-C(=O)-CH$_2$CH$_2$CH$_2$CH$_2$-O-[aryl-OMe] | MS(m/z): 789[M−Na]$^-$ |

Examples 235 to 238

The corresponding starting compounds are treated in a similar manner to any of the above Examples to give the compounds as listed in Table 34.

Example 239

The corresponding starting compound is treated in a similar manner to Example 142 to give the compound as listed in Table 35.

TABLE 34

| Ex. No. | —R² | Physical properties, etc. |
|---|---|---|
| 235 | [4-(1-methylethyl)-2-methylphenoxy]butanoic acid substituent | |
| 236 | 1-(4-methoxy-3-methylphenyl)ethoxy-butanoic acid substituent | |
| 237 | 3-methoxy-4-methyl-benzyloxy-butanoic acid substituent (with isopropyl) | |

TABLE 34-continued

| Ex. No. | —R² | Physical properties, etc. |
|---|---|---|
| 238 | 2-methoxy-3-methyl-5-(1-methylethyl)phenyl-butanoic acid substituent | |

TABLE 35

| Ex. No. | —R² | Physical properties, etc. |
|---|---|---|
| 239 | 4-methoxy-3-methyl-N,N-dimethylbenzamide substituent | MS(m/z): 757[M − Na]⁻ |

Examples 240 to 248 and 250 to 252

The corresponding starting compounds are treated in a similar manner to any of the above Examples to give the compounds as listed in Table 36.

TABLE 36
| Ex. No. | Structural formula | Physical properties, etc. |
|---|---|---|
| 240 | 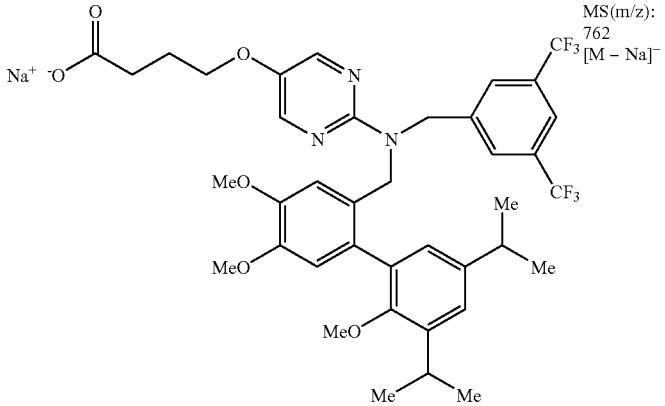 | MS(m/z): 762 [M − Na]⁻ |
| 241 | 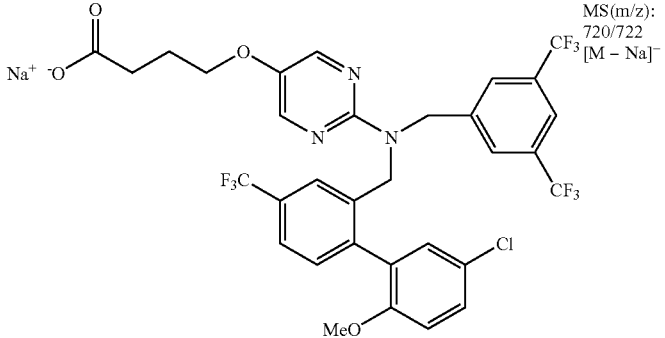 | MS(m/z): 720/722 [M − Na]⁻ |
| 242 | 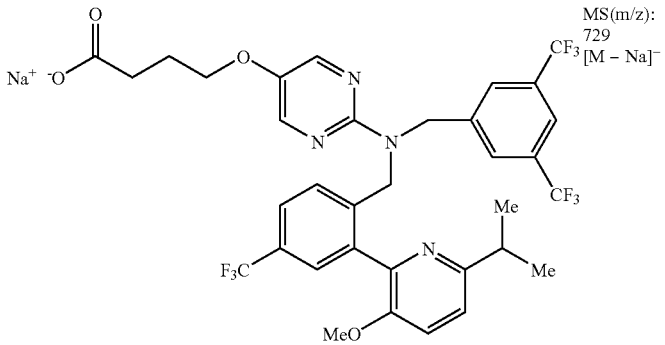 | MS(m/z): 729 [M − Na]⁻ |
| 243 | 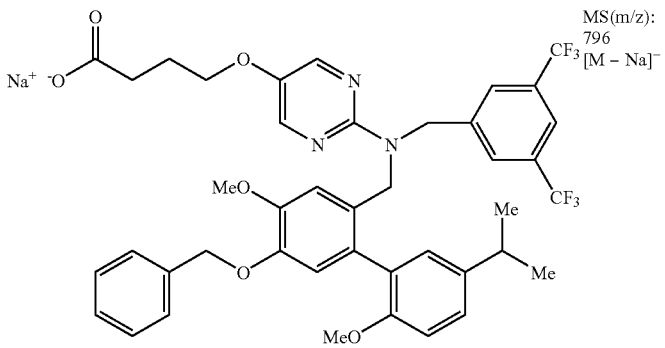 | MS(m/z): 796 [M − Na]⁻ |

TABLE 36-continued

| Ex. No. | Structural formula | Physical properties, etc. |
|---|---|---|
| 244 | (structure) | MS(m/z): 706 [M − Na]− |
| 245 | (structure) | MS(m/z): 734 [M − Na]− |
| 246 | (structure) | MS(m/z): 748 [M − Na]− |
| 247 | (structure) | MS(m/z): 764 [M − Na]− |

TABLE 36-continued
| Ex. No. | Structural formula | Physical properties, etc. |
|---|---|---|
| 248 | 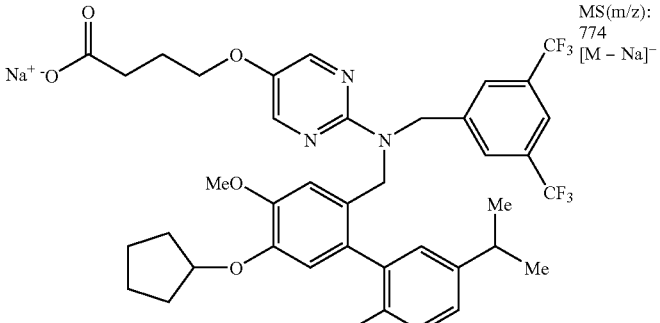 | MS(m/z): 774 [M − Na]⁻ |
| 250 | 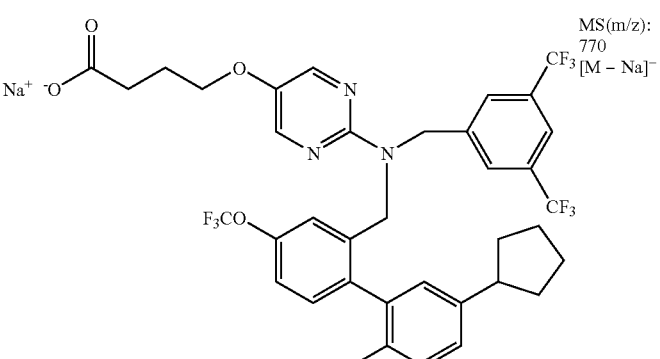 | MS(m/z): 770 [M − Na]⁻ |
| 251 | 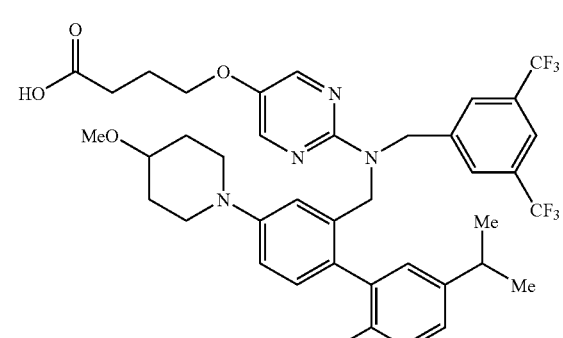 | |
| 252 | 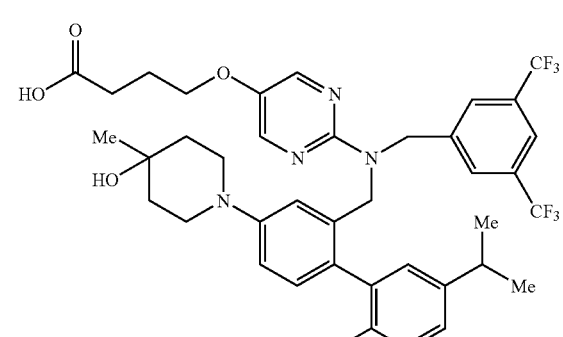 | |

Example 249

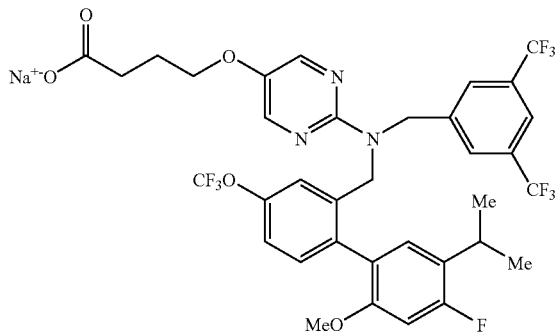

The corresponding starting compound is treated in a similar manner to Example 224 to give the above compound. MS (m/z): 762 [M−Na]⁻

Reference Example 1

Cyclohexanecarboxaldehyde (38 g), diethylamine hydrochloride (55 g) and acetic acid (29 ml) are dissolved in methylene chloride (500 ml) and thereto is added triacetoxy sodium borohydride (71.8 g) at room temperature and the mixture is stirred at room temperature overnight. To the reaction solution are added a 2N-aqueous sodium hydroxide solution and methylene chloride, and the mixture is separated, and the organic layer is washed with a saturated brine, dried over magnesium sulfate, and the mixture is concentrated under reduced pressure to give cyclohexylmethyl-ethyl-amine (40.1 g) as a crude product. MS (m/z): 142 [M+H]⁺

Reference Example 2

3,5-Bis-trifluoromethyl-benzylamine (10 g) and 5-bromo-2-chloro-pyrimidine (12 g) are dissolved in 1,4-dioxane (50 ml) and thereto is added N,N-diisopropylethylamine (10.7 ml) and the mixture is heated under reflux overnight. The reaction solution is cooled to room temperature and concentrated under reduced pressure. The resulting residue is purified by silica gel column chromatography (hexane:ethyl acetate=9:1 to 7:3) to give (3,5-bis-trifluoromethyl-benzyl)-(5-bromo-pyrimidin-2-yl)-amine (10.1 g). MS (m/z): 713 [M+H]⁺

Reference Example 3

(1) Ethylamine hydrochloride (2 g) is dissolved in methylene chloride (20 ml) and thereto are added pyridine (6 ml) and ethyl 6-(chloroformyl)hexanoate (7.6 g) and the mixture is stirred at room temperature overnight. To the reaction solution are added a saturated aqueous sodium bicarbonate solution and the mixture is separated, and the organic layer is washed successively with a 1N-hydrochloric acid, water and a saturated brine, dried over magnesium sulfate, and concentrated under reduced pressure to give ethyl 6-ethylcarbamoyl hexanoate (9.29 g) as a crude product. MS (m/z): 216 [M+H]⁺

(2) Crude ethyl 6-ethylcarbamoyl hexanoate (9.29 g) is dissolved in tetrahydrofuran (50 ml) and thereto is added sodium borohydride (7.35 g). The reaction solution is heated under reflux and thereto is added dropwise acetic acid (11 ml) and the mixture is heated under reflux for 1 hour and a half. To the reaction solution is added water under ice-cooling and the mixture is extracted with ethyl acetate. The organic layer is washed with a saturated brine, dried over magnesium sulfate, and concentrated under reduced pressure. The resulting residue is dissolved in ethanol (30 ml), and thereto is added a 4N-hydrochloric acid in ethyl acetate (7.6 ml), and the mixture is stirred at room temperature overnight. To the reaction solution are added a 2N-aqueous sodium hydroxide solution and ethyl acetate and the mixture is separated, and the organic layer is washed with a saturated brine, dried over magnesium sulfate, and concentrated under reduced pressure to give ethyl 7-ethylamino-heptanoate (3.98 g) as a crude product. MS (m/z): 216 [M+H]⁺

Reference Example 4

(1) 6-Aminohexanoic acid methyl ester hydrochloride (5 g) is dissolved in methylene chloride (20 ml) and thereto are added pyridine (4.5 ml) and acetyl chloride (2 ml), and the mixture is stirred at room temperature for 1 hour and 45 minutes. To the reaction solution are added a 1N-hydrochloric acid and chloroform, and the mixture is separated, and the organic layer is washed with a saturated brine, dried over magnesium sulfate, and concentrated under reduced pressure to give methyl 6-acetylamino-hexanoate (5.19 g) as a crude product. MS (m/z): 188 [M+H]⁺

(2) Crude methyl 6-acetylamino-hexanoate (5.19 g) is dissolved in tetrahydrofuran (50 ml) and thereto is added sodium borohydride (5.03 g). The reaction solution is heated under reflux and thereto is added dropwise acetic acid (7.6 ml) and the mixture is heated under reflux for 1 hour and 30 minutes. To the reaction solution is added water under ice-cooling and the mixture is extracted with ethyl acetate. The organic layer is washed with a saturated brine, dried over magnesium sulfate, and concentrated under reduced pressure. The resulting residue is dissolved in ethanol (30 ml) and thereto is added a 4N-hydrochloric acid in ethyl acetate (7.6 ml) and the mixture is stirred at room temperature overnight. To the reaction solution are added a 2N-aqueous sodium hydroxide solution and ethyl acetate, and the mixture is separated, and the organic layer is washed with a saturated brine, dried over magnesium sulfate, and concentrated under reduced pressure to give ethyl 6-ethylamino-hexanoate (1.74 g) as a crude product. MS (m/z): 188 [M+H]⁺

Reference Example 5

(1) (3,5-Bis-trifluoromethyl-benzyl)-(5-bromo-pyrimidin-2-yl)-amine (10 g) and triethylamine (4.18 ml) are dissolved in methylene chloride (100 mL) and thereto is added triphosgene (2.97 g) under ice-cooling. The reaction solution is stirred at the same temperature for 30 minutes and concentrated under reduced pressure. The resulting residue is dissolved in tetrahydrofuran (100 mL) and thereto are added benzyl alcohol (3.88 ml) and triethylamine (10.45 ml) at room temperature and the mixture is stirred overnight. The reaction solution is diluted with ethyl acetate and washed with a saturated aqueous sodium bicarbonate solution and a 1N-hydrochloric acid. The organic layer is washed with a saturated brine, dried over magnesium sulfate, and concentrated under reduced pressure. The resulting residue is purified by silica gel column chromatography (hexane:ethyl acetate=97:3→9:1) to give benzyl (3,5-bis-trifluoromethyl-benzyl)-(5-bromo-pyrimidin-2-yl)-carbamate (11.58 g). MS (m/z): 534/536 [M+H]⁺

(2) Benzyl (3,5-bis-trifluoromethyl-benzyl)-(5-bromo-pyrimidin-2-yl)-carbamate (11.5 g), [1,1'-bis(diphenylphosphino)ferrocene]-dichloropalladium dichloromethane complex (3.51 g), potassium acetate (6.33 g) and bis(pinacolato) diboron (10.9 g) are dissolved in dimethylsulfoxide (75 ml), and the mixture is heated to 80° C. under nitrogen atmosphere and stirred for 30 minutes. The reaction solution is cooled to room temperature and thereto are added water and ethyl acetate, and the insoluble materials are removed by filtration through Celite™, and the mixture is separated and the organic layer is washed with a saturated brine, dried over magnesium sulfate, and concentrated under reduced pressure. The resulting residue is dissolved in tetrahydrofuran (100 ml) and thereto is added dropwise a 30% aqueous hydrogen peroxide solution (50 ml) under ice-cooling and the mixture is stirred for 1 hour. Thereto is added a saturated aqueous sodium thiosulfate solution under ice-cooling to consume the excess hydrogen peroxide, followed by an addition of water and ethyl acetate, and the mixture is separated. The organic layer is washed with a saturated brine, dried over magnesium sulfate, and concentrated under reduced pressure. The resulting residue is purified by silica gel column chromatography (chloroform:methanol=1:0→9:1) to give benzyl (3,5-bis-trifluoromethyl-benzyl)-(5-hydroxy-pyrimidin-2-yl)-carbamate (9.70 g). MS (m/z): 472 [M+H]$^+$ (3) Benzyl (3,5-bis-trifluoromethyl-benzyl)-(5-hydroxy-pyrimidin-2-yl)-carbamate (9.70 g) and ethyl 4-bromobutyrate (3.53 g) are dissolved in N,N-dimethylformamide (50 mL) and thereto is added potassium carbonate (3.41 g) and the mixture is stirred at 50° C. for 1 hour. Thereto are added ethyl acetate and a saturated brine, and the mixture is separated, and the organic layer is washed with a saturated brine, dried over magnesium sulfate, and concentrated under reduced pressure. The resulting residue is purified by silica gel column chromatography (hexane:ethyl acetate=4:1→1:1) to give ethyl 4-{2-[benzyloxycarbonyl-(3,5-bis-trifluoromethyl-benzyl)-amino]-pyrimidin-5-yloxy}-butyrate (8.29 g). MS (m/z): 586 [M+H]$^+$ (4) Ethyl 4-{2-[benzyloxycarbonyl-(3,5-bis-trifluoromethyl-benzyl)-amino]-pyrimidin-5-yloxy}-butyrate (3.0 g) is dissolved in tetrahydrofuran (20 ml) and thereto is added 10% palladium-carbon (500 mg) and the mixture is stirred under hydrogen atmosphere at room temperature for 2 hours and 30 minutes. The catalyst is removed by filtration, and the filtrate is concentrated under reduced pressure. The resulting residue is purified by silica gel column chromatography (hexane:ethyl acetate=9:1→1:1) to give ethyl 4-[2-(3,5-bis-trifluoromethyl-benzylamino)-pyrimidin-5-yloxy]-butyrate (2.22 g). MS (m/z): 452 [M+H]$^+$ Reference Example 6

(1) 6-Aminohexanoic acid methyl ester hydrochloride (2.50 g) is dissolved in tetrahydrofuran (50 ml) and thereto are added water (50 ml) and sodium bicarbonate (3.44 g), followed by an addition dropwise of benzyl chloroformate (2.17 ml) under ice-cooling, and the mixture is stirred at the same temperature for 2 hours and a half. To the reaction mixture is added a saturated brine, and the mixture is extracted with ethyl acetate. The organic layer is washed twice with a saturated brine, dried over magnesium sulfate, and concentrated under reduced pressure to give methyl 6-benzyloxycarbonylamino hexanoate (4.16 g). MS (m/z): 280 [M+H]$^+$ (2) Methyl 6-benzyloxycarbonylamino-hexanoate (4.15 g) is dissolved in N,N-dimethylformamide (2.5 mL) and thereto is added sodium hydride (63%) (552 mg) under ice-cooling and the mixture is stirred at the same temperature for 1 hour and thereto is added methyl iodide (1.72 ml), and the mixture is stirred at the same temperature for an additional 2 hours. To the reaction mixture is added a saturated brine, and the mixture is extracted with ethyl acetate, and the organic layer is washed with a saturated brine, dried over magnesium sulfate, and concentrated under reduced pressure. The resulting residue is purified by silica gel column chromatography (hexane:ethyl acetate=4:1) to give methyl 6-(benzyloxycarbonyl-methyl-amino)-hexanoate (2.25 g). MS (m/z): 294 [M+H]$^+$ (3) Methyl 6-(benzyloxycarbonyl-methyl-amino)-hexanoate (2.24 g) is dissolved in methanol (35 ml) and thereto is added 10% palladium-carbon (500 mg) and the mixture is stirred at room temperature under hydrogen atmosphere for 2 hours. The reaction mixture is filtered and the filtrate is concentrated under reduced pressure to give methyl 6-methylamino hexanoate (1.11 g). MS (m/z): 160 [M+H]$^+$ Reference Example 7

Propylamine (0.65 g) is dissolved in tetrahydrofuran (5 ml) and thereto is added pyridine (0.89 ml), followed by an addition dropwise of methyl adipoyl chloride (1.96 g) under ice-cooling and the mixture is stirred at room temperature for 1 hour. To the reaction mixture is added a saturated brine, and the mixture is extracted with ethyl acetate. The organic layer is washed with a saturated brine, dried over magnesium sulfate, and concentrated under reduced pressure. The resulting residue is dissolved in tetrahydrofuran (30 ml) and thereto is added sodium borohydride (1.93 g) at room temperature and the mixture is heated to 65° C. and thereto is added dropwise acetic acid (2.92 ml) over 1 hour and the mixture is stirred at the same temperature for 9 hours. To reaction mixture is added an ice-cooled dilute hydrochloric acid, and the mixture is stirred for 30 minutes and extracted with ethyl acetate, and the organic layer is washed with a mixed solution of a saturated aqueous sodium bicarbonate solution and a saturated brine, dried over magnesium sulfate, and concentrated under reduced pressure. The resulting residue is dissolved in methanol (5 ml) and thereto is added a 4N-hydrochloric acid in dioxane (7.5 mL) and the mixture is stirred at room temperature overnight. To the reaction mixture is added a saturated aqueous sodium bicarbonate solution and a saturated brine, and the mixture is extracted six times with ethyl acetate and the collected organic layer is dried over magnesium sulfate, and concentrated under reduced pressure to give methyl 6-propylamino-hexanoate (914 mg). MS (m/z): 188 [M+H]$^+$ Reference Example 8

(1) Tert-butyl piperidine-4-ylmethyl-carbamate (2.00 g) is dissolved in tetrahydrofuran (10 ml), and thereto is added triethylamine (1.69 ml), followed by an addition dropwise of ethyl bromoacetate (1.24 mL) in water bath and the mixture is stirred at room temperature for 2 hours. To the reaction mixture is added a saturated brine, and the mixture is extracted with ethyl acetate. The organic layer is washed twice with a saturated brine, dried over magnesium sulfate, and concentrated under reduced pressure, and to the resulting crystalline residue is added isopropylether and the mixture is filtered to give ethyl [4-(tert-butoxy-carbonylamino-methyl)-piperidin-1-yl]-acetate (1.87 g). MS (m/z): 301 [M+H]$^+$ (2) Ethyl [4-(tert-butoxycarbonylamino-methyl)-piperidin-1-yl]-acetate (1.86 g) is dissolved in N,N-dimethylformamide (10 ml), and thereto are added sodium hydride (63%) (1.19 g) and ethyl iodide (6.0 ml), and the mixture is stirred at room temperature for 2 hours. The reaction mixture is made weak basic with a 10% aqueous citric acid solution and a saturated aqueous sodium bicarbonate solution, and extracted with ethyl acetate, and the organic layer is washed with a saturated brine, dried over magnesium sulfate, and concentrated under reduced pressure. The resulting residue is purified by silica gel column chromatography (hexane:ethyl acetate=2:1) to give ethyl {4-[(tert-butoxycarbonyl-ethyl-amino)-methyl]-piperidine-1-yl}-acetate (905 mg). MS (m/z): 329 [M+H]$^+$ (3) Ethyl {4-[(tert-butoxycarbonyl-ethyl-amino)-methyl]-piperidine-1-yl}-acetate (235 mg) is dissolved in methylene chloride (1 ml) and thereto is added trifluoroacetic acid (1 ml) and the mixture is stirred at room temperature overnight. The reaction mixture is concentrated under reduced pressure to give (4-ethylaminomethyl-piperidin-1-yl)-acetic acid ethyl ester bistrifluoroacetic acid salt (482 mg). MS (m/z): 229 [M+H]$^+$ Reference Example 9

(1) 2-Tert-butoxy-ethylamine (2 g) is dissolved in methylene chloride (10 ml) and thereto are added pyridine (940 μl) and ethyl 6-(chloroformyl)hexanoate (1.13 g) under ice-cooling and the mixture is stirred at room temperature overnight. To the reaction solution are added a 1N-hydrochloric acid and chloroform, and the mixture is separated, and the organic layer is washed with a saturated brine, dried over magnesium sulfate, and concentrated under reduced pressure to give ethyl 6-(2-tert-ethylcarbamoyl)-hexanoate as a crude product (2.96 g). MS (m/z): 288 [M+H]$^+$ (2) Crude ethyl 6-(2-tert-ethylcarbamoyl)-hexanoate (2.96 g) is dissolved in tetrahydrofuran (15 ml) and thereto is added sodium borohydride (1.60 g). The reaction solution is heated under reflux and thereto is added dropwise acetic acid (2.4 mL) and the mixture is heated under reflux for 1 hour. To the reaction solution is added water under ice-cooling and the mixture is extracted with ethyl acetate. The organic layer is washed with a saturated brine, dried over magnesium sulfate, and concentrated under reduced pressure. The resulting residue is dissolved in ethanol (6 ml) and thereto is added a 4N-hydrochloric acid in ethyl acetate (1.5 ml) and the mixture is stirred at room temperature for 3 days. To the reaction solution are added a saturated aqueous sodium bicarbonate solution and ethyl acetate, and the mixture is separated, and the organic layer is washed with a saturated brine, dried over magnesium sulfate, and concentrated under reduced pressure to give ethyl 7-(2-tert-butoxy-ethylamino)-heptanoate as a crude product (2.6 g). MS (m/z): 274 [M+H]$^+$ Reference Example 10

(1) 2-Bromo-pyridin-3-ol (5 g) is dissolved in water (150 ml) and thereto are added sodium carbonate (6.15 g) and iodine (7.65 g) and the mixture is stirred at room temperature for 2 hours. Thereto are added a 1N-hydrochloric acid and ethyl acetate, and the mixture is separated, and the organic layer is washed with a saturated brine, dried over magnesium sulfate, and concentrated under reduced pressure. The residue is purified by silica gel column chromatography (hexane:ethyl acetate=9:1→3:1) to give 2-bromo-6-iodo-pyridin-3-ol (4.52 g). MS (m/z): 300/302 [M+H]$^+$ (2) 2-Bromo-6-iodo-pyridin-3-ol (2.98 g) is dissolved in N,N-dimethylformamide (140 ml) and thereto are added cesium carbonate (16.3 g) and methyl iodide (1.25 mL) and the mixture is stirred at room temperature overnight. To the reaction solution are added water and ethyl acetate, and the mixture is separated, and the organic layer is washed with a saturated brine, dried over magnesium sulfate, and concentrated under reduced pressure. The resulting residue is purified by silica gel column chromatography (hexane:ethyl acetate=19:1→4:1) to give 2-bromo-6-iodo-3-methoxy-pyridine (2.45 g). MS (m/z): 314/316 [M+H]$^+$ (3) To 0.5M-isopropenyl magnesium bromide/tetrahydrofuran is added trimethyl borate (3.3 ml) and the mixture is stirred under nitrogen atmosphere at room temperature for 30 minutes. To the reaction solution are added 6N-hydrochloric acid and diethylether, and the mixture is separated. The organic layer is washed with a saturated brine, dried over magnesium sulfate, and concentrated under reduced pressure to give isopropenylboronic acid as a crude product (818 mg). The above crude isopropenyl boronic acid (287 mg) and 2-bromo-6-iodo-3-methoxy-pyridine (800 mg) are dissolved in a mixed solvent of 1,2-dimethoxy-ethane (8 ml) and ethanol (3.2 ml) and thereto are added a 1M-aqueous sodium carbonate solution (6.4 ml) and tetrakis(triphenylphosphine) palladium (240 mg) and the mixture is stirred under nitrogen atmosphere at 80° C. for 5 hours. To the reaction solution are added water and ethyl acetate, and the mixture is separated, and the organic layer is washed with a saturated brine, dried over magnesium sulfate, and concentrated under reduced pressure. The residue is purified by silica gel column chromatography (hexane:ethyl acetate=49:1→9:1), followed by NH-silica gel column chromatography (hexane:ethyl acetate=49:1→9:1) to give 2-bromo-6-isopropenyl-3-methoxy-pyridine (138 mg). MS (m/z): 228/230 [M+H]$^+$ Reference Example 11

5-Methoxy-2-methylsulfanyl-pyrimidin-4-ol (250 mg) is dissolved in acetonitrile (7 ml) and thereto are added phosphorus oxychloride (0.7 ml) and N,N-diethyl aniline (460 μl) and the mixture is heated under reflux for 5.5 hours. The reaction solution is evaporated azeotropically with toluene three times, and to the residue are added aqueous citric acid solution and chloroform, and the mixture is separated. The organic layer is washed with a saturated brine, dried over magnesium sulfate, and concentrated under reduced pressure. The resulting residue is purified by silica gel column chromatography (hexane:ethyl acetate=19:1→17:3) to give 4-chloro-5-methoxy-2-methylsulfanyl-pyrimidine (260 mg). MS (m/z): 191/193 [M+H]$^+$ Reference Example 12

(1) 3-Nitro-5-(trifluoromethyl)benzoic acid (50 g) is dissolved in tetrahydrofuran (300 ml) and thereto is added dropwise a 1.0M-borane tetrahydrofuran complex/tetrahydrofuran (300 ml) at 0° C. under nitrogen atmosphere over 2 hours and the mixture is stirred at 75° C. for 1 hour and a half. The reaction solution is allowed to cool to room temperature and concentrated under reduced pressure, and thereto is added a 1N-hydrochloric acid and the mixture is extracted with ethyl acetate. The organic layer is washed successively with water and a saturated brine, dried over magnesium sulfate, and concentrated under reduced pressure to give crude (3-nitro-5-trifluoromethyl-phenyl)-methanol. This product is dissolved in methanol (500 mL) and thereto is added 10% palladium-carbon (5 g) and the mixture is stirred under hydrogen atmosphere at room temperature overnight. The catalyst is removed by filtration, and the filtrate is concentrated under reduced pressure to give crude (3-amino-5-trifluoromethyl-phenyl)-methanol. To copper (II) bromide (53.6 g) is added acetonitrile (500 ml), followed by an addition dropwise of tert-butyl nitrite (35.7 ml) under ice-cooling and the mixture is stirred under nitrogen atmosphere for 5 minutes. To the reaction mixture is added dropwise a solution of the above crude (3-amino-5-trifluoromethyl-phenyl)-methanol in acetonitrile (200 ml) under ice-cooling over 1 hour and 15 minutes and the mixture is stirred at room temperature under nitrogen atmosphere overnight. To the reaction mixture is added a 1N-hydrochloric acid and the mixture is extracted with ethyl acetate. The organic layer is washed successively with a 1N-hydrochloric acid, water and a saturated brine, dried over magnesium sulfate, and concentrated under reduced pressure. The resulting residue is purified by silica gel column chromatography (hexane:ethyl acetate=7:1→4:1) to give (3-bromo-5-trifluoromethyl-phenyl)-methanol (40.7 g). NMR (CDCl$_3$): 1.90 (1H, t), 4.76 (2H, d), 7.56 (1H, s), 7.68 (1H, s), 7.72 (1H, s)

(2) (3-Bromo-5-trifluoromethyl-phenyl)-methanol (33.9 g) is dissolved in N,N-dimethylformamide (400 mL) and thereto are added zinc(II) cyanide (16.39 g) and tetrakis (triphenylphosphine)palladium (7.68 g) and the mixture is heated under nitrogen atmosphere at 120° C. for 2 hours. The reaction solution is allowed to cool to room temperature, and filtered through Celite™, and the filtrate is concentrated under reduced pressure. Thereto is added water and the mixture is extracted with ethyl acetate. The organic layer is washed with a saturated brine, dried over sodium sulfate, and concentrated under reduced pressure. The resulting residue is purified by silica gel column chromatography (hexane:ethyl acetate=2:1) to give 3-hydroxymethyl-5-trifluoromethyl-benzonitrile (23.4 g). NMR (CDCl$_3$): 2.09 (1H, t), 4.85 (2H, d), 7.83 (1H, s), 7.87 (2H, s)

(3) 3-Hydroxymethyl-5-trifluoromethyl-benzonitrile (23.4 g) is dissolved in methylene chloride (230 mL) and thereto is added carbon tetrabromide (42.4 g), followed by an addition of triphenylphosphine (32.0 g) under ice-cooling and the mixture is stirred at the same temperature for 30 minutes. The reaction solution is concentrated under reduced pressure. The resulting residue is purified by silica gel column chromatography (hexane:ethyl acetate=10:1) to give 3-bromo-methyl-5-trifluoromethyl-benzonitrile (25.5 g). NMR (CDCl$_3$): 4.51 (2H, s), 7.86 (1H, s), 7.88 (2H, s)

Reference Example 13

2-Chloropyrimidin-5-ol (3.89 g) is dissolved in N,N-dimethylformamide (50 ml) and thereto are added potassium carbonate (4.98 g) and tert-butyl 4-bromo-butyrate (7.36 g) and the mixture is stirred at room temperature overnight. To the reaction solution are added ethyl acetate and water, and the mixture is separated, and the organic layer is washed with a saturated brine, dried over magnesium sulfate, and concentrated under reduced pressure. The resulting residue is purified by silica gel column chromatography (hexane:ethyl acetate=24:1→4:1) to give tert-butyl 4-(2-chloropyrimidin-5-yloxy)bromobutyrate (6.22 g). MS (m/z): 273 [M+H]$^+$ Reference Example 14

2,5-Dibromopyridine (4.74 g) is dissolved in toluene (100 ml) and thereto are added 3,5-bis-trifluoromethyl-benzy-lamine (5.84 g) and palladium acetate (449.0 mg), 2,2'-bis (diphenylphosphino)-1,1'-binaphthyl (1.25 g) and sodium tert-butoxide (4.23 g) and the mixture is stirred under nitrogen atmosphere at 80° C. for 12 hours. The reaction solution is cooled to room temperature, and thereto is added a saturated aqueous sodium bicarbonate solution and the mixture is extracted with ethyl acetate twice, and the organic layer is washed successively with water and a saturated brine, dried over magnesium sulfate, and concentrated under reduced pressure. The resulting residue is purified by silica gel column chromatography (hexane:ethyl acetate=19:1→4:1) to give (3,5-bis-trifluoromethyl-benzyl)-(5-bromopyridin-2-yl)-amine (2.08 g). MS (m/z): 399/401 [M+H]$^+$ Reference Example 15

3-Bromomethyl-5-trifluoromethyl-benzonitrile (which is prepared in Reference Example 12) (15.9 g) is dissolved in 7M-ammonia/methanol (550 ml), and the mixture is stirred at 50-60° C. for 30 minutes. The reaction solution is concentrated under reduced pressure. To the resulting residue are added a saturated aqueous sodium bicarbonate solution and chloroform, and the mixture is separated, and the organic layer is dried over sodium sulfate, and concentrated under reduced pressure. The resulting residue is purified by silica gel column chromatography (chloroform:methanol=1: 0→19:1 chloroform:methanol: ammonium hydroxide solution=19:1:0.1) to give 3-aminomethyl-5-trifluoromethyl-benzonitrile (10.4 g). MS (m/z): 201 [M+H]$^+$ Reference Example 16

The corresponding starting compound is treated in a similar manner to Example 142(1) to give the compound listed in Table 37.

Reference Example 17

(1) 3-Bromo-4-methoxybenzoic acid (2.00 g) is dissolved in tetrahydrofuran (50 ml), and the mixture is cooled to −78° C., and thereto is added dropwise a 1.1M methyllithium in diethyl ether (7.7 ml). The mixture is stirred at −78° C. for 5 minutes, and thereto is added dropwise a 1.6M tert-butyl-lithium in n-pentane (13.2 ml), and the mixture is stirred at −78° C. for 15 minutes, and the mixture is allowed to warm to −45° C., and the mixture is stirred for 45 minutes, and then again cooled to −78° C. Thereto is added dropwise triisopropylborate, and the mixture is stirred at −78° C. for 15 minutes, and the mixture is allowed to warm to room temperature. The mixture is stirred at room temperature for 1.5 hours, and the mixture is concentrated under reduced pressure, and thereto are added water and hexane. The aqueous layer is adjusted to pH 4 by addition of a 6N-hydrochloric acid and a saturated aqueous sodium bicarbonate solution, and the mixture is extracted with ethyl acetate and methanol twice. The organic layer is washed with a saturated brine, dried over magnesium sulfate and concentrated under reduced pressure. To the resulting residue is added diethyl ether, and the resulting solids are collected by filtration to give 2-methoxy-5-carboxyphenylboronic acid (1.37 g) as a crude product.

(2) The crude 2-methoxy-5-carboxyphenylboronic acid (370 mg) is dissolved in N,N-dimethylformamide (10 ml), and thereto are added 2.0M-dimethylamine/tetrahydrofuran solution (1.9 ml), 1-hydroxybenzotriazole dihydrate (725 mg), 1-ethyl-3-(3-dimethylaminopropyl)carbodiimide hydrochloride (579 mg). The mixture is stirred at room temperature for 3 hours, and thereto is added a saturated aqueous sodium bicarbonate solution, and the mixture is extracted with ethyl acetate twice. The organic layer is dried over magnesium sulfate and concentrated under reduced pressure. The resulting residue is purified by silica gel column chromatography (chloroform:methanol=19:1) to give 2-methoxy-5-dimethylcarbamoylphenylboronic acid (210 mg). MS (m/z): 224 [M+H]$^+$ Reference Example 18

The corresponding starting compound is treated in a similar manner to Reference Example 17 to give the compound listed in Table 37.

Reference Example 19

(1) 4-sec-Butyl-phenol (3.0 g) is dissolved in chloroform and thereto is added bromine (1.02 ml) and the mixture is stirred at room temperature for 30 minutes. Thereto are added a saturated aqueous sodium thiosulfate solution, a saturated aqueous sodium bicarbonate solution and ethyl acetate, and the mixture is separated. The organic layer is washed with a saturated brine, dried over magnesium sulfate, and concentrated under reduced pressure to give 2-bromo-4-sec-butyl-phenol (4.57 g). NMR (CDCl$_3$): 0.81 (3H, t), 1.19 (3H, d), 1.56 (2H, m), 2.51 (1H, m), 5.33 (1H, s), 6.93 (1H, d), 7.02 (1H, d), 7.26 (1H, s).

(2) 2-Bromo-4-sec-butyl-phenol (1.50 g) is dissolved in N,N-dimethylformamide (10 ml) and thereto are added potassium carbonate (1.18 g) and iodomethane (1.12 g) and the mixture is stirred at room temperature overnight. Thereto are added ethyl acetate and water, and the mixture is separated, and the organic layer is washed with a saturated brine, dried over magnesium sulfate and concentrated under reduced pressure. The resulting residue is purified by silica gel column chromatography (hexane:ethyl acetate=1:0→20:1) to give 2-bromo-4-sec-butyl-1-methoxy-benzene (1.58 g). NMR (CDCl$_3$): 0.80 (3H, t), 1.20 (3H, d), 1.55 (2H, m), 2.51 (1H, m), 3.87 (3H, s), 6.82 (1H, d), 7.07 (1H, d), 7.35 (1H, s).

(3) 2-Bromo-4-sec-butyl-1-methoxy-benzene (1.15 g) is dissolved in tetrahydrofuran (17 ml) and the mixture is cooled to −78° C., and thereto is added dropwise 1.6M n-butyllithium in hexanes, and the mixture is stirred at −78° C. for 15 minutes. To the reaction solution is added trimethyl borate (1.47 g), and the reaction mixture is stirred at −78° C. for 30 minutes, and thereto are added a saturated aqueous ammonium chloride solution and ethyl acetate. The mixture is separated, and the organic layer is washed with a saturated brine, dried over magnesium sulfate, and concentrated under reduced pressure to give crude 5-sec-butyl-1-methoxy-benzene boronic acid (950 mg). NMR (CDCl$_3$): 0.81 (3H, t), 1.22 (3H, d), 1.58 (2H, m), 2.58 (1H, m), 3.90 (3H, s), 6.25 (2H, s), 6.85 (2H, d), 7.25 (1H, d), 7.65 (1H, s).

Reference Examples 20 to 23

The corresponding starting compounds are treated in a similar manner to Reference Example 19 to give the compounds listed in Table 37.

Reference Example 24

2-Bromo-6-iodo-3-methoxy-pyridine (500 mg) is dissolved in dry toluene (5 ml) and thereto is added dropwise 1.6M n-butyllithium in hexane (1 ml) at −78° C. under nitrogen atmosphere, and the mixture is stirred for 1 hour and thereto is added acetone (0.23 ml), and the mixture is stirred overnight. To the reaction solution are added water and ethyl acetate, and the mixture is separated, and the organic layer is washed with a saturated brine, dried over magnesium sulfate, and concentrated under reduced pressure. The resulting residue is purified by silica gel column chromatography (hexane:ethyl acetate=4:1→3:2) to give 2-(6-bromo-5-methoxy-pyridin-2-yl)-propan-2-ol (197 mg). MS (m/z): 246/248 [M+H]$^+$

TABLE 37

| Reference Ex. No. | Structural formula |
| --- | --- |
| 1 | |
| 2 | |
| 3 | |
| 4 | |

TABLE 37-continued
| Reference Ex. No. | Structural formula |
| --- | --- |
| 5 | 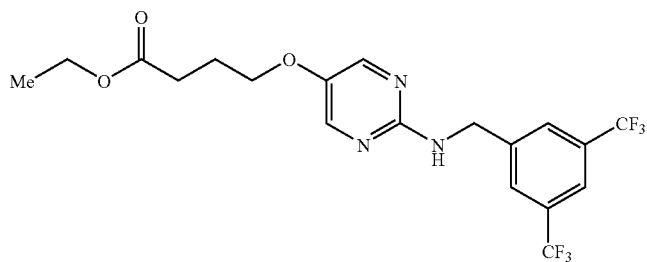 |
| 6 | 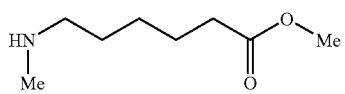 |
| 7 | 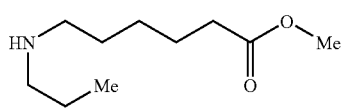 |
| 8 | 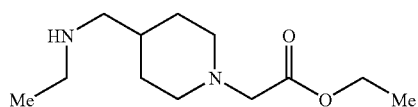 2TFA |
| 9 | 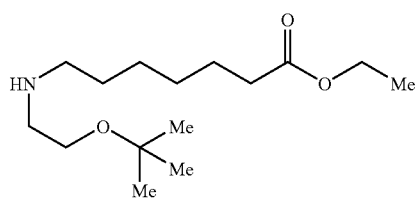 |
| 10 | 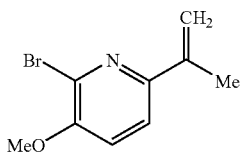 |
| 11 | 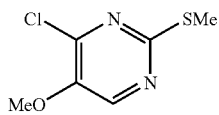 |
| 12 | 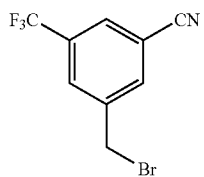 |
| 13 | 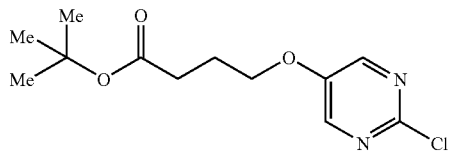 |

TABLE 37-continued
| Reference Ex. No. | Structural formula |
|---|---|
| 14 | 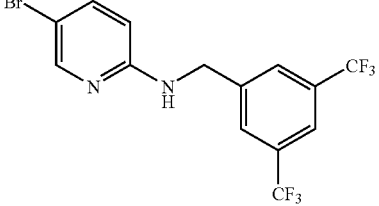 |
| 15 | 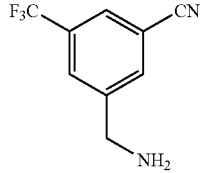 |
| 16 | 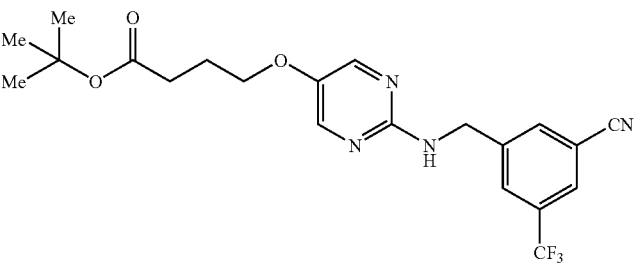 |
| 17 | 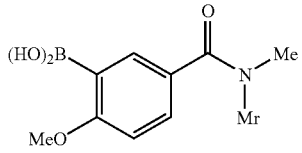 |
| 18 | 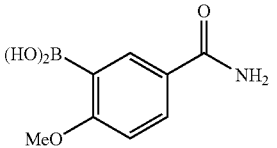 |
| 19 | 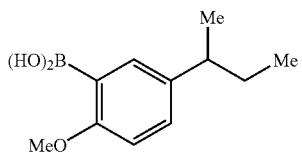 |
| 20 | 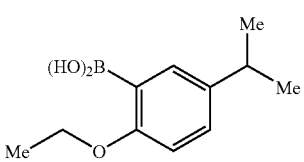 |
| 21 | 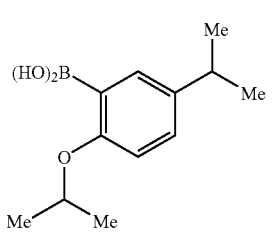 |

TABLE 37-continued

| Reference Ex. No. | Structural formula |
|---|---|
| 22 | 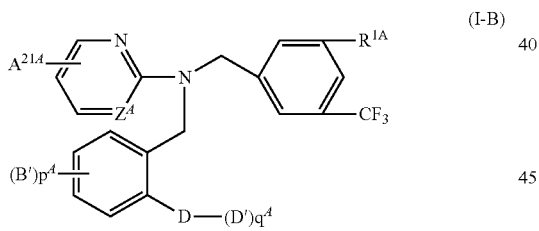 |
| 23 | |
| 24 | |

INDUSTRIAL APPLICABILITY

The present compound of formula (1) or a pharmaceutically acceptable derivative thereof has an inhibitory activity against CETP and also shows an activity of increasing HDL cholesterol level and an activity of decreasing LDL cholesterol level. Thus, the compounds of the present invention are useful for prophylaxis and/or treatment of arteriosclerotic diseases, hyperlipemia or dyslipidemia, and the like.

The invention claimed is:

1. A compound of the formula (I-B):

wherein
$Z^A$ is N or CH;
$A^{21A}$ is an optionally substituted homocyclic group, an optionally substituted alkylsulfanyl group, an optionally substituted alkylsulfinyl group, an optionally substituted alkylsulfonyl group, an optionally substituted alkyl group, a nitro group, a hydroxy group, a cyano group, an optionally substituted alkenyl group, an optionally substituted heterocyclic group, an optionally substituted alkoxy group, a halogen atom, an amino group optionally substituted by 1 to 2 substituents, a carbamoyl group optionally substituted by 1 to 2 substituents, a carboxyl group or a hydrogen atom;
$R^{1A}$ is a cyano group or an alkyl group optionally substituted by 1 to 3 halogen atoms;
B' is a group selected independently from an oxo group, a cyano group, a halogen atom, an optionally substituted alkylsulfanyl group, an optionally substituted alkylsulfinyl group, an optionally substituted alkylsulfonyl group, an amino group optionally substituted by 1 to 2 substituents, a hydroxy group, an optionally substituted heterocyclic group, an optionally substituted cycloalkoxy group, an optionally substituted cycloalkyl group, a carboxyl group, a carbamoyl group optionally substituted by 1 to 2 substituents, an optionally substituted alkyl group or an optionally substituted alkoxy group;
$p^A$ is an integer of 0 to 3;
D is a pyrimidinyl group, a pyridyl group, a phenyl group, a pyrimidinyloxy group, a tetrazolyl group or an oxazolidinyl group;
D' is a group selected independently from a halogen atom, an alkoxyalkyl group, an alkyl group substituted by 1 to 5 halogen atoms, an alkoxy group substituted by 1 to 5 halogen atoms, an alkenyl group, a carbamoyl group, a cycloalkyl group, a mono- or di-alkylaminoalkyl group, a mono- or di-alkylaminoalkoxy group, a carboxyl group, a hydroxy group, a cyano group, an oxo group, an alkyl group, a hydroxyalkyl group, an alkoxycarbonylalkyl group, a carboxyalkyl group, a morpholinylalkyl group, a phenylalkyl group, an alkanoyl group, a hydroxyalkanoyl group, an alkoxyalkanoyl group, an alkoxy group, a phenylalkoxy group, an alkoxycarbonyl group, a benzyloxycarbonyl group, a mono- or di-alkylamino group, a mono- or di-alkylcarbamoyl group, a mono- or di-alkylsulfamoyl group, an alkylsulfonyl group, a tetrazolyl group, a benzyloxyalkyl group, a cycloalkylalkyl group, a benzyloxy group, an alkoxyalkoxy group, a carboxyalkoxy group, a carboxyalkenyl group, an alkylcarbonylamino group, a carboxyalkoxyalkyl group, a morpholinyl group or a pyridylalkoxy group;
$q^A$ is an integer of 0 to 3,
or a pharmaceutically acceptable salt thereof.

2. The compound of claim 1 wherein
$A^{21A}$ is selected from the following group:
(a) a heterocyclic group selected from a piperidyl group and a morpholinyl group, respectively optionally substituted by a substitutent(s) selected from a carboxyl group, an alkoxycarbonyl group, a carboxyalkyl group or an alkyl group;
(b) an alkoxy group optionally substituted by a group selected from a carboxyl group, an alkoxycarbonyl group, a halogen atom, an alkylsulfinyl group, a mono- or di-alkylamino group, a cyano group, a tetrazolyl group, an alkylsulfonyl group, an alkylsulfanyl group, a hydroxy group or an alkoxy group;
(c) a halogen atom;
(d) an amino group optionally substituted by 1 to 2 substituents independently selected from a carboxyalkyl group, an alkoxycarbonylalkyl group, an alkylsulfonylalkyl group, an alkylsulfinylalkyl group, a hydroxyalkyl group, an alkyl group, an alkoxyalkyl group or an aminoalkyl group optionally substituted by 1 to 2 alkyl groups;
(e) a hydrogen atom;
(f) an alkyl group optionally substituted by a group selected from a carboxyl group, an alkoxycarbonyl group, a halogen atom, an alkylsulfinyl group, a mono- or di-alkylamino group, a cyano group, a tetrazolyl group, an alkylsulfonyl group, an alkylsulfanyl group, a hydroxy group or an alkoxy group;
(g) a carboxyl group;
(h) a carbamoyl group optionally substituted by a carboxyalkyl group;
(i) an alkenyl group substituted by a group selected from a carboxyl group, an alkoxycarbonyl group, an alkylsulfinyl group, a cyano group, a tetrazolyl group, an alkylsulfonyl group, an alkylsulfanyl group, a hydroxy group or an alkoxy group;
(j) a morpholinyl group;
(k) a piperidinyl group optionally substituted by a carboxyl group or a carboxyalkyl group;
B' is a group selected independently from an oxo group, a halogen atom, an alkyl group optionally substituted by 1 to 3 halogen atoms, an alkoxy group optionally substituted by 1 to 3 halogen atoms, a cyano group, a hydroxy group, a cycloalkyl group, an alkoxyalkyl group, a cycloalkoxy group, an alkylsulfanyl group optionally substituted by 1 to 3 halogen atoms, an alkylsulfinyl group optionally substituted by 1 to 3 halogen atoms or an alkylsulfonyl group optionally substituted by 1 to 3 halogen atoms;
or a pharmaceutically acceptable salt thereof.

3. The compound of claim 2 wherein
$A^{21A}$ is an alkoxy group optionally substituted by 1 to 2 groups selected from a carboxyl group, a halogen atom, an alkoxycarbonyl group, an alkoxy group, a hydroxy group, a mono or di-alkylamino group, an alkylsulfinyl group, a cyano group, a tetrazolyl group, an alkylsulfonyl group and an alkylsulfanyl group; an alkyl group optionally substituted by 1 to 2 groups selected from a carboxyl group, a halogen atom, an alkoxycarbonyl group, an alkoxy group, a hydroxy group, a mono or di-alkylamino group, an alkylsulfinyl group, a cyano group, a tetrazolyl group, an alkylsulfonyl group and an alkylsulfanyl group; a morpholinyl group; a carboxyl group or a carboxypiperidinyl group;
B' is a group selected independently from a halogen atom, an alkyl group optionally substituted by 1 to 3 halogen atoms or an alkoxy group optionally substituted by 1 to 3 halogen atoms;
D' is a group selected independently from an alkoxy group optionally substituted by 1 to 3 halogen atoms, a halogen atom, a cyano group, an alkylsulfanyl group, a mono or di-alkylamino group, an alkenyl group, an alkyl group optionally substituted by 1 to 3 halogen atoms, a carboxyl group, a hydroxy group, a carboxyalkoxy group, a carboxyalkyl group, an alkoxycarbonylalkyl group, an oxo group, a cycloalkyl group, a hydroxyalkyl group, an alkoxyalkyl group, a carbamoyl group, a mono- or di-alkylcarbamoyl group, an alkylcarbonylamino group, a morpholinyl group or a carboxyalkoxyalkyl group,
or a pharmaceutically acceptable salt thereof.

4. The compound of claim 3, wherein $Z^A$ is N, or a pharmaceutically acceptable salt thereof.

5. The compound of claim 3, wherein $R^{1A}$ is an alkyl group optionally substituted by 1 to 3 halogen atoms, or a pharmaceutically acceptable salt thereof.

6. The compound of claim 3, wherein D is a phenyl group, or a pharmaceutically acceptable salt thereof.

7. The compound of claim 3, wherein D' is a group selected independently from a halogen atom, an alkoxy group or an alkyl group, or a pharmaceutically acceptable salt thereof.

8. The compound of claim 3, wherein $A^{21A}$ is a morpholinyl group or an alkoxy group substituted by a carboxyl group, or a pharmaceutically acceptable salt thereof.

9. A pharmaceutical composition, which comprises as an active ingredient a compound according to claim 1, or a pharmaceutically acceptable salt thereof.

10. The compound of claim 1, wherein:
$A^{21A}$ is an alkoxy group substituted by a carboxyl group; or a carboxypiperidinyl group;
D is a pyridyl group, or a phenyl group;
D' is a group selected independently from an alkoxy group; a halogen atom; an alkenyl group; an alkyl group optionally substituted by 1 to 3 halogen atoms; and a hydroxyalkyl group;
or a pharmaceutically acceptable salt thereof.

11. A compound selected from the group consisting of:

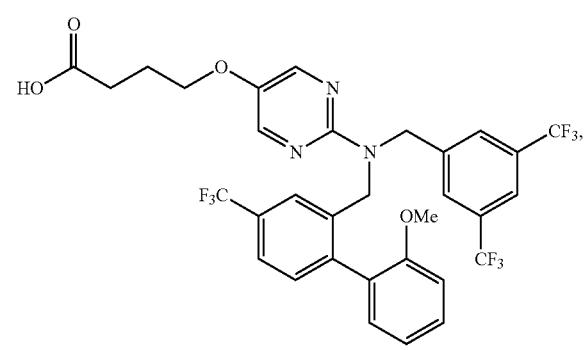

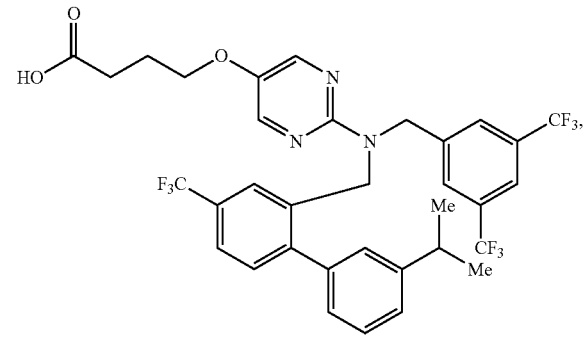

203
-continued
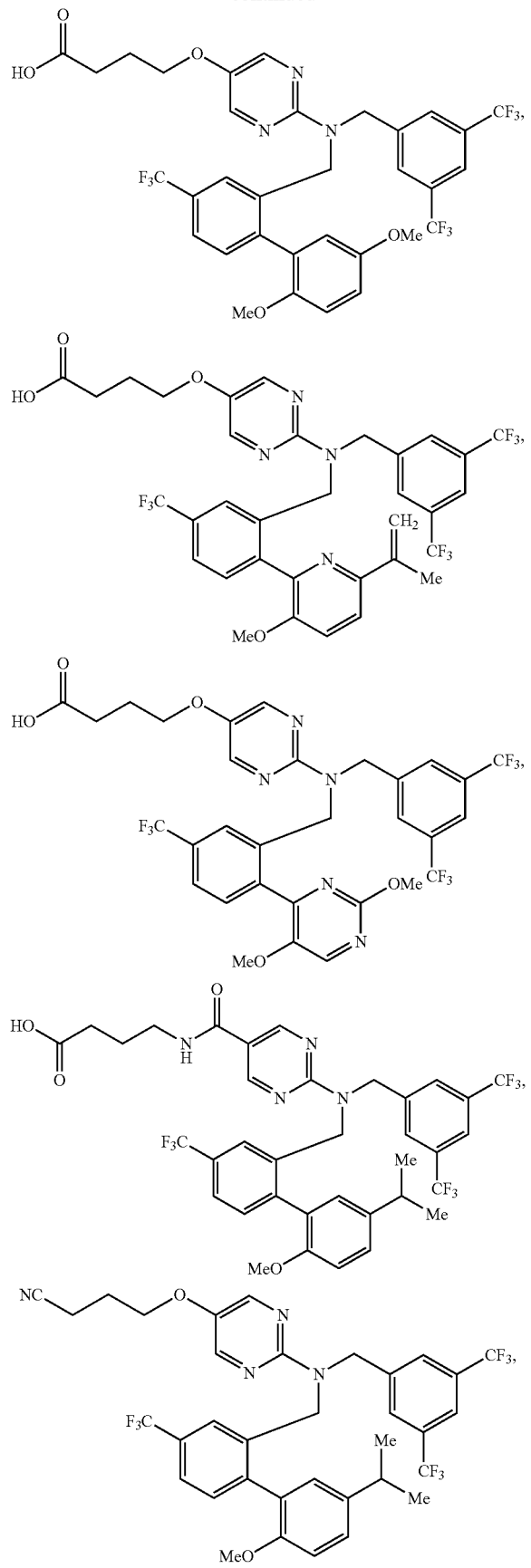
204
-continued
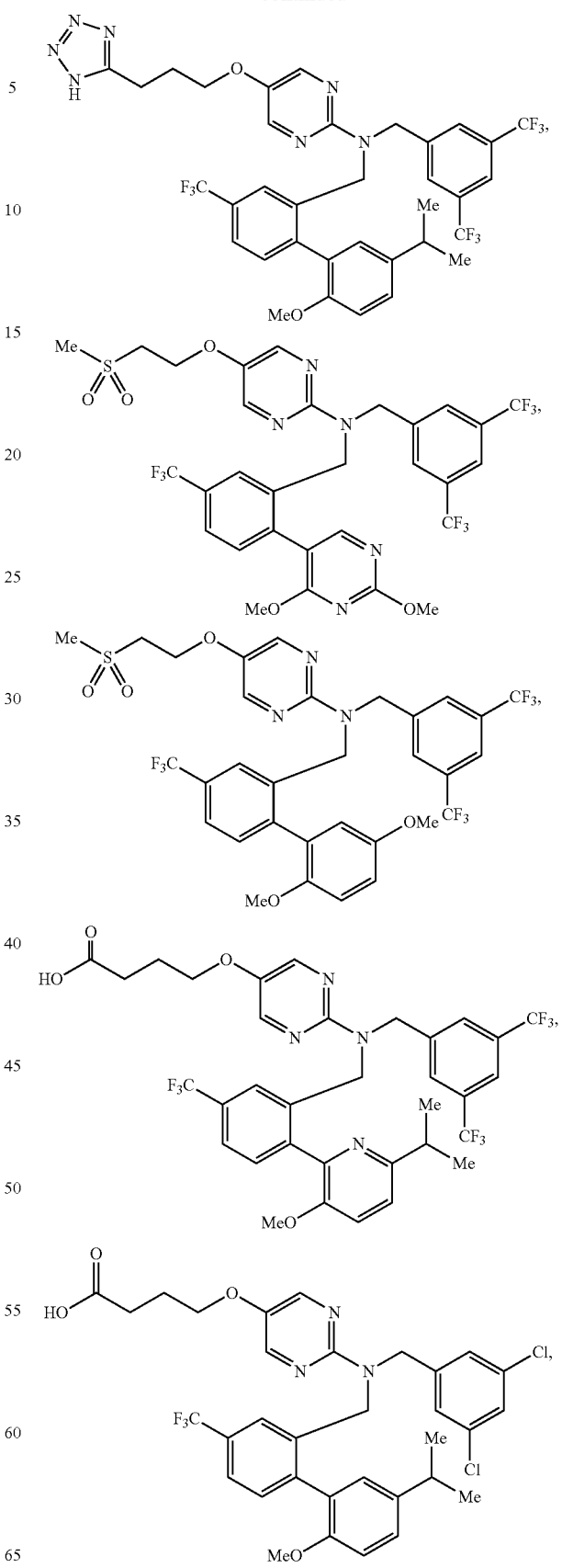

205
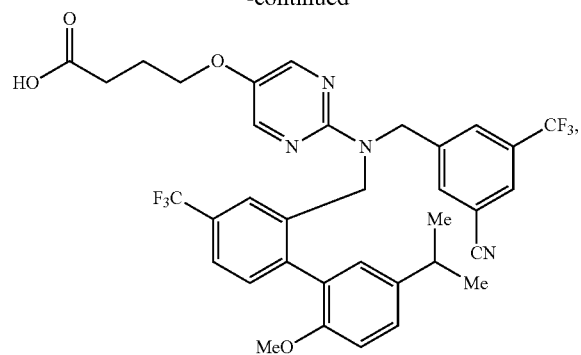
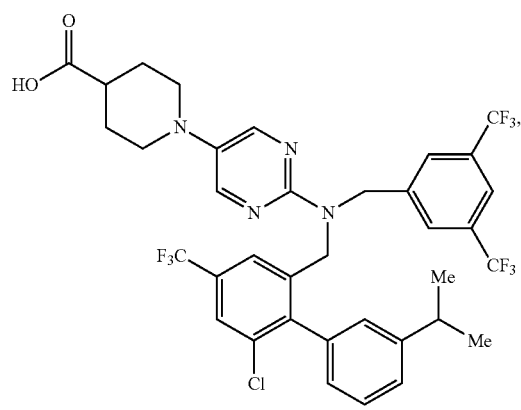
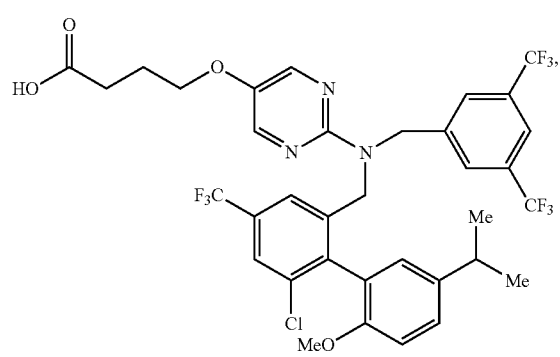
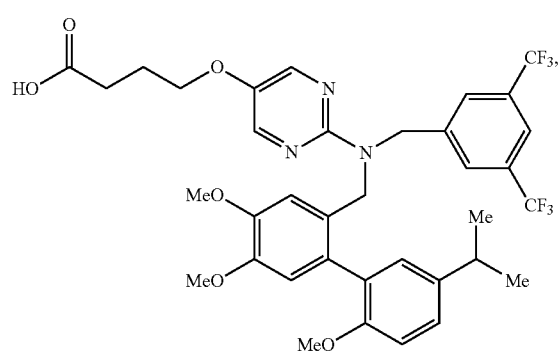
206
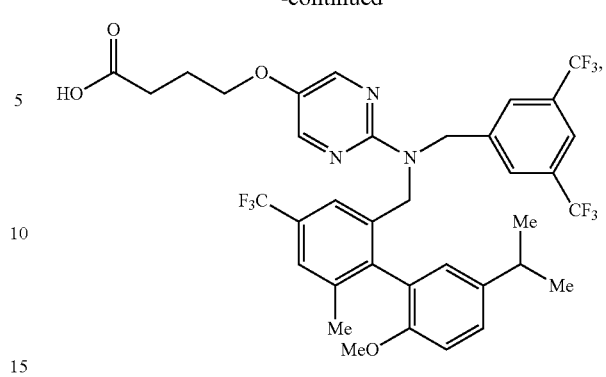
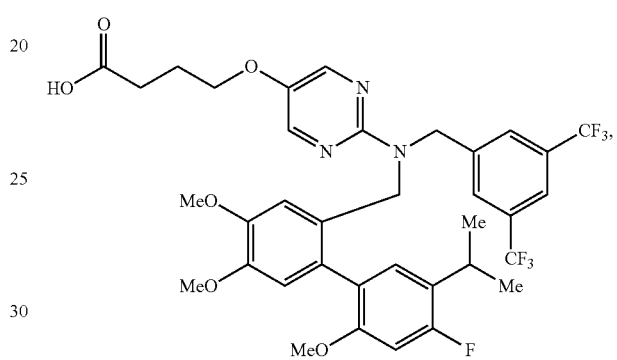
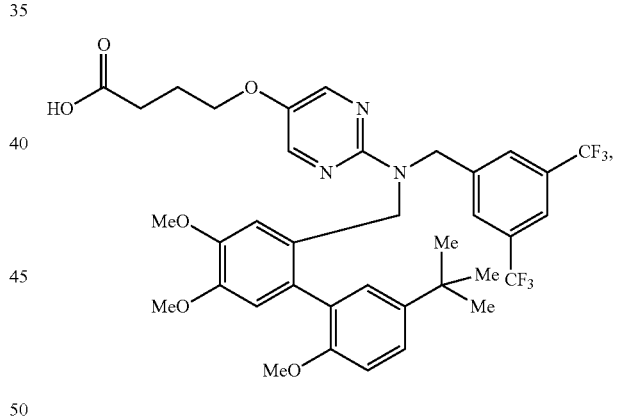
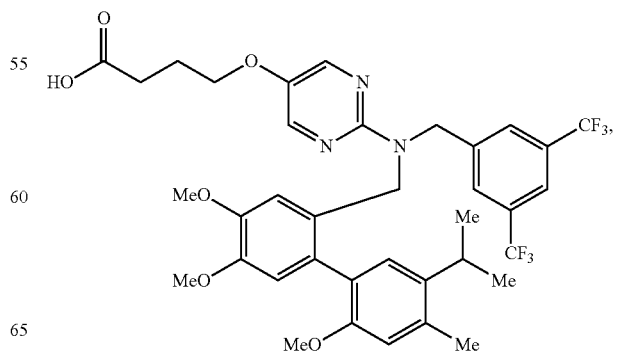

207
-continued
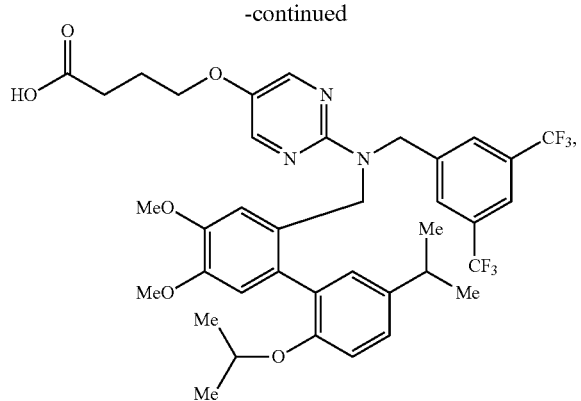
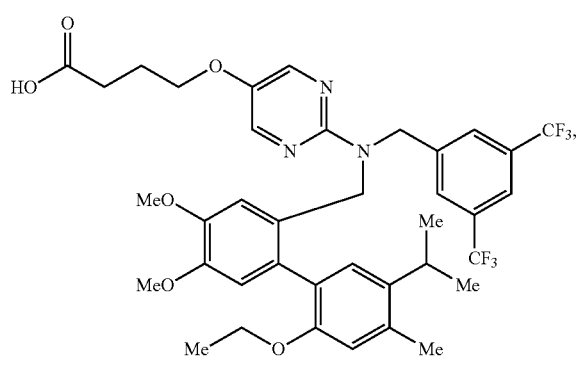
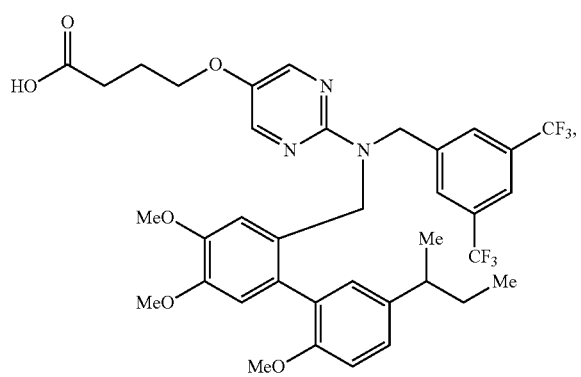
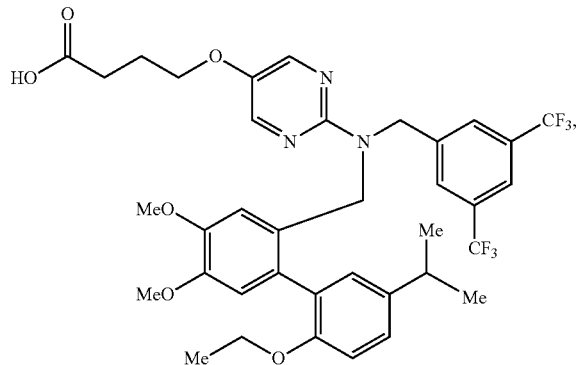
208
-continued
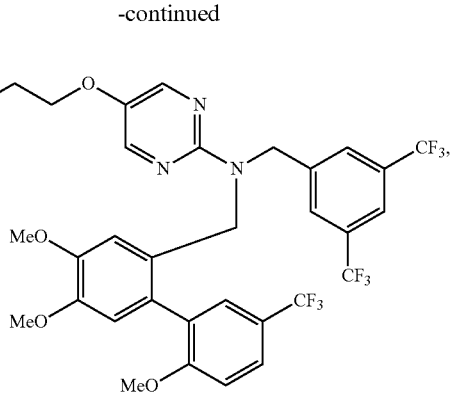
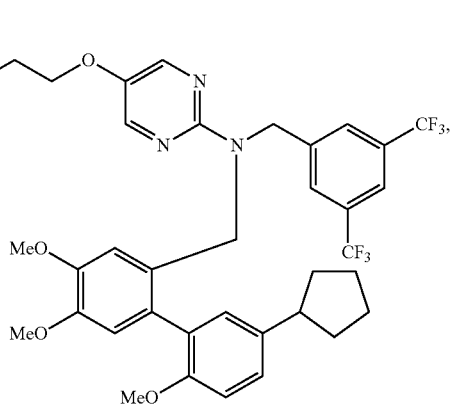

-continued
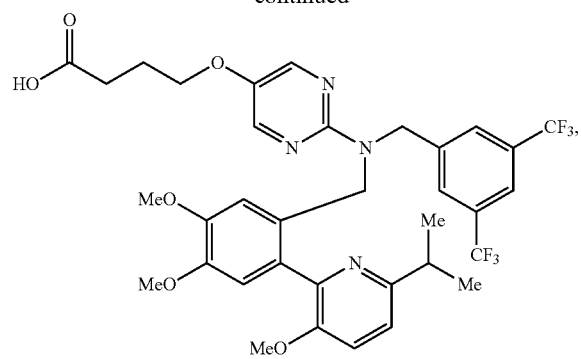
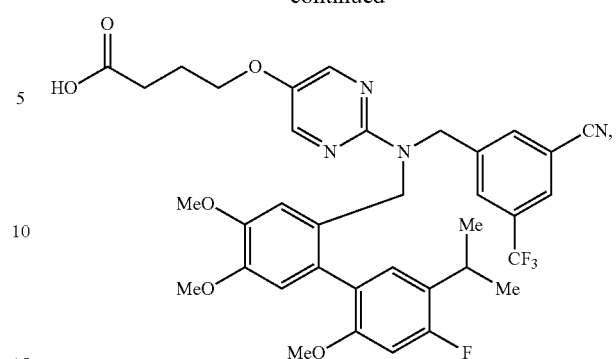
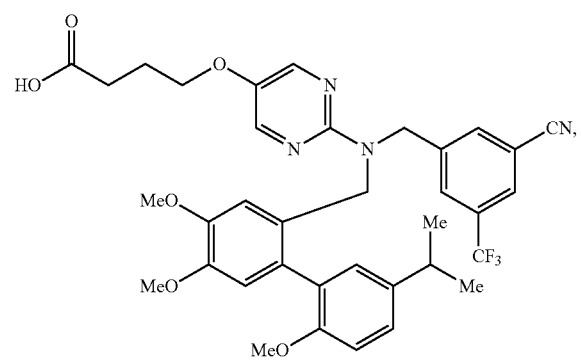
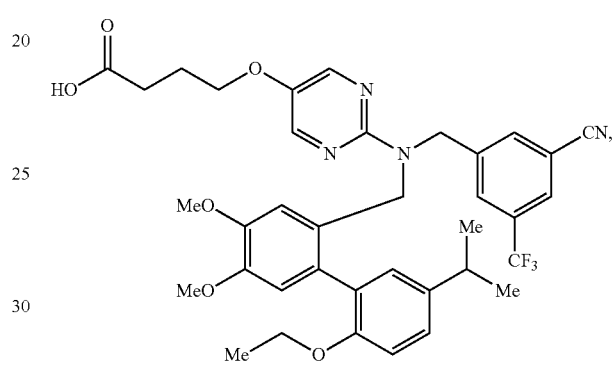
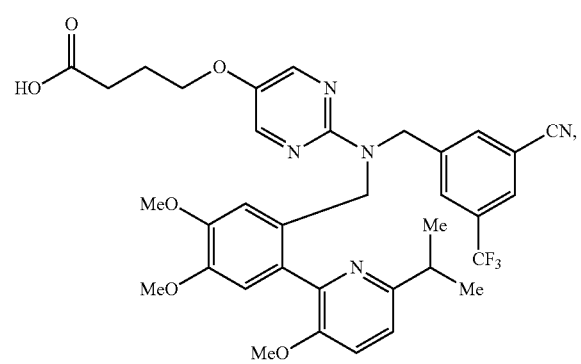
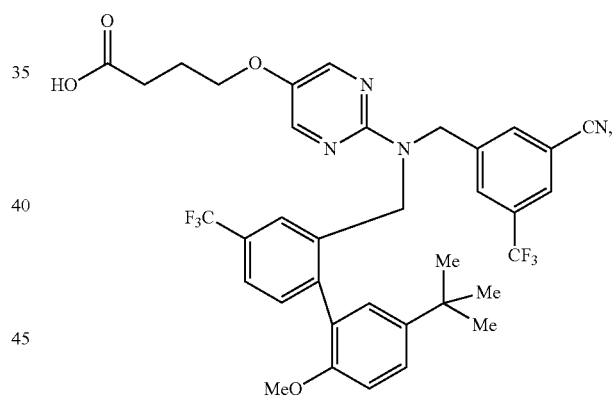
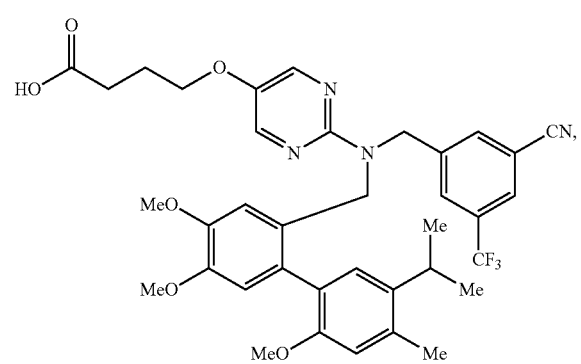
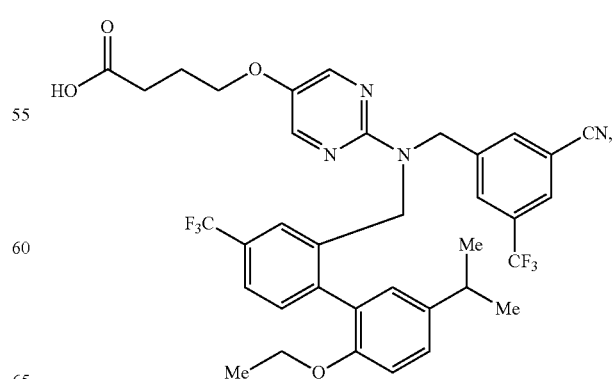

211
-continued
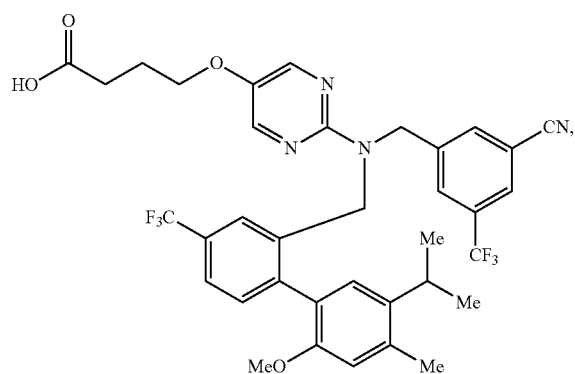
212
-continued
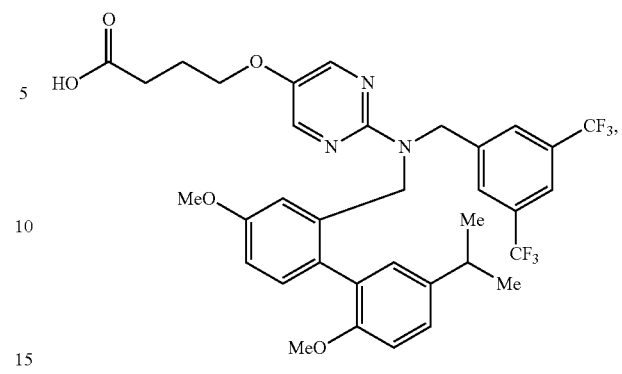
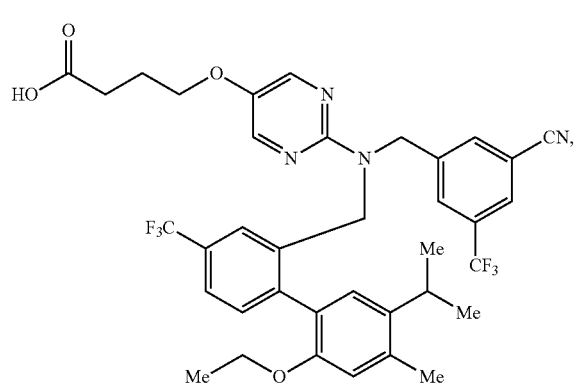
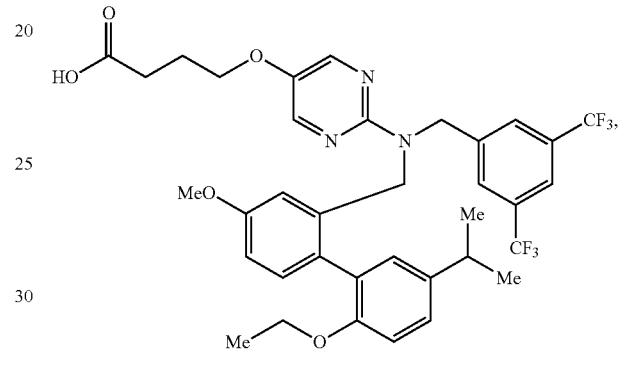
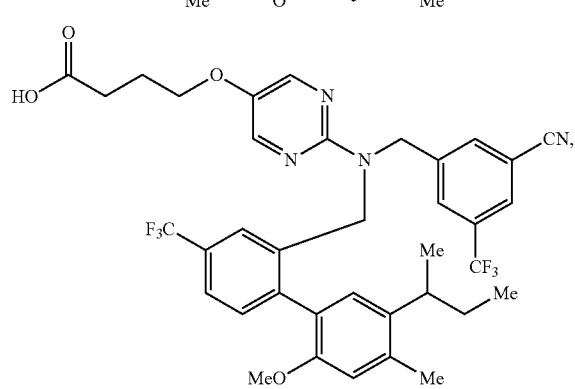
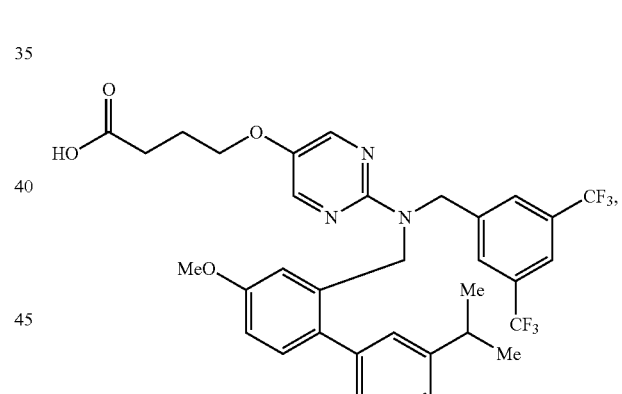
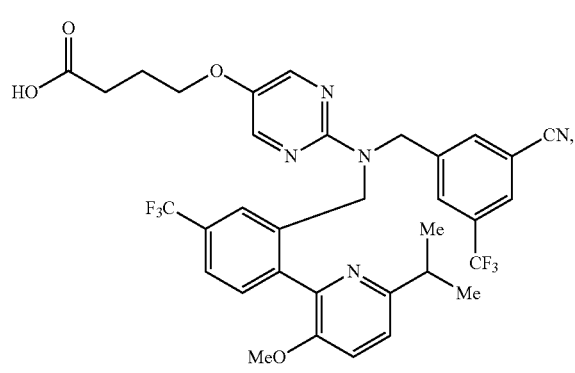
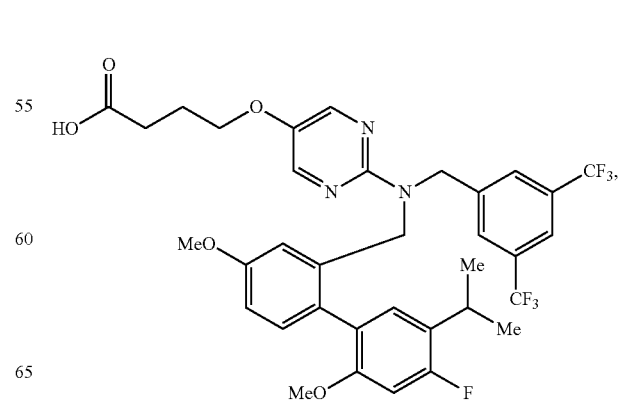

213
-continued
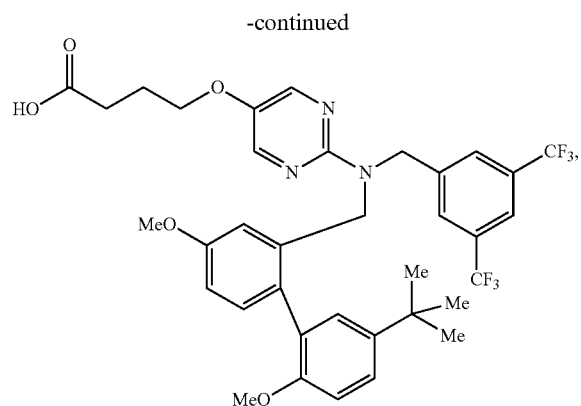
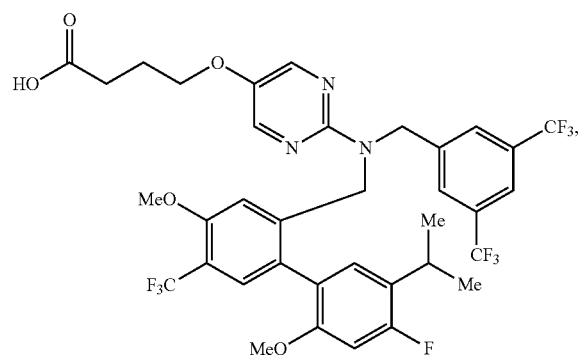
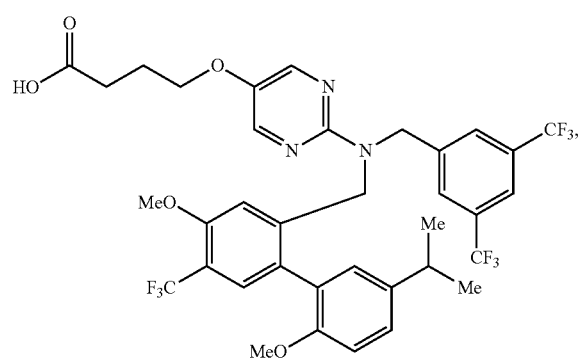
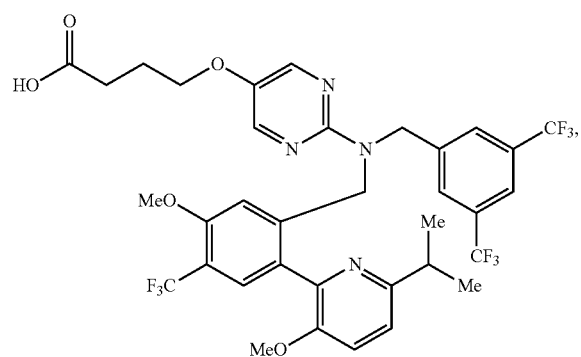
214
-continued
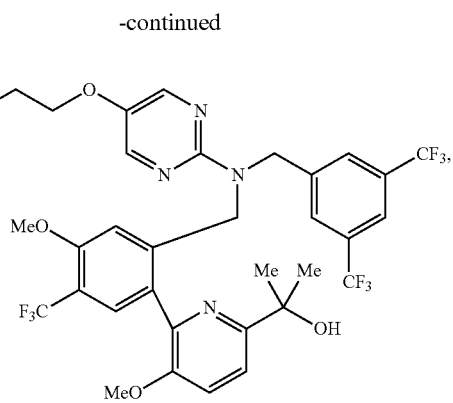
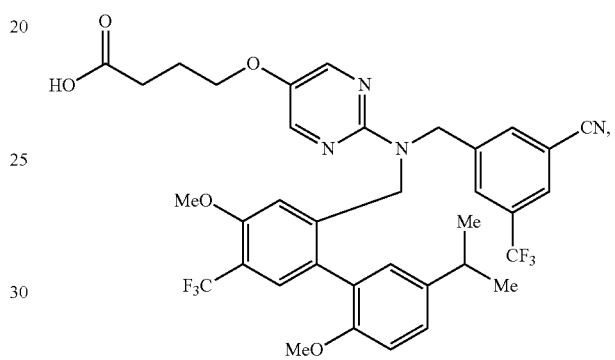
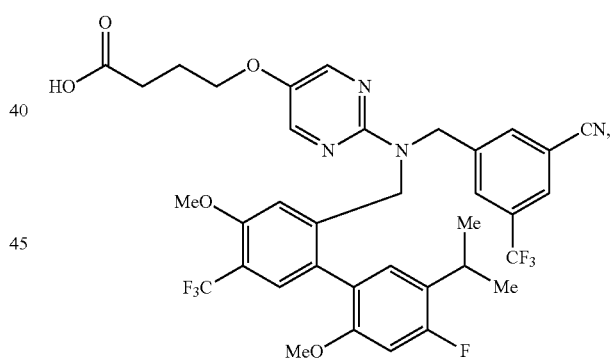
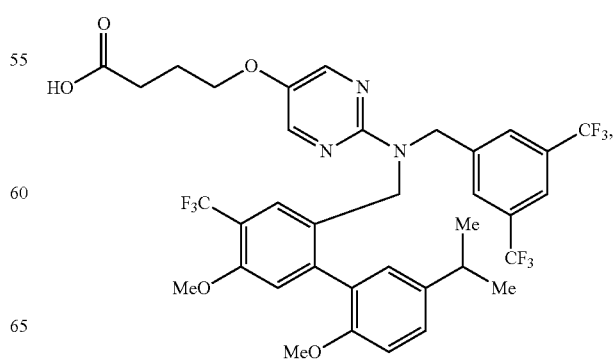

-continued
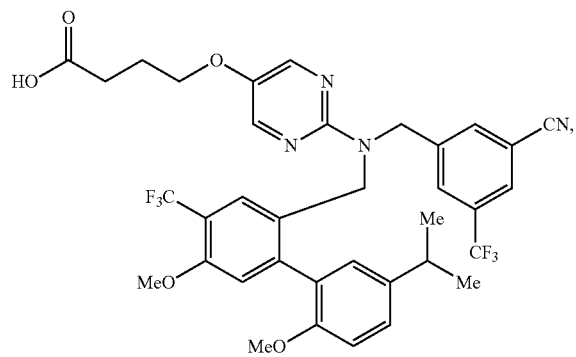
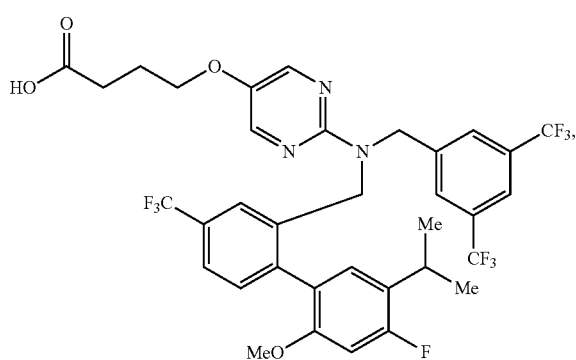
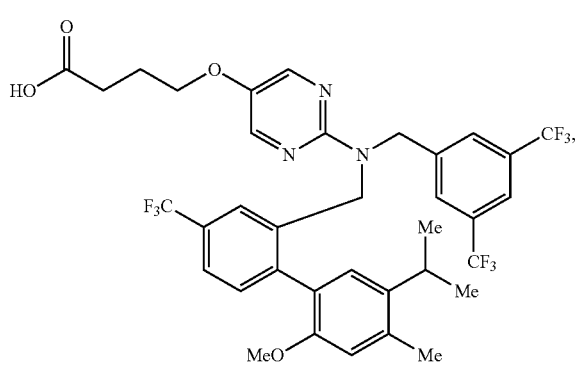
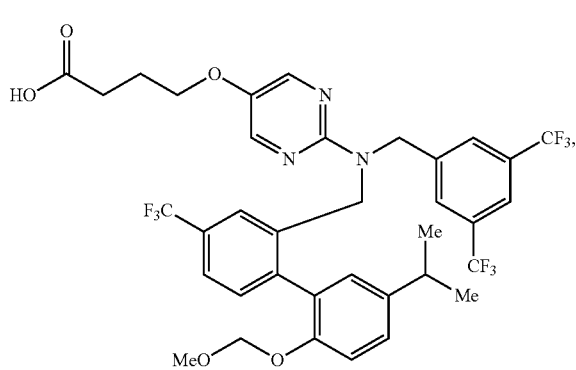
-continued
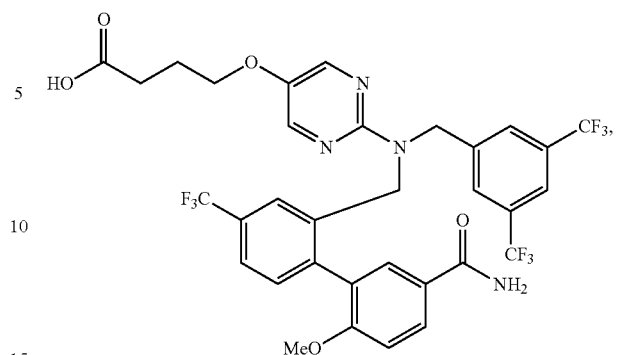
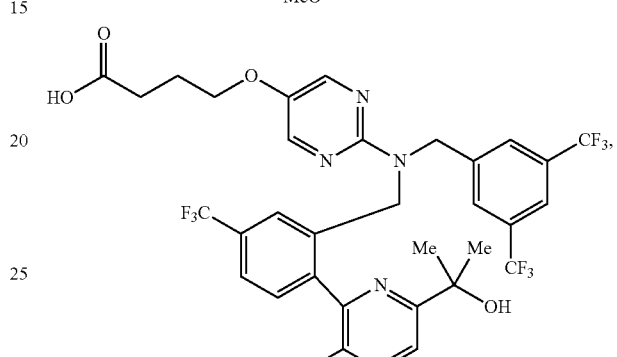
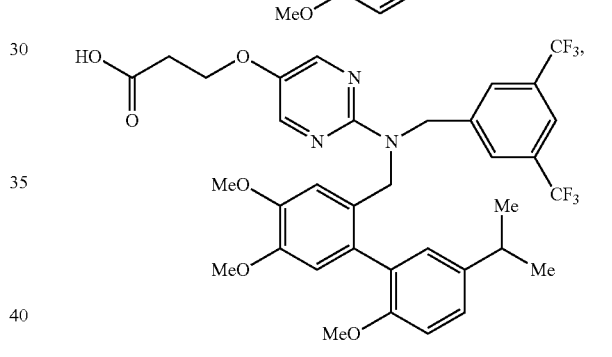
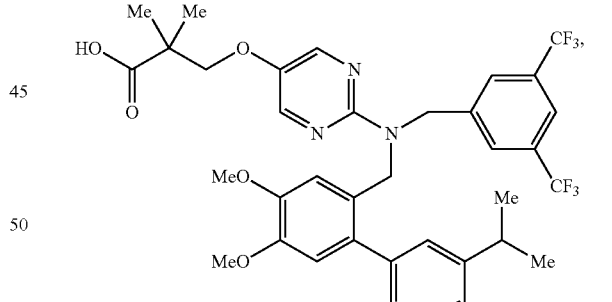
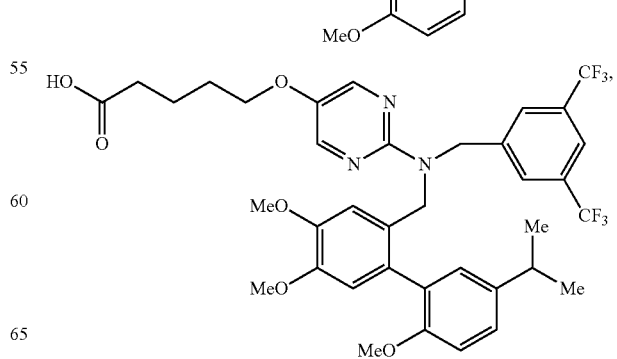

217
-continued
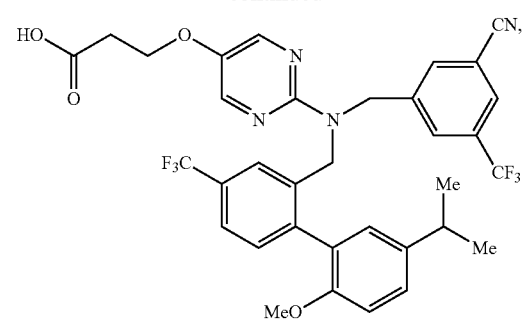
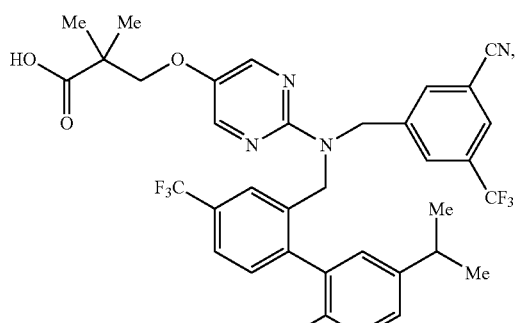
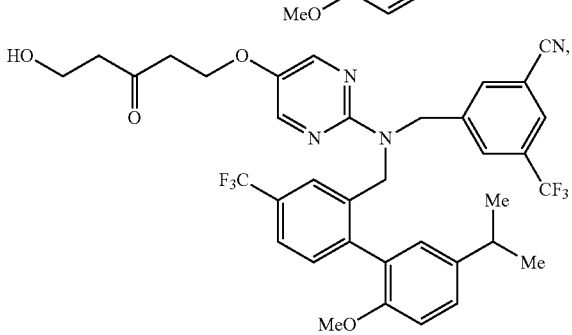
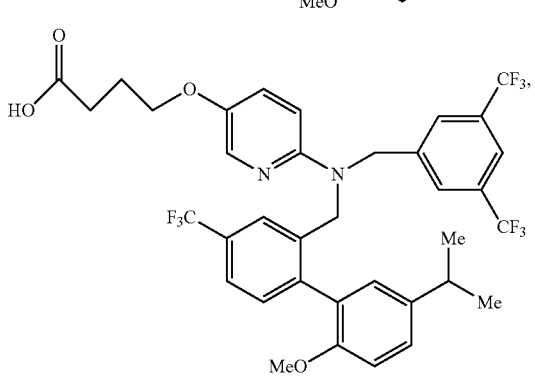
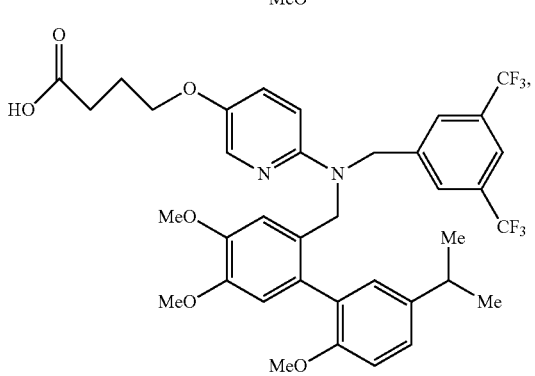
218
-continued
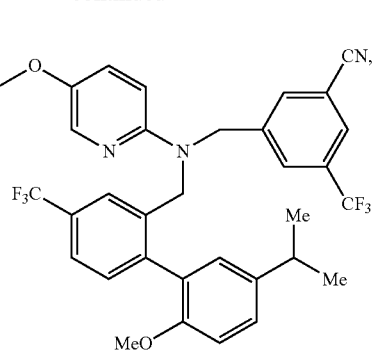
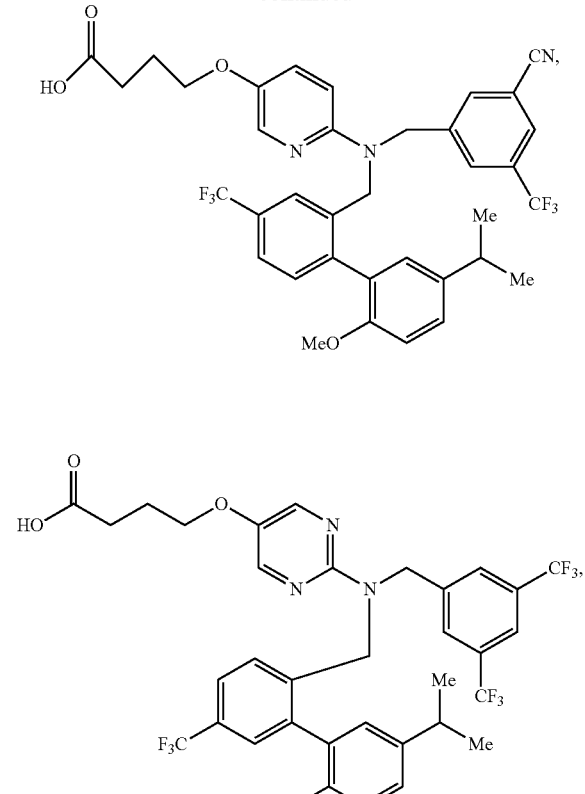
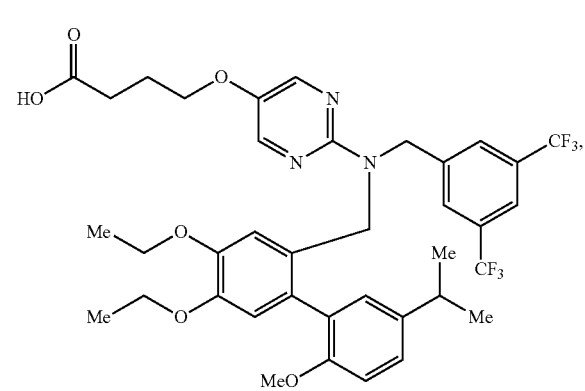
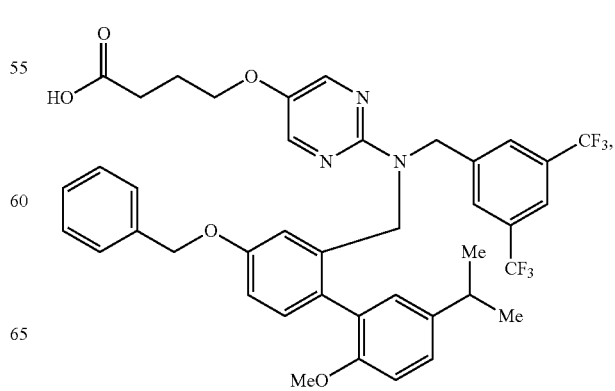

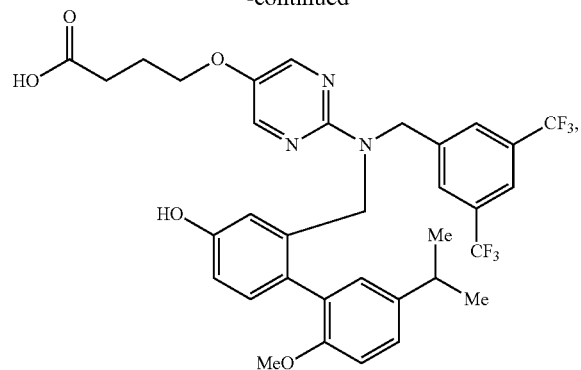
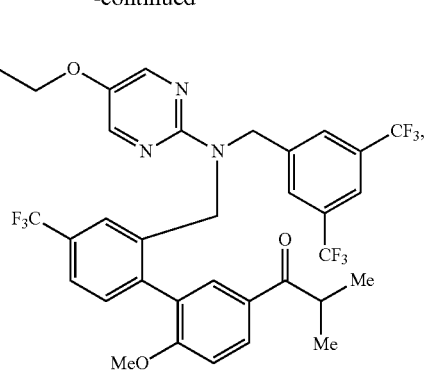
or a pharmaceutically acceptable salt thereof.
12. A compound selected from the group consisting of:
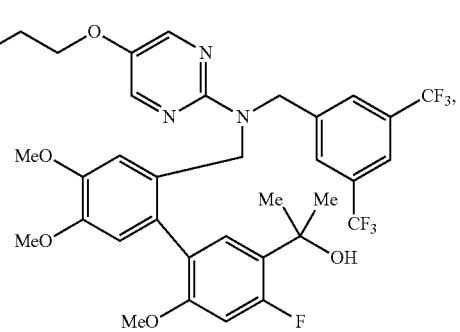

221
-continued
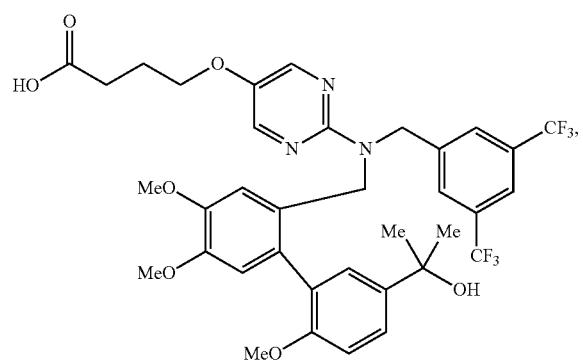
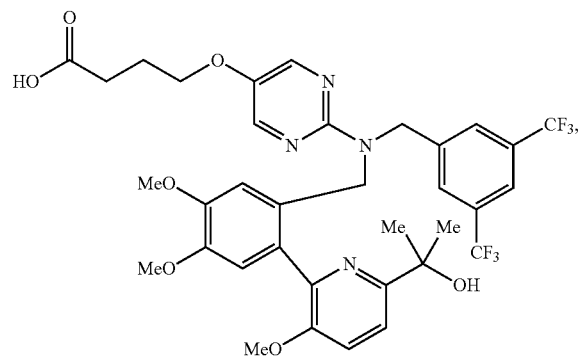
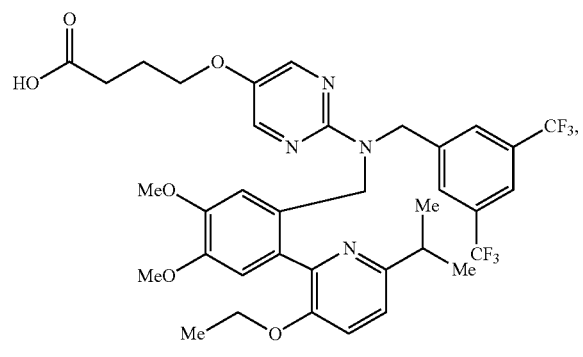
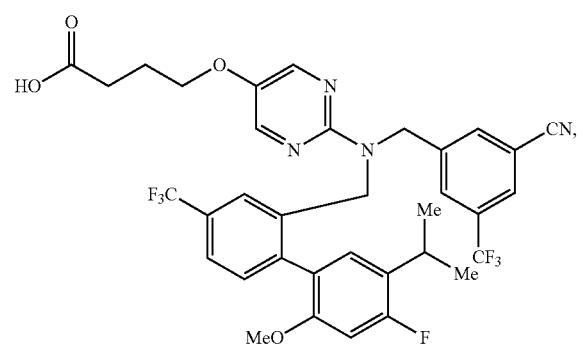
222
-continued
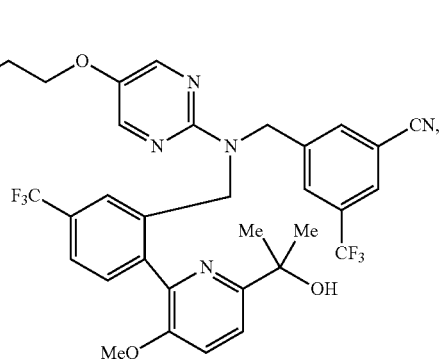
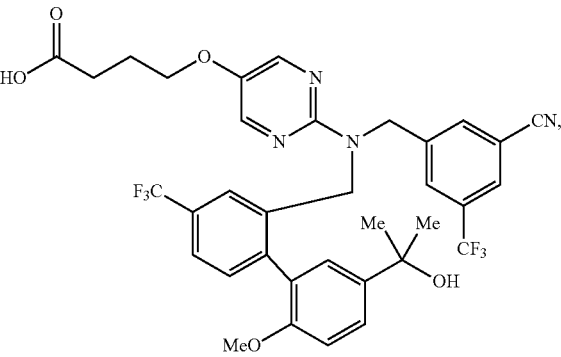
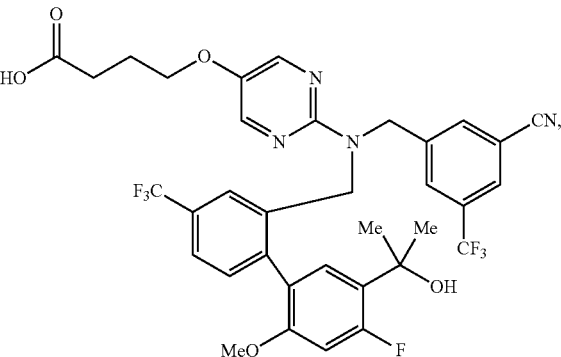
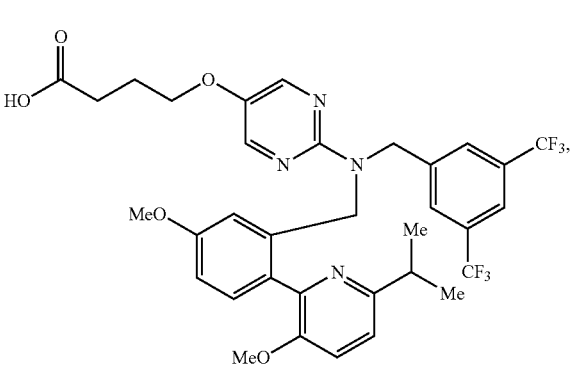

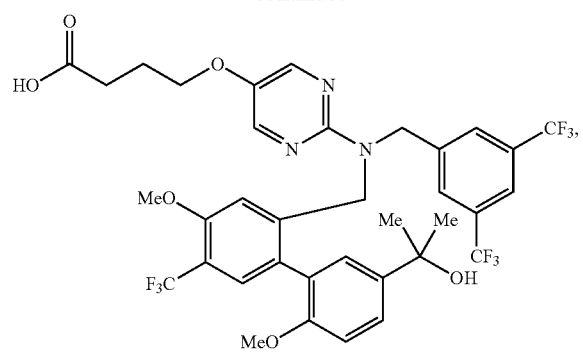
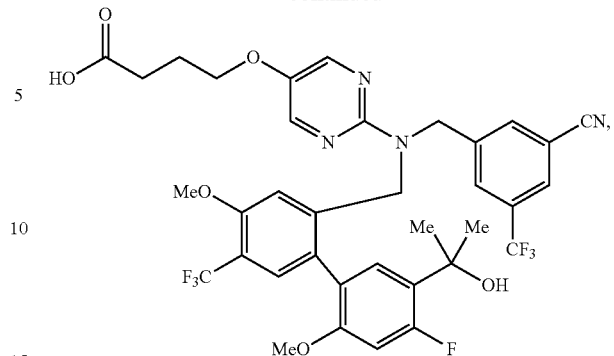
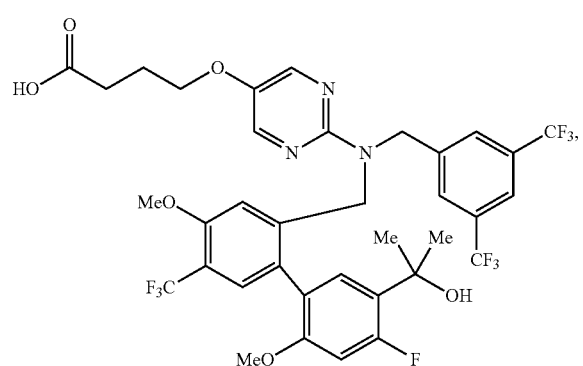
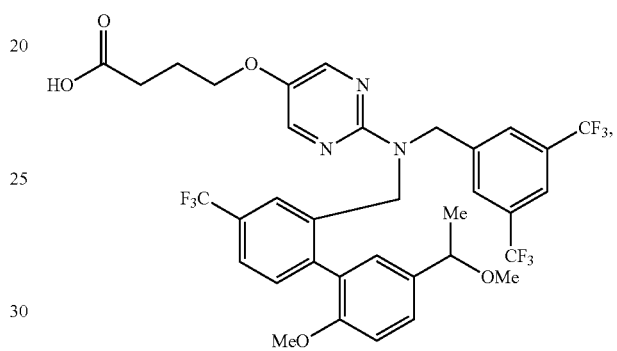
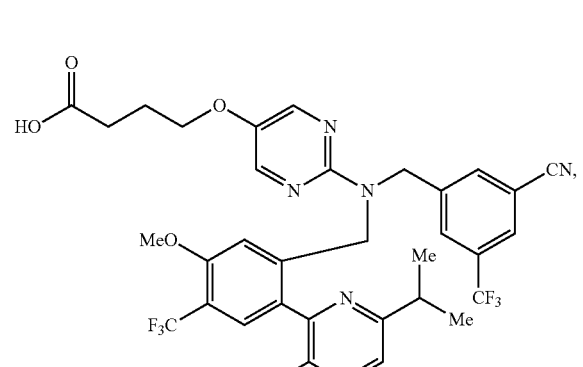
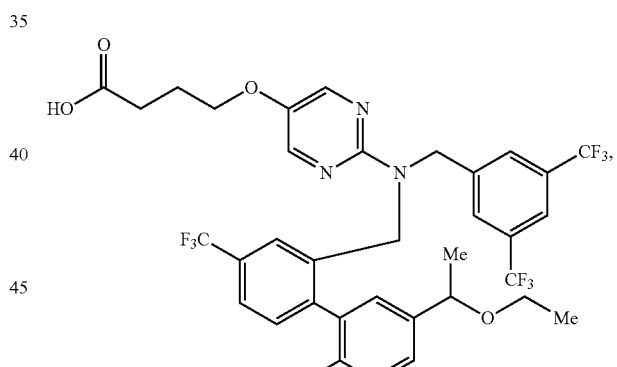
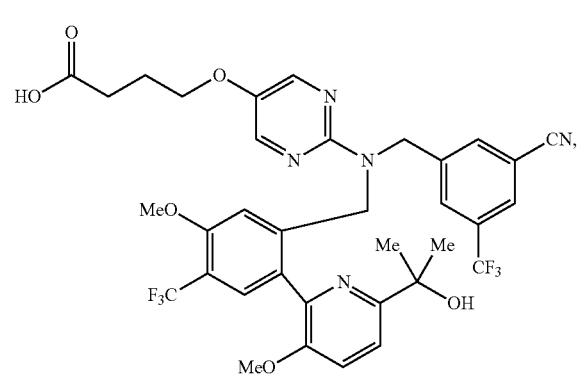
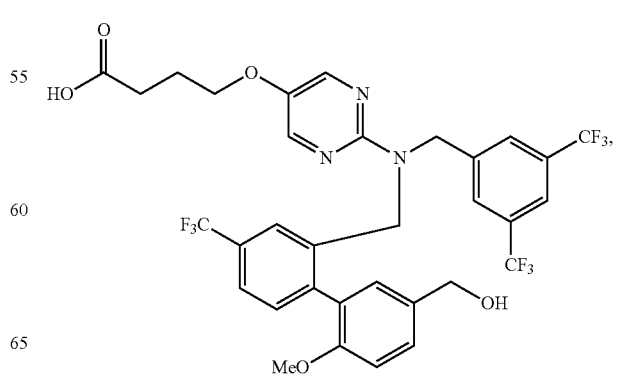

225
-continued
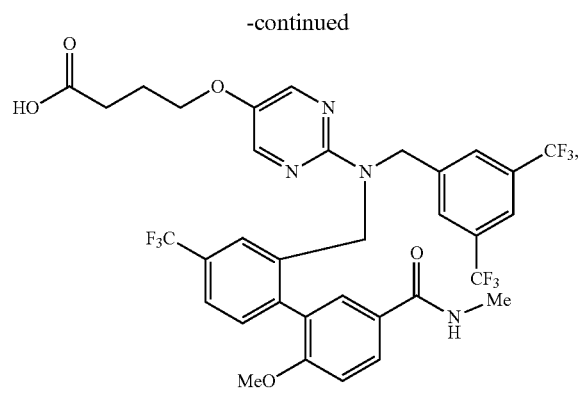
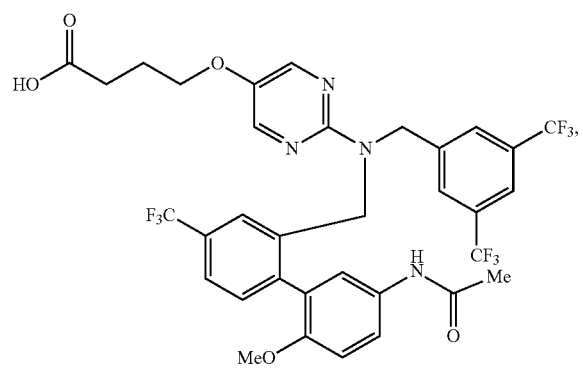
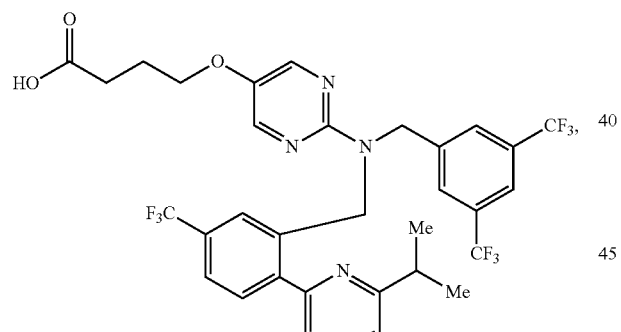
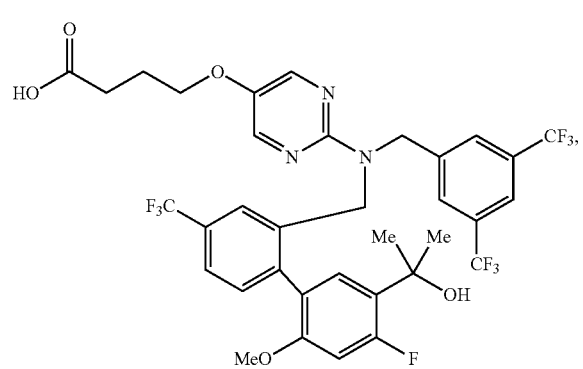
226
-continued
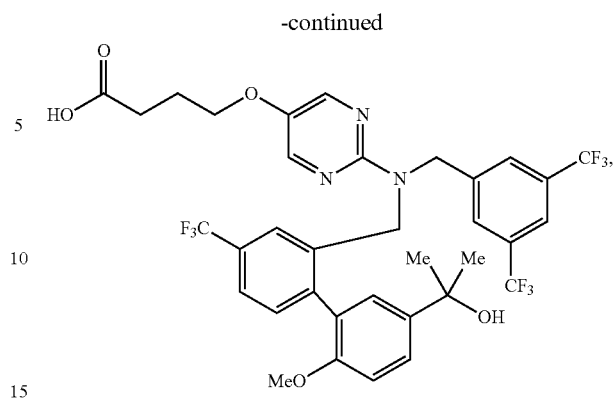
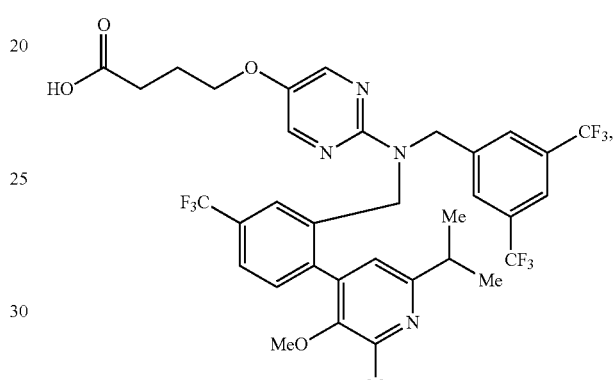
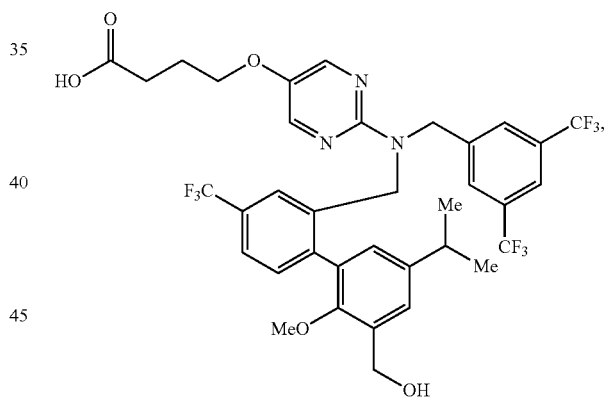
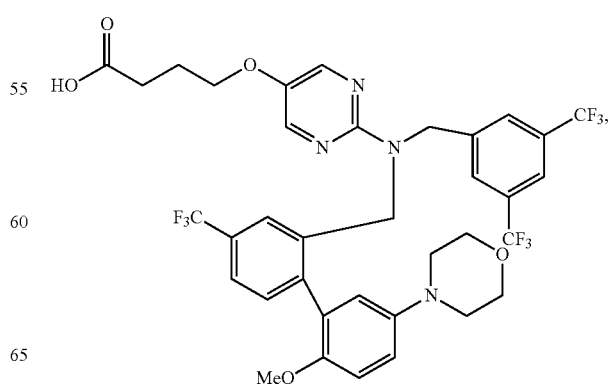

227
-continued
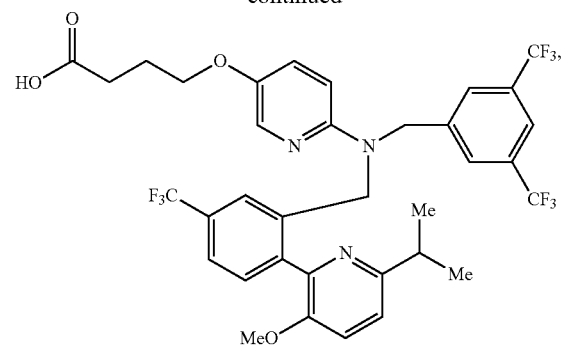
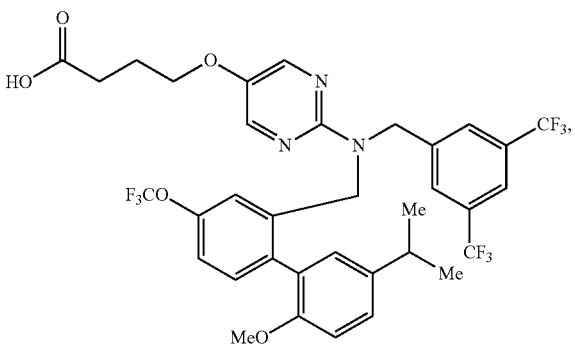
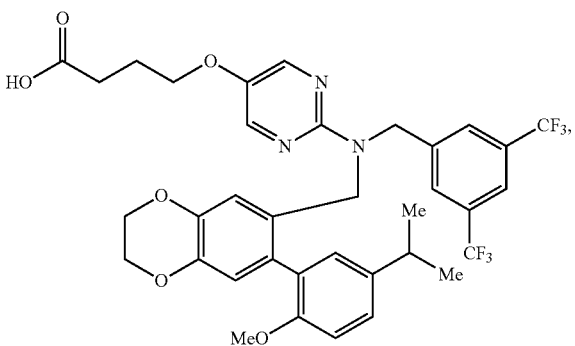
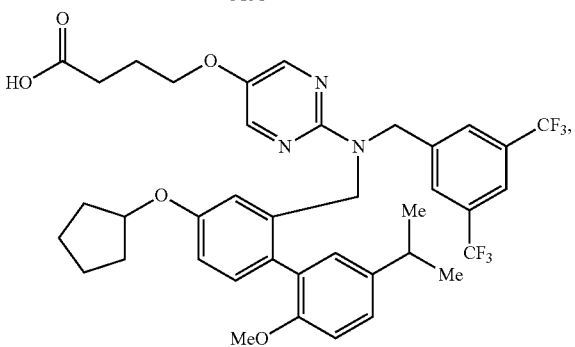
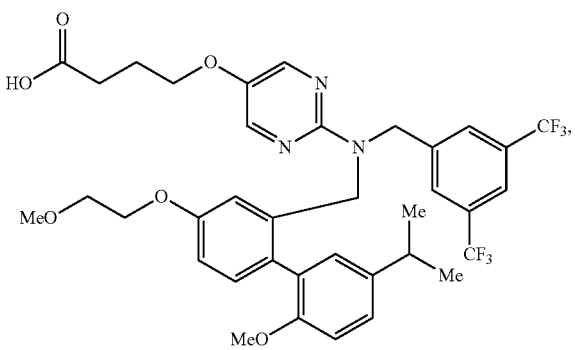
228
-continued
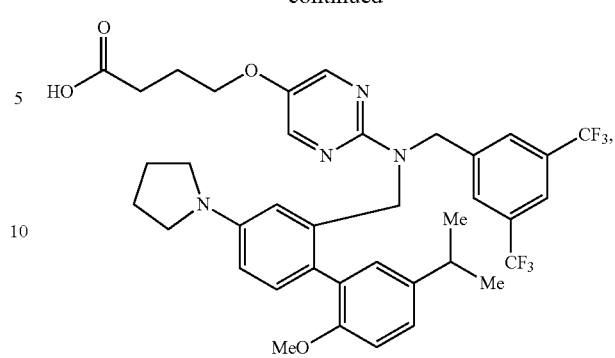
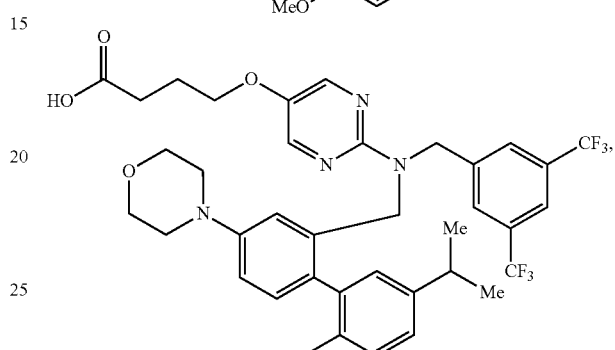
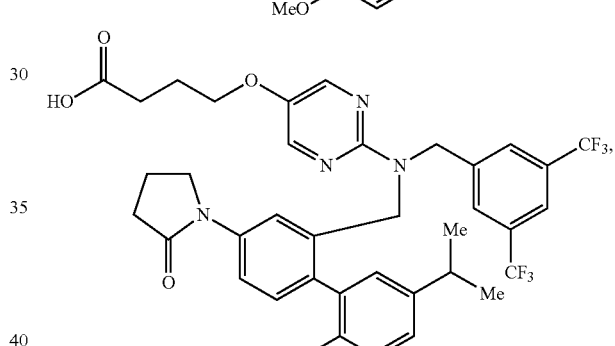
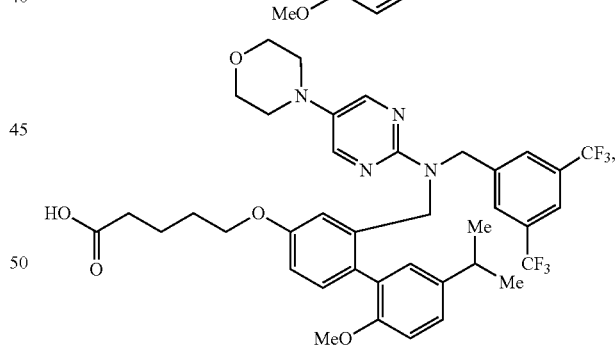
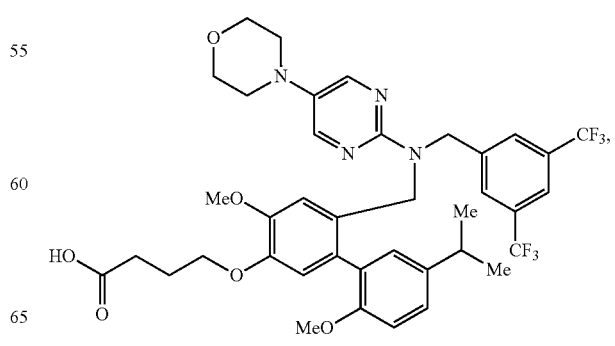

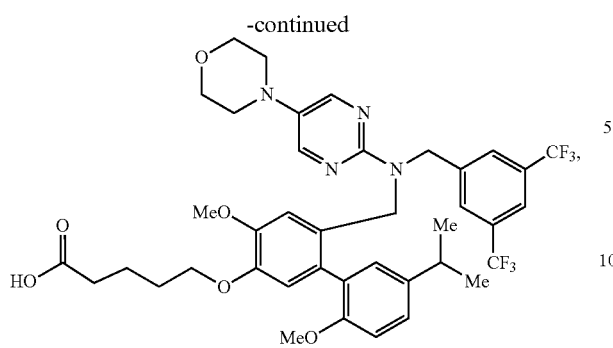
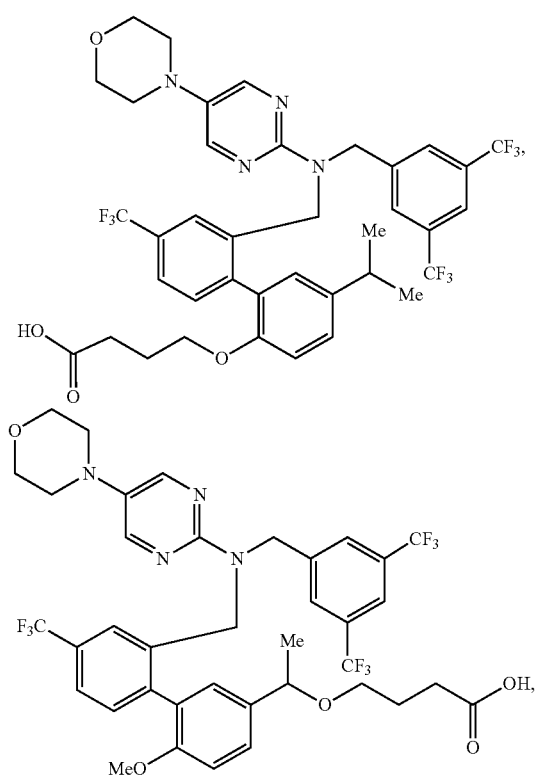
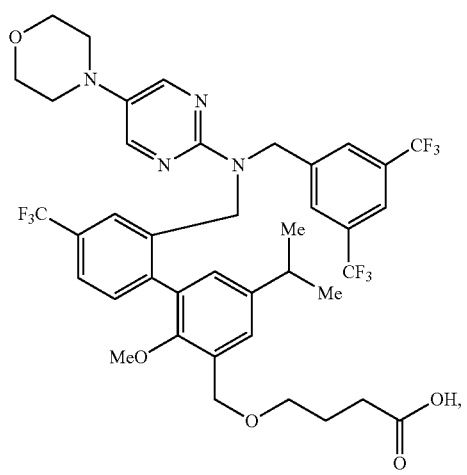
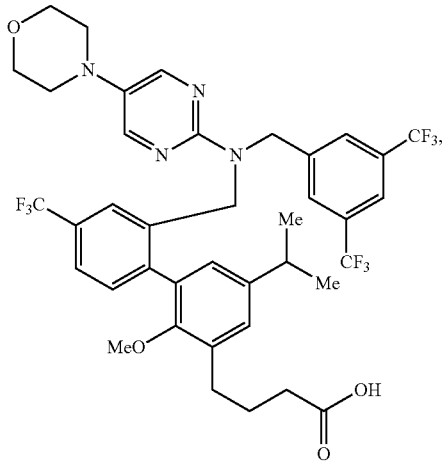
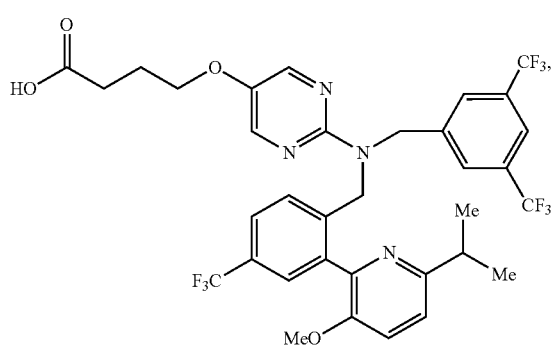
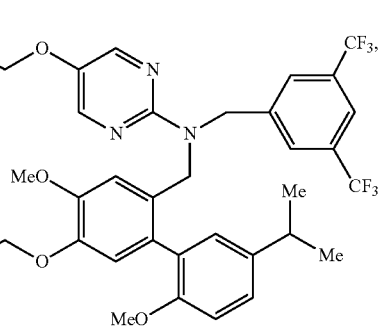
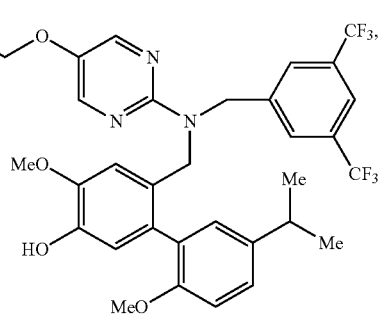

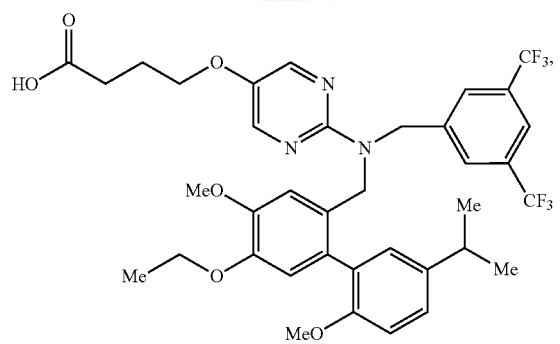
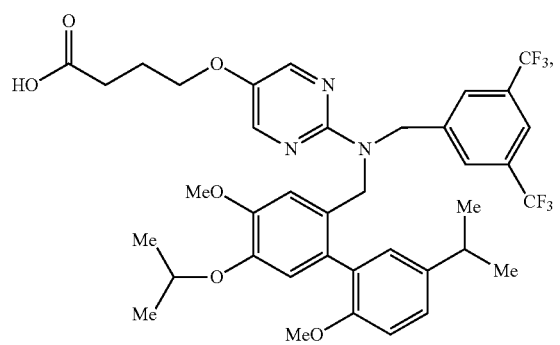
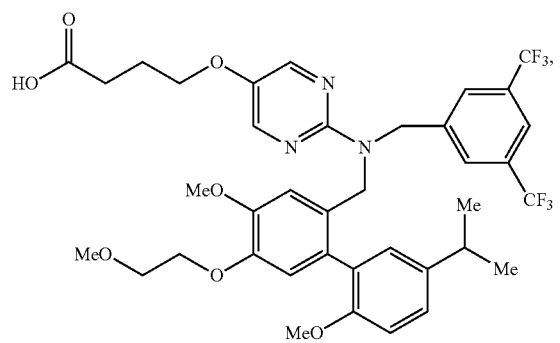
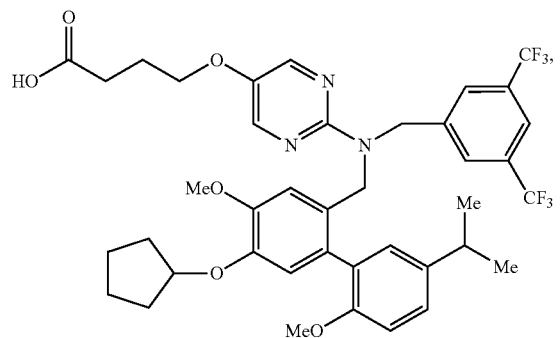
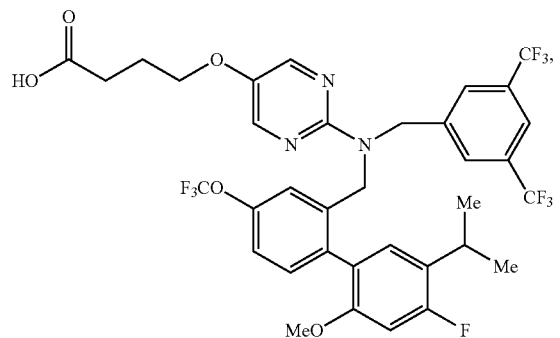
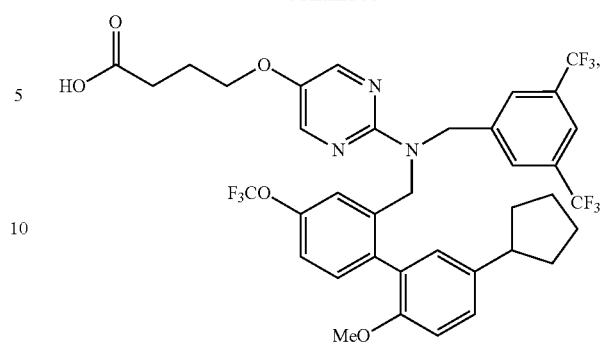
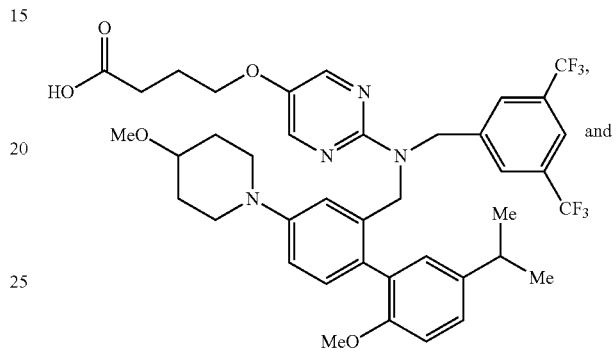
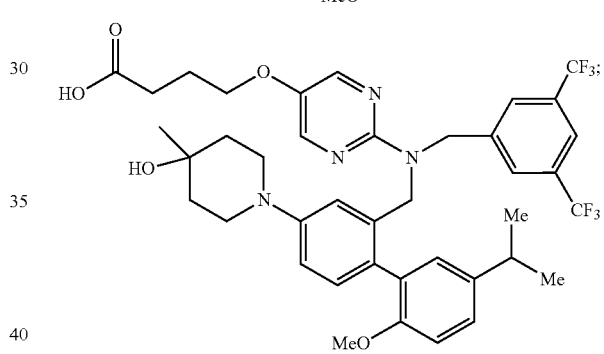
or a pharmaceutically acceptable salt thereof.
13. The compound of claim 11, which is:
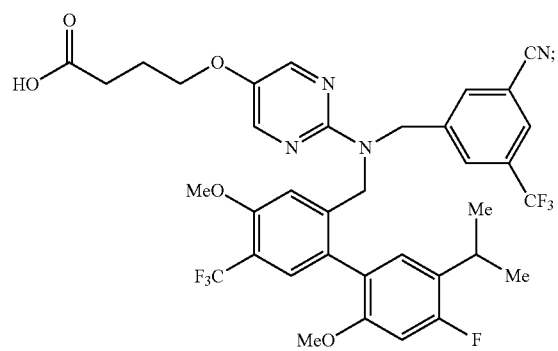
or a pharmaceutically acceptable salt thereof.
14. The compound of claim 13, which is the sodium salt of said compound.
15. The compound of claim 11, which is selected from the group consisting of:

233
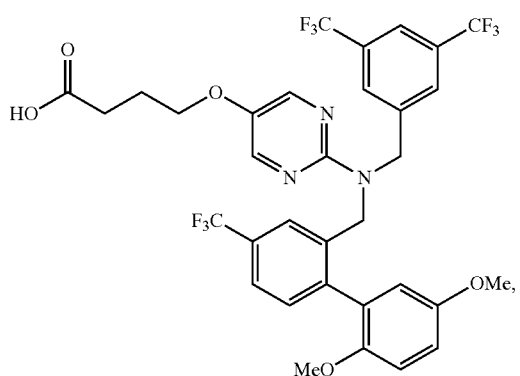
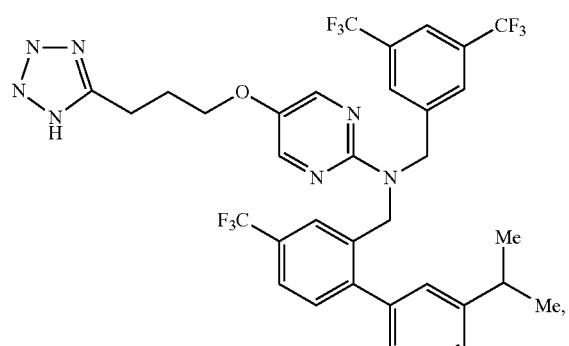
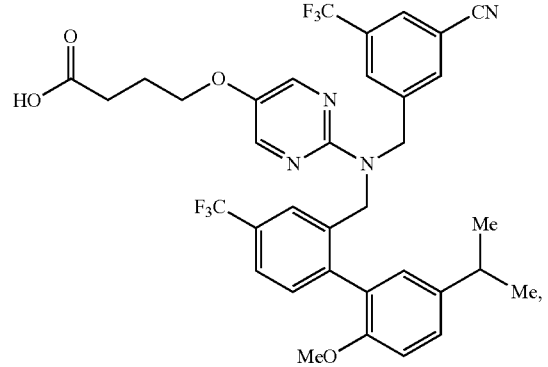
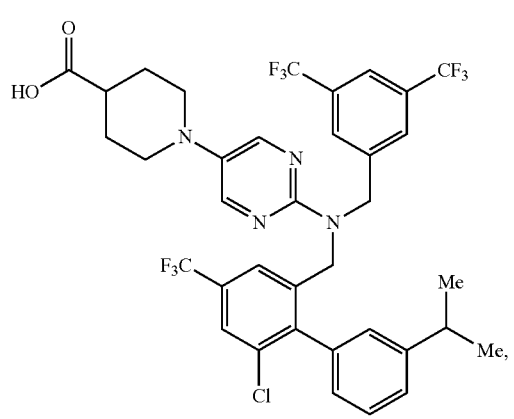
234
-continued
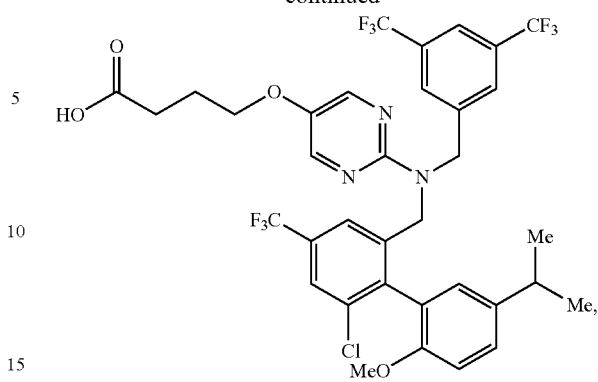
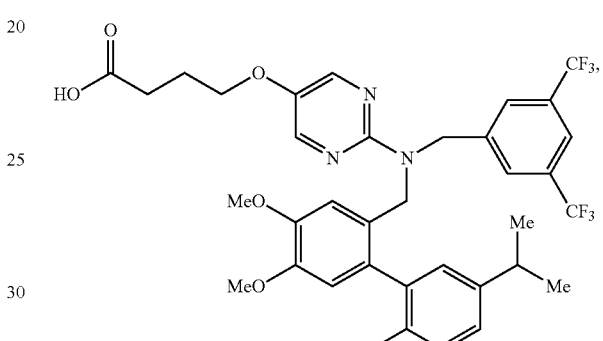
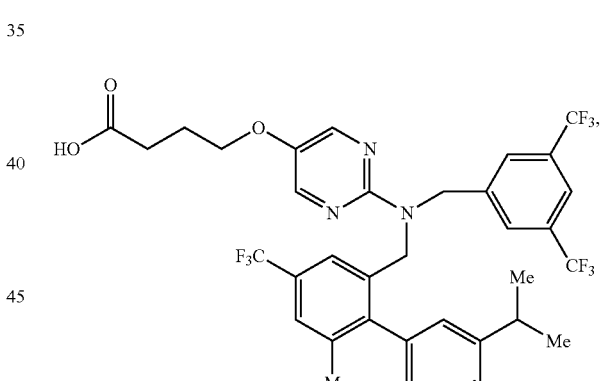
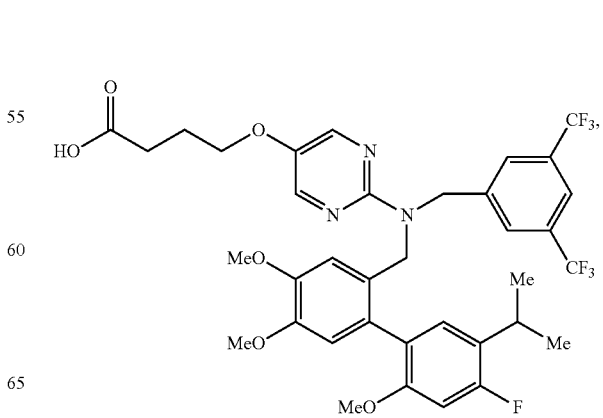

235
-continued
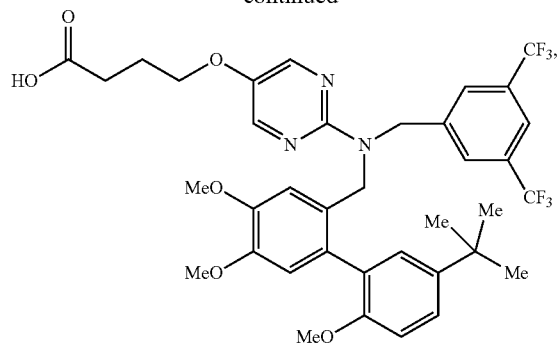
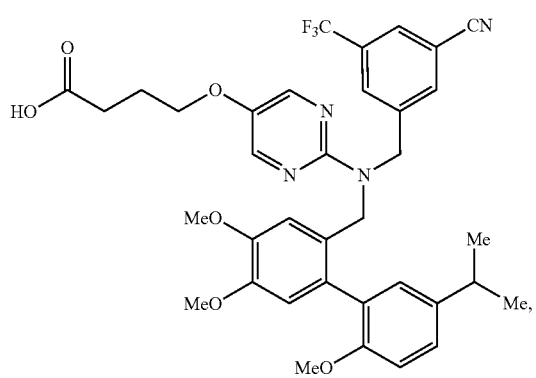
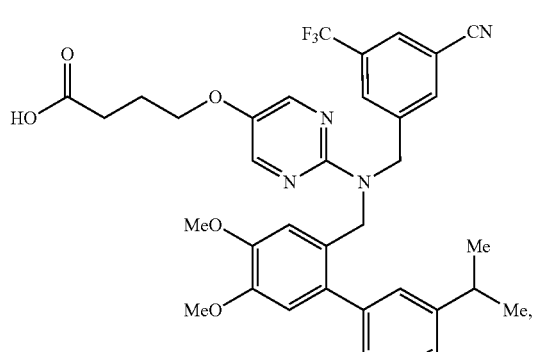
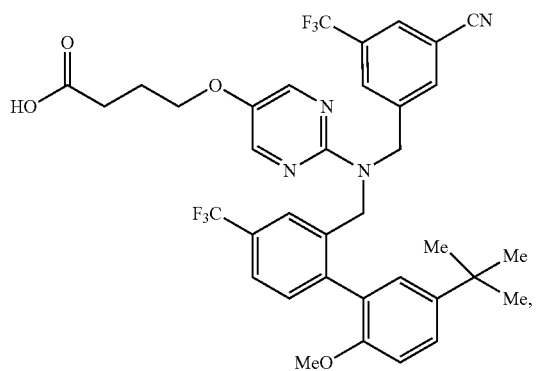
236
-continued
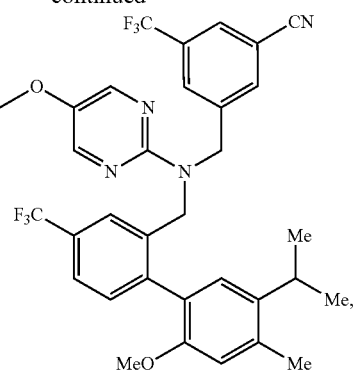
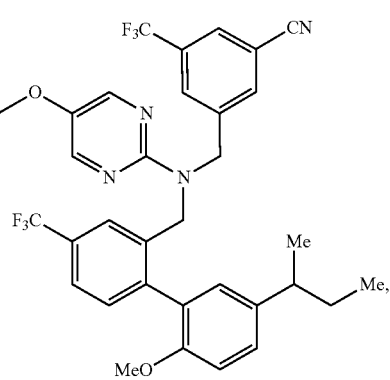
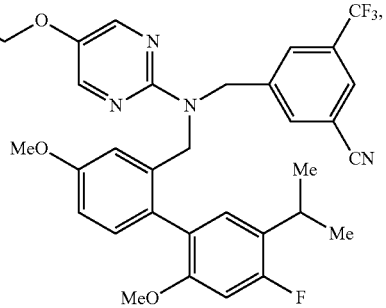
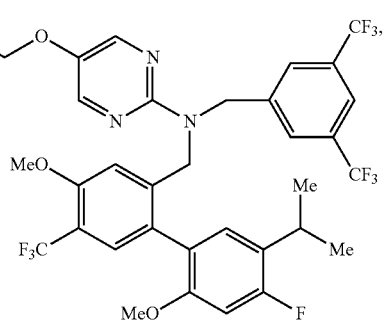

237
-continued
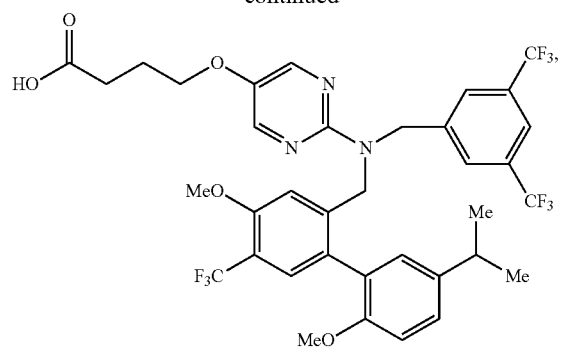
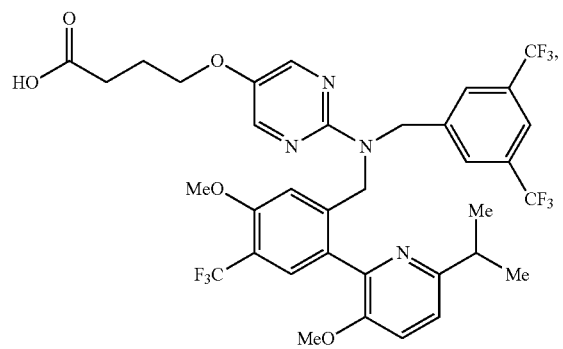
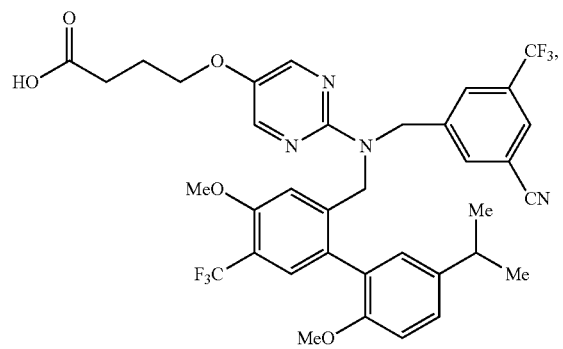
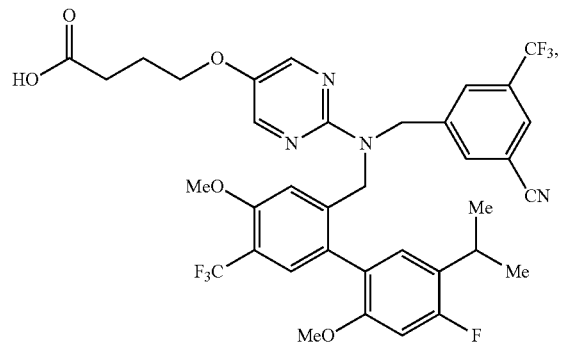
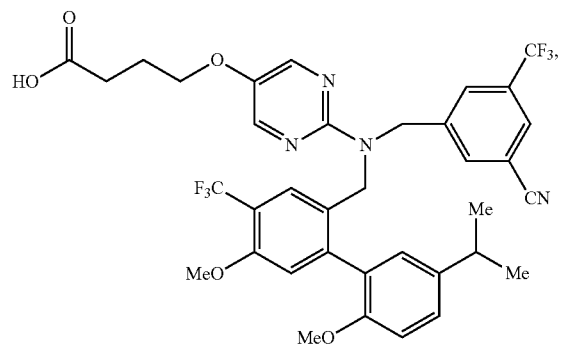
238
-continued
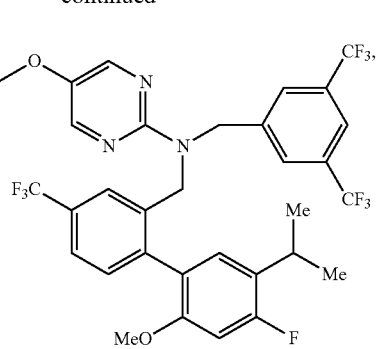
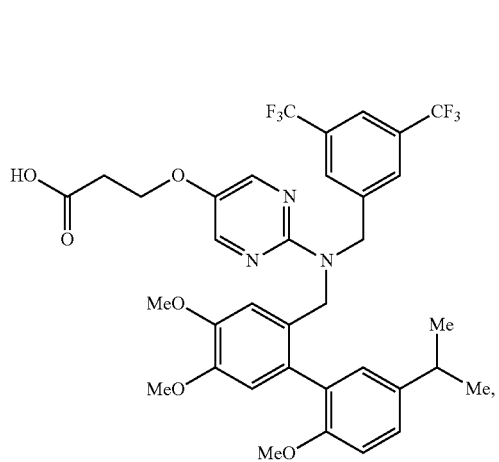
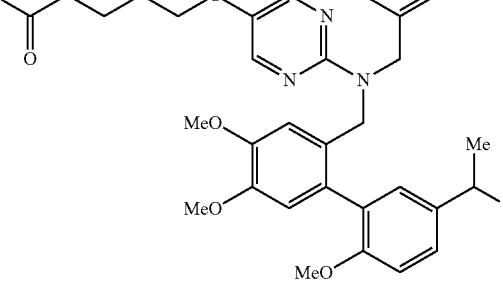
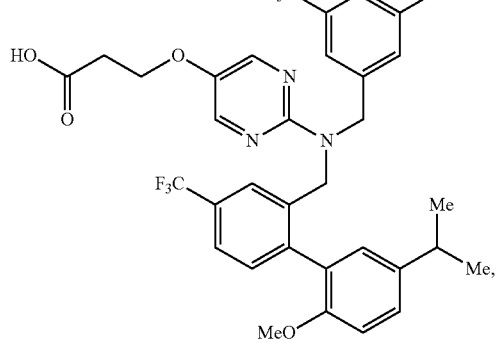

239
-continued
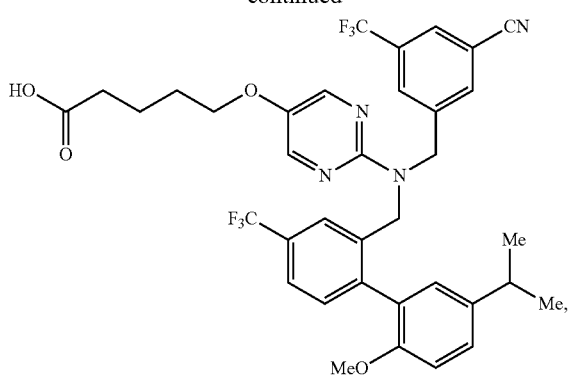
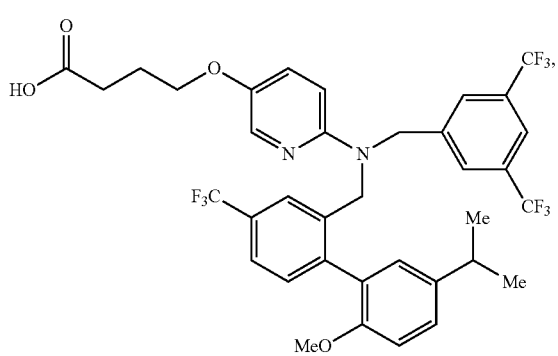
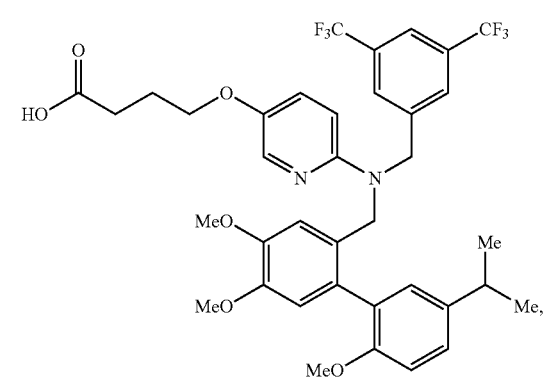
240
-continued
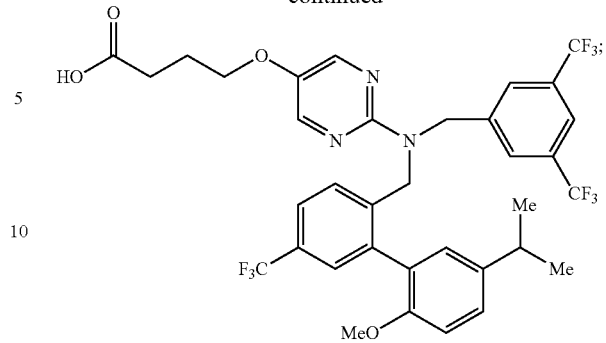
or a pharmaceutically acceptable salt thereof.
16. The compound of claim 11, which is represented by the following chemical formula:
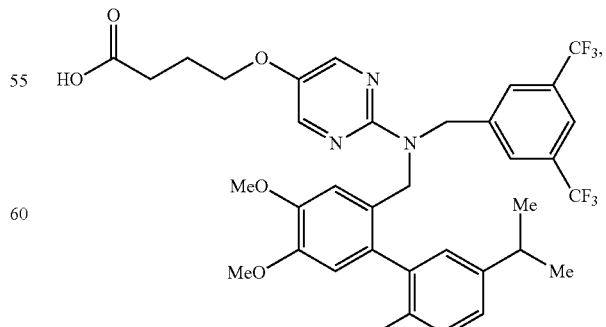
or a pharmaceutically acceptable salt thereof.
17. The compound of claim 11, which is represented by the following chemical formula:
or a pharmaceutically acceptable salt thereof.

18. A compound selected from the group consisting of:
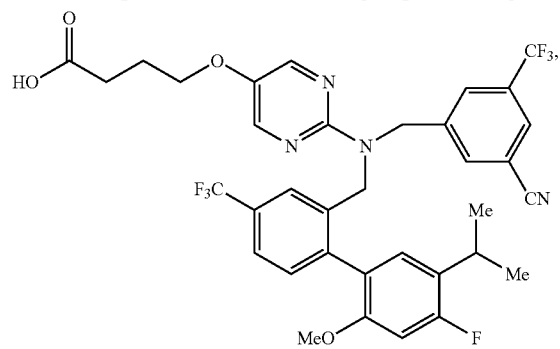
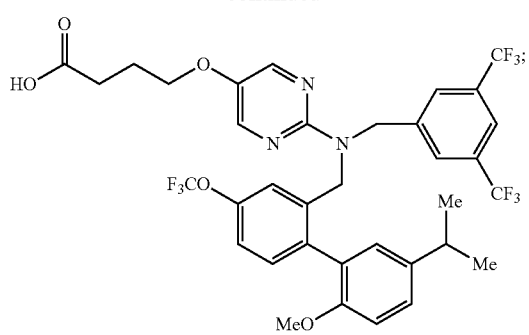
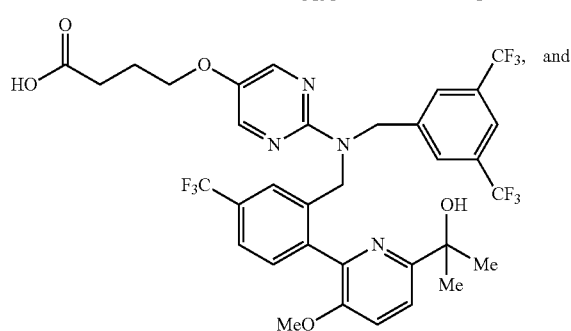
or a pharmaceutically acceptable salt thereof.
* * * * *

UNITED STATES PATENT AND TRADEMARK OFFICE
CERTIFICATE OF CORRECTION

PATENT NO. : 7,906,517 B2  Page 1 of 1
APPLICATION NO. : 12/219775
DATED : March 15, 2011
INVENTOR(S) : Yoshinori Nakamura et al.

It is certified that error appears in the above-identified patent and that said Letters Patent is hereby corrected as shown below:

Claim 11, at column 211, between lines numbered 35-50, replace the formula with the following correct formula:

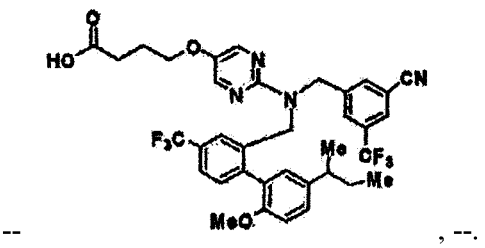

, --.

Claim 11, at column 217, between lines numbered 25-35, replace the formula with the following correct formula:

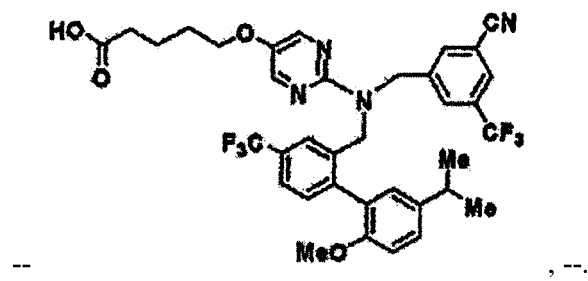

, --.

Signed and Sealed this
Twenty-first Day of June, 2011

David J. Kappos
*Director of the United States Patent and Trademark Office*